(12) United States Patent
Williams

(10) Patent No.: US 10,167,478 B2
(45) Date of Patent: *Jan. 1, 2019

(54) REPLICATIVE MINICIRCLE VECTORS WITH IMPROVED EXPRESSION

(71) Applicant: Nature Technology Corporation, Lincoln, NE (US)

(72) Inventor: James A. Williams, Lincoln, NE (US)

(73) Assignee: Nature Technology Corporation, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/096,517

(22) Filed: Apr. 12, 2016

(65) Prior Publication Data

US 2016/0215296 A1    Jul. 28, 2016

Related U.S. Application Data

(62) Division of application No. 14/432,693, filed as application No. PCT/US2013/000259 on Nov. 18, 2013.

(60) Provisional application No. 61/796,765, filed on Nov. 19, 2012.

(30) Foreign Application Priority Data

Mar. 14, 2013   (WO) ................ PCT/US2013/000067
Mar. 14, 2013   (WO) ................ PCT/US2013/000068

(51) Int. Cl.
| | | |
|---|---|---|
| *C12N 15/00* | (2006.01) |
| *C12N 15/79* | (2006.01) |
| *C12N 15/64* | (2006.01) |
| *C12P 21/00* | (2006.01) |
| *C12N 15/85* | (2006.01) |
| *C12N 15/63* | (2006.01) |
| *C12P 19/34* | (2006.01) |
| *C12N 15/67* | (2006.01) |
| *A61K 48/00* | (2006.01) |

(52) U.S. Cl.
CPC ............ *C12N 15/79* (2013.01); *C12N 15/63* (2013.01); *C12N 15/64* (2013.01); *C12N 15/67* (2013.01); *C12N 15/85* (2013.01); *C12P 19/34* (2013.01); *C12P 21/00* (2013.01); *A61K 48/00* (2013.01); *C12N 2800/107* (2013.01); *C12N 2800/24* (2013.01); *C12N 2820/55* (2013.01); *C12N 2830/42* (2013.01)

(58) Field of Classification Search
CPC ........ C12N 15/85; C12N 15/64; C12N 16/63; C12N 2820/55; C12N 2800/24; C12N 2839/42; C12N 2800/107; C12P 21/00; C12P 19/34; A61K 48/00
See application file for complete search history.

(56) References Cited

U.S. PATENT DOCUMENTS

| | | |
|---|---|---|
| 6,977,174 B2 | 12/2005 | Crouzet et al. |
| 7,611,883 B2 | 11/2009 | Cranenburgh |
| 8,871,503 B2 | 10/2014 | Hyde et al. |
| 8,993,316 B2 | 3/2015 | Hanley |
| 9,347,073 B2 | 5/2016 | Kay et al. |
| 2010/0184158 A1 | 7/2010 | Williams |
| 2010/0303859 A1 | 12/2010 | Williams |

FOREIGN PATENT DOCUMENTS

| | | |
|---|---|---|
| EP | 2333091 A2 | 6/2011 |
| WO | 2014035457 A1 | 3/2014 |

OTHER PUBLICATIONS

Abhyankar et al., Biochemical Investigations of Control of Replication Initiation of Plasmid R6K*, Journal of Biological Chemistry. vol. 279. No. 8, pp. 6711-6719, 2004.
Abhyankar et al., "Reconstitution of R6K replication in Vitro Using 22 Purified Proteins", The Journal of Biological Chemistry, vol. 278. No. 46, pp. 45476-45484, 2003.
Angulo et al., "Identification of a Boundary Domain Adjacent to the Potent Human cytomegalovirus Enhancer That Represses Transcription of the Divergent UL127 Promoter" Journal of Virology, Mar. 2000, p. 2826-2839.
Ashfield et al. "MAZ-dependent termination between closely spaced human complement genes" The EMBO Journal vol. 13 No. 23 pp. 5656-5667, 1994.
Barouch et al. "A Human T-Cell Leukemia Virus Type 1 Regulatory Element Enhances the Immunogenicity of Human Immunodeficiency Virus Type 1 DNA Vaccines in Mice and Nonhuman Primates" Journal of Virology, Jul. 2005, pp. 8828-8834 2005.
Brendel et al. "Gene structure prediction from consensus spliced alignment of multiple ESTs matching the same genomic locus" Bioinformatics vol. 20 No. 7 pp. 1157-1169, 2004.
Brunak et al. "Prediction of Human mRNA and Acceptor Sites from the DNA Sequence " J. Mol. Biol. (1991) 220, 49-65.
Carnes et al. "Critical design criteria for minimal antibiotic-free plasmid vectors necessary to combine robust RNA Pol II and Pol III-mediated eukaryotic expression with high bacterial production yields" The Journal of Gene Medicine 2010; 12: 818-831.
Carnes et al. "Plasmid DNA Fermentation Strain and Process-Specific effects on Vector Yield, Quality, and Transgene Expression" Biotechnology and Bioengineering, vol. 108, No. 2, pp. 354-363, 2011.
Carnes "Fermentation Design for the Manufacture of Therapeutic Plasmid DNA" Bioprocess International, pp. 2-7, Oct. 2005.
Chen et al. "Silencing of episomal transgene expression by plasmid bacterial DNA elements in vivo" Gene Therapy 11, 856-864, 2004.
Chenna et al. "Multiple sequence alignment with the Clustal series of programs" Nucleic Acids Research, vol. 31, No. 13, pp. 3497-3500, 2003.

(Continued)

*Primary Examiner* — Mindy G. Brown
(74) *Attorney, Agent, or Firm* — Harness, Dickey & Pierce, P.L.C.

(57) ABSTRACT

The present invention relates to the production and use of covalently closed circular (ccc) recombinant DNA molecules such as plasmids, cosmids, bacterial artificial chromosomes (BACs), bacteriophages, viral vectors and hybrids thereof, and more particularly to vector modifications that improve expression of said DNA molecules.

15 Claims, 13 Drawing Sheets
Specification includes a Sequence Listing.

(56) References Cited

OTHER PUBLICATIONS

Del Solar et al., "Replication and Control of Circular Bacterial Plasmids", Microbiology and Molecular Biology Reviews, vol. 62, No. 2, pp. 434-464, Jun. 1998.
Franch and Gerdes "U-turns and regulatory RNAs" Current Opinion in Microbiology, 3:159-164, 2000.
Garg et al. "The Hybrid Cytomegalovirus Enhancer/Chicken b-Actin Promoter along with Woodchuck Hepatitis Virus Posttranscriptional Regulatory element Enhances the Protective Efficacy of DNA Vaccines" The Journal of Immunology pp. 550-558, 2004.
Hebel et al. "Challenges in the process development of a novel Zero-CpG CFTR plasmid for human clinical use" VGX Pharmaceuticals, Inc., (1 page), 2008.
Hiraga et al. "Comparative analysis of the replicon regions of eleven COIE2-related plasmids" vol. 176, No. 23, Journal of Bacteriology, pp. 7233-7243, Dec. 1994.
Kay et al. "A robust system for production of minicircle DNA vectors" Nature Biotechnology, 2010.
Kim et al. "Improved Mammalian Expression Systems by Manipulating Transcriptional Termination Regions" Biotechnol. Prog. vol. 19, No. 5. p. 1620-1622, 2003.
Lemp et al "Cryptic transcriptps from a ubiquitous plasmid origin or replican confound tests for cis-regulatory function" Nucleic Acids Research pp. 1-11, May 2012.
Lu et al. "The Extragenic Spacer Length Between the 5' and 3' Ends of the Transgene Expression Cassette Affects Trangene Silencing from Plasmid-based Vectors" Molecular Therapy, pp. 1-9, 2012.
Luke et al. "Improved antibiotic-free DNA vaccine vectors utilizing a novel RNA based plasmid selection system" Vaccine 27, pp. 6454-6459, 2009.
Luke et al. "Improved antiobiotic-free plasmid vector design by incorporation of transient expression enhancers" Gene Therapy (2011) 18, 334-343.
Luke et al. "Vector Insert-Targeted Integrative Antisense Expression System for Plasmid Stabilization" Mol. Biotechnol, (7 pages), 2010.
Manoj et al. "Approaches to Enhance the Efficacy of DNA Vaccines" Critical Reviews in Clinical Laboratory Sciences, 41(1), pp. 1-39, 2004.
Marians et al. "Maximal Limits of the *Excherichia coli* Replication Factor Y Effector Site Sequences in pBR322 DNA" The Journal of Biological Chemistry, vol. 247, No. 10, pp. 5656-5662, May 1982.
Masai et al. "The ABC-Primosome—A Novel Priming System Employing dnaA, dnaB, dnaC, and Primase on a Hairpin containing a dnaA Box Sequence" The Journal of Biological Chemistry, vol. 265, No. 25, pp. 15134-15144, Sep. 1990.

Masai et al. "Roles of øX174 Type Primosome—and G4 Type Primase-dependent Primings in Initiation of Lagging and Leading Strand Syntheses of DNA Replication" The Journal of Biological Chemistry, vol. 265, No. 25, pp. 15124-15133, Sep. 1990.
Mutalik et al. "Rationally designed families of orthogonal RNA regulators of translation" Nature Chemical Biology, pp. 1-8, Mar. 2012.
Na et al. "Metabolic engineering of Excherichia colii using synthetic small regulatory RNAs" Nature Biotechnology, pp. 1-7, 2013.
Nomura et al. "Identification of eleven single-strand initiation sequences (ssi) for priming of DNA replication in the F, R6K, R100 and ColE2 plasmids" Gene, 108 (1991) 15-22.
Sato et al. "A Specific DNA Sequence Controls Termination of Transcription in the Gastrin Gene" Molecular and Cellular Biology, vol. 6, No. 4, pp. 1032-1043, Apr. 1986.
Soubrier et al. "pCOR: a new design of plasmid vectors for nonviral gene therapy" Gene Therapy, (1999)6, pp. 1482-1489.
Suzuki et al. "Plasmid DNA Sequences Present in Conventional Herpes Simplex Viirus Amplicon Vectors Cause Rapid Transgene Silencing by Forming Inactive Chromatin" Journal of Virology, vol. 80, No. 7, pp. 3293-3300, Apr. 2006.
Takechi et al. "Control of ColE2 plasmid replication: regulation of Rep expression by a plasmid-coded antisense RNA", Mol Gen Genet (1994) 244: pp. 49-56.
Wagner et al. "Antisense RNAs in Bacteria and Their Genetic Elements" Advances in Genetics, vol. 46, pp. 361-398, 2002.
Wang er al. "Construction and analysis of compact muscle-specific promoters for AAV vectors" Gene Therapy, (2008) 15, 1489-1499.
Williams, J. A. "Vector Design for Improved DNA Vaccine Efficacy, Safety and Production" Vaccines, vol. 1, pp. 225-249, Jun. 2013.
Williams et al. "Plasmid DNA vaccine vector design: Impact on efficacy, safety and upstream production" Biotechnology Advances, vol. 27, No. 4, pp. 353-370, 2009.
Wilson et al. "Importance of Structural Differences between Complementary RNA Molecules to Control of Replication of an IncB Plasmid" Journal of Bacteriology, vol. 179, No. 3, pp. 742-753, Feb. 1997.
Wu et al. "A DNA Segment conferring Stable Maintenance on R6K y-Origin Core Replicons" Journal of Bacteriology, vol. 177, No. 22, pp. 6338-6345, Nov. 1995.
Yagura et al. "The Rep protein binding elements of the plasmid ColE2-P9 replication origin" Biochemical and Biophysical Research Communications, vol. 345, pp. 872-877, 2006.
Yagura et al. "Anatomy of the Replication Origin of Plasmid ColE2-P9" Journal of Bacteriology, vol. 188, No. 3, pp. 999-1010, Feb. 2006.
Soubrier et al. "Improvement of pCOR plasmid copy No. For pharmaceutical applications." Appl. Microbiol. Biotechnol., vol. 66, pp. 683-688, 2005.

HTLV- IR-Rabbit Beta globin hybrid intron (SEQ ID NO: 1)

AG*gtaagt*ttaaagctcaggtcgagaccgggcctttgtccggcgctcccttggagcctacctagactca
gccggctctccacgctttgcctgaccctgcttgctcaactctagttctctcGTTAACttaatgagacag
atagaaactggtcttgtagaaacagagtagtcgcctgcttttctgccaggtgctgacttctctcccct
gggcttttttcttttctcagG M = 1- Kb Plus DNA Ladder
1) NTC9385P2-O2-EGFP (intronic AF selection and pUC origin)
2) NTC9385P2a-O2-EGFP (intronic AF selection and pUC origin)
3) NTC9385P2-O1-EGFP (intronic AF selection and pUC origin)
4) NTC9385P2a-O1-EGFP (intronic AF selection and pUC origin)
5) NTC8385-EGFP (backbone AF selection and pUC origin)

M = 1- Kb Plus DNA Ladder
1) RF383 (2.4 kb NTC9385R-EGFP; backbone AF selection and R6K origin)
2) RF377 (2.4 kb NTC9385R2-O1-EGFP; intronic AF selection and R6K origin)
3) RF378 (2.4 kb NTC9385R2-O2-EGFP; intronic AF selection and R6K origin)
4) RF379 (2.5 kb NTC9385R2a-O1-EGFP; intronic AF selection and R6K origin)
5) RF380 (2.5 kb NTC9385R2a-O2-EGFP; intronic AF selection and R6K origin)

A)

IncB RNAII-SacB synthetic gene
362 bp

B)

IncB RNAI
124 bp

A)

B)

A)

B)

SEQUENCE LISTING

```
<160> NUMBER OF SEQ ID NOS: 77

<210> SEQ ID NO 1
<211> LENGTH: 228
<212> TYPE: DNA
<213> ORGANISM: Artificial Sequence
<220> FEATURE:
<223> OTHER INFORMATION: Description of Artificial Sequence: HTLV-
      IR-Rabbit Beta globin hybrid intron

<400> SEQUENCE: 1
aggtaagttt aaagctcagg tcgagaccgg gcctttgtcc ggcgctccct tggagcctac      60
ctagactcag ccggctctcc acgctttgcc tgaccctgct tgctcaactc tagttctctc     120
```

```
gttaacttaa tgagacagat agaaactggt cttgtagaaa cagagtagtc gcctgctttt    180
ctgccaggtg ctgacttctc tccctgggc ttttttcttt ttctcagg                  228
```

<210> SEQ ID NO 2
<211> LENGTH: 227
<212> TYPE: DNA
<213> ORGANISM: Artificial Sequence
<220> FEATURE:
<223> OTHER INFORMATION: Description of Artificial Sequence: HTLV- IR
      CMV hybrid intron

<400> SEQUENCE: 2

```
aggtaagttt aaagctcagg tcgagaccgg gcctttgtcc ggcgctccct tggagcctac    60
ctagactcag ccggctctcc acgctttgcc tgaccctgct tgctcaactc tagttaacgg   120
tggagggcag tgtagtctga gcagtactcg ttgctgccgc gcgcgccacc agacataata   180
gctgacagac taacagactg ttcctttcca tgggtctttt ctgcagt                 227
```

<210> SEQ ID NO 3
<211> LENGTH: 829
<212> TYPE: DNA
<213> ORGANISM: Artificial Sequence
<220> FEATURE:
<223> OTHER INFORMATION: Description of Artificial Sequence: CMV intron

<400> SEQUENCE: 3

```
acgtaagtac cgcctataga ctctataggc acacccttt ggctcttatg catgctatac    60 tgttttggc ttggggccta tacacccccg cttccttatg ctataggtga tggtatagct   120
tagcctatag gtgtgggtta ttgaccatta ttgaccactc ccctattggt gacgatactt   180
tccattacta atccataaca tggctctttg ccacaactat ctctattggc tatatgccaa   240
tactctgtcc ttcagagact gacacggact ctgtatttt acaggatggg gtcccattta   300
ttatttacaa attcacatat acaacaacgc cgtcccccgt gcccgcagtt tttattaaac   360
atagcgtggg atctccacgc gaatctcggg tacgtgttcc ggacatgggc tcttctccgg   420
tagcggcgga gcttccacat ccgagccctg gtcccatgcc tccagcggct catggtcgct   480
cggcagctcc ttgctcctaa cagtggaggc cagacttagg cacagcacaa tgcccaccac   540
caccagtgtg ccgcacaagg ccgtggcggt agggtatgtg tctgaaaatg agcgtggaga   600
ttgggctcgc acggctgacg cagatggaag acttaaggca gcggcagaag aagatgcagg   660
cagctgagtt gttgtattct gataagagtc agaggtaact cccgttgcgg tgctgttaac   720
ggtggagggc agtgtagtct gagcagtact cgttgctgcc gcgcgcgcca ccagacataa   780
tagctgacag actaacagac tgttcctttc atgggtctt tctgcagt                 829
```

<210> SEQ ID NO 4
<211> LENGTH: 142
<212> TYPE: DNA
<213> ORGANISM: Artificial Sequence
<220> FEATURE:
<223> OTHER INFORMATION: Description of Artificial Sequence: CpG free
      intron I 140

<400> SEQUENCE: 4

```
ggtaagtcac tgactgtcta tgcctgggaa agggtgggca ggagatgggg cagtgcagga    60
aaagtggcac tatgaaccct gcagccctag gaatgcatct agacaattgt actaaccttc   120
ttctctttcc tctcctgaca gg                                            142
```

```
<210> SEQ ID NO 5
<211> LENGTH: 135
<212> TYPE: DNA
<213> ORGANISM: Artificial Sequence
<220> FEATURE:
<223> OTHER INFORMATION: Description of Artificial Sequence: Human Beta
      globin Murine IgG chimeric intron

<400> SEQUENCE: 5
ggtaagtatc aaggttacaa gacaggttta aggagaccaa tagaaactgg gcttgtcgag      60
acagagaaga ctcttgcgtt tctgataggc acctattggt cttactgaca tccactttgc    120
ctttctctcc acagg                                                      135

<210> SEQ ID NO 6
<211> LENGTH: 276
<212> TYPE: DNA
<213> ORGANISM: Artificial Sequence
<220> FEATURE:
<223> OTHER INFORMATION: Description of Artificial Sequence: Adenovirus
      leader- Murine IgG chimeric intron

<400> SEQUENCE: 6
gattcgctgt ctgcgagggc cagctgttgg ggtgagtact ccctctcaaa agcgggcatg      60
acttctgcgc taagattgtc agtttccaaa aacgaggagg atttgatatt cacctggccc    120
gcggtgatgc ctttgagggt ggccgcgtcc atctggtcag aaaagacaat cttttttgttg    180 tcaagcttga ggtgtggcag gcttgagatc tggccataca cttgagtgac aatgacatcc    240
actttgcctt tctctccaca ggtgtccact cccagg                              276

<210> SEQ ID NO 7
<211> LENGTH: 128
<212> TYPE: DNA
<213> ORGANISM: Artificial Sequence
<220> FEATURE:
<223> OTHER INFORMATION: Description of Artificial Sequence: Rabbit Beta
      globin intron

<400> SEQUENCE: 7
ggtaagtatc cttttacag cacaacttaa tgagacagat agaaactggt cttgtagaaa      60
cagagtagtc gcctgctttt ctgccaggtg ctgacttctc tcccctgggc ttttttcatt    120
ttctcagg                                                              128

<210> SEQ ID NO 8
<211> LENGTH: 273
<212> TYPE: DNA
<213> ORGANISM: Artificial Sequence
<220> FEATURE:
<223> OTHER INFORMATION: Description of Artificial Sequence: Truncated
      CMV intron

<400> SEQUENCE: 8
acgtaagtac cgcctataga ctctataggc acacccttt ggctcttatg catgctatac       60
tgtttttggc ttggggccta tacacccccg cttccttatg ctataggtga tggtatagct    120
tagcctatag gtgtgggtta ttgaccatta ttgaccactc caacggtgga gggcagtgta    180
gtctgagcag tactcgttgc tgccgcgcgc gccaccagac ataatagctg acagactaac    240
agactgttcc tttccatggg tcttttctgc agt                                  273
```

<210> SEQ ID NO 9
<211> LENGTH: 921
<212> TYPE: DNA
<213> ORGANISM: Artificial Sequence
<220> FEATURE:
<223> OTHER INFORMATION: Description of Artificial Sequence: CAG
      (Chicken Beta Actin-rabbit beta globin) intron

<400> SEQUENCE: 9

| | | | | | |
|---|---|---|---|---|---|
| ggtgagcggg | cgggacggcc | cttctcctcc | gggctgtaat | tagcgcttgg | tttaatgacg | 60 |
| gctcgtttct | tttctgtggc | tgcgtgaaag | ccttaaaggg | ctccgggagg | gcccttgtg | 120 |
| cggggggggag | cggctcgggg | ggtgcgtgcg | tgtgtgtgtg | cgtggggagc | gccgcgtgcg | 180 |
| gcccgcgctg | cccggcggct | gtgagcgctg | cgggcgcggc | gcggggcttt | gtgcgctccg | 240 |
| cgtgtgcgcg | aggggagcgc | ggccgggggc | ggtgccccgc | ggtgcggggg | ggctgcgagg | 300 |
| ggaacaaagg | ctgcgtgcgg | ggtgtgtgcg | tgggggggtg | agcaggggggt | gtgggcgcgg | 360 |
| cggtcgggct | gtaacccccc | cctgcacccc | cctccccgag | ttgctgagca | cggcccggct | 420 |
| tcgggtgcgg | ggctccgtgc | ggggcgtggc | gcggggctcg | ccgtgccggg | cggggggtgg | 480 |
| cggcaggtgg | gggtgccggg | cggggcgggg | ccgcctcggg | ccggggaggg | ctcggggggag | 540 |
| gggcgcggcg | gccccggagc | gccggcggct | gtcgaggcgc | ggcgagccgc | agccattgcc | 600 |
| ttttatggta | atcgtgcgag | agggcgcagg | gacttccttt | gtcccaaatc | tggcggagcc | 660 |
| gaaatctggg | aggcgccgcc | gcaccccctc | tagcgggcgc | gggcgaagcg | gtgcggcgcc | 720 |
| ggcaggaagg | aaatgggcgg | ggagggcctt | cgtgcgtcgc | cgcgccgccg | tcccccttctc | 780 |
| catctccagc | ctcggggctg | ccgcaggggg | acggctgcct | tcggggggga | cggggcaggg | 840 |
| cggggttcgg | cttctggcgt | gtgaccggcg | gctctagagc | ctctgctaac | catgttcatg | 900 |
| ccttcttctt | tttcctacag | c | | | | 921 |

<210> SEQ ID NO 10
<211> LENGTH: 117
<212> TYPE: DNA
<213> ORGANISM: Artificial Sequence
<220> FEATURE:
<223> OTHER INFORMATION: Description of Artificial Sequence: CMV-Rabbit
      Beta globin hybrid intron

<400> SEQUENCE: 10

| | | | | | |
|---|---|---|---|---|---|
| aggtaagtag | ttaacttaat | gagacagata | gaaactggtc | ttgtagaaac | agagtagtcg | 60 |
| cctgcttttc | tgccaggtgc | tgacttctct | cccctgggct | tttttctttt | tctcagg | 117 |

<210> SEQ ID NO 11
<211> LENGTH: 281
<212> TYPE: DNA
<213> ORGANISM: Artificial Sequence
<220> FEATURE:
<223> OTHER INFORMATION: R6K gamma Origin

<400> SEQUENCE: 11

| | | | | | |
|---|---|---|---|---|---|
| ggcttgttgt | ccacaaccgt | taaaccttaa | aagctttaaa | agccttatat | attctttttt | 60 |
| ttcttataaa | acttaaaacc | ttagaggcta | tttaagttgc | tgatttatat | taatttatt | 120 |
| gttcaaacat | gagagcttag | tacgtgaaac | atgagagctt | agtacgttag | ccatgagagc | 180 |
| ttagtacgtt | agccatgagg | gtttagttcg | ttaaacatga | gagcttagta | cgttaaacat | 240 |
| gagagcttag | tacgtactat | caacaggttg | aactgctgat | c | | 281 |

```
<210> SEQ ID NO 12
<211> LENGTH: 260
<212> TYPE: DNA
<213> ORGANISM: Artificial Sequence
<220> FEATURE:
<223> OTHER INFORMATION: Description of Artificial Sequence: CpG free
      R6K gamma origin

<400> SEQUENCE: 12
aaaccttaaa acctttaaaa gccttatata ttcttttttt tcttataaaa cttaaaacct      60
tagaggctat ttaagttgct gatttatatt aatttattg ttcaaacatg agagcttagt     120
acatgaaaca tgagagctta gtacattagc catgagagct tagtacatta gccatgaggg    180
tttagttcat taaacatgag agcttagtac attaaacatg agagcttagt acatactatc    240
aacaggttga actgctgatc                                                260

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: ColE2
      Origin (+7)

<400> SEQUENCE: 13
caaaagggcg ctgttatctg ataaggctta tctggtctca ttttg                     45

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: ColE2
      Origin (Min)

<400> SEQUENCE: 14
ggcgctgtta tctgataagg cttatctggt ctcatttt                             38

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: ColE2
      origin (Core)

<400> SEQUENCE: 15
ggcgctgtta tctgataagg cttatctggt ct                                   32

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: CpG free
      ColE2 Origin (+7, CpG free)

<400> SEQUENCE: 16
caaaaggggg ctgttatctg ataaggctta tctggtctca ttttg                     45

<210> SEQ ID NO 17
<211> LENGTH: 76
<212> TYPE: DNA
<213> ORGANISM: Artificial Sequence
```

```
<220> FEATURE:
<223> OTHER INFORMATION: Description of Artificial Sequence: CpG free
      ssiA [from plasmid R6K]

<400> SEQUENCE: 17
tacaatggct catgtggaaa aaccattggc agaaaaacac ctgccaacag ttttaccaca      60
attgccactt aaccca                                                     76

<210> SEQ ID NO 18
<211> LENGTH: 121
<212> TYPE: DNA
<213> ORGANISM: Artificial Sequence
<220> FEATURE:
<223> OTHER INFORMATION: Description of Artificial Sequence: +7(CpG
      free) ColE2 origin-CpG free ssiA

<400> SEQUENCE: 18
tacaatggct catgtggaaa aaccattggc agaaaaacac ctgccaacag ttttaccaca      60
attgccactt aacccacaaa aggggctgt tatctgataa ggcttatctg gtctcatttt     120
g                                                                    121

<210> SEQ ID NO 19
<211> LENGTH: 132
<212> TYPE: DNA
<213> ORGANISM: Artificial Sequence
<220> FEATURE:
<223> OTHER INFORMATION: Description of Artificial Sequence: +7(CpG
      free) ColE2 origin-CpG free ssiA -flanked by SphI and KpnI sites

<400> SEQUENCE: 19
gcatgctaca atggctcatg tggaaaaacc attggcagaa aaacacctgc caacagtttt      60
accacaattg ccacttaacc cacaaaaggg ggctgttatc tgataaggct tatctggtct    120
cattttggta cc                                                        132

<210> SEQ ID NO 20
<211> LENGTH: 139
<212> TYPE: DNA
<213> ORGANISM: Artificial Sequence
<220> FEATURE:
<223> OTHER INFORMATION: Description of Artificial Sequence: RNA-OUT
      Selectable Marker

<400> SEQUENCE: 20
gtagaattgg taaagagagt cgtgtaaaat atcgagttcg cacatcttgt tgtctgatta      60 ttgattttg gcgaaaccat ttgatcatat gacaagatgt gtatctacct taacttaatg    120
attttgataa aaatcatta                                                 139

<210> SEQ ID NO 21
<211> LENGTH: 70
<212> TYPE: DNA
<213> ORGANISM: Artificial Sequence
<220> FEATURE:
<223> OTHER INFORMATION: Description of Artificial Sequence: RNA-OUT
      antisense repressor RNA

<400> SEQUENCE: 21
ttcgcacatc ttgttgtctg attattgatt tttggcgaaa ccatttgatc atatgacaag      60
atgtgtatct                                                            70
```

<210> SEQ ID NO 22
<211> LENGTH: 139
<212> TYPE: DNA
<213> ORGANISM: Artificial Sequence
<220> FEATURE:
<223> OTHER INFORMATION: Description of Artificial Sequence: CpG free
      RNA-OUT selection marker

<400> SEQUENCE: 22

```
gtagaattgg taaagagagt tgtgtaaaat attgagttag cacatcttgt tgtctgatta      60 ttgattttttg gggaaaccat ttgatcatat gacaagatgt gtatctacct taacttaatg    120
attttgataa aaatcatta                                                  139
```

<210> SEQ ID NO 23
<211> LENGTH: 281
<212> TYPE: DNA
<213> ORGANISM: Artificial Sequence
<220> FEATURE:
<223> OTHER INFORMATION: Description of Artificial Sequence: RNA-OUT-
      ColE2 origin Bacterial region [NheI site-ssiA-ColE2 Origin (+7)-
      RNA-OUT-KpnI site]

<400> SEQUENCE: 23

```
gctagctaca atggctcatg tggaaaaacc attggcagaa aaacacctgc caacagtttt      60
accacaattg ccacttaacc cacaaaaggg cgctgttatc tgataaggct tatctggtct    120
cattttgcac gttgtggtag aattggtaaa gagagtcgtg taaatatcg agttcgcaca     180 tcttgttgtc tgattattga ttttttggcga aaccatttga tcatatgaca agatgtgtat   240
ctaccttaac ttaatgattt tgataaaaat cattaggtac c                        281
```

<210> SEQ ID NO 24
<211> LENGTH: 275
<212> TYPE: DNA
<213> ORGANISM: Artificial Sequence
<220> FEATURE:
<223> OTHER INFORMATION: Description of Artificial Sequence: NTC9385C2
      and NTC9385C2a intronic Bacterial region [filled NheI site-ssiA-
      ColE2 Origin (+7)-RNA-OUT-chewed KpnI site] Sequence shown is O1;
      O2 is reverse complement

<400> SEQUENCE: 24

```
ctagctacaa tggctcatgt ggaaaaacca ttggcagaaa aacacctgcc aacagtttta      60
ccacaattgc cacttaaccc acaaaagggc gctgttatct gataaggctt atctggtctc    120
attttgcacg ttgtggtaga attggtaaag agagtcgtgt aaatatcga gttcgcacat     180 cttgttgtct gattattgat ttttggcgaa accatttgat catatgacaa gatgtgtatc    240
taccttaact taatgatttt gataaaaatc attag                                275
```

<210> SEQ ID NO 25
<211> LENGTH: 280
<212> TYPE: DNA
<213> ORGANISM: Artificial Sequence
<220> FEATURE:
<223> OTHER INFORMATION: Description of Artificial Sequence: CpG free
      ColE2 RNA-OUT bacterial region. (CpG free ssiA-CpG free ColE2
      origin-CpG free RNA-OUT selection marker)- - flanked by SphI and
      BglII restriction sites

<400> SEQUENCE: 25

```
agcatgctac aatggctcat gtggaaaaac cattggcaga aaacacctg ccaacagttt       60 taccacaatt gccacttaac ccacaaaagg gggctgttat ctgataaggc ttatctggtc    120
tcattttggt acctggtaga attggtaaag agagttgtgt aaaatattga gttagcacat    180
```

```
cttgttgtct gattattgat ttttggggaa accatttgat catatgacaa gatgtgtatc    240
taccttaact taatgatttt gataaaaatc attaagatct                         280
```

<210> SEQ ID NO 26
<211> LENGTH: 466
<212> TYPE: DNA
<213> ORGANISM: Artificial Sequence
<220> FEATURE:
<223> OTHER INFORMATION: Description of Artificial Sequence: RNA-OUT-R6K
      gamma origin Bacterial region [NheI site-trpA terminator-R6K
      Origin-RNA-OUT-KpnI site]

<400> SEQUENCE: 26

```
gctagcccgc ctaatgagcg ggcttttttt tggcttgttg tccacaaccg ttaaacctta    60
aaagctttaa aagccttata tattcttttt tttcttataa acttaaaaac cttagaggct   120
atttaagttg ctgatttata ttaattttat tgttcaaaca tgagagctta gtacgtgaaa   180
catgagagct tagtacgtta gccatgagag cttagtacgt tagccatgag ggtttagttc   240
gttaaacatg agagcttagt acgttaaaca tgagagctta gtacgtacta tcaacaggtt   300
gaactgctga tccacgttgt ggtagaattg gtaaagagag tcgtgtaaaa tatcgagttc   360
gcacatcttg ttgtctgatt attgattttt ggcgaaacca tttgatcata tgacaagatg   420
tgtatctacc ttaacttaat gattttgata aaaatcatta ggtacc                 466
```

<210> SEQ ID NO 27
<211> LENGTH: 460
<212> TYPE: DNA
<213> ORGANISM: Artificial Sequence
<220> FEATURE:
<223> OTHER INFORMATION: Description of Artificial Sequence: NTC9385R2
      and NTC9385R2a intronic R6K gamma origin- RNA-OUT Bacterial region
      [filled NheI site-trpA terminator-R6K Origin-RNA-OUT-chewed KpnI
      site] Sequence shown is O1; O2 is reverse complement

<400> SEQUENCE: 27

```
ctagcccgcc taatgagcgg gcttttttttt ggcttgttgt ccacaaccgt taaaccttaa    60
aagctttaaa agccttatat attcttttttt ttcttataaa acttaaaacc ttagaggcta   120
tttaagttgc tgatttatat taattttatt gttcaaacat gagagcttag tacgtgaaac   180
atgagagctt agtacgttag ccatgagagc ttagtacgtt agccatgagg gtttagttcg   240
ttaaacatga gagcttagta cgttaaacat gagagcttag tacgtactat caacaggttg   300
aactgctgat ccacgttgtg gtagaattgg taaagagagt cgtgtaaaat atcgagttcg   360
cacatcttgt tgtctgatta ttgattttg gcgaaaccat ttgatcatat gacaagatgt   420
gtatctacct taacttaatg attttgataa aaatcattag                         460
```

<210> SEQ ID NO 28
<211> LENGTH: 420
<212> TYPE: DNA
<213> ORGANISM: Artificial Sequence
<220> FEATURE:
<223> OTHER INFORMATION: Description of Artificial Sequence: CpG free
      R6K gamma origin - RNA-OUT bacterial region flanked by SphI and
      BglII restriction sites

<400> SEQUENCE: 28

```
agcatgcaaa ccttaaaacc tttaaaagcc ttatatattc ttttttttct tataaaactt    60
aaaaccttag aggctattta agttgctgat ttatattaat tttattgttc aaacatgaga   120
gcttagtaca tgaaacatga gagcttagta cattagccat gagagcttag tacattagcc   180
```

```
atgagggttt agttcattaa acatgagagc ttagtacatt aaacatgaga gcttagtaca    240
tactatcaac aggttgaact gctgatcggt acctggtaga attggtaaag agagttgtgt    300
aaaatattga gttagcacat cttgttgtct gattattgat ttttggggaa accatttgat    360
catatgacaa gatgtgtatc taccttaact taatgatttt gataaaaatc attaagatct    420
```

<210> SEQ ID NO 29
<211> LENGTH: 1210
<212> TYPE: DNA
<213> ORGANISM: Artificial Sequence
<220> FEATURE:
<223> OTHER INFORMATION: Description of Artificial Sequence: NTC9385P2
and NTC9385P2a intronic pUC origin- RNA-OUT Bacterial region
[filled NheI site-trpA terminator-pUC Origin-RNA-OUT-chewed KpnI
site] Sequence shown is O1; O2 is reverse complement

<400> SEQUENCE: 29

```
ctagcccgcc taatgagcgg gcttttttt cttaggcctt cttccgcttc ctcgctcact    60
gactcgctgc gctcggtcgt tcggctgcgg cgagcggtat cagctcactc aaaggcggta    120
atacggttat ccacagaatc aggggataac gcaggaaaga acatgtgagc aaaaggccag    180
caaaaggcca ggaaccgtaa aaaggccgcg ttgctggcgt ttttccatag gctccgcccc    240
cctgacgagc atcacaaaaa tcgacgctca agtcagaggt ggcgaaaccc gacaggacta    300
taaagatacc aggcgtttcc ccctggaagc tccctcgtgc gctctcctgt tccgaccctg    360
ccgcttaccg gatacctgtc cgcctttctc ccttcgggaa gcgtggcgct ttctcatagc    420
tcacgctgta ggtatctcag ttcggtgtag gtcgttcgct ccaagctggg ctgtgtgcac    480
gaaccccccg ttcagcccga ccgctgcgcc ttatccggta actatcgtct tgagtccaac    540
ccggtaagac acgacttatc gccactggca gcagccactg gtaacaggat tagcagagcg    600
aggtatgtag gcggtgctac agagttcttg aagtggtggc ctaactacgg ctacactaga    660
agaacagtat ttggtatctg cgctctgctg aagccagtta ccttcggaaa aagagttggt    720
agctcttgat ccggcaaaca aaccaccgct ggtagcggtg gtttttttgt ttgcaagcag    780
cagattacgc gcagaaaaaa aggatctcaa gaagatcctt tgatcttttc tacggggtct    840
gacgctcagt ggaacgaaaa ctcacgttaa gggattttgg tcatgagatt atcaaaaagg    900
atcttcacct agatcctttt aaattaaaaa tgaagtttta aatcaatcta agtatatat    960 gagtaaactt ggtctgacag ttaccaatgc ttaatcagtg aggcacctat ctcagcgatc    1020
tgtctatttc gttcatccat agttgcctga ctccctgcaaa ccacgttgtg gtagaattgg    1080
taaagagagt cgtgtaaaat atcgagttcg cacatcttgt tgtctgatta ttgattttg    1140 gcgaaaccat tgatcatat gacaagatgt gtatctacct taacttaatg attttgataa    1200
aaatcattag                                                          1210
```

<210> SEQ ID NO 30
<211> LENGTH: 1196
<212> TYPE: DNA
<213> ORGANISM: Artificial Sequence
<220> FEATURE:
<223> OTHER INFORMATION: Description of Artificial Sequence: NTC9385C2,
NTC9385R2, NTC9385P2 and NTC9385P2(0.85) Eukaryotic region. Bp 1
is start of CMV enhancer, bp 1196 is end of polyadenylation site.
Exon 2 encoded SalI (GTCGAC) and BglII (AGATCT) transgene cloning
sites.

<400> SEQUENCE: 30

```
ttattaatag taatcaatta cggggtcatt agttcatagc ccatatatgg agttccgcgt    60
tacataactt acggtaaatg gcccgcctgg ctgaccgccc aacgaccccc gcccattgac   120
gtcaataatg acgtatgttc ccatagtaac gccaataggg actttccatt gacgtcaatg   180
ggtggagtat ttacggtaaa ctgcccactt ggcagtacat caagtgtatc atatgccaag   240
tacgccccct attgacgtca atgacggtaa atggcccgcc tggcattatg cccagtacat   300
gaccttatgg gactttccta cttggcagta catctacgta ttagtcatcg ctattaccat   360
ggtgatgcgg ttttggcagt acatcaatgg gcgtggatag cggtttgact cacggggatt   420
tccaagtctc caccccattg acgtcaatgg gagtttgttt tggcaccaaa atcaacggga   480
ctttccaaaa tgtcgtaaca actccgcccc attgacgcaa atgggcggta ggcgtgtacg   540
gtgggaggtc tatataagca gagctcgttt agtgaaccgt cagatcgcct ggagacgcca   600
tccacgctgt tttgacctcc atagaagaca ccgggaccga tccagcctcc gcggctcgca   660
tctctccttc acgcgcccgc cgccctacct gaggccgcca tccacgccgg ttgagtcgcg   720
ttctgccgcc tcccgcctgt ggtgcctcct gaactgcgtc cgccgtctag gtaagtttaa   780
agctcaggtc gagaccgggc ctttgtccgg cgctcccttg gagcctacct agactcagcc   840
ggctctccac gctttgcctg accctgcttg ctcaactcta gttctctcgt taacttaatg   900
agacagatag aaactggtct gtagaaaca gagtagtcgc ctgcttttct gccaggtgct   960
gacttctctc ccctgggctt ttttcttttt ctcaggttga aagaagaag acgaagaaga  1020
cgaagaagac aaaccgtcgt cgacagatct ttttccctct gccaaaaatt atggggacat  1080
catgaagccc cttgagcatc tgacttctgg ctaataaagg aaatttattt tcattgcaat  1140
agtgtgttgg aattttttgt gtctctcact cggaaggaca taagggcggc cgctag      1196
```

<210> SEQ ID NO 31
<211> LENGTH: 1292
<212> TYPE: DNA
<213> ORGANISM: Artificial Sequence
<220> FEATURE:
<223> OTHER INFORMATION: Description of Artificial Sequence: NTC9385C2a, NTC9385R2a, NTC9385P2a and NTC9385P2a(0.85) Eukaryotic region. Bp 1 start of CMV enhancer encoded boundary region, bp 1292 is end of polyadenylation site. Exon 2 encoded SalI and BglII transgene

<400> SEQUENCE: 31

```
atggccattg catacgttgt atccatatca taatatgtac atttatattg gctcatgtcc    60
aacattaccg ccatgttgac attgattatt gactagttat taatagtaat caattacggg   120
gtcattagtt catagcccat atatggagtt ccgcgttaca taacttacgg taaatggccc   180
gcctggctga ccgcccaacg acccccgccc attgacgtca ataatgacgt atgttcccat   240
agtaacgcca atagggactt tccattgacg tcaatgggtg gagtatttac ggtaaactgc   300
ccacttggca gtacatcaag tgtatcatat gccaagtacg ccccctattg acgtcaatga   360
cggtaaatgg cccgcctggc attatgccca gtacatgacc ttatgggact ttcctacttg   420
gcagtacatc tacgtattag tcatcgctat taccatggtg atgcggtttt ggcagtacat   480
caatgggcgt ggatagcggt ttgactcacg gggatttcca gtctccacc ccattgacgt   540
caatgggagt ttgttttggc accaaaatca acgggacttt ccaaaatgtc gtaacaactc   600
cgccccattg acgcaaatgg gcggtaggcg tgtacggtgg gaggtctata taagcagagc   660
tcgtttagtg aaccgtcaga tcgcctggag acgccatcca cgctgttttg acctccatag   720
```

```
aagacaccgg gaccgatcca gcctccgcgg ctcgcatctc tccttcacgc gcccgccgcc    780
ctacctgagg ccgccatcca cgccggttga gtcgcgttct gccgcctccc gcctgtggtg    840
cctcctgaac tgcgtccgcc gtctaggtaa gtttaaagct caggtcgaga ccgggccttt    900
gtccggcgct cccttggagc ctacctagac tcagccggct ctccacgctt tgcctgaccc    960
tgcttgctca actctagttc tctcgttaac ttaatgagac agatagaaac tggtcttgta   1020
gaaacagagt agtcgcctgc ttttctgcca ggtgctgact tctctcccct gggctttttt   1080 cttttctca ggttgaaaag aagaagacga agaagacgaa gaagacaaac cgtcgtcgac    1140
agatcttttt ccctctgcca aaaattatgg ggacatcatg aagccccttg agcatctgac   1200
ttctggctaa taaaggaaat ttattttcat tgcaatagtg tgttggaatt ttttgtgtct   1260
ctcactcgga aggacataag ggcggccgct ag                                  1292
```

```
<210> SEQ ID NO 32
<211> LENGTH: 230
<212> TYPE: DNA
<213> ORGANISM: Artificial Sequence
<220> FEATURE:
<223> OTHER INFORMATION: Description of Artificial Sequence: CpG free
      HTLV- IR-Rabbit Beta globin hybrid intron

<400> SEQUENCE: 32
aggtaagttt aaagctcagg tcagagacca gggcctttgt ccaggcagct cccttggagc     60
ctacctagac tcagccaggc tctccagctt gcctgaccc tgcttgctca actctagttc    120
tctgttaact taatgagaca gatagaaact ggtcttgtag aaacagagta gtgcctgctt    180
ttctgccagg tgctgacttc tctcccctgg ctttttttct ttttctcagg                230

<210> SEQ ID NO 33
<211> LENGTH: 108
<212> TYPE: DNA
<213> ORGANISM: Artificial Sequence
<220> FEATURE:
<223> OTHER INFORMATION: Description of Artificial Sequence: RNAI
      antisense repressor RNA (pMB1 plasmid origin RNAII antisense
      partner)

<400> SEQUENCE: 33
acagtatttg gtatctgcgc tctgctgaag ccagttacct tcggaaaaag agttggtagc     60
tcttgatccg gcaaacaaac caccgctggt agcggtggtt ttttgtt                  108

<210> SEQ ID NO 34
<211> LENGTH: 156
<212> TYPE: DNA
<213> ORGANISM: Artificial Sequence
<220> FEATURE:
<223> OTHER INFORMATION: Description of Artificial Sequence: RNAI
      selectable Marker

<400> SEQUENCE: 34
ttgaagtggt ggcctaacta cggctacact agaagaacag tatttggtat ctgcgctctg     60
ctgaagccag ttaccttcgg aaaaagagtt ggtagctctt gatccggcaa acaaaccacc   120
gctggtagcg gtggtttttt tgtttgcaag cagcag                              156

<210> SEQ ID NO 35
<211> LENGTH: 73
<212> TYPE: DNA
<213> ORGANISM: Artificial Sequence
```

```
<220> FEATURE:
<223> OTHER INFORMATION: Description of Artificial Sequence: IncB RNAI
      antisense repressor RNA (IncB plasmid origin RNAII antisense
      partner)

<400> SEQUENCE: 35
gtattctgtg aggcccccat tatttttctg cgttccgcca agttcgagga aaaatagtgg      60
gggttttcct tta                                                        73

<210> SEQ ID NO 36
<211> LENGTH: 109
<212> TYPE: DNA
<213> ORGANISM: Artificial Sequence
<220> FEATURE:
<223> OTHER INFORMATION: Description of Artificial Sequence: IncB RNAI
      selectable Marker, RNAI  RNA (Sense strand).

<400> SEQUENCE: 36
ttgaatctct ggtacggttt catatatact tatcccgtat tctgtgaggc ccccattatt      60
tttctgcgtt ccgccaagtt cgaggaaaaa tagtgggggt tttccttta               109

<210> SEQ ID NO 37
<211> LENGTH: 362
<212> TYPE: DNA
<213> ORGANISM: Artificial Sequence
<220> FEATURE:
<223> OTHER INFORMATION: Description of Artificial Sequence: IncB RNAII-
      SacB. PstI-MamI restriction fragment

<400> SEQUENCE: 37
ctgcagttca agcggtgga aaagggtat attgcggatc gttattcagt ggcttttggg        60
atcctcgcgg tccggaaagc cagaaaacgg cagaatgcgc cataaggcat tcaggacgta    120
tggcagaaac gacggcagtt tgccggtgcc ggaaggctga aaaaagtttc agaagaccat    180
aaaggaaaac ccccactatt tttcctcgaa cttggcggaa cgcagaaaaa taatgggggc    240
ctcacagaat acgggatagg gcccatgaaa ccgtaccaga gattgggccc tgtgcagtgt    300
ataaatacac ggcacaatcg ctccgccata agcgacagct tgtggcaggt ctgatgaaca    360
tc                                                                  362

<210> SEQ ID NO 38
<211> LENGTH: 67
<212> TYPE: DNA
<213> ORGANISM: Artificial Sequence
<220> FEATURE:
<223> OTHER INFORMATION: Description of Artificial Sequence: RNA
      selection marker (RSM) antisense repressor RNA

<400> SEQUENCE: 38
atgttcatgt tcttgtctcc ttattgattt ttggggaaac catttgatca tatgagaaca     60
tgaacta                                                              67

<210> SEQ ID NO 39
<211> LENGTH: 139
<212> TYPE: DNA
<213> ORGANISM: Artificial Sequence
<220> FEATURE:
<223> OTHER INFORMATION: Description of Artificial Sequence: RNA
      selectable marker (RSM)
```

<400> SEQUENCE: 39

```
gttgacatgg taaagagagt tgtgtaaaat attgagtatg ttcatgttct tgtctcctta    60
ttgatttttg gggaaaccat ttgatcatat gagaacatga actactacct taacttaatg   120
attttgataa aaatcatta                                                 139
```

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: RSM
      complement

<400> SEQUENCE: 40

```
cccaaaaatc aataaggaga caagaacatg aacat                               35
```

<210> SEQ ID NO 41
<211> LENGTH: 1497
<212> TYPE: DNA
<213> ORGANISM: Artificial Sequence
<220> FEATURE:
<223> OTHER INFORMATION: Description of Artificial Sequence: RNA
      selection-sacB (P5/6 4/6) PstI/BamHI restriction fragment

<400> SEQUENCE: 41

```
ctgcaggtag acatttatcc cttgcggcga tagattggtt tccccaaaaa tcaataagga    60
gacaagaaca tgaacatcaa aaaattcgcc aaacaggcaa ccgtcttgac cttcaccacc   120
gcactgctgg caggcggtgc aacccaggca tttgcaaaag aaaccaatca gaagccgtac   180
aaagaaacct atggcattag ccacatcaca cgccatgaca tgctgcaaat tccggaacag   240
cagaaaaacg agaagtacaa agtgccggaa ttcgatagca gcaccattaa aaacattagc   300
agcgcaaaag gtctggatgt tgggatagc tggcctctgc aaaataccga tggcaccgtt   360
gcaaattacc acggctatca cattgttttt gcactggctg gtgatccgaa aaatgcagac   420
gacaccagca tctacatgtt ttatcagaaa gttggcgaaa ccagcatcga cagctggaag   480
aacgccggtc gtgtttttaa agatagcgat aaatttgatg ccaacgatag catcctgaaa   540
gatcagaccc aagagtggtc tggtagcgcc acctttacct cagatggcaa gattcgtctg   600
ttctacaccg atttcagcgg taaacattat ggtaaacaga ccttgaccac agcccaggtt   660
aacgtcagcg caagcgatag cagtctgaat attaacggtg tggaggacta caaaagcatc   720
tttgatggtg atggcaaaac ctatcagaac gtgcagcagt ttattgatga aggcaattac   780
agcagcggtg acaaccatac cctgcgtgat ccgcattatg ttgaagataa aggccataaa   840
tatctggtgt ttgaagcaaa taccggcacc gaagacggtt atcagggtga agaaagcctg   900
tttaacaaag cctactacgg caaaagcacc agctttttc gccaagaaag ccagaaactg   960
ctgcaaagcg acaagaaacg taccgcagaa ctggcaaatg gtgcactggg catgattgaa  1020
ctgaatgatg actacacccc tgaaaaagtg atgaaaccgc tgattgcaag caataccgtt  1080
accgacgaga ttgaacgtgc caacgtgttc aagatgaacg gtaagtggta cctgtttacc  1140
gatagccgtg gtagcaaaat gaccattgat ggtattacga gcaacgatat ttacatgctg  1200
ggttacgtca gcaatagctt aaccggtccg tacaaacctc tgaataaaac cggtctggtt  1260
ctgaaaatgg atctggaccc gaatgacgtc accttcacct attcacactt cgcagttccg  1320
caggccaaag gcaataacgt tgttatcact agctacatga ccaaccgtgg tttctacgca  1380
```

```
gataaacaga gcacctttgc accgagcttt ctgctgaaca ttaaaggtaa aaaaaccagc    1440
gtggtgaaag acagcatcct ggaacagggc cagcttaccg tgaacaagtg aggatcc      1497
```

<210> SEQ ID NO 42
<211> LENGTH: 1497
<212> TYPE: DNA
<213> ORGANISM: Artificial Sequence
<220> FEATURE:
<223> OTHER INFORMATION: Description of Artificial Sequence: RNA
      selection-sacB (P5/6 5/6) PstI/BamHI restriction fragment

<400> SEQUENCE: 42

```
ctgcaggtag acacacatct tgtcatatga tagaatggtt tccccaaaaa tcaataagga     60
gacaagaaca tgaacatcaa aaaattcgcc aaacaggcaa ccgtcttgac cttcaccacc   120
gcactgctgg caggcggtgc aacccaggca tttgcaaaag aaaccaatca gaagccgtac   180
aaagaaacct atggcattag ccacatcaca cgccatgaca tgctgcaaat tccggaacag   240
cagaaaaacg agaagtacaa agtgccggaa ttcgatagca gcaccattaa aaacattagc   300
agcgcaaaag gtctggatgt ttgggatagc tggcctctgc aaaataccga tggcaccgtt   360
gcaaattacc acggctatca cattgttttt gcactggctg gtgatccgaa aaatgcagac   420
gacaccagca tctacatgtt ttatcagaaa gttggcgaaa ccagcatcga cagctggaag   480
aacgccggtc gtgtttttaa agatagcgat aaatttgatg ccaacgatag catcctgaaa   540
gatcagaccc aagagtggtc tggtagcgcc acctttacct cagatggcaa gattcgtctg   600
ttctacaccg atttcagcgg taaacattat ggtaaacaga ccttgaccac agcccaggtt   660
aacgtcagcg caagcgatag cagtctgaat attaacggtg tggaggacta caaaagcatc   720
tttgatggtg atggcaaaac ctatcagaac gtgcagcagt ttattgatga aggcaattac   780
agcagcggtg acaaccatac cctgcgtgat ccgcattatg ttgaagataa aggccataaa   840
tatctggtgt ttgaagcaaa taccggcacc gaagacggtt atcagggtga agaaagcctg   900
tttaacaaag cctactacgg caaaagcacc agcttttttc gccaagaaag ccagaaactg   960
ctgcaaagcg acaagaaacg taccgcagaa ctggcaaatg gtgcactggg catgattgaa  1020
ctgaatgatg actacacccct gaaaaaagtg atgaaaccgc tgattgcaag caataccgtt  1080
accgacgaga ttgaacgtgc caacgtgttc aagatgaacg gtaagtggta cctgtttacc  1140
gatagccgtg gtagcaaaat gaccattgat ggtattacga gcaacgatat ttacatgctg  1200
ggttacgtca gcaatagctt aaccggtccg tacaaacctc tgaataaaac cggtctggtt  1260
ctgaaaatgg atctggaccc gaatgacgtc accttcacct attcacactt cgcagttccg  1320
caggccaaag gcaataacgt tgttatcact agctacatga ccaaccgtgg tttctacgca  1380
gataaacaga gcacctttgc accgagcttt ctgctgaaca ttaaaggtaa aaaaaccagc  1440
gtggtgaaag acagcatcct ggaacagggc cagcttaccg tgaacaagtg aggatcc     1497
```

<210> SEQ ID NO 43
<211> LENGTH: 4015
<212> TYPE: DNA
<213> ORGANISM: Artificial Sequence
<220> FEATURE:
<223> OTHER INFORMATION: Description of Artificial Sequence: pINT-RNAS
      integration vector (P5/6 4/6)

<400> SEQUENCE: 43

```
ctgcaggtag acatttatcc cttgcggcga tagattggtt tccccaaaaa tcaataagga    60
gacaagaaca tgaacatcaa aaaattcgcc aaacaggcaa ccgtcttgac cttcaccacc  120
```

```
gcactgctgg caggcggtgc aacccaggca tttgcaaaag aaaccaatca gaagccgtac    180
aaagaaacct atggcattag ccacatcaca cgccatgaca tgctgcaaat tccggaacag    240
cagaaaaacg agaagtacaa agtgccggaa ttcgatagca gcaccattaa aacattagc    300 agcgcaaaag gtctggatgt ttgggatagc tggcctctgc aaaataccga tggcaccgtt    360
gcaaattacc acggctatca cattgttttt gcactggctg gtgatccgaa aaatgcagac    420
gacaccagca tctacatgtt ttatcagaaa gttggcgaaa ccagcatcga cagctggaag    480
aacgccggtc gtgtttttaa agatagcgat aaatttgatg ccaacgatag catcctgaaa    540
gatcagaccc aagagtggtc tggtagcgcc acctttacct cagatggcaa gattcgtctg    600
ttctacaccg atttcagcgg taaacattat ggtaaacaga ccttgaccac agcccaggtt    660
aacgtcagcg caagcgatag cagtctgaat attaacggtg tggaggacta caaaagcatc    720
tttgatggtg atggcaaaac ctatcagaac gtgcagcagt ttattgatga aggcaattac    780
agcagcggtg acaaccatac cctgcgtgat ccgcattatg ttgaagataa aggccataaa    840
tatctggtgt ttgaagcaaa taccggcacc gaagacggtt atcagggtga agaaagcctg    900
tttaacaaag cctactacgg caaaagcacc agcttttttc gccaagaaag ccagaaactg    960
ctgcaaagcg acaagaaacg taccgcagaa ctggcaaatg gtgcactggg catgattgaa   1020
ctgaatgatg actacaccct gaaaaaagtg atgaaccgc tgattgcaag caataccgtt   1080
accgacgaga ttgaacgtgc caacgtgttc aagatgaacg gtaagtggta cctgtttacc   1140
gatagccgtg gtagcaaaat gaccattgat ggtattacga gcaacgatat ttacatgctg   1200
ggttacgtca gcaatagctt aaccggtccg tacaaacctc tgaataaaac cggtctggtt   1260
ctgaaaatgg atctggaccc gaatgacgtc accttcacct attcacactt cgcagttccg   1320
caggccaaag gcaataacgt tgttatcact agctacatga ccaaccgtgg tttctacgca   1380
gataaacaga gcacctttgc accgagcttt ctgctgaaca ttaaaggtaa aaaaaccagc   1440
gtggtgaaag acagcatcct ggaacagggc cagcttaccg tgaacaagtg aggatccccg   1500
gaattaattc tcatgtttga cagcttatca ctgatcagtg aattaatggc gatgacgcat   1560
cctcacgata atatccgggt aggcgcaatc actttcgtct ctactccgtt acaaagcgag   1620
gctgggtatt cccggccctt tctgttatcc gaaatccact gaaagcacag cggctggctg   1680
aggagataaa taataaacga ggggctgtat gcacaaagca tcttctgttg agttaagaac   1740
gagtatcgag atggcacata gccttgctca aattggaatc aggtttgtgc caataccagt   1800
agaaacagac gaagaagcta gctttgcact ggattgcgag gctttgtgct tctctggagt   1860
gcgacaggtt tgatgacaaa aaattagcgc aagaagacaa aaatcacctt gcgctaatgc   1920
tctgttacag gtcactaata ccatctaagt agttgattca tagtgactgc atatatgttg   1980
tgttttacag tattatgtag tctgtttttt atgcaaaatc taatttaata tattgatatt   2040
tatatcattt tacgtttctc gttcagcttt tttatactaa gttggcatta taaaaaagca   2100
ttgcttatca atttgttgca acgaacaggt cactatcagt caaaataaaa tcattatttg   2160
atttcaattt tgtcccactc cctgcctctg tcatcacgat actgtgatgc catggctaat   2220
tcccatgtca gccgttaagt gttcctgtgt cactcaaaat tgctttgaga ggctctaagg   2280
gcttctcagt gcgttacatc cctggcttgt tgtccacaac cgttaaacct taaaagcttt   2340
aaaagcctta tatattcttt ttttctttat aaaacttaaa accttagagg ctatttaagt   2400
tgctgattta tattaatttt attgttcaaa catgagagct tagtacgtga acatgagag    2460 cttagtacgt tagccatgag agcttagtac gttagccatg agggtttagt tcgttaaaca   2520
```

```
tgagagctta gtacgttaaa catgagagct tagtacgtga aacatgagag cttagtacgt    2580
actatcaaca ggttgaactg ctgatcttca gatcctctac gccggacgca tcgtggccgg    2640
atcttgcggc cgcaaaaatt aaaaatgaag ttttaaatca atctaaagta tatatgagta    2700
aacttggtct gacagttacc aatgcttaat cagtgaggca ccataactg ccttaaaaaa     2760 attacgcccc gccctgccac tcatcgcagt actgttgtaa ttcattaagc attctgccga    2820
catggaagcc atcacagacg gcatgatgaa cctgaatcgc cagcggcatc agcaccttgt    2880
cgccttgcgt ataatatttg cccatggtga aaacggggc gaagaagttg tccatattgg     2940
ccacgtttaa atcaaaactg gtgaaactca cccagggatt ggctgagacg aaaaacatat    3000
tctcaataaa cccttttaggg aaataggcca ggttttcacc gtaacacgcc acatcttgcg   3060
aatatatgtg tagaaactgc cggaaatcgt cgtggtattc actccagagc gatgaaaacg    3120
tttcagtttg ctcatggaaa acggtgtaac aagggtgaac actatcccat atcaccagct    3180
caccgtcttt cattgccata cggaatttcg gatgagcatt catcaggcgg gcaagaatgt    3240
gaataaaggc cggataaaac ttgtgcttat ttttctttac ggtctttaaa aaggccgtaa    3300
tatccagctg aacggtctgg ttataggtac attgagcaac tgactgaaat gcctcaaaat    3360
gttctttacg atgccattgg gatatatcaa cggtggtata ccagtgatt tttttctcca     3420 ttttagcttc cttagctcct gaaaatctcg ataactcaaa aaatacgccc ggtagtgatc    3480
ttatttcatt atggtgaaag ttggaacctc ttacgtgccg atcaacgtct catttttcgcc   3540 aaaagttggc ccagggcttc ccggtatcaa cagggacacc aggattttatt tattctgcga   3600 agtgatcttc cgtcacaggt atttattcgg cgcaaagtgc gtcgggtgat gctgccaact    3660
tactgattta gtgtatgatg gtgtttttga ggtgctccag tggcttctgt ttctatcagc    3720
atcgatggcc cccgatggta gtgtggggtc tccccatgcg agagtaggga actgccaggc    3780
atcaaataaa acgaaaggct cagtcgaaag actgggcctt tcgttttatc tgttgttgt    3840 cggtgaacgc tctcctgagt aggacaaatc cgccgggagc ggatttgaac gttgcgaagc   3900
aacggcccgg agggtggcgg gcaggacgcc cgccataaac tgccaggcat caaattaagc   3960
agaaggccat cctgacggat ggcctttttg cgtggccagt gccaagcttg catgc         4015
```

<210> SEQ ID NO 44
<211> LENGTH: 4015
<212> TYPE: DNA
<213> ORGANISM: Artificial Sequence
<220> FEATURE:
<223> OTHER INFORMATION: Description of Artificial Sequence: pINT-RNAS
      integration vector (P5/6 5/6)

<400> SEQUENCE: 44

```
ctgcaggtag acacacatct tgtcatatga tagaatggtt tccccaaaaa tcaataagga      60
gacaagaaca tgaacatcaa aaaattcgcc aaacaggcaa ccgtcttgac cttcaccacc    120
gcactgctgg caggcggtgc aacccaggca tttgcaaaag aaaccaatca gaagccgtac    180
aaagaaacct atggcattag ccacatcaca cgccatgaca tgctgcaaat tccggaacag    240
cagaaaaacg agaagtacaa agtgccggaa ttcgatagca gcaccattaa aaacattagc    300
agcgcaaaag gtctggatgt ttgggatagc tggcctctgc aaaataccga tggcaccgtt    360
gcaaattacc acggctatca cattgttttt gcactggctg gtgatccgaa aaatgcagac    420
gacaccagca tctacatgtt ttatcagaaa gttggcgaaa ccagcatcga cagctggaag    480
aacgccggtc gtgttttaa agatagcgat aaatttgatg ccaacgatag catcctgaaa    540
```

-continued

```
gatcagaccc aagagtggtc tggtagcgcc acctttacct cagatggcaa gattcgtctg    600
ttctacaccg atttcagcgg taaacattat ggtaaacaga ccttgaccac agcccaggtt    660
aacgtcagcg caagcgatag cagtctgaat attaacggtg tggaggacta caaaagcatc    720
tttgatggtg atggcaaaac ctatcagaac gtgcagcagt ttattgatga aggcaattac    780
agcagcggtg acaaccatac cctgcgtgat ccgcattatg ttgaagataa aggccataaa    840
tatctggtgt ttgaagcaaa taccggcacc gaagacggtt atcagggtga agaaagcctg    900
tttaacaaag cctactacgg caaaagcacc agctttttc gccaagaaag ccagaaactg     960
ctgcaaagcg acaagaaacg taccgcagaa ctggcaaatg gtgcactggg catgattgaa   1020
ctgaatgatg actacaccct gaaaaagtg atgaaccgc tgattgcaag caataccgtt     1080
accgacgaga ttgaacgtgc caacgtgttc aagatgaacg gtaagtggta cctgtttacc   1140
gatagccgtg gtagcaaaat gaccattgat ggtattacga gcaacgatat ttacatgctg   1200
ggttacgtca gcaatagctt aaccggtccg tacaaacctc tgaataaaac cggtctggtt   1260
ctgaaaatgg atctggaccc gaatgacgtc accttcacct attcacactt cgcagttccg   1320
caggccaaag gcaataacgt tgttatcact agctacatga ccaaccgtgg tttctacgca   1380
gataaacaga gcacctttgc accgagcttt ctgctgaaca ttaaaggtaa aaaaaccagc   1440
gtggtgaaag acagcatcct ggaacagggc cagcttaccg tgaacaagtg aggatccccg   1500
gaattaattc tcatgtttga cagcttatca ctgatcagtg aattaatggc gatgacgcat   1560
cctcacgata atatccgggt aggcgcaatc actttcgtct ctactccgtt acaaagcgag   1620
gctgggtatt tcccggcctt tctgttatcc gaaatccact gaaagcacag cggctggctg   1680
aggagataaa taataaacga ggggctgtat gcacaaagca tcttctgttg agttaagaac   1740
gagtatcgag atggcacata gccttgctca aattggaatc aggtttgtgc caataccagt   1800
agaaacagac gaagaagcta gctttgcact ggattgcgag gctttgtgct tctctggagt   1860
gcgacaggtt tgatgacaaa aaattagcgc aagaagacaa aaatcacctt gcgctaatgc   1920
tctgttacag gtcactaata ccatctaagt agttgattca tagtgactgc atatatgttg   1980
tgttttacag tattatgtag tctgttttt atgcaaaatc taatttaata tattgatatt    2040
tatatcattt tacgtttctc gttcagcttt tttatactaa gttggcatta taaaaaagca   2100
ttgcttatca atttgttgca acgaacaggt cactatcagt caaaataaaa tcattatttg   2160
atttcaattt tgtcccactc cctgcctctg tcatcacgat actgtgatgc catggctaat   2220
tcccatgtca gccgttaagt gttcctgtgt cactcaaaat tgctttgaga ggctctaagg   2280
gcttctcagt gcgttacatc cctggcttgt tgtccacaac cgttaaacct aaaagctttt   2340
aaaagcctta tatattcttt tttttcttat aaaacttaaa accttagagg ctatttaagt   2400
tgctgattta tattaatttt attgttcaaa catgagagct tagtacgtga acatgagag    2460 cttagtacgt tagccatgag agcttagtac gttagccatg agggtttagt tcgttaaaca   2520
tgagagctta gtacgttaaa catgagagct tagtacgtga acatgagag cttagtacgt    2580 actatcaaca ggttgaactg ctgatcttca gatcctctac gccggacgca tcgtggccgg   2640
atcttgcggc cgcaaaaatt aaaaatgaag ttttaaatca atctaaagta tatatgagta   2700
aacttggtct gacagttacc aatgcttaat cagtgaggca ccaataactg ccttaaaaaa   2760
attacgcccc gccctgccac tcatcgcagt actgttgtaa ttcattaagc attctgccga   2820
catggaagcc atcacagacg gcatgatgaa cctgaatcgc cagcggcatc agcaccttgt   2880
cgccttgcgt ataatatttg cccatggtga aaacgggggc gaagaagttg tccatattgg   2940
```

```
ccacgtttaa atcaaaactg gtgaaactca cccagggatt ggctgagacg aaaaacatat    3000
tctcaataaa ccctttaggg aaataggcca ggttttcacc gtaacacgcc acatcttgcg    3060
aatatatgtg tagaaactgc cggaaatcgt cgtggtattc actccagagc gatgaaaacg    3120
tttcagtttg ctcatggaaa acggtgtaac aagggtgaac actatcccat atcaccagct    3180
caccgtcttt cattgccata cggaatttcg gatgagcatt catcaggcgg gcaagaatgt    3240
gaataaaggc cggataaaac ttgtgcttat ttttctttac ggtctttaaa aaggccgtaa    3300
tatccagctg aacggtctgg ttataggtac attgagcaac tgactgaaat gcctcaaaat    3360
gttctttacg atgccattgg gatatatcaa cggtggtata tccagtgatt ttttctcca    3420 ttttagcttc cttagctcct gaaaatctcg ataactcaaa aaatacgccc ggtagtgatc    3480
ttatttcatt atggtgaaag ttggaacctc ttacgtgccg atcaacgtct catttccgcc    3540
aaaagttggc ccagggcttc ccggtatcaa cagggacacc aggatttatt tattctgcga    3600
agtgatcttc cgtcacaggt atttattcgg cgcaaagtgc gtcgggtgat gctgccaact    3660
tactgattta gtgtatgatg gtgttttga ggtgctccag tggcttctgt ttctatcagc    3720
atcgatggcc cccgatggta gtgtggggtc tccccatgcg agagtaggga actgccaggc    3780
atcaaataaa acgaaaggct cagtcgaaag actgggcctt tcgttttatc tgttgtttgt    3840
cggtgaacgc tctcctgagt aggacaaatc cgccgggagc ggatttgaac gttgcgaagc    3900 aacgcccgg agggtggcgg gcaggacgcc cgccataaac tgccaggcat caaattaagc    3960
agaaggccat cctgacggat ggccttttg cgtggccagt gccaagcttg catgc          4015

<210> SEQ ID NO 45
<211> LENGTH: 678
<212> TYPE: DNA
<213> ORGANISM: Artificial Sequence
<220> FEATURE:
<223> OTHER INFORMATION: Description of Artificial Sequence: Pmin pUC
      replication origin (minimal)

<400> SEQUENCE: 45
cgcgttgctg gcgtttttca taggctccgc cccctgacg agcatcacaa aaatcgacgc      60
tcaagtcaga ggtggcgaaa cccgacagga ctataaagat accaggcgtt ccccctgga    120 agctccctcg tgcgctctcc tgttccgacc ctgccgctta ccggatacct gtccgccttt    180
ctcccttcgg gaagcgtggc gctttctcat agctcacgct gtaggtatct cagttcggtg    240
taggtcgttc gctccaagct gggctgtgtg cacgaacccc ccgttcagcc cgaccgctgc    300
gccttatccg gtaactatcg tcttgagtcc aacccggtaa gacacgactt atcgccactg    360
gcagcagcca ctggtaacag gattagcaga gcgaggtatg taggcggtgc tacagagttc    420
ttgaagtggt ggcctaacta cggctacact agaagaacag tatttggtat ctgcgctctg    480
ctgaagccag ttaccttcgg aaaaagagtt ggtagctctt gatccggcaa acaaaccacc    540
gctggtagcg gtggtttttt tgtttgcaag cagcagatta cgcgcagaaa aaaggatct    600 caagaagatc ctttgatctt ttctacgggg tctgacgctc agtggaacga aaactcacgt    660
taagggattt tggtcatg                                                678

<210> SEQ ID NO 46
<211> LENGTH: 860
<212> TYPE: DNA
<213> ORGANISM: Artificial Sequence
```

-continued

<220> FEATURE:
<223> OTHER INFORMATION: NTC9385P2(0.85) and NTC9385P2a(0.85) intronic
pUC (0.85) Bacterial region [filled NheI site-trpA terminator-
Pmin pUC replication origin-RNA-OUT-chewed KpnI site] Sequence
shown is O1; O2 is

<400> SEQUENCE: 46

```
ctagcccgcc taatgagcgg gcttttttt cttaggcctc gcgttgctgg cgttttcat        60
aggctccgcc ccctgacga gcatcacaaa atcgacgct caagtcagag gtggcgaaac       120
ccgacaggac tataaagata ccaggcgttt ccccctggaa gctccctcgt gcgctctcct    180
gttccgaccc tgccgcttac cggatacctg tccgccttc tcccttcggg aagcgtggcg     240
ctttctcata gctcacgctg taggtatctc agttcggtgt aggtcgttcg ctccaagctg    300
ggctgtgtgc acgaaccccc cgttcagccc gaccgctgcg ccttatccgg taactatcgt    360
cttgagtcca acccggtaag acacgactta tcgccactgg cagcagccac tggtaacagg    420
attagcagag cgaggtatgt aggcggtgct acagagttct tgaagtggtg cctaactac     480
ggctacacta gaagaacagt atttggtatc tgcgctctgc tgaagccagt taccttcgga   540
aaaagagttg gtagctcttg atccggcaaa caaaccaccg ctggtagcgg tggttttttt    600
gtttgcaagc agcagattac gcgcagaaaa aaggatctc aagaagatcc tttgatcttt    660
tctacggggt ctgacgctca gtggaacgaa aactcacgtt aagggatttt ggtcatggtg   720
gtagaattgg taaagagagt cgtgtaaaat atcgagttcg cacatcttgt tgtctgatta   780
ttgattttg gcgaaaccat ttgatcatat gacaagatgt gtatctacct taacttaatg    840
attttgataa aaatcattag                                                860
```

<210> SEQ ID NO 47
<211> LENGTH: 1751
<212> TYPE: DNA
<213> ORGANISM: Artificial Sequence
<220> FEATURE:
<223> OTHER INFORMATION: Description of Artificial Sequence: NTC9385RbF
vector backbone

<400> SEQUENCE: 47

```
atggccattg catacgttgt atccatatca taatatgtac atttatattg gctcatgtcc       60
aacattaccg ccatgttgac attgattatt gactagttat taatagtaat caattacggg    120
gtcattagtt catagcccat atatggagtt ccgcgttaca taacttacgg taaatggccc    180
gcctggctga ccgcccaacg acccccgccc attgacgtca ataatgacgt atgttcccat   240
agtaacgcca tagggactt tccattgacg tcaatgggtg gagtatttac ggtaaactgc    300
ccacttggca gtacatcaag tgtatcatat gccaagtacg ccccctattg acgtcaatga   360
cggtaaatgg cccgcctggc attatgccca gtacatgacc ttatgggact ttcctacttg    420
gcagtacatc tacgtattag tcatcgctat taccatggtg atgcggtttt ggcagtacat    480
caatgggcgt ggatagcggt ttgactcacg gggatttcca agtctccacc ccattgacgt    540
caatgggagt ttgttttggc accaaaatca acgggacttt ccaaaatgtc gtaacaactc   600
cgccccattg acgcaaatgg gcggtaggcg tgtacggtgg gaggtctata taagcagagc    660
tcgtttagtg aaccgtcaga tcgcctggag acgccatcca cgctgttttg acctccatag   720
aagacaccgg gaccgatcca gcctccgcgg ctcgcatctc tccttcacgc gcccgccgcc   780
ctacctgagg ccgccatcca cgccggttga gtcgcgttct gccgcctccc gcctgtggtg   840
cctcctgaac tgcgtccgcc gtctaggtaa gtttaaagct caggtcgaga ccgggccttt   900
```

```
gtccggcgct cccttggagc ctacctagac tcagccggct ctccacgctt tgcctgaccc    960
tgcttgctca actctagttc tctcgttgtg gtagaattgg taaagagagt cgtgtaaaat   1020
atcgagttcg cacatcttgt tgtctgatta ttgattttg gcgaaaccat ttgatcatat    1080
gacaagatgt gtatctacct taacttaatg attttgataa aaatcattag aacttaatga   1140
gacagataga aactggtctt gtagaaacag agtagtcgcc tgcttttctg ccaggtgctg   1200
acttctctcc cctgggcttt tttcttttc tcaggttgaa agaagaagaa cgaagaagac    1260
gaagaagaca aaccgtcgtc gacagatcta gcccgcctaa tgagcgggct tttttttggc   1320
ttgttgtcca caaccgttaa acctaaaaag ctttaaaagc cttatatatt ctttttttc    1380
ttataaaact taaaaccta gaggctattt aagttgctga tttatattaa ttttattgtt    1440
caaacatgag agcttagtac gtgaaacatg agagcttagt acgttagcca tgagagctta   1500
gtacgttagc catgagggtt tagttcgtta acatgagag cttagtacgt taaacatgag    1560
agcttagtac gtactatcaa caggttgaac tgctgatcca catcttttc cctctgccaa    1620
aaattatggg gacatcatga gccccttga gcatctgact tctggctaat aaaggaaatt    1680
tattttcatt gcaatagtgt gttggaattt tttgtgtctc tcactcggaa ggacataagg   1740
gcggccgcta g                                                        1751

<210> SEQ ID NO 48
<211> LENGTH: 1751
<212> TYPE: DNA
<213> ORGANISM: Artificial Sequence
<220> FEATURE:
<223> OTHER INFORMATION: Description of Artificial Sequence: NTC9385RbF-
      RSM vector backbone

<400> SEQUENCE: 48
atggccattg catacgttgt atccatatca taatatgtac atttatattg gctcatgtcc     60
aacattaccg ccatgttgac attgattatt gactagttat taatagtaat caattacggg    120
gtcattagtt catagcccat atatggagtt ccgcgttaca taacttacgg taaatggccc    180
gcctggctga ccgcccaacg acccccgccc attgacgtca ataatgacgt atgttcccat    240
agtaacgcca atagggactt tccattgacg tcaatgggtg gagtatttac ggtaaactgc    300
ccacttggca gtacatcaag tgtatcatat gccaagtacg ccccctattg acgtcaatga    360
cggtaaatgg cccgcctggc attatgccca gtacatgacc ttatgggact ttcctacttg    420
gcagtacatc tacgtattag tcatcgctat taccatggta tgcggttttt ggcagtacat    480
caatgggcgt ggatagcggt ttgactcacg gggatttcca agtctccacc ccattgacgt    540
caatgggagt ttgttttggc accaaaatca acgggacttt ccaaaatgtc gtaacaactc    600
cgccccattg acgcaaatgg gcggtaggcg tgtacggtgg gaggtctata taagcagagc    660
tcgtttagtg aaccgtcaga tcgcctggag acgccatcca cgctgttttg acctccatag    720
aagacaccgg gaccgatcca gcctccgcgg ctcgcatctc tccttcacgc gcccgccgcc    780
ctacctgagg ccgccatcca gccggttga gtcgcgttct gccgcctccc gcctgtggtg    840
cctcctgaac tgcgtccgcc gtctaggtaa gtttaaagct caggtcgaga ccgggccttt    900
gtccggcgct cccttggagc ctacctagac tcagccggct ctccacgctt tgcctgaccc    960
tgcttgctca actctagttc tctcgttgtg gttgacatgg taaagagagt tgtgtaaaat   1020
attgagtatg ttcatgttct tgtctcctta ttgatttttg gggaaaccat ttgatcatat   1080
gagaacatga actactacct taacttaatg attttgataa aaatcattag aacttaatga   1140
```

-continued

```
gacagataga aactggtctt gtagaaacag agtagtcgcc tgcttttctg ccaggtgctg    1200
acttctctcc cctgggcttt tttcttttc tcaggttgaa agaagaaga cgaagaagac      1260 gaagaagaca aaccgtcgtc gacagatcta gcccgcctaa tgagcgggct ttttttggc     1320 ttgttgtcca caaccgttaa accttaaaag ctttaaaagc cttatatatt ctttttttc     1380 ttataaaact taaaacctta gaggctattt aagttgctga tttatattaa ttttattgtt   1440
caaacatgag agcttagtac gtgaaacatg agagcttagt acgttagcca tgagagctta   1500
gtacgttagc catgagggtt tagttcgtta acatgagag cttagtacgt taaacatgag    1560
agcttagtac gtactatcaa caggttgaac tgctgatcca catctttttc cctctgccaa   1620
aaattatggg gacatcatga agcccttga gcatctgact tctggctaat aaaggaaatt    1680
tattttcatt gcaatagtgt gttggaattt tttgtgtctc tcactcggaa ggacataagg   1740
gcggccgcta g                                                         1751
```

<210> SEQ ID NO 49
<211> LENGTH: 1770
<212> TYPE: DNA
<213> ORGANISM: Artificial Sequence
<220> FEATURE:
<223> OTHER INFORMATION: Description of Artificial Sequence: NTC9385RbF-
    RNAI vector backbone

<400> SEQUENCE: 49

```
atggccattg catacgttgt atccatatca taatatgtac atttatattg gctcatgtcc     60
aacattaccg ccatgttgac attgattatt gactagttat taatagtaat caattacggg    120
gtcattagtt catagcccat atatggagtt ccgcgttaca taacttacgg taaatggccc    180
gcctggctga ccgcccaacg accccgccc attgacgtca ataatgacgt atgttcccat    240
agtaacgcca atagggactt tccattgacg tcaatgggtg gagtatttac ggtaaactgc    300
ccacttggca gtacatcaag tgtatcatat gccaagtacg cccctattg acgtcaatga    360 cggtaaatgg cccgcctggc attatgccca gtacatgacc ttatgggact ttcctacttg    420
gcagtacatc tacgtattag tcatcgctat taccatggtg atgcggtttt ggcagtacat    480
caatgggcgt ggatagcggt ttgactcacg gggatttcca agtctccacc ccattgacgt    540
caatgggagt ttgttttggc accaaaatca acgggacttt ccaaaatgtc gtaacaactc    600
cgccccattg acgcaaatgg gcggtaggcg tgtacggtgg gaggtctata taagcagagc    660
tcgtttagtg aaccgtcaga tcgcctggag acgccatcca cgctgttttg acctccatag    720
aagacaccgg gaccgatcca gcctccgcgg ctcgcatctc tccttcacgc gcccgccgcc    780
ctacctgagg ccgccatcca cgccggttga gtcgcgttct gccgcctccc gctgtggtg    840 cctcctgaac tgcgtccgcc gtctaggtaa gtttaaagct caggtcgaga ccgggccttt    900
gtccggcgct cccttggagc ctacctagac tcagccggct ctccacgctt tgcctgaccc    960
tgcttgctca actctagttc tctcgttaac ttgaagtggt ggcctaacta cggctacact   1020
agaagaacag tatttggtat ctgcgctctg ctgaagccag ttaccttcgg aaaagagtt    1080 ggtagctctt gatccggcaa acaaaccacc gctggtagcg tggttttttt tgtttgcaag   1140
cagcaggtta acttaatgag acagatagaa actggtcttg tagaaacaga gtagtcgcct   1200
gcttttctgc caggtgctga cttctctccc ctgggcttt ttcttttct caggttgaaa    1260 agaagaagac gaagaagacg aagaagacaa accgtcgtcg acagatctag cccgcctaat   1320
gagcgggctt ttttttggct tgttgtccac aaccgttaaa ccttaaaagc tttaaaagcc   1380
```

```
ttatatattc tttttttct  tataaaactt  aaaaccttag  aggctattta  agttgctgat   1440
ttatattaat  tttattgttc  aaacatgaga  gcttagtacg  tgaaacatga  gagcttagta   1500
cgttagccat  gagagcttag  tacgttagcc  atgagggttt  agttcgttaa  acatgagagc   1560
ttagtacgtt  aaacatgaga  gcttagtacg  tactatcaac  aggttgaact  gctgatccac   1620
atctttttcc  ctctgccaaa  aattatgggg  acatcatgaa  gccccttgag  catctgactt   1680
ctggctaata  aaggaaattt  attttcattg  caatagtgtg  ttggaatttt  ttgtgtctct   1740
cactcggaag  gacataaggg  cggccgctag                                     1770
```

<210> SEQ ID NO 50
<211> LENGTH: 1660
<212> TYPE: DNA
<213> ORGANISM: Artificial Sequence
<220> FEATURE:
<223> OTHER INFORMATION: Description of Artificial Sequence: NTC9385Ra-O1 vector backbone

<400> SEQUENCE: 50

```
ccgcctaatg  agcgggcttt  ttttggcttt  gttgtccaca  accgttaaac  cttaaaagct    60
ttaaaagcct  tatatattct  tttttttctt  ataaaactta  aaaccttaga  ggctatttaa   120
gttgctgatt  tatattaatt  ttattgttca  acatgagag   cttagtacgt  gaaacatgag   180
agcttagtac  gttagccatg  agagcttagt  acgttagcca  tgagggttta  gttcgttaaa   240
catgagagct  tagtacgtta  aacatgagag  cttagtacgt  actatcaaca  ggttgaactg   300
ctgatccacc  ccggctctag  ttattaatag  taatcaatta  cggggtcatt  agttcatagc   360
ccatatatgg  agttccgcgt  tacataactt  acggtaaatg  gcccgcctgg  ctgaccgccc   420
aacgaccccc  gcccattgac  gtcaataatg  acgtatgttc  ccatagtaac  gccaataggg   480
actttccatt  gacgtcaatg  ggtggagtat  ttacggtaaa  ctgcccactt  ggcagtacat   540
caagtgtatc  atatgccaag  tacgccccct  attgacgtca  atgacggtaa  atggcccgcc   600
tggcattatg  cccagtacat  gaccttatgg  gactttccta  cttggcagta  catctacgta   660
ttagtcatcg  ctattaccat  ggtgatgcgg  ttttggcagt  acatcaatgg  gcgtggatag   720
cggtttgact  cacggggatt  tccaagtctc  cacccattg   acgtcaatgg  gagtttgttt   780
tggcaccaaa  atcaacggga  ctttccaaaa  tgtcgtaaca  actccgcccc  attgacgcaa   840
atgggcggta  ggcgtgtacg  gtgggaggtc  tatataagca  gagctcgttt  agtgaaccgt   900
cagatcgcct  ggagacgcca  tccacgctgt  tttgacctcc  atagaagaca  ccgggaccga   960
tccagcctcc  gcggctcgca  tctctccttc  acgcgcccgc  cgccctacct  gaggccgcca  1020
tccacgccgg  ttgagtcgcg  ttctgccgcc  tcccgcctgt  ggtgcctcct  gaactgcgtc  1080
cgccgtctag  gtaagtttaa  agctcaggtc  gagaccgggc  ctttgtccgg  cgctcccttg  1140
gagcctacct  agactcagcc  ggctctccac  gctttgcctg  accctgcttg  ctcaactcta  1200
gttctctcgt  tgtggtagaa  ttggtaaaga  gagtcgtgta  aaatatcgag  ttcgcacatc  1260
ttgttgtctg  attattgatt  tttggcgaaa  ccatttgatc  atatgacaag  atgtgtatct  1320
accttaactt  aatgattttg  ataaaaatca  ttagaactta  atgagacaga  tagaaactgg  1380
tcttgtagaa  acagagtagt  cgcctgcttt  tctgccaggt  gctgacttct  ctcccctggg  1440
cttttttctt  tttctcaggt  tgaaagaag   aagacgaaga  agacgaagaa  gacaaaccgt  1500
cgtcgacaga  tcttttccc   tctgccaaaa  attatgggga  catcatgaag  ccccttgagc  1560
```

<210> SEQ ID NO 51
<211> LENGTH: 1660
<212> TYPE: DNA
<213> ORGANISM: Artificial Sequence
<220> FEATURE:
<223> OTHER INFORMATION: Description of Artificial Sequence: NTC9385Ra-O2 vector backbone

<400> SEQUENCE: 51

```
ccgcctaatg agcgggcttt tttttggctt gttgtccaca accgttaaac cttaaaagct      60
ttaaaagcct tatatattct ttttttttctt ataaaactta aaaccttaga ggctatttaa    120
gttgctgatt tatattaatt ttattgttca aacatgagag cttagtacgt gaaacatgag    180
agcttagtac gttagccatg agagcttagt acgttagcca tgagggttta gttcgttaaa    240
catgagagct tagtacgtta aacatgagag cttagtacgt actatcaaca ggttgaactg    300
ctgatccacc ccggctctag ttattaatag taatcaatta cggggtcatt agttcatagc    360
ccatatatgg agttccgcgt tacataactt acggtaaatg gcccgcctgg ctgaccgccc    420
aacgaccccc gcccattgac gtcaataatg acgtatgttc ccatagtaac gccaataggg    480
actttccatt gacgtcaatg ggtggagtat ttacggtaaa ctgcccactt ggcagtacat    540
caagtgtatc atatgccaag tacgccccct attgacgtca atgacggtaa atggcccgcc    600
tggcattatg cccagtacat gaccttatgg actttcctta cttggcagta catctacgta    660
ttagtcatcg ctattaccat ggtgatgcgg ttttggcagt acatcaatgg gcgtggatag    720
cggtttgact cacggggatt tccaagtctc cacccccattg acgtcaatgg gagtttgttt    780
tggcaccaaa atcaacggga ctttccaaaa tgtcgtaaca actccgcccc attgacgcaa    840
atgggcggta ggcgtgtacg gtgggaggtc tatataagca gagctcgttt agtgaaccgt    900
cagatcgcct ggagacgcca tccacgctgt tttgacctcc atagaagaca ccgggaccga    960
tccagcctcc gcggctcgca tctctccttc acgcgcccgc cgccctacct gaggccgcca   1020
tccacgccgg ttgagtcgcg ttctgccgcc tcccgcctgt ggtgcctcct gaactgcgtc   1080
cgccgtctag gtaagtttaa agctcaggtc gagaccgggc ctttgtccgg cgctccttg    1140
gagcctacct agactcagcc ggctctccac gctttgcctg accctgcttg ctcaactcta   1200
gttctctcgt tctaatgatt tttatcaaaa tcattaagtt aaggtagata cacatcttgt   1260
catatgatca aatggtttcg ccaaaaatca ataatcagac aacaagatgt gcgaactcga   1320
tattttacac gactctcttt accaattcta ccacaactta atgagacaga tagaaactgg   1380
tcttgtagaa acagagtagt cgcctgcttt tctgccaggt gctgacttct ctcccctggg   1440
cttttttctt tttctcaggt tgaaaagaag aagacgaaga agacgaagaa gacaaaccgt   1500
cgtcgacaga tctttttccc tctgccaaaa attatgggga catcatgaag ccccttgagc   1560
atctgacttc tggctaataa aggaaattta ttttcattgc aatagtgtgt tggaattttt   1620
tgtgtctctc actcggaagg acataagggc ggccgctagc                         1660
```

<210> SEQ ID NO 52
<211> LENGTH: 1660
<212> TYPE: DNA
<213> ORGANISM: Artificial Sequence
<220> FEATURE:
<223> OTHER INFORMATION: Description of Artificial Sequence: NTC9385Ra-O1-RSM vector backbone

```
<400> SEQUENCE: 52
ccgcctaatg agcgggcttt tttttggctt gttgtccaca accgttaaac cttaaaagct      60
ttaaaagcct tatatattct ttttttttctt ataaaactta aaaccttaga ggctatttaa    120
gttgctgatt tatattaatt ttattgttca aacatgagag cttagtacgt gaaacatgag    180
agcttagtac gttagccatg agagcttagt acgttagcca tgagggttta gttcgttaaa    240
catgagagct tagtacgtta aacatgagag cttagtacgt actatcaaca ggttgaactg    300
ctgatccacc ccggctctag ttattaatag taatcaatta cggggtcatt agttcatagc    360
ccatatatgg agttccgcgt tacataactt acggtaaatg gcccgcctgg ctgaccgccc    420 aacgacccc gcccattgac gtcaataatg acgtatgttc ccatagtaac gccaataggg     480
actttccatt gacgtcaatg ggtggagtat ttacggtaaa ctgcccactt ggcagtacat    540
caagtgtatc atatgccaag tacgccccct attgacgtca atgacggtaa atggcccgcc    600
tggcattatg cccagtacat gaccttatgg gactttccta cttggcagta catctacgta    660
ttagtcatcg ctattaccat ggtgatgcgg ttttggcagt acatcaatgg gcgtggatag    720
cggtttgact cacggggatt tccaagtctc cacccattg acgtcaatgg gagtttgttt     780
tggcaccaaa atcaacggga ctttccaaaa tgtcgtaaca actccgcccc attgacgcaa    840
atgggcggta ggcgtgtacg gtgggaggtc tatataagca gagctcgttt agtgaaccgt    900
cagatcgcct ggagacgcca tccacgctgt tttgacctcc atagaagaca ccgggaccga    960
tccagcctcc gcggctcgca tctctccttc acgcgcccgc cgcctacct gaggccgcca    1020 tccacgccgg ttgagtcgcg ttctgccgcc tcccgcctgt ggtgcctcct gaactgcgtc   1080
cgccgtctag gtaagtttaa agctcaggtc gagaccgggc ctttgtccgg cgctcccttg   1140
gagcctacct agactcagcc ggctctccac gctttgcctg accctgcttg ctcaactcta   1200
gttctctcgt tgtggttgac atggtaaaga gagttgtgta aaatattgag tatgttcatg   1260
ttcttgtctc cttattgatt tttggggaaa ccatttgatc atatgagaac atgaactact   1320
accttaactt aatgattttg ataaaaatca ttagaactta atgagacaga tagaaactgg   1380
tcttgtagaa acagagtagt cgcctgcttt tctgccaggt gctgacttct ctcccctggg   1440 ctttttttctt tttctcaggt tgaaaagaag aagacgaaga agacgaagaa gacaaaccgt   1500
cgtcgacaga tctttttccc tctgccaaaa attatgggga catcatgaag ccccttgagc   1560
atctgacttc tggctaataa aggaaattta ttttcattgc aatagtgtgt tggaattttt   1620
tgtgtctctc actcggaagg acataagggc ggccgctagc                          1660

<210> SEQ ID NO 53
<211> LENGTH: 1660
<212> TYPE: DNA
<213> ORGANISM: Artificial Sequence
<220> FEATURE:
<223> OTHER INFORMATION: Description of Artificial Sequence: NTC9385Ra-
      O2-RSM  vector backbone

<400> SEQUENCE: 53
ccgcctaatg agcgggcttt tttttggctt gttgtccaca accgttaaac cttaaaagct      60
ttaaaagcct tatatattct ttttttttctt ataaaactta aaaccttaga ggctatttaa    120
gttgctgatt tatattaatt ttattgttca aacatgagag cttagtacgt gaaacatgag    180
agcttagtac gttagccatg agagcttagt acgttagcca tgagggttta gttcgttaaa    240
catgagagct tagtacgtta aacatgagag cttagtacgt actatcaaca ggttgaactg    300
```

```
ctgatccacc ccggctctag ttattaatag taatcaatta cggggtcatt agttcatagc    360
ccatatatgg agttccgcgt tacataactt acggtaaatg gcccgcctgg ctgaccgccc    420 aacgacccccc gcccattgac gtcaataatg acgtatgttc ccatagtaac gccaataggg   480
actttccatt gacgtcaatg ggtggagtat ttacggtaaa ctgcccactt ggcagtacat    540
caagtgtatc atatgccaag tacgccccct attgacgtca atgacggtaa atggcccgcc    600
tggcattatg cccagtacat gaccttatgg gactttccta cttggcagta catctacgta    660
ttagtcatcg ctattaccat ggtgatgcgg ttttggcagt acatcaatgg gcgtggatag    720
cggtttgact cacggggatt tccaagtctc cacccccattg acgtcaatgg gagtttgttt   780
tggcaccaaa atcaacggga ctttccaaaa tgtcgtaaca actccgcccc attgacgcaa    840
atgggcggta ggcgtgtacg gtgggaggtc tatataagca gagctcgttt agtgaaccgt    900
cagatcgcct ggagacgcca tccacgctgt tttgacctcc atagaagaca ccgggaccga    960
tccagcctcc gcggctcgca tctctccttc acgcgcccgc cgccctacct gaggccgcca   1020
tccacgccgg ttgagtcgcg ttctgccgcc tcccgcctgt ggtgcctcct gaactgcgtc   1080
cgccgtctag gtaagtttaa agctcaggtc gagaccgggc ctttgtccgg cgctcccttg   1140
gagcctacct agactcagcc ggctctccac gctttgcctg accctgcttg ctcaactcta   1200
gttctctcgt tctaatgatt tttatcaaaa tcattaagtt aaggtagtag ttcatgttct   1260
catatgatca aatggtttcc ccaaaaatca ataaggagaa agaacatga acatactcaa    1320 tattttacac aactctcttt accatgtcaa ccacaactta atgagacaga tagaaactgg   1380
tcttgtagaa acagagtagt cgcctgcttt tctgccaggt gctgacttct ctccctggg    1440 cttttttctt tttctcaggt tgaaaagaag aagacgaaga agacgaagaa gacaaaccgt   1500
cgtcgacaga tcttttttccc tctgccaaaa attatgggga catcatgaag cccccttgagc  1560 atctgacttc tggctaataa aggaaattta ttttcattgc aatagtgtgt tggaattttt    1620
tgtgtctctc actcggaagg acataagggc ggccgctagc                         1660
```

<210> SEQ ID NO 54
<211> LENGTH: 1673
<212> TYPE: DNA
<213> ORGANISM: Artificial Sequence
<220> FEATURE:
<223> OTHER INFORMATION: Description of Artificial Sequence: NTC9385Ra-
      01-RNAI vector backbone

<400> SEQUENCE: 54

```
ccgcctaatg agcgggcttt ttttttggctt gttgtccaca accgttaaac cttaaaagct    60
ttaaaagcct tatatattct ttttttttctt ataaaactta aaaccttaga ggctatttaa   120
gttgctgatt tatattaatt ttattgttca aacatgagag cttagtacgt gaaacatgag   180
agcttagtac gttagccatg agagcttagt acgttagcca tgagggttta gttcgttaaa    240
catgagagct tagtacgtta acatgagagg cttagtacgt actatcaaca ggttgaactg    300
ctgatccacc ccggctctag ttattaatag taatcaatta cggggtcatt agttcatagc    360
ccatatatgg agttccgcgt tacataactt acggtaaatg gcccgcctgg ctgaccgccc   420 aacgacccccc gcccattgac gtcaataatg acgtatgttc ccatagtaac gccaataggg   480
actttccatt gacgtcaatg ggtggagtat ttacggtaaa ctgcccactt ggcagtacat    540
caagtgtatc atatgccaag tacgccccct attgacgtca atgacggtaa atggcccgcc    600
tggcattatg cccagtacat gaccttatgg gactttccta cttggcagta catctacgta    660
```

```
ttagtcatcg ctattaccat ggtgatgcgg ttttggcagt acatcaatgg gcgtggatag      720
cggtttgact cacggggatt tccaagtctc cacccattg acgtcaatgg gagtttgttt      780
tggcaccaaa atcaacggga ctttccaaaa tgtcgtaaca actccgcccc attgacgcaa      840
atgggcggta ggcgtgtacg gtgggaggtc tatataagca gagctcgttt agtgaaccgt      900
cagatcgcct ggagacgcca tccacgctgt tttgacctcc atagaagaca ccgggaccga      960
tccagcctcc gcggctcgca tctctccttc acgcgcccgc cgccctacct gaggccgcca     1020
tccacgccgg ttgagtcgcg ttctgccgcc tcccgcctgt ggtgcctcct gaactgcgtc     1080
cgccgtctag gtaagtttaa agctcaggtc gagaccgggc ctttgtccgg cgctcccttg     1140
gagcctacct agactcagcc ggctctccac gctttgcctg accctgcttg ctcaactcta     1200
gttctctcgt tttgaagtgg tggcctaact acggctacac tagaagaaca gtatttggta     1260
tctgcgctct gctgaagcca gttaccttcg gaaaagagt tggtagctct tgatccggca     1320
aacaaaccac cgctggtagc ggtggttttt tgtttgcaa gcagcagaac ttaatgagac     1380
agatagaaac tggtcttgta gaaacagagt agtcgcctgc ttttctgcca ggtgctgact     1440
tctctcccct gggcttttt cttttctca ggttgaaaag aagaagacga agaagacgaa      1500
gaagacaaac cgtcgtcgac agatctttt ccctctgcca aaaattatgg ggacatcatg      1560
aagccccttg agcatctgac ttctggctaa taaggaaat ttattttcat tgcaatagtg      1620
tgttggaatt ttttgtgtct ctcactcgga aggacataag ggcggccgct agc            1673
```

<210> SEQ ID NO 55
<211> LENGTH: 1673
<212> TYPE: DNA
<213> ORGANISM: Artificial Sequence
<220> FEATURE:
<223> OTHER INFORMATION: Description of Artificial Sequence: NTC9385Ra-O2-RNAI vector backbone

<400> SEQUENCE: 55

```
ccgcctaatg agcgggcttt ttttggctt gttgtccaca accgttaaac cttaaaagct       60
ttaaaagcct tatatattct tttttttctt ataaaactta aaaccttaga ggctatttaa      120
gttgctgatt tatattaatt ttattgttca aacatgagag cttagtacgt gaaacatgag      180
agcttagtac gttagccatg agagcttagt acgttagcca tgagggttta gttcgttaaa      240
catgagagct tagtacgtta acatgagag cttagtacgt actatcaaca ggttgaactg      300
ctgatccacc ccggctctag ttattaatag taatcaatta cggggtcatt agttcatagc      360
ccatatatgg agttccgcgt tacataactt acggtaaatg gcccgcctgg ctgaccgccc      420
aacgaccccc gcccattgac gtcaataatg acgtatgttc ccatagtaac gccaataggg      480
actttccatt gacgtcaatg ggtggagtat ttacggtaaa ctgcccactt ggcagtacat      540
caagtgtatc atatgccaag tacgccccct attgacgtca atgacggtaa atggcccgcc      600
tggcattatg cccagtacat gaccttatgg gactttccta cttggcagta catctacgta      660
ttagtcatcg ctattaccat ggtgatgcgg ttttggcagt acatcaatgg gcgtggatag      720
cggtttgact cacggggatt tccaagtctc cacccattg acgtcaatgg gagtttgttt      780
tggcaccaaa atcaacggga ctttccaaaa tgtcgtaaca actccgcccc attgacgcaa      840
atgggcggta ggcgtgtacg gtgggaggtc tatataagca gagctcgttt agtgaaccgt      900
cagatcgcct ggagacgcca tccacgctgt tttgacctcc atagaagaca ccgggaccga      960
tccagcctcc gcggctcgca tctctccttc acgcgcccgc cgccctacct gaggccgcca     1020
```

```
tccacgccgg ttgagtcgcg ttctgccgcc tcccgcctgt ggtgcctcct gaactgcgtc    1080
cgccgtctag gtaagtttaa agctcaggtc gagaccgggc ctttgtccgg cgctcccttg    1140
gagcctacct agactcagcc ggctctccac gctttgcctg accctgcttg ctcaactcta    1200
gttctctcgt tctgctgctt gcaaacaaaa aaaccaccgc taccagcggt ggtttgtttg    1260
ccggatcaag agctaccaac tcttttttcc g aaggtaactg gcttcagcag agcgcagata    1320
ccaaatactg ttcttctagt gtagccgtag ttaggccacc acttcaaaac ttaatgagac    1380
agatagaaac tggtcttgta gaaacagagt agtcgcctgc ttttctgcca ggtgctgact    1440
tctctcccct gggcttttt cttttctca ggttgaaaag aagaagacga agaagacgaa    1500
gaagacaaac cgtcgtcgac agatcttttt ccctctgcca aaaattatgg ggacatcatg    1560
aagccccttg agcatctgac ttctggctaa taaaggaaat ttattttcat tgcaatagtg    1620
tgttggaatt ttttgtgtct ctcactcgga aggacataag ggcggccgct agc    1673

<210> SEQ ID NO 56
<211> LENGTH: 1665
<212> TYPE: DNA
<213> ORGANISM: Artificial Sequence
<220> FEATURE:
<223> OTHER INFORMATION: Description of Artificial Sequence: NTC9385RaF
      vector backbone

<400> SEQUENCE: 56
ccgcctaatg agcgggcttt ttttggctt gttgtccaca accgttaaac cttaaaagct     60
ttaaaagcct tatatattct ttttttctt ataaaactta aaaccttaga ggctatttaa    120
gttgctgatt tatattaatt ttattgttca acatgagag cttagtacgt gaaacatgag    180
agcttagtac gttagccatg agagcttagt acgttagcca tgagggttta gttcgttaaa    240
catgagagct tagtacgtta acatgagag cttagtacg actatcaaca ggttgaactg    300
ctgatccacc ccggctctag ttattaatag taatcaatta cggggtcatt agttcatagc    360
ccatatatgg agttccgcgt tacataactt acggtaaatg gcccgcctgg ctgaccgccc    420 aacgacccc gcccattgac gtcaataatg acgtatgttc ccatagtaac gccaataggg    480
actttccatt gacgtcaatg ggtggagtat ttacggtaaa ctgcccactt ggcagtacat    540
caagtgtatc atatgccaag tacgcccct attgacgtca atgacggtaa atggcccgcc    600
tggcattatg cccagtacat gaccttatgg gactttccta cttggcagta catctacgta    660
ttagtcatcg ctattaccat ggtgatgcgg ttttggcagt acatcaatgg gcgtggatag    720
cggtttgact cacggggatt tccaagtctc cacccattg acgtcaatgg gagtttgttt    780
tggcaccaaa atcaacggga ctttccaaa tgtcgtaaca actccgcccc attgacgcaa    840
atgggcggta ggcgtgtacg gtgggaggtc tatataagca gagctcgttt agtgaaccgt    900
cagatcgcct ggagacgcca tccacgctgt tttgacctcc atagaagaca ccgggaccga    960
tccagcctcc gcggctcgca tctctccttc acgcgcccgc cgccctacct gaggccgcca   1020
tccacgccgg ttgagtcgcg ttctgccgcc tcccgcctgt ggtgcctcct gaactgcgtc   1080
cgccgtctag gtaagtttaa agctcaggtc gagaccgggc ctttgtccgg cgctcccttg   1140
gagcctacct agactcagcc ggctctccac gctttgcctg accctgcttg ctcaactcta   1200
gttctctcgt taacttaatg agacagatag aaactggtct tgtagaaaca gagtagtcgc   1260
ctgcttttct gccaggtgct gacttctctc ccctgggctt ttttcttttt ctcaggttga   1320
aaagaagaag acgaagaaga cgaagaagac aaaccgtcgt cgacagatct gtggtagaat   1380
```

| | |
|---|---|
| tggtaaagag agtcgtgtaa aatatcgagt tcgcacatct tgttgtctga ttattgattt | 1440 |
| ttggcgaaac catttgatca tatgacaaga tgtgtatcta ccttaactta atgatttga | 1500 |
| taaaaatcat taggatcttt ttccctctgc caaaaattat ggggacatca tgaagcccct | 1560 |
| tgagcatctg acttctggct aataaaggaa atttattttc attgcaatag tgtgttggaa | 1620 |
| ttttttgtgt ctctcactcg aaggacata agggcggccg ctagc | 1665 |

<210> SEQ ID NO 57
<211> LENGTH: 1665
<212> TYPE: DNA
<213> ORGANISM: Artificial Sequence
<220> FEATURE:
<223> OTHER INFORMATION: Description of Artificial Sequence: NTC9385RaF-RSM vector backbone

<400> SEQUENCE: 57

| | |
|---|---|
| ccgcctaatg agcgggcttt ttttggctt gttgtccaca accgttaaac cttaaaagct | 60 |
| ttaaaagcct tatatattct tttttttctt ataaaactta aaccttaga ggctatttaa | 120 |
| gttgctgatt tatattaatt ttattgttca acatgagag cttagtacgt gaaacatgag | 180 |
| agcttagtac gttagccatg agagcttagt acgttagcca tgagggttta gttcgttaaa | 240 |
| catgagagct tagtacgtta acatgagag cttagtacgt actatcaaca ggttgaactg | 300 |
| ctgatccacc ccggctctag ttattaatag taatcaatta cggggtcatt agttcatagc | 360 |
| ccatatatgg agttccgcgt tacataactt acggtaaatg gcccgcctgg ctgaccgccc | 420 |
| aacgacccc gcccattgac gtcaataatg acgtatgttc ccatagtaac gccaataggg | 480 |
| actttccatt gacgtcaatg ggtggagtat ttacggtaaa ctgcccactt ggcagtacat | 540 |
| caagtgtatc atatgccaag tacgccccct attgacgtca atgacggtaa atggcccgcc | 600 |
| tggcattatg cccagtacat gaccttatgg actttccta cttggcagta catctacgta | 660 |
| ttagtcatcg ctattaccat ggtgatgcgg ttttggcagt acatcaatgg gcgtggatag | 720 |
| cggtttgact cacggggatt tccaagtctc cacccattg acgtcaatgg gagtttgttt | 780 |
| tggcaccaaa atcaacggga ctttccaaaa tgtcgtaaca actccgcccc attgacgcaa | 840 |
| atgggcggta ggcgtgtacg gtgggaggtc tatataagca gagctcgttt agtgaaccgt | 900 |
| cagatcgcct ggagacgcca tccacgctgt tttgacctcc atagaagaca ccgggaccga | 960 |
| tccagcctcc gcggctcgca tctctccttc acgcgcccgc cgccctacct gaggccgcca | 1020 |
| tccacgccgg ttgagtcgcg ttctgccgcc tcccgcctgt ggtgcctcct gaactgcgtc | 1080 |
| cgccgtctag gtaagtttaa agctcaggtc gagaccgggc ctttgtccgg cgctcccttg | 1140 |
| gagcctacct agactcagcc ggctctccac gctttgcctg accctgcttg ctcaactcta | 1200 |
| gttctctcgt taacttaatg agacagatag aaactggtct tgtagaaaca gagtagtcgc | 1260 |
| ctgctttct gccaggtgct gacttctctc ccctgggctt ttttctttt ctcaggttga | 1320 |
| aaagaagaag acgaagaaga cgaagaagac aaaccgtcgt cgacagatct gtggttgaca | 1380 |
| tggtaaagag agttgtgtaa aatattgagt atgttcatgt tcttgtctcc ttattgattt | 1440 |
| ttggggaaac catttgatca tatgagaaca tgaactacta ccttaactta atgatttga | 1500 |
| taaaaatcat taggatcttt ttccctctgc caaaaattat ggggacatca tgaagcccct | 1560 |
| tgagcatctg acttctggct aataaaggaa atttattttc attgcaatag tgtgttggaa | 1620 |
| ttttttgtgt ctctcactcg aaggacata agggcggccg ctagc | 1665 |

<210> SEQ ID NO 58
<211> LENGTH: 1695
<212> TYPE: DNA
<213> ORGANISM: Artificial Sequence
<220> FEATURE:
<223> OTHER INFORMATION: Description of Artificial Sequence: NTC9385RaF-
      RNAI vector backbone

<400> SEQUENCE: 58

| ccgcctaatg agcgggcttt ttttggctt gttgtccaca accgttaaac cttaaaagct | 60 |
| ttaaaagcct tatatattct tttttttctt ataaaactta aaaccttaga ggctatttaa | 120 |
| gttgctgatt tatattaatt ttattgttca acatgagag cttagtacgt gaaacatgag | 180 |
| agcttagtac gttagccatg agagcttagt acgttagcca tgagggttta gttcgttaaa | 240 |
| catgagagct tagtacgtta acatgagag cttagtacgt actatcaaca ggttgaactg | 300 |
| ctgatccacc ccggctctag ttattaatag taatcaatta cggggtcatt agttcatagc | 360 |
| ccatatatgg agttccgcgt tacataactt acggtaaatg gcccgcctgg ctgaccgccc | 420 |
| aacgacccc gcccattgac gtcaataatg acgtatgttc ccatagtaac gccaataggg | 480 |
| actttccatt gacgtcaatg ggtggagtat ttacggtaaa ctgcccactt ggcagtacat | 540 |
| caagtgtatc atatgccaag tacgccccct attgacgtca atgacggtaa atggcccgcc | 600 |
| tggcattatg cccagtacat gaccttatgg gactttccta cttggcagta catctacgta | 660 |
| ttagtcatcg ctattaccat ggtgatgcgg ttttggcagt acatcaatgg gcgtggatag | 720 |
| cggtttgact cacggggatt tccaagtctc cacccccattg acgtcaatgg gagtttgttt | 780 |
| tggcaccaaa atcaacggga ctttccaaaa tgtcgtaaca actccgcccc attgacgcaa | 840 |
| atgggcggta ggcgtgtacg gtgggaggtc tatataagca gagctcgttt agtgaaccgt | 900 |
| cagatcgcct ggagacgcca tccacgctgt tttgacctcc atagaagaca ccgggaccga | 960 |
| tccagcctcc gcggctcgca tctctccttc acgcgcccgc cgccctacct gaggccgcca | 1020 |
| tccacgccgg ttgagtcgcg ttctgccgcc tcccgcctgt ggtgcctcct gaactgcgtc | 1080 |
| cgccgtctag gtaagtttaa agctcaggtc gagaccgggc ctttgtccgg cgctcccttg | 1140 |
| gagcctacct agactcagcc ggctctccac gctttgcctg accctgcttg ctcaactcta | 1200 |
| gttctctcgt taacttaatg agacagatag aaactggtct tgtagaaaca gagtagtcgc | 1260 |
| ctgcttttct gccaggtgct gacttctctc ccctgggctt ttttcttttt ctcaggttga | 1320 |
| aaagaagaag acgaagaaga cgaagaagac aaaccgtcgt cgacagatct accgttaacc | 1380 |
| tgctgcttgc aaacaaaaaa accaccgcta ccagcggtgg tttgtttgcc ggatcaagag | 1440 |
| ctaccaactc tttttccgaa ggtaactggc ttcagcagag cgcagatacc aaatactgtt | 1500 |
| cttctagtgt agccgtagtt aggccaccac ttcaagttaa cacgatcttt ttccctctgc | 1560 |
| caaaaattat ggggacatca tgaagcccct tgagcatctg acttctggct aataaaggaa | 1620 |
| atttattttc attgcaatag tgtgttggaa ttttttgtgt ctctcactcg aaggacata | 1680 |
| agggcggccg ctagc | 1695 |

<210> SEQ ID NO 59
<211> LENGTH: 99
<212> TYPE: DNA
<213> ORGANISM: Artificial Sequence
<220> FEATURE:
<223> OTHER INFORMATION: Description of Artificial Sequence: Anti-RNAI
      (10-108)

<400> SEQUENCE: 59

```
aacaaaaaaa ccaccgctac cagcggtggt ttgtttgccg gatcaagagc taccaactct    60
ttttccgaag gtaactggct tcagcagagc gcagatacc                           99
```

<210> SEQ ID NO 60
<211> LENGTH: 114
<212> TYPE: DNA
<213> ORGANISM: Artificial Sequence
<220> FEATURE:
<223> OTHER INFORMATION: Description of Artificial Sequence: Anti-RNAI
       (10-108)-weak RBS-ATG

<400> SEQUENCE: 60

```
aacaaaaaaa ccaccgctac cagcggtggt ttgtttgccg gatcaagagc taccaactct    60
ttttccgaag gtaactggct tcagcagagc gcagataccg tcgacaagaa catg         114
```

<210> SEQ ID NO 61
<211> LENGTH: 121
<212> TYPE: DNA
<213> ORGANISM: Artificial Sequence
<220> FEATURE:
<223> OTHER INFORMATION: Description of Artificial Sequence: Anti-RNAI
       (10-108)-strong RBS-ATG

<400> SEQUENCE: 61

```
aacaaaaaaa ccaccgctac cagcggtggt ttgtttgccg gatcaagagc taccaactct    60
ttttccgaag gtaactggct tcagcagagc gcagataccg tcgacaggag acaagaacat   120
g                                                                   121
```

<210> SEQ ID NO 62
<211> LENGTH: 1667
<212> TYPE: DNA
<213> ORGANISM: Artificial Sequence
<220> FEATURE:
<223> OTHER INFORMATION: Description of Artificial Sequence: NTC9385R
       vector backbone. Bp 1 is start of trpA terminator upstream of R6K
       origin, last bp is end of polyadenylation signal. Exon 2 encoded
       SalI (GTCGAC) and BglII (AGATCT) transgene cloning sites are
       juxtaposed

<400> SEQUENCE: 62

```
ccgcctaatg agcgggcttt ttttttggctt gttgtccaca accgttaaac cttaaaagct    60
ttaaaagcct tatatattct ttttttttctt ataaaactta aaaccttaga ggctatttaa   120
gttgctgatt tatattaatt ttattgttca acatgagag cttagtacgt gaaacatgag     180
agcttagtac gttagccatg agagcttagt acgttagcca tgagggttta gttcgttaaa   240
catgagagct tagtacgtta acatgagag cttagtacgt actatcaaca ggttgaactg    300
ctgatccacg ttgtggtaga attggtaaag agagtcgtgt aaaatatcga gttcgcacat  360
cttgttgtct gattattgat ttttggcgaa accatttgat catatgacaa gatgtgtatc   420
taccttaact taatgatttt gataaaaatc attaggtacc ccggctctag ttattaatag   480
taatcaatta cggggtcatt agttcatagc ccatatatgg agttccgcgt tacataactt   540
acggtaaatg gcccgcctgg ctgaccgccc aacgacccc gcccattgac gtcaataatg   600
acgtatgttc ccatagtaac gccaataggg actttccatt gacgtcaatg ggtggagtat   660
ttacggtaaa ctgcccactt ggcagtacat caagtgtatc atatgccaag tacgccccct   720
attgacgtca atgacggtaa atggcccgcc tggcattatg cccagtacat gaccttatgg   780
gactttccta cttggcagta catctacgta ttagtcatcg ctattaccat ggtgatgcgg   840
```

```
ttttggcagt acatcaatgg gcgtggatag cggtttgact cacggggatt ccaagtctc    900
caccccattg acgtcaatgg gagtttgttt tggcaccaaa atcaacggga ctttccaaaa   960
tgtcgtaaca actccgcccc attgacgcaa atgggcggta ggcgtgtacg gtgggaggtc  1020
tatataagca gagctcgttt agtgaaccgt cagatcgcct ggagacgcca tccacgctgt  1080
tttgacctcc atagaagaca ccgggaccga tccagcctcc gcggctcgca tctctccttc  1140
acgcgcccgc cgccctacct gaggccgcca tccacgccgg ttgagtcgcg ttctgccgcc  1200
tcccgcctgt ggtgcctcct gaactgcgtc cgccgtctag gtaagtttaa agctcaggtc  1260
gagaccgggc ctttgtccgg cgctcccttg agcctacctt agactcagcc ggctctccac  1320
gctttgcctg accctgcttg ctcaactcta gttctctcgt taacttaatg agacagatag  1380
aaactggtct tgtagaaaca gagtagtcgc ctgcttttct gccaggtgct gacttctctc  1440
ccctgggctt ttttcttttt ctcaggttga aagaagaag acgaagaaga cgaagaagac  1500
aaaccgtcgt cgacagatct ttttccctct gccaaaaatt atgggacat catgaagccc  1560
cttgagcatc tgacttctgg ctaataaagg aaatttattt tcattgcaat agtgtgttgg  1620
aatttttgt gtctctcact cggaaggaca taagggcggc cgctagc              1667
```

<210> SEQ ID NO 63
<211> LENGTH: 1482
<212> TYPE: DNA
<213> ORGANISM: Artificial Sequence
<220> FEATURE:
<223> OTHER INFORMATION: Description of Artificial Sequence: NTC9385C
     vector backbone. Bp 1 is start of ssiA upstream of ColE2 origin,
     last bp is end of polyadenylation signal. Exon 2 encoded SalI
     (GTCGAC) and BglII (AGATCT) transgene cloning sites are juxtaposed

<400> SEQUENCE: 63

```
tacaatggct catgtggaaa aaccattggc agaaaaacac ctgccaacag ttttaccaca    60
attgccactt aacccacaaa agggcgctgt tatctgataa ggcttatctg gtctcatttt   120
gcacgttgtg gtagaattgg taagagagt cgtgtaaaat atcgagttcg cacatcttgt   180
tgtctgatta ttgattttg gcgaaaccat ttgatcatat gacaagatgt gtatctacct   240
taacttaatg attttgataa aaatcattag gtaccccggc tctagttatt aatagtaatc   300
aattacgggg tcattagttc atagcccata tatggagttc cgcgttacat aacttacggt   360
aaatggcccg cctggctgac cgcccaacga ccccgccca ttgacgtcaa taatgacgta    420
tgttcccata gtaacgccaa tagggacttt ccattgacgt caatgggtgg agtatttacg   480
gtaaactgcc cacttggcag tacatcaagt gtatcatatg ccaagtacgc cccctattga   540
cgtcaatgac ggtaaatggc ccgcctggca ttatgcccag tacatgacct tatgggactt   600
tcctacttgg cagtacatct acgtattagt catcgctatt accatggtga tgcggttttg   660
gcagtacatc aatgggcgtg gatagcggtt tgactcacgg ggatttccaa gtctccaccc   720
cattgacgtc aatgggagtt tgttttggca ccaaaatcaa cgggactttc caaaatgtcg   780
taacaactcc gccccattga cgcaaatggg cggtaggcgt gtacggtggg aggtctatat   840
aagcagagct cgtttagtga accgtcagat cgcctggaga cgccatccac gctgttttga   900
cctccataga agacaccggg accgatccag cctccgcggc tcgcatctct ccttcacgcg   960
cccgccgccc tacctgaggc cgccatccac gccggttgag tcgcgttctg ccgcctcccg  1020
cctgtggtgc ctcctgaact gcgtccgccg tctaggtaag tttaaagctc aggtcgagac  1080
cgggcctttg tccggcgctc ccttggagcc tacctagact cagccggctc tccacgcttt  1140
```

```
gcctgaccct gcttgctcaa ctctagttct ctcgttaact taatgagaca gatagaaact    1200
ggtcttgtag aaacagagta gtcgcctgct tttctgccag gtgctgactt ctctcccctg    1260
ggcttttttc tttttctcag gttgaaaaga agaagacgaa aagacgaag aagacaaacc    1320 gtcgtcgaca gatcttttc cctctgccaa aaattatggg gacatcatga agcccttga     1380 gcatctgact tctggctaat aaaggaaatt tattttcatt gcaatagtgt gttggaattt    1440
tttgtgtctc tcactcggaa ggacataagg gcggccgcta gc                      1482

<210> SEQ ID NO 64
<211> LENGTH: 1486
<212> TYPE: DNA
<213> ORGANISM: Artificial Sequence
<220> FEATURE:
<223> OTHER INFORMATION: Description of Artificial Sequence: NTC9385R-
      intron vector backbone. Bp 1 is start of trpA terminator upstream
      of R6K origin, last bp is end of polyadenylation signal. Exon 2
      encoded SalI (GTCGAC) and BglII (AGATCT) transgene cloning sites
      are

<400> SEQUENCE: 64
ccgcctaatg agcgggcttt ttttggctt gttgtccaca accgttaaac cttaaaagct     60
ttaaaagcct tatatattct tttttttctt ataaaactta aaaccttaga ggctatttaa   120
gttgctgatt tatattaatt ttattgttca aacatgagag cttagtacgt gaaacatgag   180
agcttagtac gttagccatg agagcttagt acgttagcca tgagggttta gttcgttaaa   240
catgagagct tagtacgtta acatgagag cttagtacgt actatcaaca ggttgaactg    300
ctgatccacg ttgtggtaga attggtaaag agagtcgtgt aaaatatcga gttcgcacat   360
cttgttgtct gattattgat ttttggcgaa accatttgat catatgacaa gatgtgtatc   420
taccttaact taatgatttt gataaaaatc attaggtacc ccggctctag ttattaatag   480
taatcaatta cggggtcatt agttcatagc ccatatatgg agttccgcgt tacataactt   540
acggtaaatg gcccgcctgg ctgaccgccc aacgaccccc gcccattgac gtcaataatg   600
acgtatgttc ccatagtaac gccaataggg actttccatt gacgtcaatg ggtggagtat   660
ttacggtaaa ctgcccactt ggcagtacat caagtgtatc atatgccaag tacgcccct    720 attgacgtca atgacggtaa atggcccgcc tggcattatg cccagtacat gaccttatgg   780
gactttccta cttggcagta catctacgta ttagtcatcg ctattaccat ggtgatgcgg   840
ttttggcagt acatcaatgg gcgtggatag cggtttgact cacggggatt tccaagtctc   900
caccccattg acgtcaatgg gagtttgttt tggcaccaaa atcaacggga ctttccaaaa   960
tgtcgtaaca actccgcccc attgacgcaa atgggcggta ggcgtgtacg gtgggaggtc   1020
tatataagca gagctcgttt agtgaaccgt cagatcgcct ggagacgcca tccacgctgt   1080
tttgacctcc atagaagaca ccgggaccga tccagcctcc gcggccggga acggtgcatt   1140
ggaacgcgga ttccccgtgc caagagtcag gtaagtagtt aacttaatga gacagataga   1200
aactggtctt gtagaaacag agtagtcgcc tgctttctg ccaggtgctg acttctctcc    1260
cctgggcttt tttcttttc tcaggttgaa agaagaaga cgaagaagac gaagaagaca    1320
aaccgtcgtc gacagatctt tttccctctg ccaaaaatta tggggacatc atgaagcccc   1380
ttgagcatct gacttctggc taataaagga aattttttt cattgcaata gtgtgttgga   1440
attttttgtg tctctcactc ggaaggacat aagggcggcc gctagc                  1486
```

<210> SEQ ID NO 65
<211> LENGTH: 1486
<212> TYPE: DNA
<213> ORGANISM: Artificial Sequence
<220> FEATURE:
<223> OTHER INFORMATION: Description of Artificial Sequence: NTC9385R-
intron RSM vector backbone. Bp 1 is start of trpA terminator
upstream of R6K origin, last bp is end of polyadenylation signal.
Exon 2 encoded SalI (GTCGAC) and BglII (AGATCT) transgene cloning
sites are

<400> SEQUENCE: 65

| | | | | | |
|---|---|---|---|---|---|
| ccgcctaatg | agcgggcttt | tttttggctt | gttgtccaca | accgttaaac | cttaaaagct | 60 |
| ttaaaagcct | tatatattct | tttttttctt | ataaaactta | aaaccttaga | ggctatttaa | 120 |
| gttgctgatt | tatattaatt | ttattgttca | aacatgagag | cttagtacgt | gaaacatgag | 180 |
| agcttagtac | gttagccatg | agagcttagt | acgttagcca | tgagggttta | gttcgttaaa | 240 |
| catgagagct | tagtacgtta | aacatgagag | cttagtacgt | actatcaaca | ggttgaactg | 300 |
| ctgatccacg | ttgtggttga | catggtaaag | agagttgtgt | aaaatattga | gtatgttcat | 360 |
| gttcttgtct | ccttattgat | ttttggggaa | accatttgat | catatgagaa | catgaactac | 420 |
| taccttaact | taatgatttt | gataaaaatc | attaggtacc | ccggctctag | ttattaatag | 480 |
| taatcaatta | cggggtcatt | agttcatagc | ccatatatgg | agttccgcgt | tacataactt | 540 |
| acggtaaatg | gcccgcctgg | ctgaccgccc | aacgaccccc | gcccattgac | gtcaataatg | 600 |
| acgtatgttc | ccatagtaac | gccaataggg | actttccatt | gacgtcaatg | ggtggagtat | 660 |
| ttacggtaaa | ctgcccactt | ggcagtacat | caagtgtatc | atatgccaag | tacgccccct | 720 |
| attgacgtca | atgacggtaa | atggcccgcc | tggcattatg | cccagtacat | gaccttatgg | 780 |
| gactttccta | cttggcagta | catctacgta | ttagtcatcg | ctattaccat | ggtgatgcgg | 840 |
| ttttggcagt | acatcaatgg | gcgtggatag | cggtttgact | cacggggatt | tccaagtctc | 900 |
| cacccccattg | acgtcaatgg | gagtttgttt | tggcaccaaa | atcaacggga | ctttccaaaa | 960 |
| tgtcgtaaca | actccgcccc | attgacgcaa | atgggcggta | ggcgtgtacg | gtgggaggtc | 1020 |
| tatataagca | gagctcgttt | agtgaaccgt | cagatcgcct | ggagacgcca | tccacgctgt | 1080 |
| tttgacctcc | atagaagaca | ccgggaccga | tccagcctcc | gcggccggga | acggtgcatt | 1140 |
| ggaacgcgga | ttccccgtgc | caagagtcag | gtaagtagtt | aacttaatga | gacagataga | 1200 |
| aactggtctt | gtagaaacag | agtagtcgcc | tgcttttctg | ccaggtgctg | acttctctcc | 1260 |
| cctgggcttt | tttcttttc | tcaggttgaa | aagaagaaga | cgaagaagac | gaagaagaca | 1320 |
| aaccgtcgtc | gacagatctt | tttccctctg | ccaaaaatta | tggggacatc | atgaagcccc | 1380 |
| ttgagcatct | gacttctggc | taataaagga | aatttatttt | cattgcaata | gtgtgttgga | 1440 |
| atttttgtg | tctctcactc | ggaaggacat | aagggcggcc | gctagc | | 1486 |

<210> SEQ ID NO 66
<211> LENGTH: 1514
<212> TYPE: DNA
<213> ORGANISM: Artificial Sequence
<220> FEATURE:
<223> OTHER INFORMATION: Description of Artificial Sequence: NTC9385R-
intron RNAI vector backbone. Bp 1 is start of trpA terminator
upstream of R6K origin, last bp is end of polyadenylation signal.
Exon 2 encoded SalI (GTCGAC) and BglII (AGATCT) transgene cloning
sites are

<400> SEQUENCE: 66

```
ccgcctaatg agcgggcttt ttttggctt gttgtccaca accgttaaac cttaaaagct      60
ttaaaagcct tatatattct ttttttctt ataaaactta aaaccttaga ggctatttaa     120
gttgctgatt tatattaatt ttattgttca aacatgagag cttagtacgt gaaacatgag    180
agcttagtac gttagccatg agagcttagt acgttagcca tgagggttta gttcgttaaa    240
catgagagct tagtacgtta aacatgagag cttagtacgt actatcaaca ggttgaactg    300
ctgatccacg ttgtgttaac ttgaagtggt ggcctaacta cggctacact agaagaacag    360
tatttggtat ctgcgctctg ctgaagccag ttaccttcgg aaaagagtt ggtagctctt     420
gatccggcaa acaaaccacc gctggtagcg tggtttttt tgtttgcaag cagcaggtta     480
acggtacccc ggctctagtt attaatagta atcaattacg gggtcattag ttcatagccc    540
atatatggag ttccgcgtta cataacttac ggtaaatggc ccgcctggct gaccgcccaa    600
cgacccccgc ccattgacgt caataatgac gtatgttccc atagtaacgc caatagggac    660
tttccattga cgtcaatggg tggagtattt acggtaaact gcccacttgg cagtacatca    720
agtgtatcat atgccaagta cgccccctat tgacgtcaat gacggtaaat ggcccgcctg    780
gcattatgcc cagtacatga ccttatggga ctttcctact tggcagtaca tctacgtatt    840
agtcatcgct attaccatgg tgatgcggtt ttggcagtac atcaatgggc gtggatagcg    900
gtttgactca cggggatttc caagtctcca ccccattgac gtcaatggga gtttgttttg    960
gcaccaaaat caacgggact ttccaaaatg tcgtaacaac tccgccccat tgacgcaaat   1020
gggcggtagg cgtgtacggt gggaggtcta tataagcaga gctcgtttag tgaaccgtca   1080
gatcgcctgg agacgccatc cacgctgttt tgacctccat agaagacacc gggaccgatc   1140
cagcctccgc ggccgggaac ggtgcattgg aacgcggatt ccccgtgcca agagtcaggt   1200
aagtagttaa cttaatgaga cagatagaaa ctggtcttgt agaaacagag tagtcgcctg   1260
cttttctgcc aggtgctgac ttctctcccc tgggcttttt tcttttctc aggttgaaaa    1320
gaagaagacg aagaagacga agaagacaaa ccgtcgtcga cagatctttt tccctctgcc   1380
aaaaattatg gggacatcat gaagccccctt gagcatctga cttctggcta ataaggaaa   1440
tttattttca ttgcaatagt gtgttggaat ttttgtgtc tctcactcgg aaggacataa    1500
gggcggccgc tagc                                                     1514
```

<210> SEQ ID NO 67
<211> LENGTH: 1301
<212> TYPE: DNA
<213> ORGANISM: Artificial Sequence
<220> FEATURE:
<223> OTHER INFORMATION: Description of Artificial Sequence: NTC9385C-intron vector backbone. Bp 1 is start of ssiA upstream of ColE2 origin, last bp is end of polyadenylation signal. Exon 2 encoded SalI (GTCGAC) and BglII (AGATCT) transgene cloning sites are juxtaposed

<400> SEQUENCE: 67

```
tacaatggct catgtggaaa aaccattggc agaaaaacac ctgccaacag ttttaccaca      60
attgccactt aacccacaaa agggcgctgt tatctgataa ggcttatctg gtctcatttt    120
gcacgttgtg gtagaattgg taagagagt cgtgtaaaat atcgagttcg cacatcttgt     180
tgtctgatta ttgattttttg gcgaaaccat ttgatcatat gacaagatgt gtatctacct    240
taacttaatg attttgataa aaatcattag gtaccccggc tctagttatt aatagtaatc    300
aattacgggg tcattagttc atagcccata tatggagttc cgcgttacat aacttacggt    360
```

```
aaatggcccg cctggctgac cgcccaacga cccccgccca ttgacgtcaa taatgacgta    420
tgttcccata gtaacgccaa tagggacttt ccattgacgt caatgggtgg agtatttacg    480
gtaaactgcc cacttggcag tacatcaagt gtatcatatg ccaagtacgc ccctattga    540 cgtcaatgac ggtaaatggc ccgcctggca ttatgcccag tacatgacct tatgggactt    600
tcctacttgg cagtacatct acgtattagt catcgctatt accatggtga tgcggttttg    660
gcagtacatc aatgggcgtg gatagcggtt tgactcacgg ggatttccaa gtctccaccc    720
cattgacgtc aatgggagtt tgttttggca ccaaaatcaa cgggactttc caaaatgtcg    780
taacaactcc gccccattga cgcaaatggg cggtaggcgt gtacggtggg aggtctatat    840
aagcagagct cgtttagtga accgtcagat cgcctggaga cgccatccac gctgttttga    900
cctccataga agacaccggg accgatccag cctccgcggc cgggaacggt gcattggaac    960
gcggattccc cgtgccaaga gtcaggtaag tagttaactt aatgagacag atagaaactg   1020
gtcttgtaga acagagtag tcgcctgctt ttctgccagg tgctgacttc tctcccctgg    1080
gcttttttct ttttctcagg ttgaaaagaa gaagacgaag aagacgaaga agacaaaccg   1140
tcgtcgacag atcttttttcc ctctgccaaa aattatgggg acatcatgaa gccccttgag   1200
catctgactt ctggctaata aaggaaattt attttcattg caatagtgtg ttggaatttt   1260
ttgtgtctct cactcggaag gacataaggg cggccgctag c                      1301
```

<210> SEQ ID NO 68
<211> LENGTH: 1301
<212> TYPE: DNA
<213> ORGANISM: Artificial Sequence
<220> FEATURE:
<223> OTHER INFORMATION: Description of Artificial Sequence: NTC9385C-intron RSM vector backbone. Bp 1 is start of ssiA upstream of ColE2 origin, last bp is end of polyadenylation signal. Exon 2 encoded SalI (GTCGAC) and BglII (AGATCT) transgene cloning sites are juxtaposed

<400> SEQUENCE: 68

```
tacaatggct catgtggaaa aaccattggc agaaaaacac ctgccaacag ttttaccaca    60
attgccactt aacccacaaa agggcgctgt tatctgataa ggcttatctg gtctcatttt   120
gcacgttgtg gttgacatgg taaagagagt tgtgtaaaat attgagtatg ttcatgttct   180
tgtctcctta ttgatttttg gggaaaccat ttgatcatat gagaacatga actactacct   240
taacttaatg attttgataa aaatcattag gtaccccggc tctagttatt aatagtaatc   300
aattacgggg tcattagttc atagcccata tatggagttc cgcgttacat aacttacggt   360
aaatggcccg cctggctgac cgcccaacga cccccgccca ttgacgtcaa taatgacgta   420
tgttcccata gtaacgccaa tagggacttt ccattgacgt caatgggtgg agtatttacg   480
gtaaactgcc cacttggcag tacatcaagt gtatcatatg ccaagtacgc ccctattga    540 cgtcaatgac ggtaaatggc ccgcctggca ttatgcccag tacatgacct tatgggactt    600
tcctacttgg cagtacatct acgtattagt catcgctatt accatggtga tgcggttttg    660
gcagtacatc aatgggcgtg gatagcggtt tgactcacgg ggatttccaa gtctccaccc    720
cattgacgtc aatgggagtt tgttttggca ccaaaatcaa cgggactttc caaaatgtcg    780
taacaactcc gccccattga cgcaaatggg cggtaggcgt gtacggtggg aggtctatat    840
aagcagagct cgtttagtga accgtcagat cgcctggaga cgccatccac gctgttttga    900
cctccataga agacaccggg accgatccag cctccgcggc cgggaacggt gcattggaac    960
gcggattccc cgtgccaaga gtcaggtaag tagttaactt aatgagacag atagaaactg   1020
```

```
gtcttgtaga acagagtag tcgcctgctt ttctgccagg tgctgacttc tctcccctgg    1080
gcttttttct ttttctcagg ttgaaaagaa gaagacgaag aagacgaaga agacaaaccg    1140
tcgtcgacag atcttttccc ctctgccaaa aattatgggg acatcatgaa gccccttgag    1200
catctgactt ctggctaata aaggaaattt attttcattg caatagtgtg ttggaatttt    1260
ttgtgtctct cactcggaag gacataaggg cggccgctag c                        1301
```

<210> SEQ ID NO 69
<211> LENGTH: 1329
<212> TYPE: DNA
<213> ORGANISM: Artificial Sequence
<220> FEATURE:
<223> OTHER INFORMATION: Description of Artificial Sequence: NTC9385C-
  intron RNAI vector backbone. Bp 1 is start of ssiA upstream of
  ColE2 origin, last bp is end of polyadenylation signal. Exon 2
  encoded SalI (GTCGAC) and BglII (AGATCT) transgene cloning sites
  are juxtaposed

<400> SEQUENCE: 69

```
tacaatggct catgtggaaa aaccattggc agaaaaacac ctgccaacag ttttaccaca     60
attgccactt aacccacaaa agggcgctgt tatctgataa ggcttatctg gtctcatttt    120
gcacgttgtg ttaacttgaa gtggtggcct aactacggct acactagaag aacagtattt    180
ggtatctgcg ctctgctgaa gccagttacc ttcggaaaaa gagttggtag ctcttgatcc    240
ggcaaacaaa ccaccgctgg tagcggtggt ttttttgttt gcaagcagca ggttaacggt    300
accccggctc tagttattaa tagtaatcaa ttacggggtc attagttcat agcccatata    360
tggagttccg cgttacataa cttacggtaa atggcccgcc tggctgaccg cccaacgacc    420
cccgcccatt gacgtcaata atgacgtatg ttcccatagt aacgccaata gggactttcc    480
attgacgtca atgggtggag tatttacggt aaactgccca cttggcagta catcaagtgt    540
atcatatgcc aagtacgccc cctattgacg tcaatgacgg taaatggccc gcctggcatt    600
atgcccagta catgacctta tgggactttc ctacttggca gtacatctac gtattagtca    660
tcgctattac catggtgatg cggttttggc agtacatcaa tgggcgtgga tagcggtttg    720
actcacgggg atttccaagt ctccacccca ttgacgtcaa tgggagtttg ttttggcacc    780
aaaatcaacg ggactttcca aatgtcgta caactccgc cccattgacg caaatgggcg    840
gtaggcgtgt acggtgggag gtctatataa gcagagctcg tttagtgaac cgtcagatcg    900
cctggagacg ccatccacgc tgttttgacc tccatagaag acaccgggac cgatccagcc    960
tccgcggccg ggaacggtgc attggaacgc ggattcccc gtgccaagag caggtaagta    1020
gttaacttaa tgagacagat agaaactggt cttgtagaaa cagagtagtc gcctgctttt    1080
ctgccaggtg ctgacttctc tcccctgggc tttttttctt ttctcaggtt gaaaagaaga    1140
agacgaagaa gacgaagaag acaaaccgtc gtcgacagat cttttccct ctgccaaaaa    1200 ttatggggac atcatgaagc cccttgagca tctgacttct ggctaataaa ggaaatttat    1260
tttcattgca atagtgtgtt ggaatttttt gtgtctctca ctcggaagga cataagggcg    1320
gccgctagc                                                           1329
```

<210> SEQ ID NO 70
<211> LENGTH: 466
<212> TYPE: DNA
<213> ORGANISM: Artificial Sequence
<220> FEATURE:
<223> OTHER INFORMATION: Description of Artificial Sequence: RSM-R6K
  gamma origin bacterial region. [NheI site-trpA terminator-R6K
  Origin-RSM-KpnI site]

<400> SEQUENCE: 70

```
gctagcccgc ctaatgagcg ggcttttttt tggcttgttg tccacaaccg ttaaaccttta       60 aaagctttaa aagccttata tattcttttt tttcttataa aacttaaaac cttagaggct      120
atttaagttg ctgatttata ttaattttat tgttcaaaca tgagagctta gtacgtgaaa      180
catgagagct tagtacgtta gccatgagag cttagtacgt tagccatgag ggtttagttc      240
gttaaacatg agagcttagt acgttaaaca tgagagctta gtacgtacta tcaacaggtt      300
gaactgctga tccacgttgt ggttgacatg gtaaagagag ttgtgtaaaa tattgagtat      360
gttcatgttc ttgtctcctt attgattttt ggggaaacca tttgatcata tgagaacatg      420
aactactacc ttaacttaat gattttgata aaaatcatta ggtacc                     466
```

<210> SEQ ID NO 71
<211> LENGTH: 494
<212> TYPE: DNA
<213> ORGANISM: Artificial Sequence
<220> FEATURE:
<223> OTHER INFORMATION: Description of Artificial Sequence: RNAI-R6K
      gamma origin bacterial region. [NheI site-trpA terminator-R6K
      Origin-RNAI-KpnI site]

<400> SEQUENCE: 71

```
gctagcccgc ctaatgagcg ggcttttttt tggcttgttg tccacaaccg ttaaaccttta       60 aaagctttaa aagccttata tattcttttt tttcttataa aacttaaaac cttagaggct      120
atttaagttg ctgatttata ttaattttat tgttcaaaca tgagagctta gtacgtgaaa      180
catgagagct tagtacgtta gccatgagag cttagtacgt tagccatgag ggtttagttc      240
gttaaacatg agagcttagt acgttaaaca tgagagctta gtacgtacta tcaacaggtt      300
gaactgctga tccacgttgt gttaacttga agtggtggcc taactacggc tacactagaa      360
gaacagtatt tggtatctgc gctctgctga agccagttac cttcggaaaa agagttggta      420
gctcttgatc cggcaaacaa accaccgctg gtagcggtgg ttttttttgtt tgcaagcagc      480 aggttaacgg tacc                                                        494
```

<210> SEQ ID NO 72
<211> LENGTH: 454
<212> TYPE: DNA
<213> ORGANISM: Artificial Sequence
<220> FEATURE:
<223> OTHER INFORMATION: Description of Artificial Sequence: NTC9385R2
      and NTC9385R2a intronic R6K gamma origin- RSM bacterial region.
      Sequence show is O1; O2 is reverse complement

<400> SEQUENCE: 72

```
ccgcctaatg agcgggcttt ttttggctt gttgtccaca accgttaaac cttaaaagct         60
ttaaaagcct tatatattct tttttttctt ataaaactta aaaccttaga ggctatttaa      120
gttgctgatt tatattaatt ttattgttca acatgagag cttagtacgt gaaacatgag      180
agcttagtac gttagccatg agagcttagt acgttagcca tgagggttta gttcgttaaa      240
catgagagct tagtacgtta aacatgagag cttagtacgt actatcaaca ggttgaactg      300
ctgatccacg ttgtggttga catggtaaag agagttgtgt aaaatattga gtatgttcat      360
gttcttgtct ccttattgat ttttggggaa accatttgat catatgagaa catgaactac      420
taccttaact taatgatttt gataaaaatc atta                                  454
```

<210> SEQ ID NO 73
<211> LENGTH: 482
<212> TYPE: DNA
<213> ORGANISM: Artificial Sequence
<220> FEATURE:
<223> OTHER INFORMATION: Description of Artificial Sequence: NTC9385R2
and NTC9385R2a intronic R6K gamma origin- RNAI bacterial region.
Sequence show is O1; O2 is reverse complement

<400> SEQUENCE: 73

```
ccgcctaatg agcgggcttt tttttggctt gttgtccaca accgttaaac cttaaaagct      60
ttaaaagcct tatatattct ttttttttctt ataaaactta aaaccttaga ggctatttaa    120
gttgctgatt tatattaatt ttattgttca aacatgagag cttagtacgt gaaacatgag    180
agcttagtac gttagccatg agagcttagt acgttagcca tgagggttta gttcgttaaa    240
catgagagct tagtacgtta aacatgagag cttagtacgt actatcaaca ggttgaactg    300
ctgatccacg ttgtgttaac ttgaagtggt ggcctaacta cggctacact agaagaacag    360
tatttggtat ctgcgctctg ctgaagccag ttaccttcgg aaaaagagtt ggtagctctt    420
gatccggcaa acaaaccacc gctggtagcg gtggtttttt tgtttgcaag cagcaggtta    480
ac                                                                    482
```

<210> SEQ ID NO 74
<211> LENGTH: 281
<212> TYPE: DNA
<213> ORGANISM: Artificial Sequence
<220> FEATURE:
<223> OTHER INFORMATION: Description of Artificial Sequence: RSM-ColE2
origin bacterial region. [NheI site-ssiA-ColE2 Origin-RSM-KpnI
site]

<400> SEQUENCE: 74

```
gctagctaca atggctcatg tggaaaaacc attggcagaa aaacacctgc caacagtttt      60
accacaattg ccacttaacc cacaaaaggg cgctgttatc tgataaggct tatctggtct    120
cattttgcac gttgtggttg acatggtaaa gagagttgtg taaatattg agtatgttca    180
tgttcttgtc tccttattga ttttggggga aaccatttga tcatatgaga acatgaacta    240
ctaccttaac ttaatgattt tgataaaaat cattaggtac c                        281
```

<210> SEQ ID NO 75
<211> LENGTH: 309
<212> TYPE: DNA
<213> ORGANISM: Artificial Sequence
<220> FEATURE:
<223> OTHER INFORMATION: Description of Artificial Sequence: RNAI-ColE2
origin bacterial region. [NheI site-ssiA-ColE2 Origin-RNAI-KpnI
site]

<400> SEQUENCE: 75

```
gctagctaca atggctcatg tggaaaaacc attggcagaa aaacacctgc caacagtttt      60
accacaattg ccacttaacc cacaaaaggg cgctgttatc tgataaggct tatctggtct    120
cattttgcac gttgtgttaa cttgaagtgg tggcctaact acggctacac tagaagaaca    180
gtatttggta tctgcgctct gctgaagcca gttaccttcg gaaaaagagt tggtagctct    240
tgatccggca aacaaaccac cgctggtagc ggtggttttt ttgtttgcaa gcagcaggtt    300
aacggtacc                                                             309
```

```
<210> SEQ ID NO 76
<211> LENGTH: 269
<212> TYPE: DNA
<213> ORGANISM: Artificial Sequence
<220> FEATURE:
<223> OTHER INFORMATION: Description of Artificial Sequence: NTC9385C2
      and NTC9385C2a intronic C2 origin- RSM bacterial region. Sequence
      show is O1; O2 is reverse complement

<400> SEQUENCE: 76
tacaatggct catgtggaaa aaccattggc agaaaaacac ctgccaacag ttttaccaca      60
attgccactt aacccacaaa agggcgctgt tatctgataa ggcttatctg gtctcatttt     120
gcacgttgtg gttgacatgg taaagagagt tgtgtaaaat attgagtatg ttcatgttct     180
tgtctcctta ttgatttttg gggaaaccat ttgatcatat gagaacatga actactacct     240
taacttaatg attttgataa aaatcatta                                       269

<210> SEQ ID NO 77
<211> LENGTH: 297
<212> TYPE: DNA
<213> ORGANISM: Artificial Sequence
<220> FEATURE:
<223> OTHER INFORMATION: Description of Artificial Sequence: NTC9385C2
      and NTC9385C2a intronic C2 origin- RNAI bacterial region. Sequence
      show is O1; O2 is reverse complement

<400> SEQUENCE: 77
tacaatggct catgtggaaa aaccattggc agaaaaacac ctgccaacag ttttaccaca      60
attgccactt aacccacaaa agggcgctgt tatctgataa ggcttatctg gtctcatttt     120
gcacgttgtg ttaacttgaa gtggtggcct aactacggct acactagaag aacagtattt     180
ggtatctgcg ctctgctgaa gccagttacc ttcggaaaaa gagttggtag ctcttgatcc     240
ggcaaacaaa ccaccgctgg tagcggtggt tttttgttt gcaagcagca ggttaac        297
```

REPLICATIVE MINICIRCLE VECTORS WITH IMPROVED EXPRESSION

CROSS REFERENCE TO RELATED APPLICATIONS

This application is a divisional application of U.S. Ser. No. 14/432,693, filed on Mar. 31, 2015 entitled "Replicative Minicircle Vectors with Improved Expressions" which is a 371 U.S. National Phase of International Application PCT/US2013/000259, filed Nov. 18, 2013, which claims the benefit of U.S. Provisional Patent Application Ser. No. 61/796,765, entitled "Replicative Minicircle vectors with improved expression" filed Nov. 19, 2012, the entire contents of which are incorporated herein by reference.

This application also claims priority to International Application PCT/US13/00067, entitled "Replicative Minicircle vectors with improved expression" filed Mar. 14, 2013, and International Patent Application PCT/US13/00068, entitled "DNA plasmids with improved expression" filed Mar. 14, 2013, the entire contents of which are incorporated herein by reference.

STATEMENT REGARDING FEDERALLY SPONSORED RESEARCH OR DEVELOPMENT

This invention was supported in part with government support under Grant No. R44GM080768, awarded by the National Institutes of Health. The government has certain rights in this invention.

INCORPORATION-BY-REFERENCE

The accompanying Sequence Listing incorporates by reference the material in the ASCII text file identified by the file name: Seq_listing.txt, creation date: Apr. 4, 2016, size: 95 kilobytes.

FIELD OF THE INVENTION

The present invention relates to a family of eukaryotic expression plasmids useful for gene therapy, obtaining improved genetic immunization, natural interferon production, and more particularly, for improving the expression of plasmid encoded antigens or therapeutic genes.

Such recombinant DNA molecules are useful in biotechnology, transgenic organisms, gene therapy, therapeutic vaccination, agriculture and DNA vaccines.

BACKGROUND OF THE INVENTION

E. coli plasmids have long been an important source of recombinant DNA molecules used by researchers and by industry. Today, plasmid DNA is becoming increasingly important as the next generation of biotechnology products (e.g. gene medicines and DNA vaccines) make their way into clinical trials, and eventually into the pharmaceutical marketplace. Plasmid DNA vaccines may find application as preventive vaccines for viral, bacterial, or parasitic diseases; immunizing agents for the preparation of hyper immune globulin products; therapeutic vaccines for infectious diseases; or as cancer vaccines. Plasmids are also utilized in gene therapy or gene replacement applications, wherein the desired gene product is expressed from the plasmid after administration to the patient.

Therapeutic plasmids often contain a pMB1, ColE1 or pBR322 derived replication origin. Common high copy number derivatives have mutations affecting copy number regulation, such as ROP (Repressor of primer gene) deletion, with a second site mutation that increases copy number (e.g. pMB1 pUC G to A point mutation, or ColE1 pMM1). Higher temperature (42° C.) can be employed to induce selective plasmid amplification with pUC and pMM1 replication origins.

U.S. Pat. No. 7,943,377 (Carnes, A E and Williams, J A, 2011) disclose methods for fed-batch fermentation, in which plasmid-containing E. coli cells were grown at a reduced temperature during part of the fed-batch phase, during which growth rate was restricted, followed by a temperature upshift and continued growth at elevated temperature in order to accumulate plasmid; the temperature shift at restricted growth rate improved plasmid yield and purity. Other fermentation processes for plasmid production are described in Carnes A. E. 2005 *BioProcess Intl* 3:36-44, which is incorporated herein by reference in its entirety.

The art teaches that one of the limitations of application of plasmid therapies and plasmid vaccines is regulatory agency (e.g. Food and Drug Administration, European Medicines Agency) safety concerns regarding 1) plasmid transfer and replication in endogenous bacterial flora, or 2) plasmid encoded selection marker expression in human cells, or endogenous bacterial flora. Additionally, regulatory agency guidance's recommend removal of all non essential sequences in a vector. Plasmids containing a pMB1, ColE1 or pBR322 derived replication origin can replicate promiscuously in *E. coli* hosts. This presents a safety concern that a plasmid therapeutic gene or antigen will be transferred and replicated to a patient's endogenous flora. Ideally, a therapeutic or vaccine plasmid would be replication incompetent in endogenous *E. coli* strains. This requires replacement of the pMB1, ColE1 or pBR322 derived replication origin with a conditional replication origin that requires a specialized cell line for propagation. As well, regulatory agencies such as the EMEA and FDA are concerned with utilization of antibiotic resistance or alternative protein markers in gene therapy and gene vaccine vectors, due to concerns that the gene (antibiotic resistance marker or protein marker) may be expressed in a patients cells. Ideally, plasmid therapies and plasmid vaccines would: 1) be replication incompetent in endogenous *E. coli* strains, 2) not encode a protein based selection marker and 3) be minimalized to eliminate all non essential sequences.

The art further teaches that one of the limitations of application of plasmid therapies and vaccines is that transgene expression is generally very low. Vector modifications that improve antigen expression (e.g. codon optimization of the gene, inclusion of an intron, use of the strong constitutive CMV or CAG promoters versus weaker or cell line specific promoter) are highly correlative with improved in vivo expression and, where applicable, immune responses (reviewed in Manoj S, Babiuk L A, van Drunen Little-van den Hurk S. 2004 *Crit Rev Clin Lab Sci* 41: 1-39). A hybrid CMV promoter (CMV/R), which increased antigen expression, also improved cellular immune responses to HIV DNA vaccines in mice and nonhuman primates (Barouch D H, Yang Z Y, Kong W P, Korioth-Schmitz B, Sumida S M, Truitt D M, Kishko M G, Arthur J C, Miura A, Mascola J R, Letvin N L, Nabel G J. 2005 *J Virol.* 79: 8828-8834). A plasmid containing the woodchuck hepatitis virus posttranscriptional regulatory element (a 600 bp element that increases stability and extranuclear transport of RNA resulting in enhanced levels of mRNA for translation) enhanced antigen expression and protective immunity to influenza hemagglutinin (HA) in mice (Garg S, Oran A E, Hon H, Jacob J. 2004 *J Immunol.* 173: 550-558). These studies teach that improvement in expression beyond that of current CMV based vectors may generally improve immunogenicity and, in the case of gene therapeutics, efficacy.

Transgene expression duration from plasmid vectors is reduced due to promoter inactivation mediated by the bacterial region (i.e. region encoding bacterial replication origin and selectable marker which is encoded in the spacer region) of the vector (Chen Z Y, He C Y, Meuse L, Kay M A. 2004. *Gene Ther* 11:856-864; Suzuki M, Kasai K, Saeki Y. 2006. *J Virol* 80:3293-3300). This results in short duration transgene expression. A strategy to improve transgene expression duration is to remove the bacterial region of the plasmid. For example, minicircle and 'linear Minimalistic immunogenic defined gene expression' (MIDGE) vectors have been developed which do not contain a bacterial region. Removal of the bacterial region in minicircle vectors improved transgene expression duration (Chen et al., Supra, 2004). In minicircle vectors, the eukaryotic region polyadenylation signal is covalently linked to the eukaryotic region promoter. This linkage (spacer region) can tolerate a spacer sequence of at least 500 bp since in vivo expression duration is improved with plasmid vectors in which the bacterial region is removed or replaced with a spacer sequence (spacer region) up to 500 bp in length (Lu J, Zhang F, Xu S, Fire A Z, Kay M A. 2012. *Mol Ther.* 20:2111-9).

However, methods to manufacture MIDGE and minicircle vectors are expensive and not easily scalable. Creating terminal loops on MIDGE vectors in vitro is problematic, requiring in vitro ligation of annealed primers to restriction digested vector. For minicircle vectors, *E. coli* based manufacturing systems have been developed in which, after plasmid production, the bacterial region and the eukaryotic region are separated and circularized into a minicircle (eukaryotic region) and a bacterial region circle via the action of phage recombinases on recognition sequences in the plasmid. In some methods, a restriction enzyme is then utilized to digest the bacterial region circle at a unique site to eliminate this difficult to remove contaminant. These production procedures are very inefficient. For example, optimal manufacture of minicircle vectors yields only 5 mg of minicircle per liter culture (Kay M A, He C Y, Chen Z Y. 2010. *Nat Biotechnol* 28:1287-1289).

A solution is needed to develop eukaryotic expression vectors that contain short spacer regions preferably less than 500 bp that can be efficiently manufactured. These vectors should not encode a protein based selection marker and should be minimalized to eliminate all non essential sequences.

SUMMARY OF THE INVENTION

The present invention relates to a family of minimalized eukaryotic expression plasmids with short spacer regions that preferably are replication incompetent in endogenous flora and surprisingly have dramatically improved in vivo expression and high yield manufacture. These vectors are useful for gene therapy, genetic immunization and or interferon therapy.

Improved vector methods and compositions that utilize novel spacer region encoded bacterial propagation and selection sequences are disclosed.

Improved vector methods and compositions that utilize novel spacer region encoded bacterial propagation sequences with selection sequences encoded within the eukaryotic expression cassette are disclosed.

Improved vector methods and compositions that utilize novel spacer region encoded bacterial selection sequences with propagation sequences encoded within the eukaryotic expression cassette are disclosed.

Improved vector methods and compositions that utilize novel intronic bacterial regions in which bacterial propagation and selection sequences are encoded within an intron within the eukaryotic expression cassette are disclosed.

Improved vector methods and compositions that utilize novel bacterial selection sequences encoded within an intron while propagation sequences are encoded within the spacer region or within the 3' UTR of the eukaryotic expression cassette are disclosed.

Improved vector methods and compositions that utilize novel bacterial replication sequences encoded within an intron while selection sequences are encoded within the spacer region or within the 3' UTR of the eukaryotic expression cassette are disclosed.

Improved vector methods and compositions that utilize novel 3'UTR bacterial regions in which bacterial propagation and selection sequences are encoded within a 3' UTR within the eukaryotic expression cassette are disclosed.

Improved vector methods and compositions that utilize novel bacterial selection sequences encoded within an 3'UTR while propagation sequences are encoded within the spacer region or within an intron of the eukaryotic expression cassette are disclosed.

Improved vector methods and compositions that utilize novel intronic bacterial replication sequences encoded within an 3'UTR while selection sequences are encoded within the spacer region or within an intron of the eukaryotic expression cassette are disclosed.

Improved vector methods and compositions wherein a bacterial replication origin and a RNA selectable marker are not both positioned within a single intron, spacer region or 3'UTR are disclosed. In these improved vectors the replication origin and RNA selection marker are positioned separately (i.e. without the other) in either an intron, a 3' UTR or a spacer region. For example, in one embodiment the replication origin is positioned in the spacer region and the RNA selection marker is positioned in a intron. For example, in one embodiment the replication origin is positioned in the spacer region and the RNA selection marker is positioned in a 3' UTR. For example, in one embodiment the replication origin is positioned in a intron and the RNA selection marker is positioned in a second intron. For example, in one embodiment the replication origin is positioned in a intron and the RNA selection marker is positioned in a 3' UTR. For example, in one embodiment the replication origin is positioned in a intron and the RNA selection marker is positioned in a spacer region. For example, in one embodiment the replication origin is positioned in a 3'UTR and the RNA selection marker is positioned in a intron. For example, in one embodiment the replication origin is positioned in a 3'UTR and the RNA selection marker is positioned in a spacer region.

One object of the invention is to provide improved transgene expression plasmid vectors.

Another object of the invention is to provide eukaryotic expression vectors containing short spacer regions less than 500 bp that may be efficiently manufactured.

According to one object of the invention, a method of increasing expression from an expression plasmid vector comprises modifying the plasmid DNA to replace the pMB1, ColE1 or pBR322 derived replication origin and selectable marker with an alternative replication origin selected from the group consisting of a R6K gamma replication origin, a ColE2-P9 replication origin, and a ColE2-P9 related replication origin and an RNA selectable marker; transforming the modified plasmid DNA into a bacterial cell line rendered competent for transformation; and isolating the resultant transformed bacterial cells. The resultant plasmid surprisingly has higher in vivo expression levels than the parent pMB1, ColE1 or pBR322 derived replication origin expression plasmid vector.

According to one object of the invention, a composition for construction of a eukaryotic expression vector comprises an R6K origin with at least 90% sequence identity to the sequence set forth as SEQ ID NO: 11 or SEQ ID NO: 12, and a RNA selectable marker, wherein said R6K origin is operably linked to said RNA selectable marker and a eukaryotic region. According to still another object of the invention, the RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. According to still another object of the invention, a RNA-OUT selectable marker selected from the group consisting of: SEQ ID NO: 20 and SEQ ID NO: 22 is incorporated into the vector adjacent to the R6K origin. According to still another object of the invention, the RNA-OUT selectable marker—R6K origin is selected from the group consisting of: SEQ ID NO: 26, SEQ ID NO: 27 and SEQ ID NO: 28. According to still another object of the invention, the synthetic RNA selectable marker—R6K origin is selected from the group consisting of: SEQ ID NO: 70, SEQ ID NO: 72. According to still another object of the invention, the RNAI selectable marker—R6K origin is selected from the group consisting of: SEQ ID NO: 71, SEQ ID NO: 73. According to another object of the invention, said R6K origin-RNA selectable marker improves said vector expression in vivo compared to a corresponding vector containing a pMB1, ColE1 or pBR322 derived replication origin. According to still another object of the invention, said vector has at least 95% sequence identity to a sequence selected from the group consisting of: SEQ ID NO: 62, SEQ ID NO: 64, SEQ ID NO:65, SEQ ID NO:66.

According to one object of the invention, a composition for construction of a eukaryotic expression vector comprises a ColE2-P9 origin with at least 90% sequence identity to the sequence set forth as SEQ ID NO: 13, SEQ ID NO: 14, SEQ ID NO: 15, or SEQ ID NO: 16, and a a RNA selectable marker, wherein said ColE2-P9 origin—a RNA selectable marker is operably linked to a eukaryotic region. According to another object of the invention, said ColE2-P9 origin-RNA selectable marker improves said vector expression in vivo compared to a corresponding vector containing a pMB1, ColE1 or pBR322 derived replication origin. According to still another object of the invention, a primosomal assembly site (ssiA) is optionally incorporated into the vector adjacent to the ColE2-P9 origin. According to still another object of the invention, a RNA selectable marker is incorporated into the vector adjacent to the ColE2-P9 replication origin. According to still another object of the invention, the RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. According to still another object of the invention, a RNA-OUT selectable marker selected from the group consisting of: SEQ ID NO: 20 and SEQ ID NO: 22 is incorporated into the vector adjacent to the ColE2-P9 origin. According to still another object of the invention, the RNA-OUT selectable marker—ColE2-P9 is selected from the group consisting of: SEQ ID NO: 23, SEQ ID NO: 24 and SEQ ID NO: 25. According to still another object of the invention, the synthetic RNA selectable marker—ColE2-P9 origin is selected from the group consisting of: SEQ ID NO: 74, SEQ ID NO: 76. According to still another object of the invention, the RNAI selectable marker—ColE2-P9 origin is selected from the group consisting of: SEQ ID NO: 75, SEQ ID NO: 77. According to still another object of the invention, said vector has at least 95% sequence identity to SEQ ID NO: 63, SEQ ID NO: 67, SEQ ID NO:68, SEQ ID NO: 69.

According to one object of the invention, a method of improving expression from an expression plasmid vector comprises modifying the plasmid DNA to replace the spacer region encoded pMB1, ColE1, pBR322, R6K, ColE2-P9 or ColE2-P9 related derived replication origin with an alternative intronic encoded replication origin selected from the group consisting of an R6K gamma replication origin, a ColE2-P9 replication origin, a ColE2-P9 related replication origin, a pUC replication origin, a $P_{min}$ pUC replication origin; transforming the modified plasmid DNA into a bacterial cell line rendered competent for transformation; and isolating the resultant transformed bacterial cells.

According to one object of the invention, a composition for construction of a short spacer region eukaryotic expression vector with high yield manufacture comprises an R6K origin with at least 90% sequence identity to a sequence selected from the group consisting of: SEQ ID NO: 11 and SEQ ID NO: 12, and a plasmid DNA encoded eukaryotic region, wherein said R6K origin is operably linked to an intron within said plasmid DNA eukaryotic region. According to still another object of the invention, a RNA selectable marker is incorporated into the vector adjacent to the R6K replication origin. According to still another object of the invention, a RNA selectable marker is incorporated into the vector within a second intron or within the spacer region or within the 3' UTR. According to still another object of the invention, the RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. According to still another object of the invention, a RNA-OUT selectable marker selected from the group consisting of: SEQ ID NO: 20 and SEQ ID NO: 22 is incorporated into the vector adjacent to the R6K origin. According to still another object of the invention, a RNA-OUT selectable marker selected from the group consisting of: SEQ ID NO:

20 and SEQ ID NO: 22 is incorporated into the vector within a second intron. According to still another object of the invention, a RNA-OUT selectable marker selected from the group consisting of: SEQ ID NO: 20 and SEQ ID NO: 22 is incorporated into the vector within the spacer region. According to still another object of the invention, a RNA-OUT selectable marker selected from the group consisting of: SEQ ID NO: 20 and SEQ ID NO: 22 is incorporated into the vector within a 3' UTR. According to still another object of the invention, the RNA-OUT selectable marker—R6K origin operably linked to the intron is selected from the group consisting of: SEQ ID NO: 26, SEQ ID NO: 27 and SEQ ID NO: 28. According to still another object of the invention, the synthetic RNA selectable marker—R6K origin operably linked to the intron is selected from the group consisting of: SEQ ID NO: 70, SEQ ID NO: 72. According to still another object of the invention, the RNAI selectable marker—R6K origin operably linked to the intron is selected from the group consisting of: SEQ ID NO: 71, SEQ ID NO: 73. According to another object of the invention, said intronic R6K origin improves said vector expression compared to a corresponding vector containing a pMB1, ColE1 or pBR322 derived replication origin encoded in the spacer region. According to still another object of the invention, said eukaryotic region has at least 95% sequence identity to a sequence selected from the group consisting of: SEQ ID NO: 30, SEQ ID NO: 31.

According to one object of the invention, a composition for construction of a short spacer region eukaryotic expression vector with high yield manufacture comprises a ColE2-P9 origin with at least 90% sequence identity to a sequence selected from the group consisting of: SEQ ID NO: 13, SEQ ID NO: 14, SEQ ID NO: 15, or SEQ ID NO: 16, and a plasmid DNA encoded eukaryotic region, wherein said ColE2-P9 origin is operably linked to an intron within said plasmid DNA encoded eukaryotic region. According to still another object of the invention, a primosomal assembly site (ssiA) is optionally incorporated into the vector adjacent to the ColE2-P9 origin. According to still another object of the invention, a RNA selectable marker is incorporated into the vector adjacent to the ColE2-P9 replication origin. According to still another object of the invention, a RNA selectable marker is incorporated into the vector within a second intron or within the spacer region or within the 3' UTR. According to still another object of the invention, the RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. According to still another object of the invention, a RNA-OUT selectable marker selected from the group consisting of: SEQ ID NO: 20 and SEQ ID NO: 22 is incorporated into the vector adjacent to the ColE2-P9 origin. According to still another object of the invention, a RNA-OUT selectable marker selected from the group consisting of: SEQ ID NO: 20 and SEQ ID NO: 22 is incorporated into the vector within a second intron. According to still another object of the invention, a RNA-OUT selectable marker selected from the group consisting of: SEQ ID NO: 20 and SEQ ID NO: 22 is incorporated into the vector within the spacer region. According to still another object of the invention, a RNA-OUT selectable marker selected from the group consisting of: SEQ ID NO: 20 and SEQ ID NO: 22 is incorporated into the vector within a 3' UTR. According to still another object of the invention, the RNA-OUT selectable marker—ColE2-P9 origin operably linked to the intron is selected from the group consisting of: SEQ ID NO: 23, SEQ ID NO: 24 and SEQ ID NO: 25. According to still another object of the invention, the synthetic RNA selectable marker—ColE2-P9 origin operably linked to the intron is selected from the group consisting of: SEQ ID NO: 74, SEQ ID NO: 76. According to still another object of the invention, the RNAI selectable marker—ColE2-P9 origin operably linked to the intron is selected from the group consisting of: SEQ ID NO: 75, SEQ ID NO: 77. According to another object of the invention, said intronic ColE2-P9 origin improves said vector expression compared to a corresponding vector containing a pMB1, ColE1 or pBR322 derived replication origin encoded in the spacer region. According to still another object of the invention, said eukaryotic region has at least 95% sequence identity to a sequence selected from the group consisting of: SEQ ID NO: 30, SEQ ID NO: 31.

According to one object of the invention, a composition for construction of a short spacer region eukaryotic expression vector with high yield manufacture comprises a pUC origin, and a plasmid DNA encoded eukaryotic region, wherein said pUC origin is operably linked to an intron within said plasmid DNA eukaryotic region. According to still another object of the invention, a RNA selectable marker is incorporated into the vector adjacent to the pUC replication origin. According to still another object of the invention, a RNA selectable marker is incorporated into the vector within a second intron or within the spacer region or within the 3' UTR. According to still another object of the invention, the RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. According to still another object of the invention, a RNA-OUT selectable marker selected from the group consisting of: SEQ ID NO: 20 and SEQ ID NO: 22 is incorporated into the vector adjacent to the pUC origin. According to still another object of the invention, a RNA-OUT selectable marker selected from the group consisting of: SEQ ID NO: 20 and SEQ ID NO: 22 is incorporated into the vector within a second intron. According to still another object of the invention, a RNA-OUT selectable marker selected from the group consisting of: SEQ ID NO: 20 and SEQ ID NO: 22 is incorporated into the vector within the spacer region. According to still another object of the invention, a RNA-OUT selectable marker selected from the group consisting of: SEQ ID NO: 20 and SEQ ID NO: 22 is incorporated into the vector within a 3' UTR. According to still another object of the invention, the RNA-OUT selectable marker—pUC origin operably linked to the intron is SEQ ID NO: 29. According to another object of the invention, said intronic pUC origin improves said vector expression compared to a corresponding vector containing a pMB1, ColE1 or pBR322 derived replication origin encoded in the spacer region. According to still another object of the invention, said eukaryotic region has at least 95% sequence identity to a sequence selected from the group consisting of: SEQ ID NO: 30, SEQ ID NO: 31.

According to one object of the invention, a composition for construction of a short spacer region eukaryotic expression vector with high yield manufacture comprises a $P_{min}$ pUC origin with at least 90% sequence identity to SEQ ID NO: 45, and a plasmid DNA encoded eukaryotic region, wherein said $P_{min}$ pUC origin is operably linked to an intron within said plasmid DNA eukaryotic region. According to still another object of the invention, a RNA selectable marker is incorporated into the vector adjacent to the $P_{min}$ pUC replication origin. According to still another object of the invention, a RNA selectable marker is incorporated into the vector within a second intron or within the spacer region or within the 3' UTR. According to still another object of the invention, the RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. According to still another object of the invention, a RNA-OUT selectable marker selected from the group consisting of: SEQ ID NO: 20 and SEQ ID NO: 22 is incorporated into the vector adjacent to the $P_{min}$ pUC origin. According to still another object of the invention, a RNA-OUT selectable marker selected from the group consisting of: SEQ ID NO: 20 and SEQ ID NO: 22 is incorporated into the vector within a second intron. According to still another object of the invention, a RNA-OUT selectable marker selected from the group consisting of: SEQ ID NO: 20 and SEQ ID NO: 22 is incorporated into the vector within the spacer region. According to still another object of the invention, a RNA-OUT selectable marker selected from the group consisting of: SEQ ID NO: 20 and SEQ ID NO: 22 is incorporated into the vector within a 3' UTR. According to still another object of the invention, the RNA-OUT selectable marker—$P_{min}$ pUC origin operably linked to the intron is SEQ ID NO: 46. According to another object of the invention, said intronic $P_{min}$ pUC origin improves said vector expression compared to a corresponding vector containing a pMB1, ColE1 or pBR322 derived replication origin encoded in the spacer region. According to still another object of the invention, said eukaryotic region has at least 95% sequence identity to a sequence selected from the group consisting of: SEQ ID NO: 30, SEQ ID NO: 31.

According to one object of the invention, a method of improving expression from an expression plasmid vector comprises modifying the plasmid DNA to replace the spacer region encoded pMB1, ColE1, pBR322, R6K, ColE2-P9 or ColE2-P9 related derived replication origin with an alternative 3' UTR encoded replication origin selected from the group consisting of an R6K gamma replication origin, a ColE2-P9 replication origin, a ColE2-P9 related replication origin transforming the modified plasmid DNA into a bacterial cell line rendered competent for transformation; and isolating the resultant transformed bacterial cells.

According to one object of the invention, a composition for construction of a short spacer region eukaryotic expression vector with high yield manufacture comprises an R6K origin with at least 90% sequence identity to a sequence selected from the group consisting of: SEQ ID NO: 11 and SEQ ID NO: 12, and a plasmid DNA encoded eukaryotic region, wherein said R6K origin is operably linked to a 3' UTR within said plasmid DNA eukaryotic region. According to still another object of the invention, a RNA selectable marker is incorporated into the vector adjacent to the R6K replication origin. According to still another object of the invention, a RNA selectable marker is incorporated into the vector within an intron or within the spacer region. According to still another object of the invention, the RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. According to still another object of the invention, a RNA-OUT selectable marker selected from the group consisting of: SEQ ID NO: 20 and SEQ ID NO: 22 is incorporated into the vector adjacent to the R6K origin. According to still another object of the invention, a RNA-OUT selectable marker selected from the group consisting of: SEQ ID NO: 20 and SEQ ID NO: 22 is incorporated into the vector within an intron. According to still another object of the invention, a RNA-OUT selectable marker selected from the group consisting of: SEQ ID NO: 20 and SEQ ID NO: 22 is incorporated into the vector within the spacer region. According to still another object of the invention, the RNA-OUT selectable marker—R6K origin operably linked to the 3' UTR is selected from the group consisting of: SEQ ID NO: 26, SEQ ID NO: 27 and SEQ ID NO: 28. According to still another object of the invention, the synthetic RNA selectable marker—R6K origin operably linked to the 3' UTR is selected from the group consisting of: SEQ ID NO: 70, SEQ ID NO: 72. According to still another object of the invention, the RNAI selectable marker—R6K origin operably linked to the 3' UTR is selected from the group consisting of: SEQ ID NO: 71, SEQ ID NO: 73. According to another object of the invention, said 3' UTR R6K origin improves said vector expression compared to a corresponding vector containing a pMB1, ColE1 or pBR322 derived replication origin encoded in the spacer region. According to still another object of the invention, said eukaryotic region has at least 95% sequence identity to a sequence selected from the group consisting of: SEQ ID NO: 30, SEQ ID NO: 31.

According to one object of the invention, a composition for construction of a short spacer region eukaryotic expression vector with high yield manufacture comprises a ColE2-P9 origin with at least 90% sequence identity to a sequence selected from the group consisting of: SEQ ID NO: 13, 14, 15, or 16, and a plasmid DNA encoded eukaryotic region, wherein said ColE2-P9 origin is operably linked to an 3' UTR within said plasmid DNA encoded eukaryotic region. According to still another object of the invention, a primosomal assembly site (ssiA) is optionally incorporated into the vector adjacent to the ColE2-P9 origin. According to still another object of the invention, a RNA selectable marker is incorporated into the vector adjacent to the ColE2-P9 replication origin. According to still another object of the invention, a RNA selectable marker is incorporated into the vector within a intron, or within the spacer region. According to still another object of the invention, the RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. According to still another object of the invention, a RNA-OUT selectable marker selected from the group consisting of: SEQ ID NO: 20 and SEQ ID NO: 22 is incorporated into the vector adjacent to the ColE2-P9 origin. According to still another object of the invention, a RNA-OUT selectable marker selected from the group consisting of: SEQ ID NO: 20 and SEQ ID NO: 22 is incorporated into the vector within an intron. According to still another object of the invention, a RNA-OUT selectable marker selected from the group consisting of: SEQ ID NO: 20 and SEQ ID NO: 22 is incorporated into the vector within the spacer region. According to still another object of the invention, the RNA-OUT selectable marker—ColE2-P9 origin operably linked to the 3' UTR is selected from the group consisting of: SEQ ID NO: 23, SEQ ID NO: 24 and SEQ ID NO: 25. According to still another object of the invention, the synthetic RNA selectable marker—ColE2-P9 origin operably linked to the 3'UTR is selected from the group consisting of: SEQ ID NO: 74, SEQ ID NO: 76. According to still another object of the invention, the RNAI selectable marker—ColE2-P9 origin operably linked to the 3'UTR is selected from the group consisting of: SEQ ID NO: 75, SEQ ID NO: 77. According to another object of the invention, said intronic ColE2-P9 origin improves said vector expression compared to a corresponding vector containing a pMB1, ColE1 or pBR322 derived replication origin encoded in the spacer region. According to still another object of the invention, said eukaryotic region has at least 95% sequence identity to a sequence selected from the group consisting of: SEQ ID NO: 30, SEQ ID NO: 31.

In one embodiment, the present invention contemplates a method of constructing a eukaryotic replicative minicircle expression vector comprising: a. combining, under conditions so as to create a eukaryotic replicative minicircle expression vector, i) a eukaryotic region encoding a gene of interest and comprising an intron, a 3' UTR and 5' and 3' ends, with ii) a spacer region linking the 5' and 3' ends of the eukaryotic region, said spacer region less than 500 basepairs in length, and with iii) a bacterial replication origin and a RNA selectable marker positioned separately within said intron, 3' UTR or the spacer region linking the 5' and 3' ends of the eukaryotic region sequences, wherein said bacterial replication origin and said RNA selectable marker are not both positioned within a single intron, spacer region or 3' UTR; and b. expressing said gene of interest in said vector, wherein said gene of interest in said vector is expressed at a higher level than a vector comprising a spacer region greater than 500 basepairs. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said vector has at least 95% sequence identity to a sequence selected from the group consisting of SEQ ID NO: 47, SEQ ID NO: 48, SEQ ID NO: 49; SEQ ID NO: 50, SEQ ID NO: 51, SEQ ID NO: 52, SEQ ID NO: 53, SEQ ID NO: 54, SEQ ID NO: 55, SEQ ID NO:56, SEQ ID NO:57, SEQ ID NO: 58.

In one embodiment, the present invention contemplates a method of constructing a eukaryotic replicative minicircle expression vector comprising: a. providing a vector comprising i) a eukaryotic region encoding a gene of interest and comprising an intron, a 3' UTR and 5' and 3' ends and ii) a first spacer region linking the 5' and 3' ends of the eukaryotic region sequences that encodes a selectable marker and a bacterial replication origin, said spacer region greater than 500 basepairs in length and capable of expressing said gene of interest at a first level; b. replacing said first spacer region with a second spacer region of less than 500 basepairs in length, to produce a modified vector wherein a bacterial replication origin and a RNA selectable marker are positioned separately within said intron, 3' UTR or the spacer region linking the 5' and 3' ends of the eukaryotic region sequences and are not both positioned within a single intron, spacer region or 3' UTR; and c. expressing said gene of interest in said modified vector, wherein said gene of interest in said modified vector is expressed at a higher level than said vector comprising a spacer region greater than 500 basepairs. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin in said modified vector is an R6K replication origin with at least 95% sequence identity to a sequence selected from the group consisting of SEQ ID NO: 11, SEQ ID NO: 12. In a further embodiment said bacterial replication origin in said modified vector is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said modified vector has at least 95% sequence identity to a sequence selected from the group consisting of SEQ ID NO: 47, SEQ ID NO: 48, SEQ ID NO: 49; SEQ ID NO: 50, SEQ ID NO: 51, SEQ ID NO: 52, SEQ ID NO: 53, SEQ ID NO: 54, SEQ ID NO: 55, SEQ ID NO:56, SEQ ID NO:57, SEQ ID NO: 58.

In one embodiment, the present invention contemplates a method of constructing a eukaryotic replicative minicircle expression vector comprising: a. combining, under conditions so as to create a eukaryotic replicative minicircle expression vector, i) a eukaryotic region encoding a gene of interest and comprising an intron, a 3' UTR and 5' and 3' ends, with ii) a spacer region linking the 5' and 3' ends of the eukaryotic region sequences and comprising a bacterial replication origin and a RNA selectable marker, said spacer region less than 500 basepairs in length and said bacterial replication origin and said RNA selectable marker positioned separately within said intron, 3' UTR or the spacer region linking the 5' and 3' ends of the eukaryotic region sequences and wherein said bacterial replication origin and said RNA selectable marker are not both positioned within a single intron, spacer region or 3' UTR; b. transforming said replicative minicircle expression vector into cells of an RNA selectable marker regulated bacterial cell line; c. isolating the resultant transformed bacterial cells by selection; and d. propagating the resultant transformed bacterial cells in culture under conditions such as to manufacture said vector in yields of greater than 100 mg vector per liter culture. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said vector has at least 95% sequence identity to a sequence selected from the group consisting of SEQ ID NO: 47, SEQ ID NO: 48, SEQ ID NO: 49; SEQ ID NO: 50, SEQ ID NO: 51, SEQ ID NO: 52, SEQ ID NO: 53, SEQ ID NO: 54, SEQ ID NO: 55, SEQ ID NO:56, SEQ ID NO:57, SEQ ID NO: 58.

In one embodiment, the present invention contemplates a eukaryotic replicative minicircle expression vector comprising i) a eukaryotic region sequence comprising an intron, a 3' UTR, and 5' and 3' ends and ii) a spacer region of less than 500 basepairs in length linking the 5' and 3' ends of the eukaryotic region sequences and iii) a bacterial replication origin and a RNA selectable marker positioned separately within an said intron, 3' UTR or the spacer region linking the 5' and 3' ends of the eukaryotic region sequences wherein said bacterial replication origin and said RNA selectable marker are not both positioned within a single intron, spacer region or 3' UTR. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said vector has at least 95% sequence identity to a sequence selected from the group consisting of SEQ ID NO: 47, SEQ ID NO: 48, SEQ ID NO: 49; SEQ ID NO: 50, SEQ ID NO: 51, SEQ ID NO: 52, SEQ ID NO: 53, SEQ ID NO: 54, SEQ ID NO: 55, SEQ ID NO:56, SEQ ID NO:57, SEQ ID NO: 58.

In one embodiment, the present invention contemplates a method of controlling cell growth, comprising: a. providing an isolated transformed bacterial host cell comprising: 1) a chromosomal gene which inhibits cell growth operably linked to a antisense sequence that is complementary to a portion of an RNA selectable marker; and 2) a eukaryotic replicative minicircle expression vector comprising i) eukaryotic region sequences comprising an intron, a 3' UTR, and 5' and 3' ends; and ii) a spacer region of less than 500 basepairs in length linking the 5' and 3' ends of the eukaryotic region sequences and iii) a bacterial replication origin and a RNA selectable marker positioned separately within said intron, 3' UTR or the spacer region linking the 5' and 3' ends of the eukaryotic region sequences, wherein said bacterial replication origin and said RNA selectable marker are not both positioned within a single intron, spacer region or 3' UTR; and b. culturing said bacterial host cell under conditions such that said RNA selectable marker binds to said antisense sequence, wherein binding of said RNA selectable marker to said antisense sequence inhibits the expression of the chromosomal gene, thereby permitting cell growth. In a further embodiment said vector has at least 95% sequence identity to a sequence selected from the group consisting of SEQ ID NO: 47, SEQ ID NO: 48, SEQ ID NO: 49; SEQ ID NO: 50, SEQ ID NO: 51, SEQ ID NO: 52, SEQ ID NO: 53, SEQ ID NO: 54, SEQ ID NO: 55, SEQ ID NO:56, SEQ ID NO:57, SEQ ID NO: 58. In a further embodiment a method of manufacture comprising culturing said isolated transformed bacterial host cell in culture media under conditions such that said transformed bacterial host cell manufactures vector in yields of greater than 100 mg vector per liter culture media. In a further embodiment said transformed bacterial host cell manufactures vector in yields up to 745 mg vector per liter culture media. In a further embodiment said RNA selectable marker is an RNA-IN regulating RNA-OUT functional variant with at least 95% sequence identity to a sequence selected from the group consisting of SEQ ID NO:20, SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38.

In one embodiment, the present invention contemplates a method of constructing a eukaryotic replicative minicircle expression vector comprising: a. combining, under conditions so as to create a eukaryotic replicative minicircle expression vector, 1) a eukaryotic region encoding a gene of interest and comprising an intron, a 3' UTR and 5' and 3' ends and a bacterial replication origin and a RNA selectable marker with 2) a spacer region linking the 5' and 3' ends of the eukaryotic region of less than 500 basepairs in length and encoding no bacterial sequences, wherein said bacterial replication origin and said RNA selectable marker positioned separately within said intron or said 3' UTR and wherein said bacterial replication origin and said RNA selectable marker are not both positioned within a single intron, or 3' UTR and neither of said bacterial replication origin and said RNA selectable marker are positioned within said spacer region linking the 5' and 3' ends of the eukaryotic region sequences; and b. expressing said gene of interest in said vector, wherein said gene of interest in said vector is expressed at a higher level than a vector comprising a spacer region linking the 5' and 3' ends of the eukaryotic region of greater than 500 basepairs.

In one embodiment, the present invention contemplates a method of constructing a eukaryotic replicative minicircle expression vector comprising: a. combining, under conditions so as to create a eukaryotic replicative minicircle expression vector, 1) a eukaryotic region encoding a gene of interest and comprising an intron, a 3' UTR and 5' and 3' ends and a bacterial replication origin and a RNA selectable marker with 2) a spacer region linking the 5' and 3' ends of the eukaryotic region of less than 500 basepairs in length and encoding no bacterial sequences, wherein said bacterial replication origin and said RNA selectable marker positioned separately within said intron or said 3' UTR and said bacterial replication origin and said RNA selectable marker are not both positioned within a single intron, or 3' UTR and neither of said bacterial replication origin and said RNA selectable marker are positioned within a spacer region linking the 5' and 3' ends of the eukaryotic region sequences; b. transforming said replicative minicircle expression vector into cells of an RNA selectable marker regulated bacterial cell line; c. isolating the resultant transformed bacterial cells by selection; and d. propagating the resultant transformed bacterial cells to manufacture said vector in yields of greater than 100 mg vector per liter culture.

In one embodiment, the present invention contemplates an isolated transformed bacterial host cell comprising: 1) a chromosomal gene which inhibits cell growth operably linked to a antisense sequence that is complementary to a portion of an RNA selectable marker; and 2) a eukaryotic replicative minicircle expression vector comprising i) eukaryotic region sequences comprising an intron, a 3' UTR, and 5' and 3' ends; and ii) a spacer region of less than 500 basepairs in length linking the 5' and 3' ends of the eukaryotic region sequences and iii) a bacterial replication origin and a RNA selectable marker positioned separately within said intron, 3' UTR or the spacer region linking the 5' and 3' ends of the eukaryotic region sequences, wherein said bacterial replication origin and said RNA selectable marker are not both positioned within a single intron, spacer region or 3' UTR. In a further embodiment said vector has at least 95% sequence identity to a sequence selected from the group consisting of SEQ ID NO: 47, SEQ ID NO: 48, SEQ ID NO: 49; SEQ ID NO: 50, SEQ ID NO: 51, SEQ ID NO: 52, SEQ ID NO: 53, SEQ ID NO: 54, SEQ ID NO: 55, SEQ ID NO:56, SEQ ID NO:57, SEQ ID NO: 58. In a further embodiment a method of manufacture comprising culturing the isolated transformed bacterial host cell in culture media under conditions such that said transformed bacterial host cell manufactures vector in yields of greater than 100 mg vector per liter culture media. In a further embodiment said transformed bacterial host cell manufactures vector in yields up to 745 mg vector per liter culture media. In a further embodiment said RNA selectable marker is an RNA-IN regulating RNA-OUT functional variant with at least 95% sequence identity to a sequence selected from the group consisting of SEQ ID NO:20, SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38.

In one embodiment, the present invention contemplates a method of constructing a eukaryotic replicative pUC-free minicircle expression vector comprising: a. combining, under conditions so as to create a eukaryotic replicative pUC-free minicircle expression vector, i) a eukaryotic region encoding a gene of interest and comprising an intron and 5' and 3' ends, with ii) a spacer region linking the 5' and 3' ends of the eukaryotic region, said spacer region less than 500 basepairs in length, and with iii) a bacterial replication origin that is not the pUC origin and a RNA selectable marker positioned within said intron; and b. expressing said gene of interest in said vector, wherein said gene of interest in said pUC-free vector is expressed at a higher level than a vector comprising a pUC origin encoding spacer region greater than 500 basepairs. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said eukaryotic region has at least 95% sequence identity to a sequence selected from the group consisting of SEQ ID NO: 30, SEQ ID NO: 31.

In one embodiment, the present invention contemplates a method of constructing a eukaryotic replicative pUC-free minicircle expression vector comprising: a. providing a vector comprising i) a eukaryotic region encoding a gene of interest and comprising an intron and 5' and 3' ends and ii) a first spacer region linking the 5' and 3' ends of the eukaryotic region sequences that encodes a selectable marker and a bacterial replication origin, said spacer region greater than 500 basepairs in length and capable of expressing said gene of interest at a first level; b. replacing said first spacer region with a second spacer region of less than 500 basepairs in length that does not encode a selectable marker or a bacterial replication origin, c. cloning into said intron a bacterial replication origin that is not the pUC origin and a RNA selectable marker to produce a modified pUC-free minicircle expression vector; and d. expressing said gene of interest in said modified vector, wherein said gene of interest in said modified vector is expressed at a higher level than said vector comprising a spacer region greater than 500 basepairs. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin in said modified vector is an R6K replication origin with at least 95% sequence identity to a sequence selected from the group consisting of SEQ ID NO: 11, SEQ ID NO: 12. In a further embodiment said bacterial replication origin in said modified vector is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said eukaryotic region has at least 95% sequence identity to a sequence selected from the group consisting of SEQ ID NO: 30, SEQ ID NO: 31.

In one embodiment, the present invention contemplates a method of constructing a eukaryotic replicative pUC-free minicircle expression vector comprising: a. combining, under conditions so as to create a eukaryotic replicative pUC-free minicircle expression vector, i) a eukaryotic region encoding a gene of interest and comprising an intron and 5' and 3' ends, with ii) a spacer region linking the 5' and 3' ends of the eukaryotic region sequences and a bacterial replication origin that is not the pUC origin and a RNA selectable marker, said spacer region less than 500 basepairs in length and said bacterial replication origin and said RNA selectable marker positioned within said intron; b. transforming said replicative minicircle expression vector into cells of an RNA selectable marker regulated bacterial cell line; c. isolating the resultant transformed bacterial cells by selection; and d. propagating the resultant transformed bacterial cells in culture under conditions such as to manufacture said vector in yields of greater than 100 mg vector per liter culture. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said eukaryotic region has at least 95% sequence identity to a sequence selected from the group consisting of SEQ ID NO: 30, SEQ ID NO: 31.

In one embodiment, the present invention contemplates a eukaryotic replicative pUC-free minicircle expression vector comprising i) a eukaryotic region sequence comprising an intron and 5' and 3' ends and ii) a spacer region of less than 500 basepairs in length linking the 5' and 3' ends of the eukaryotic region sequences and iii) a bacterial replication origin that is not the pUC origin and a RNA selectable marker positioned within said intron. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said eukaryotic region has at least 95% sequence identity to a sequence selected from the group consisting of SEQ ID NO: 30, SEQ ID NO: 31.

In one embodiment, the present invention contemplates a method of controlling cell growth, comprising: a. providing an isolated transformed bacterial host cell comprising: 1) a chromosomal gene which inhibits cell growth operably linked to a antisense sequence that is complementary to a portion of an RNA selectable marker; and 2) a eukaryotic replicative minicircle expression vector comprising i) eukaryotic region sequences comprising an intron and 5' and 3' ends; and ii) a spacer region of less than 500 basepairs in length linking the 5' and 3' ends of the eukaryotic region sequences and iii) a bacterial replication origin that is not the pUC origin and a RNA selectable marker positioned within said intron; and b. culturing said bacterial host cell under conditions such that said RNA selectable marker binds to said antisense sequence, wherein binding of said RNA selectable marker to said antisense sequence inhibits the expression of the chromosomal gene, thereby permitting cell growth. In a further embodiment said eukaryotic region has at least 95% sequence identity to a sequence selected from the group consisting of SEQ ID NO: 30, SEQ ID NO: 31. In a further embodiment a method of manufacture comprising culturing the isolated transformed bacterial host cell in culture media under conditions such that said transformed bacterial host cell manufactures vector in yields of greater than 100 mg vector per liter culture media. In a further embodiment said transformed bacterial host cell manufactures vector in yields up to 745 mg vector per liter culture media. In a further embodiment said RNA selectable marker is an RNA-IN regulating RNA-OUT functional variant with at least 95% sequence identity to a sequence selected from the group consisting of SEQ ID NO:20, SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38.

In one embodiment, the present invention contemplates a method of constructing a eukaryotic replicative pUC-free minicircle expression vector comprising: a. combining, under conditions so as to create a eukaryotic replicative pUC-free minicircle expression vector, 1) a eukaryotic region encoding a gene of interest and comprising an intron and 5' and 3' ends and a bacterial replication origin that is not the pUC origin and a RNA selectable marker with 2) a spacer region linking the 5' and 3' ends of the eukaryotic region of less than 500 basepairs in length and encoding no bacterial sequences and said bacterial replication origin and said RNA selectable marker are positioned within said intron; and b. expressing said gene of interest in said pUC-free vector, wherein said gene of interest in said vector is expressed at a higher level than a vector comprising a spacer region linking the 5' and 3' ends of the eukaryotic region of greater than 500 basepairs.

In one embodiment the present invention contemplates a method of constructing a eukaryotic replicative pUC-free minicircle expression vector comprising: a. combining, under conditions so as to create a eukaryotic replicative pUC-free minicircle expression vector, 1) a eukaryotic region encoding a gene of interest and comprising an intron and 5' and 3' ends and a bacterial replication origin that is not the pUC origin and a RNA selectable marker with 2) a spacer region linking the 5' and 3' ends of the eukaryotic region of less than 500 basepairs in length and encoding no bacterial sequences wherein said bacterial replication origin and said RNA selectable marker are positioned within said intron; b. transforming said replicative pUC-free minicircle expression vector into cells of an RNA selectable marker regulated bacterial cell line; c. isolating the resultant transformed bacterial cells by selection; and d. propagating the resultant transformed bacterial cells to manufacture said vector in yields of greater than 100 mg vector per liter culture.

In one embodiment, the present invention contemplates a isolated transformed bacterial host cell comprising: 1) a chromosomal gene which inhibits cell growth operably linked to a antisense sequence that is complementary to a portion of an RNA selectable marker; and 2) a eukaryotic replicative minicircle expression vector comprising i) eukaryotic region sequences comprising an intron and 5' and 3' ends; and ii) a spacer region of less than 500 basepairs in length linking the 5' and 3' ends of the eukaryotic region sequences and iii) a bacterial replication origin that is not the pUC origin and a RNA selectable marker positioned within said intron. In a further embodiment the isolated transformed bacterial host cell said eukaryotic region has at least 95% sequence identity to a sequence selected from the group consisting of SEQ ID NO: 30, SEQ ID NO: 31. In a further embodiment a method of manufacture comprising culturing the isolated transformed bacterial host cell in culture media under conditions such that said transformed bacterial host cell manufactures vector in yields of greater than 100 mg vector per liter culture media. In a further embodiment said transformed bacterial host cell manufactures vector in yields up to 745 mg vector per liter culture media. In a further embodiment said RNA selectable marker is an RNA-IN regulating RNA-OUT functional variant with at least 95% sequence identity to a sequence selected from the group consisting of SEQ ID NO:20, SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38.

In one embodiment, the present invention contemplates a method of constructing a eukaryotic replicative pUC-free minicircle expression vector comprising: a. combining, under conditions so as to create a eukaryotic replicative pUC-free minicircle expression vector, i) a eukaryotic region encoding a gene of interest and comprising an 3' UTR and 5' and 3' ends, with ii) a spacer region linking the 5' and 3' ends of the eukaryotic region, said spacer region less than 500 basepairs in length, and with iii) a bacterial replication origin that is not the pUC origin and a RNA selectable marker positioned within said 3' UTR; and b. expressing said gene of interest in said pUC-free vector, wherein said gene of interest in said vector is expressed at a higher level than a vector comprising a pUC origin containing spacer region greater than 500 basepairs. said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said eukaryotic region has at least 95% sequence identity to a sequence selected from the group consisting of SEQ ID NO: 30, SEQ ID NO: 31.

In one embodiment, the present invention contemplates a method of constructing a eukaryotic replicative pUC-free minicircle expression vector comprising: a. providing a vector comprising i) a eukaryotic region encoding a gene of interest and comprising an 3' UTR and 5' and 3' ends and ii) a first spacer region linking the 5' and 3' ends of the eukaryotic region sequences that encodes a selectable marker and a bacterial replication origin, said spacer region greater than 500 basepairs in length and capable of expressing said gene of interest at a first level; b. replacing said first spacer region with a second spacer region of less than 500 basepairs in length that does not encode a selectable marker or a bacterial replication origin, c. cloning into said 3' UTR a bacterial replication origin that is not the pUC origin and a RNA selectable marker to produce a modified pUC-free minicircle expression vector; and d. expressing said gene of interest in said modified pUC-free vector, wherein said gene of interest in said modified vector is expressed at a higher level than said vector comprising a spacer region greater than 500 basepairs. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin in said modified vector is an R6K replication origin with at least 95% sequence identity to a sequence selected from the group consisting of SEQ ID NO: 11, SEQ ID NO: 12. In a further embodiment said bacterial replication origin in said modified vector is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said eukaryotic region has at least 95% sequence identity to a sequence selected from the group consisting of SEQ ID NO: 30, SEQ ID NO: 31.

In one embodiment, the present invention contemplates a method of constructing a eukaryotic replicative pUC-free minicircle expression vector comprising: a. combining, under conditions so as to create a eukaryotic pUC-free replicative minicircle expression vector, i) a eukaryotic region encoding a gene of interest and comprising an 3' UTR and 5' and 3' ends, with ii) a spacer region linking the 5' and 3' ends of the eukaryotic region sequences and a bacterial replication origin that is not the pUC origin and a RNA selectable marker, said spacer region less than 500 basepairs in length and said bacterial replication origin and said RNA selectable marker positioned within said 3' UTR; b. transforming said replicative pUC-free minicircle expression vector into cells of an RNA selectable marker regulated bacterial cell line; c. isolating the resultant transformed bacterial cells by selection; and d. propagating the resultant transformed bacterial cells in culture under conditions such as to manufacture said vector in yields of greater than 100 mg vector per liter culture. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said eukaryotic region has at least 95% sequence identity to a sequence selected from the group consisting of SEQ ID NO: 30, SEQ ID NO: 31.

In one embodiment, the present invention contemplates a eukaryotic replicative pUC-free minicircle expression vector comprising i) a eukaryotic region sequence comprising an 3' UTR and 5' and 3' ends and ii) a spacer region of less than 500 basepairs in length linking the 5' and 3' ends of the eukaryotic region sequences and iii) a bacterial replication origin that is not the pUC origin and a RNA selectable marker positioned within said 3' UTR. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said eukaryotic region has at least 95% sequence identity to a sequence selected from the group consisting of SEQ ID NO: 30, SEQ ID NO: 31.

In one embodiment, the present invention contemplates a method of controlling cell growth, comprising: a. providing an isolated transformed bacterial host cell comprising: 1) a chromosomal gene which inhibits cell growth operably linked to a antisense sequence that is complementary to a portion of an RNA selectable marker; and 2) a eukaryotic replicative minicircle expression vector comprising i) eukaryotic region sequences comprising an 3' UTR and 5' and 3' ends; and ii) a spacer region of less than 500 basepairs in length linking the 5' and 3' ends of the eukaryotic region sequences and iii) a bacterial replication origin that is not the pUC origin and a RNA selectable marker positioned within said 3' UTR; and b. culturing said transformed bacterial host cell under conditions such that said RNA selectable marker binds to said antisense sequence, wherein binding of said RNA selectable marker to said antisense sequence inhibits the expression of the chromosomal gene, thereby permitting cell growth. In a further embodiment said eukaryotic region has at least 95% sequence identity to a sequence selected from the group consisting of SEQ ID NO: 30, SEQ ID NO: 31. In a further embodiment a method of manufacture comprising culturing the isolated transformed bacterial host cell in culture media under conditions such that said transformed bacterial host cell manufactures vector in yields of greater than 100 mg vector per liter culture media. In a further embodiment said transformed bacterial host cell manufactures vector in yields up to 745 mg vector per liter culture media. In a further embodiment said RNA selectable marker is an RNA-IN regulating RNA-OUT functional variant with at least 95% sequence identity to a sequence selected from the group consisting of SEQ ID NO:20, SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38.

In one embodiment, the present invention contemplates a method of constructing a eukaryotic replicative pUC-free minicircle expression vector comprising: a. combining, under conditions so as to create a eukaryotic replicative pUC-free minicircle expression vector, 1) a eukaryotic region encoding a gene of interest and comprising an 3' UTR and 5' and 3' ends and a bacterial replication origin that is not the pUC origin and a RNA selectable marker with 2) a spacer region linking the 5' and 3' ends of the eukaryotic region of less than 500 basepairs in length and encoding no bacterial sequences and said bacterial replication origin and said RNA selectable marker are positioned within said 3' UTR; and b. expressing said gene of interest in said vector, wherein said gene of interest in said vector is expressed at a higher level than a vector comprising a spacer region linking the 5' and 3' ends of the eukaryotic region of greater than 500 basepairs.

In one embodiment, the present invention contemplates a method of constructing a eukaryotic replicative pUC-free minicircle expression vector comprising: a. combining, under conditions so as to create a eukaryotic replicative pUC-free minicircle expression vector, 1) a eukaryotic region encoding a gene of interest and comprising an 3' UTR and 5' and 3' ends and a bacterial replication origin that is not the pUC origin and a RNA selectable marker with 2) a spacer region linking the 5' and 3' ends of the eukaryotic region of less than 500 basepairs in length and encoding no bacterial sequences wherein said bacterial replication origin and said RNA selectable marker are positioned within said 3' UTR; b. transforming said replicative pUC-free minicircle expression vector into cells of an RNA selectable marker regulated bacterial cell line; c. isolating the resultant transformed bacterial cells by selection; and d. propagating the resultant transformed bacterial cells to manufacture said vector in yields of greater than 100 mg vector per liter culture.

In one embodiment, the present invention contemplates an isolated transformed bacterial host cell comprising: 1) a chromosomal gene which inhibits cell growth operably linked to a antisense sequence that is complementary to a portion of an RNA selectable marker; and 2) a eukaryotic replicative minicircle expression vector comprising i) eukaryotic region sequences comprising an 3' UTR and 5' and 3' ends; and ii) a spacer region of less than 500 basepairs in length linking the 5' and 3' ends of the eukaryotic region sequences and iii) a bacterial replication origin that is not the pUC origin and a RNA selectable marker positioned within said 3' UTR. In a further embodiment said eukaryotic region has at least 95% sequence identity to a sequence selected from the group consisting of SEQ ID NO: 30, SEQ ID NO: 31. In a further embodiment a method of manufacture comprising culturing the isolated transformed bacterial host cell in culture media under conditions such that said transformed bacterial host cell manufactures vector in yields of greater than 100 mg vector per liter culture media. In a further embodiment said transformed bacterial host cell manufactures vector in yields up to 745 mg vector per liter culture media. In a further embodiment said RNA selectable marker is an RNA-IN regulating RNA-OUT functional variant with at least 95% sequence identity to a sequence selected from the group consisting of SEQ ID NO:20, SEQ ID NO:22. said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38.

In one embodiment, the present invention contemplates a method of constructing a eukaryotic replicative pUC-free minicircle expression vector comprising: a. combining, under conditions so as to create a eukaryotic replicative pUC-free minicircle expression vector, i) a eukaryotic region encoding a gene of interest and 5' and 3' ends, with ii) a spacer region linking the 5' and 3' ends of the eukaryotic region, said spacer comprising a bacterial replication origin that is not the pUC origin and a RNA selectable marker, said spacer region less than 500 basepairs in length; and b. expressing said gene of interest in said pUC-free vector, wherein said gene of interest in said pUC-free vector is expressed at a higher level than a vector comprising a spacer region comprising pUC. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said vector has at least 95% sequence identity to a sequence selected from the group consisting of SEQ ID NO: 62, SEQ ID NO: 63, SEQ ID NO: 64; SEQ ID NO: 65, SEQ ID NO: 66, SEQ ID NO: 67, SEQ ID NO: 68, SEQ ID NO: 69.

In one embodiment, the present invention contemplates a method of constructing a eukaryotic replicative pUC-free minicircle expression vector comprising: a. providing a vector comprising i) a eukaryotic region encoding a gene of interest and comprising 5' and 3' ends and ii) a first spacer region linking the 5' and 3' ends of the eukaryotic region sequences that encodes a selectable marker and a bacterial replication origin, said spacer region greater than 500 basepairs in length and capable of expressing said gene of interest at a first level; b. replacing said first spacer region with a second spacer region of less than 500 basepairs in length, to produce a pUC-free modified vector wherein the bacterial replication origin is not the pUC origin and the RNA selectable marker are both positioned within said spacer region; and c. expressing said gene of interest in said pUC-free modified vector, wherein said gene of interest in said pUC-free modified vector is expressed at a higher level than said vector comprising a spacer region greater than 500 basepairs. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin in said modified vector is an R6K replication origin with at least 95% sequence identity to a sequence selected from the group consisting of SEQ ID NO: 11, SEQ ID NO: 12. In a further embodiment said bacterial replication origin in said modified vector is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said modified vector has at least 95% sequence identity to a sequence selected from the group consisting of SEQ ID NO: 62, SEQ ID NO: 63, SEQ ID NO: 64; SEQ ID NO: 65, SEQ ID NO: 66, SEQ ID NO: 67, SEQ ID NO: 68, SEQ ID NO: 69.

In one embodiment, the present invention contemplates a method of constructing a eukaryotic replicative pUC-free minicircle expression vector comprising: a. combining, under conditions so as to create a eukaryotic replicative pUC-free minicircle expression vector, i) a eukaryotic region encoding a gene of interest and comprising 5' and 3' ends, with ii) a spacer region linking the 5' and 3' ends of the eukaryotic region sequences, said spacer comprising a bacterial replication origin that is not the pUC origin and a RNA selectable marker, said spacer region less than 500 basepairs in length; b. transforming said replicative pUC-free minicircle expression vector into cells of an RNA selectable marker regulated bacterial cell line; c. isolating the resultant transformed bacterial cells by selection; and d. propagating the resultant transformed bacterial cells in culture under conditions such as to manufacture said vector in yields of greater than 100 mg vector per liter culture. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said vector has at least 95% sequence identity to a sequence selected from the group consisting of SEQ ID NO: 62, SEQ ID NO: 63, SEQ ID NO: 64; SEQ ID NO: 65, SEQ ID NO: 66, SEQ ID NO: 67, SEQ ID NO: 68, SEQ ID NO: 69.

In one embodiment, the present invention contemplates a eukaryotic replicative pUC-free minicircle expression vector comprising i) a eukaryotic region sequence comprising 5' and 3' ends and ii) a spacer region of less than 500 basepairs in length linking the 5' and 3' ends of the eukaryotic region sequences and comprising a bacterial replication origin that is not the pUC origin and a RNA selectable marker. In a further embodiment said RNA selectable marker is an RNA-IN regulating RNA-OUT functional variant with at least 95% sequence identity to a sequence selected from the group consisting of SEQ ID NO:20, and SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38. In a further embodiment said bacterial replication origin is an R6K replication origin with at least 95% sequence identity to a sequence selected from the group consisting of SEQ ID NO: 11, SEQ ID NO: 12. In a further embodiment said bacterial replication origin is an ColE2-P9 replication origin with at least 95% sequence identity to a sequence selected from the group consisting of SEQ ID NO: 13, SEQ ID NO: 14, SEQ ID NO: 15, SEQ ID NO: 16. In a further embodiment said vector has at least 95% sequence identity to a sequence selected from the group consisting of SEQ ID NO: 62, SEQ ID NO: 63, SEQ ID NO: 64; SEQ ID NO: 65, SEQ ID NO: 66, SEQ ID NO: 67, SEQ ID NO: 68, SEQ ID NO: 69.

In one embodiment, the present invention contemplates a method of controlling cell growth, comprising: a. providing an isolated transformed bacterial host cell comprising: 1) a chromosomal gene which inhibits cell growth operably linked to a antisense sequence that is complementary to a portion of an RNA selectable marker; and 2) a eukaryotic replicative minicircle expression vector comprising i) eukaryotic region sequences comprising 5' and 3' ends; and ii) a spacer region of less than 500 basepairs in length linking the 5' and 3' ends of the eukaryotic region sequences and comprising a bacterial replication origin that is not the pUC origin and a RNA selectable marker; and b. culturing said bacterial host cell under conditions such that said RNA selectable marker binds to said antisense sequence, wherein binding of said RNA selectable marker to said antisense sequence inhibits the expression of the chromosomal gene, thereby permitting cell growth. In a further embodiment said vector has at least 95% sequence identity to a sequence selected from the group consisting of SEQ ID NO: 62, SEQ ID NO: 63, SEQ ID NO: 64; SEQ ID NO: 65, SEQ ID NO: 66, SEQ ID NO: 67, SEQ ID NO: 68, SEQ ID NO: 69. In a further embodiment a method of manufacture comprising culturing the isolated transformed bacterial host cell in culture media under conditions such that said transformed bacterial host cell manufactures vector in yields of greater than 100 mg vector per liter culture media. In a further embodiment said transformed bacterial host cell manufactures vector in yields up to 745 mg vector per liter culture media. In a further embodiment said RNA selectable marker is an RNA-IN regulating RNA-OUT functional variant with at least 95% sequence identity to a sequence selected from the group consisting of SEQ ID NO:20, SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38.

In one embodiment, the present invention contemplates an isolated transformed bacterial host cell comprising: 1) a chromosomal gene which inhibits cell growth operably linked to a antisense sequence that is complementary to a portion of an RNA selectable marker; and 2) a eukaryotic replicative minicircle expression vector comprising i) eukaryotic region sequences comprising 5' and 3' ends; and ii) a spacer region of less than 500 basepairs in length linking the 5' and 3' ends of the eukaryotic region sequences and comprising a bacterial replication origin that is not the pUC origin and a RNA selectable marker. In a further embodiment said vector has at least 95% sequence identity to a sequence selected from the group consisting of SEQ ID NO: 62, SEQ ID NO: 63, SEQ ID NO: 64; SEQ ID NO: 65, SEQ ID NO: 66, SEQ ID NO: 67, SEQ ID NO: 68, SEQ ID NO: 69. In a further embodiment a method of manufacture comprising culturing the isolated transformed bacterial host cell in culture media under conditions such that said transformed bacterial host cell manufactures vector in yields of greater than 100 mg vector per liter culture media. In a further embodiment said transformed bacterial host cell manufactures vector in yields up to 745 mg vector per liter culture media. In a further embodiment said RNA selectable marker is an RNA-IN regulating RNA-OUT functional variant with at least 95% sequence identity to a sequence selected from the group consisting of SEQ ID NO:20, SEQ ID NO:22. In a further embodiment said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38.

Further objects and advantages of the invention will become apparent from a consideration of the drawings and ensuing description.

Table 1: gWIZ, NTC9385C and NTC9385R Nanoplasmid expression compared to NTC8685

Table 2: Intron encoded RNA-OUT selection/replication origin does not prevent transgene expression;

Table 3: Improved expression with intron encoded RNA-OUT selection/replication origin;

Table 4: Intron functional analysis—Splicing accuracy and export efficiency;

Table 5: Intron vector expression efficiency;

Table 6: Replicative minicircle vector expression in vitro (lipofectamine) and in vivo (intradermal delivery with electroporation);

Table 7: Intronic RNA-OUT AF selection plasmid fermentation yields;

Table 8: High level expression with vectors with pMB1 RNAI encoded in the spacer region or intron;

Table 9: Accurate splicing with replicative minicircle vectors with pMB1 RNAI and minimal pUC origin encoded in the intron;

Table 10: SR vector expression in vitro and in vivo;

Table 11: Robust expression with P2 (0.85) replicative minicircles;

Table 12: High level expression with R6K replication origin and/or RNA-OUT encoded in the 3' UTR;

Table 13: High level expression with R6K replication origin encoded in the 3' UTR;

Table 14: High level expression with RNAI encoded in the 3' UTR;

Table 15: Spacer region, intron or 3' UTR encoded RSM selection/replication origin short spacer region replicative minicircle vector configurations; and Table 16: Spacer region, intron or 3' UTR encoded separated RSM selection/replication origin short spacer region replicative minicircle vector configurations.

Figure 1:
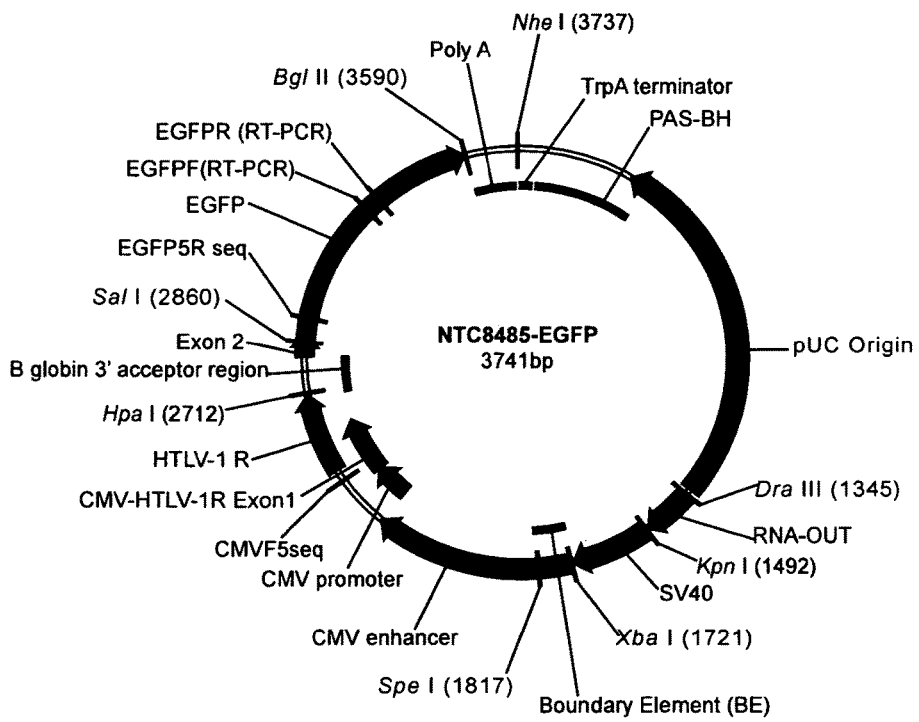
FIG. 1 depicts the NTC8485 pUC origin expression vector.

SEQ ID NO:1: HTLV-IR-Rabbit β globin hybrid intron
SEQ ID NO:2: HTLV-IR CMV hybrid intron
SEQ ID NO:3: CMV intron
SEQ ID NO:4: CpG free intron I 140
SEQ ID NO:5: Human β globin Murine IgG chimeric intron
SEQ ID NO:6: Adenovirus leader-Murine IgG chimeric intron
SEQ ID NO:7: Rabbit β globin intron
SEQ ID NO:8: Truncated CMV intron
SEQ ID NO:9: CAG (Chicken β Actin-rabbit β globin) intron
SEQ ID NO:10: CMV-Rabbit β globin hybrid intron
SEQ ID NO:11: R6K gamma origin
SEQ ID NO:12: CpG free R6K gamma origin
SEQ ID NO:13: ColE2 Origin (+7)
SEQ ID NO:14: ColE2 Origin (Min)
SEQ ID NO:15: ColE2 origin (Core)
SEQ ID NO:16: CpG free ColE2 Origin (+7, CpG free)
SEQ ID NO:17: CpG free ssiA [from plasmid R6K]
SEQ ID NO:18: +7(CpG free) ColE2 origin-CpG free ssiA
SEQ ID NO:19: +7(CpG free) ColE2 origin-CpG free ssiA-flanked by SphI and KpnI restriction sites
SEQ ID NO:20: RNA-OUT Selectable Marker
SEQ ID NO:21: RNA-OUT antisense repressor RNA
SEQ ID NO:22: CpG free RNA-OUT RNA selectable marker
SEQ ID NO:23: RNA-OUT-ColE2 origin bacterial region. [NheI site-ssiA-ColE2 Origin (+7)-RNA-OUT-KpnI site]
SEQ ID NO:24: NTC9385C2 and NTC9385C2a intronic bacterial region. [filled NheI site-ssiA-ColE2 Origin (+7)-RNA-OUT-chewed KpnI site] Sequence show is O1; O2 is reverse complement
SEQ ID NO:25: CpG free ColE2 RNA-OUT bacterial region. (CpG free ssiA-CpG free ColE2 origin-CpG free RNA-OUT RNA selectable marker)—flanked by SphI and BglII restriction sites
SEQ ID NO:26: RNA-OUT-R6K gamma origin bacterial region. [NheI site-trpA terminator-R6K Origin-RNA-OUT-KpnI site]
SEQ ID NO:27: NTC9385R2 and NTC9385R2a intronic R6K gamma origin-RNA-OUT bacterial region. [filled NheI site-trpA terminator-R6K Origin-RNA-OUT-chewed KpnI site] Sequence show is O1; O2 is reverse complement
SEQ ID NO:28: CpG free R6K gamma origin RNA-OUT bacterial region. Flanked by SphI and BglII restriction sites
SEQ ID NO:29: NTC9385P2 and NTC9385P2a intronic pUC origin-RNA-OUT Bacterial region. [filled NheI site-trpA terminator-pUC Origin-RNA-OUT-chewed KpnI site] Sequence show is O1; O2 is reverse complement
SEQ ID NO:30: NTC9385C2, NTC9385R2, NTC9385P2, NTC9385P2(0.85) Eukaryotic region. Bp 1 is start of CMV enhancer, bp 1196 is end of polyadenylation signal. Exon 2 encoded SalI (GTCGAC) and BglII (AGATCT) transgene cloning sites. Intron encoded HpaI (GTTAAC) bacterial region cloning site
SEQ ID NO:31: NTC9385C2a, NTC9385R2a, NTC9385P2a and NTC9385P2a(0.85) Eukaryotic region. Bp 1 is start of CMV enhancer encoded boundary region, bp 1292 is end of polyadenylation signal. Exon 2 encoded SalI (GTCGAC) and BglII (AGATCT) transgene cloning sites. Intron encoded HpaI (GTTAAC) bacterial region cloning site
SEQ ID NO:32: CpG free HTLV-IR-Rabbit β globin hybrid intron
SEQ ID NO:33: RNAI antisense repressor RNA (pMB 1 plasmid origin RNAII antisense partner)
SEQ ID NO:34: RNAI selectable Marker
SEQ ID NO:35: IncB RNAI antisense repressor RNA (IncB plasmid origin RNAII antisense partner)
SEQ ID NO:36: IncB RNAI selectable Marker, RNAI RNA
SEQ ID NO:37: IncB RNAII-SacB, PstI-MamI restriction fragment
SEQ ID NO:38: RNA selectable marker (RSM) antisense repressor RNA
SEQ ID NO:39: RNA selectable marker (RSM)
SEQ ID NO:40: RSM complement SEQ ID NO:41: RNA selection-sacB (P5/6 4/6)
SEQ ID NO:42: RNA selection-sacB (P5/6 5/6)
SEQ ID NO:43: pINT-RNAS integration vector (P5/6 4/6)
SEQ ID NO:44: pINT-RNAS integration vector (P5/6 5/6)
SEQ ID NO:45: $P_{min}$ pUC replication origin (minimal)
SEQ ID NO:46: NTC9385P2(0.85) and NTC9385P2a (0.85) intronic pUC (0.85) Bacterial region [[filled NheI site-trpA terminator-$P_{min}$ pUC replication origin-RNA-OUT-chewed KpnI site] Sequence shown is O1; O2 is reverse complement
SEQ ID NO:47: NTC9385RbF vector backbone. Bp 1 is start of CMV enhancer, last bp is end of polyadenylation signal. Exon 2 encoded SalI (GTCGAC) and BglII (AGATCT) transgene cloning sites are juxtaposed
SEQ ID NO:48: NTC9385RbF-RSM vector backbone. Bp 1 is start of CMV enhancer, last bp is end of polyadenylation signal. Exon 2 encoded SalI (GTCGAC) and BglII (AGATCT) transgene cloning sites are juxtaposed
SEQ ID NO:49: NTC9385RbF-RNAI vector backbone. Bp 1 is start of CMV enhancer, last bp is end of polyadenylation signal. Exon 2 encoded SalI (GTCGAC) and BglII (AGATCT) transgene cloning sites are juxtaposed
SEQ ID NO:50: NTC9385Ra-O1 vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:51: NTC9385Ra-O2 vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:52: NTC9385Ra-O1-RSM vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:53: NTC9385Ra-O2-RSM vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:54: NTC9385Ra-O1-RNAI vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:55: NTC9385Ra-O2-RNAI vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:56: NTC9385RaF vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:57: NTC9385RaF-RSM vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:58: NTC9385RaF-RNAI vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:59: Anti-RNAI (10-108)
SEQ ID NO:60: Anti-RNAI (10-108)-weak RBS-ATG
SEQ ID NO:61: Anti-RNAI (10-108)-strong RBS-ATG
SEQ ID NO:62: NTC9385R vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:63: NTC9385C vector backbone. Bp 1 is start of ssiA upstream of ColE2 origin, last bp is end of polyadenylation signal. Exon 2 encoded SalI (GTCGAC) and BglII (AGATCT) transgene cloning sites are juxtaposed
SEQ ID NO:64: NTC9385R-intron vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:65: NTC9385R-intron RSM vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:66: NTC9385R-intron RNAI vector backbone. Bp 1 is start of trpA terminator upstream of R6K origin, last bp is end of polyadenylation signal. Exon 2 encoded SalI (GTCGAC) and BglII (AGATCT) transgene cloning sites are juxtaposed
SEQ ID NO:67: NTC9385C-intron vector backbone. Bp 1 is start of ssiA upstream of ColE2 origin, last bp is end of polyadenylation signal. Exon 2 encoded SalI (GTCGAC) and BglII (AGATCT) transgene cloning sites are juxtaposed
SEQ ID NO:68: NTC9385C-intron RSM vector backbone. Bp 1 is start of ssiA upstream of ColE2 origin, last bp is end of polyadenylation signal. Exon 2 encoded SalI (GTCGAC) and BglII (AGATCT) transgene cloning sites are juxtaposed
SEQ ID NO:69: NTC9385C-intron RNAI vector backbone. Bp 1 is start of ssiA upstream of ColE2 origin, last bp is end of polyadenylation signal. Exon 2 encoded SalI (GTCGAC) and BglII (AGATCT) transgene cloning sites are juxtaposed
SEQ ID NO:70: RSM-R6K gamma origin bacterial region. [NheI site-trpA terminator-R6K Origin-RSM-KpnI site]
SEQ ID NO:71: RNAI-R6K gamma origin bacterial region. [NheI site-trpA terminator-R6K Origin-RNAI-KpnI site]
SEQ ID NO:72: NTC9385R2 and NTC9385R2a intronic R6K gamma origin-RSM bacterial region. Sequence show is O1; O2 is reverse complement
SEQ ID NO:73: NTC9385R2 and NTC9385R2a intronic R6K gamma origin-RNAI bacterial region. Sequence show is O1; O2 is reverse complement
SEQ ID NO:74: RSM-ColE2 origin bacterial region. [NheI site-ssiA-ColE2 Origin-RSM-KpnI site]
SEQ ID NO:75: RNAI-ColE2 origin bacterial region. [NheI site-ssiA-ColE2 Origin-RNAI-KpnI site]
SEQ ID NO:76: NTC9385C2 and NTC9385C2a intronic C2 origin-RSM bacterial region. Sequence show is O1; O2 is reverse complement
SEQ ID NO:77: NTC9385C2 and NTC9385C2a intronic C2 origin-RNAI bacterial region. Sequence show is O1; O2 is reverse complement Definition of Terms
$A_{405}$: Absorbance at 405 nanometers
AF: Antibiotic-free
APC: Antigen Processing Cell, for example, langerhans cells, plasmacytoid or conventional dendritic cells Approximately: As used herein, the term "approximately" or "about," as applied to one or more values of interest, refers to a value that is the same or similar to a stated reference value BAC: Bacterial artificial chromosome Bacterial region: Region of a plasmid vector required for propagation and selection in the bacterial host BE: Boundary element: Eukaryotic sequence that blocks the interaction between enhancers and promoters. Also referred to as insulator element. An example is the AT-rich unique region upstream of the CMV enhancer (XbaI to SpeI region; FIG. 1) that can function as an insulator/boundary element (Angulo A, Kerry D, Huang H, Borst E M, Razinsky A, Wu J et al. 2000 *J Virol* 74: 2826-2839)

bp: basepairs ccc: Covalently Closed Circular cI: Lambda repressor cITs857: Lambda repressor further incorporating a C to T (Ala to Thr) mutation that confers temperature sensitivity. cITs857 is a functional repressor at 28-30° C., but is mostly inactive at 37-42° C. Also called cI857

$Cm^R$: Chloramphenicol resistance cmv: Cytomegalovirus

CMV promoter boundary element: AT-rich region of the human cytomegalovirus (CMV) genome between the UL127 open reading frame and the major immediate-early (MIE) enhancer. Also referred to as unique region (Angulo et al., Supra, 2000)

ColE2-P9 replication origin: a region which is specifically recognized by the ColE2-P9 Rep protein to initiate DNA replication. Includes but not limited to ColE2-P9 replication origin sequences disclosed in SEQ ID NO:13: ColE2 Origin (+7), SEQ ID NO:16: ColE2 Origin (+7, CpG free), SEQ ID NO:14: ColE2 Origin (Min) and SEQ ID NO:15: ColE2 Origin (core) and replication functional mutations as disclosed in Yagura et al., 2006, *J Bacteriol* 188:999 included herein by reference ColE2 related replication origin: The ColE2-P9 origin is highly conserved across the ColE2-related plasmid family. Fifteen ColE2 related plasmid members including ColE3 are compared in Hiraga et al., 1994, *J Bacteriol.* 176:7233 and 53 ColE2 related plasmid members including ColE3 are compared in Yagura et al., Supra, 2006. These sequences are included herein by reference ColE2-P9 plasmid: a circular duplex DNA molecule of about 7 kb that is maintained at about 10 to 15 copies per host chromosome. The plasmid encodes an initiator protein (Rep protein), which is the only plasmid-specified trans-acting factor essential for ColE2-P9 plasmid replication ColE2-P9 replication origin RNA-OUT bacterial region: Contains a ColE2-P9 replication origin for propagation and the RNA-OUT selectable marker (e.g. SEQ ID NO: 23; SEQ ID NO: 24; SEQ ID NO: 25). Optionally includes a PAS, for example, the R6K plasmid CpG free ssiA primosomal assembly site (SEQ ID NO:17) or alternative ØX174 type or ABC type primosomal assembly sites, such as those disclosed in Nomura et al., 1991 *Gene* 108:15

ColE2 plasmid: NTC9385C, NTC9685C, NTC9385C2-O1, NTC9385C2-O2, NTC9385C2a-O1 and NTC9385C2a-O2 vectors, as well as modifications and alternative vectors containing a ColE2-P9 replication origin that were disclosed in patent application PCT/US 13/00068 (Filing No. 61/743,219) entitled 'DNA plasmids with improved expression' and included herein by reference delivery methods: Methods to deliver gene vectors [e.g. poly(lactide-co-glycolide) (PLGA), ISCOMs, liposomes, niosomes, virosomes, chitosan, and other biodegradable polymers, electroporation, piezoelectric permeabilization, sonoporation, iontophoresis, ultrasound, corona plasma, plasma facilitated delivery, tissue tolerable plasma, laser microporation, shock wave energy, magnetic fields, contactless magneto-permeabilization, gene gun, microneedles, microdermabrasion, topical DNA application, naked DNA injection, hydrodynamic delivery, high pressure tail vein injection, needle free biojector, liposomes, microparticles, microspheres, nanoparticles, nanocapsules, virosomes, bacterial ghosts, bacteria, attenuated bacteria, etc] as known in the art and included herein by reference DNA replicon: A genetic element that can replicate under its own control; examples include plasmids, cosmids, bacterial artificial chromosomes (BACs), bacteriophages, viral vectors and hybrids thereof

*E. coli*: *Escherichia coli*, a gram negative bacteria

EGFP: Enhanced green fluorescent protein

EP: Electroporation

Eukaryotic expression vector: A vector for expression of mRNA, protein antigens, protein therapeutics, shRNA, RNA or microRNA genes in a target eukaryotic organism using RNA Polymerase I, II or III promoters Eukaryotic replicative minicircle: a replicative minicircle eukaryotic expression vector Eukaryotic replicative pUC-free minicircle: a replicative minicircle eukaryotic expression vector that does not encode the pUC origin Eukaryotic region: The region of a plasmid that encodes eukaryotic sequences and/or sequences required for plasmid function in the target organism. This includes the region of a plasmid vector required for expression of one or more transgenes in the target organism including RNA Pol II enhancers, promoters, transgenes and polyA sequences. This also includes the region of a plasmid vector required for expression of one or more transgenes in the target organism using RNA Pol I or RNA Pol III promoters, RNA Pol I or RNA Pol III expressed transgenes or RNAs. The eukaryotic region may optionally include other functional sequences, such as eukaryotic transcriptional terminators, supercoiling-induced DNA duplex destabilized (SIDD) structures, S/MARs, boundary elements, etc Exon: A nucleotide sequence encoded by a gene that is transcribed and present within a mature mRNA product after RNA splicing to remove introns has been completed Expression vector: A vector for expression of mRNA, protein antigens, protein therapeutics, shRNA, RNA or microRNA genes in a target organism.

FU: Fluorescence units g: Gram, kg for kilogram gene of interest: gene to be expressed in the target organism. Includes mRNA genes that encode protein or peptide antigens, protein or peptide therapeutics, and mRNA, shRNA, RNA or microRNA that encode RNA therapeutics, and mRNA, shRNA, RNA or microRNA that encode RNA vaccines, etc Hr(s): Hour(s)

HTLV-I R: HTLV-I R 5' untranslated region (UTR). Sequences and compositions were disclosed in Williams, J A 2008 World Patent Application WO2008153733 and included herein by reference ID: Intradermal IM: Intramuscular immune response: Antigen reactive cellular (e.g. antigen reactive T cells) or antibody (e.g. antigen reactive IgG) responses IncB RNAI: plasmid pMU720 origin encoded RNAI (SEQ ID NO: 35) that represses RNA II regulated targets (Wilson I W, Siemering K R, Praszkier J, Pittard A J. 1997. *J Bacteriol* 179:742)

Intron: A nucleotide sequence encoded by a gene that is transcribed and subsequently removed from a mature mRNA product by RNA splicing kan: Kanamycin kanR: Kanamycin Resistance gene Kd: Kilodalton kozak sequence: Optimized consensus DNA sequence gccRccATG (R=G or A) immediately upstream of an ATG start codon that ensures efficient tranlation initiation. A SalI site (GTCGAC) immediately upstream of the ATG start codon (GTCGACATG) is an effective kozak sequence minicircle: Covalently closed circular plasmid derivatives in which the bacterial region has been removed from the parent plasmid by in vivo or in vitro site specific recombination or in vitro restriction digestion/ligation. Minicircle vectors are replication incompetent in bacterial cells mRNA: Messenger RNA mSEAP: Murine secreted alkaline phosphatase Nanoplasmid vector: Vector combining an RNA selectable marker with a R6K, ColE2 or ColE2 related replication origin. For example, NTC9385C, NTC9685C, NTC9385R, NTC9685R vectors and modifications disclosed in patent application PCT/US 13/00068 (Filing No. 61/743,219) entitled 'DNA plasmids with improved expression' and included herein by reference and the NTC9385C2 NTC9385C2a, NTC9385R2, NTC9385R2a, NTC9385R2b, NTC9385Ra, NTC9385RaF and NTC9385RbF replicative minicircle vectors of the invention disclosed herein NTC7382 promoter: A chimeric promoter comprising the CMV enhancer-CMV promoter-HTLV R-synthetic rabbit β globin 3' intron acceptor-exon 2-SR protein binding site (three copies of GAAGAAGAC)-kozak sequence, with or without an upstream SV40 enhancer. The creation and application of this chimeric promoter is disclosed in Williams, Supra, 2008

NTC8385: NTC8385, NTC8485 and NTC8685 plasmids are antibiotic-free vectors that contain a short RNA (RNA-OUT) selectable marker instead of an antibiotic resistance marker such as kanR. The creation and application of these RNA-OUT based antibiotic-free vectors are disclosed in Williams, Supra, 2008 and included herein by reference NTC8485: NTC8485 is an antibiotic-free vector that contains a short RNA (RNA-OUT) selectable marker instead of an antibiotic resistance marker such as kanR. The creation and application of NTC8485 is disclosed in Williams, J A 2010 US Patent Application 20100184158 and included herein by reference NTC8685: NTC8685 is an antibiotic-free vector that contains a short RNA (RNA-OUT) selectable marker instead of an antibiotic resistance marker such as kanR. The creation and application of NTC8685 is disclosed in Williams, Supra, 2010 and included herein by reference NTC9385C: The NTC9385C vector disclosed in patent application PCT/US 13/00068 (Filing No. 61/743,219) entitled 'DNA plasmids with improved expression' and included herein by reference has a spacer region encoded NheI-ssiA-ColE2 origin (+7) RNA-OUT-KpnI bacterial region (SEQ ID NO:23) linked through the flanking NheI and KpnI sites to the SEQ ID NO: 30 eukaryotic region. Transgenes are cloned into NTC9385C between the SalI and BglII sites as described for the NTC9385P2, NTC9385P2a, NTC9385C2, NTC9385C2a, NTC9385R2, and NTC9385R2a vectors NTC9385R: The NTC9385R vector disclosed in patent application PCT/US 13/00068 (Filing No. 61/743,219) entitled 'DNA plasmids with improved expression' and included herein by reference has a spacer region encoded NheI-trpA terminator-R6K origin RNA-OUT-KpnI bacterial region (SEQ ID NO:26) linked through the flanking NheI and KpnI sites to the SEQ ID NO: 30 eukaryotic region. Transgenes are cloned into NTC9385R between the SalI and BglII sites as described for the NTC9385P2, NTC9385P2a, NTC9385C2, NTC9385C2a, NTC9385R2, and NTC9385R2a vectors $OD_{600}$: optical density at 600 nm PAS: Primosomal assembly site. Priming of DNA synthesis on a single stranded DNA ssi site. ØX174 type PAS: DNA hairpin sequence that binds priA, which, in turn, recruits the remaining proteins to form the preprimosome [priB, dnaT, recruits dnaB (delivered by dnaC)], which then also recruits primase (dnaG), which then, finally, makes a short RNA substrate for DNA polymerase I. ABC type PAS: DNA hairpin binds dnaA, recruits dnaB (delivered by dnaC) which then also recruits primase (dnaG), which then, finally, makes a short RNA substrate for DNA polymerase I. See Masai et al., 1990 *J Biol Chem* 265:15134. For example, the R6K plasmid CpG free ssiA primosomal assembly site (SEQ ID NO:17) or alternative ØX174 type or ABC type primosomal assembly sites, such as those disclosed in Nomura et al., Supra, 1991

PAS-BH: Primosomal assembly site on the heavy (leading) strand

PAS-BH region: pBR322 origin region between ROP and PAS-BL (approximately pBR322 2067-2351)

PAS-BL: Primosomal assembly site on the light (lagging) strand

PBS: Phosphate buffered Saline

PCR: Polymerase Chain Reaction pDNA: Plasmid DNA pINT pR pL vector: The pINT pR pL integration expression vector is disclosed in Luke et al., 2011 *Mol Biotechnol* 47:43 and included herein by reference. The target gene to be expressed is cloned downstream of the pL promoter. The vector encodes the temperature inducible cI857 repressor, allowing heat inducible target gene expression $P_L$ promoter: Lambda promoter left. $P_L$ is a strong promoter that is repressed by the cI repressor binding to OL1, OL2 and OL3 repressor binding sites. The temperature sensitive cI857 repressor allows control of gene expression by heat induction since at 30° C. the cI857 repressor is functional and it represses gene expression, but at 37-42° C. the repressor is inactivated so expression of the gene ensues Plasmid: An extra chromosomal DNA molecule separate from the chromosomal DNA which is capable of replicating independently from the chromosomal DNA pMB1 RNAI: pMB1 plasmid origin encoded RNAI (SEQ ID NO: 33) and RNA selectable marker (SEQ ID NO: 34) that represses RNAII regulated targets such as those described in Grabherr R, Pfaffenzeller I. 2006 US patent application US20060063232 and Cranenburgh R M. 2009; U.S. Pat. No. 7,611,883

$P_{min}$: Minimal 678 bp pUC replication origin SEQ ID NO:45 and functional variants with base substitutions and/or base deletions. Vectors described herein incorporating $P_{min}$ include NTC9385P2(0.85)-O1, NTC9385P2(0.85)-O2, NTC9385P2a(0.85)-O1, and NTC9385P2a(0.85)-02

Pol: Polymerase polyA: Polyadenylation signal or site. Polyadenylation is the addition of a poly(A) tail to an RNA molecule. The polyadenylation signal contains the sequence motif recognized by the RNA cleavage complex. Most human polyadenylation signals contain an AAUAAA motif and conserved sequences 5' and 3' to it. Commonly utilized polyA signals are derived from the rabbit β globin (NTC8485; FIG. 1), bovine growth hormone (gWIZ; pVAX1), SV40 early, or SV40 late polyA signals pUC origin: pBR322-derived replication origin, with G to A transition that increases copy number at elevated temperature and deletion of the ROP negative regulator pUC free: Plasmid that does not contain the pUC origin. Non replicative fragments of the pUC origin may be included, for example the RNAI selectable marker (SEQ ID NO:34)

pUC plasmid: Plasmid containing the pUC origin

R6K plasmid: NTC9385R, NTC9685R, NTC9385R2-O1, NTC9385R2-O2, NTC9385R2a-O1, NTC9385R2a-O2, NTC9385R2b-O1, NTC9385R2b-O2, NTC9385Ra-O1, NTC9385Ra-O2, NTC9385RaF, and NTC9385RbF vectors as well as modifications and alternative vectors containing a R6K replication origin that were disclosed in patent application PCT/US 13/00068 (Filing No. 61/743,219) entitled 'DNA plasmids with improved expression' and included herein by reference. Alternative R6K vectors known in the art including, but not limited to, pCOR vectors (Gencell), pCpGfree vectors (Invivogen), and CpG free University of Oxford vectors including pGM169

R6K replication origin: a region which is specifically recognized by the R6K Rep protein to initiate DNA replication. Includes but not limited to R6K replication origin sequence disclosed as SEQ ID NO:11, and CpG free versions (e.g. SEQ ID NO:12) as disclosed in Drocourt et al., U.S. Pat. No. 7,244,609 and incorporated herein by reference R6K replication origin-RNA-OUT bacterial region: Contains a R6K replication origin for propagation and the RNA-OUT selectable marker (e.g. SEQ ID NO:26; SEQ ID NO:27; SEQ ID NO:28)

Rep: Replication

Replicative minicircle: Covalently closed circular plasmid vector with a short spacer region linking the 5' and 3' ends of the eukaryotic region sequences in which the replication origin and/or the selection marker are encoded within an intron or 3' UTR of a eukaryotic region or within the spacer region linking the 5' and 3' ends of the eukaryotic region sequences. For dual eukaryotic region vectors, the replication origin and/or the selectable marker may be cloned within an intron or 3' UTR of either of the eukaryotic regions within the vector. In replicative minicircle vectors of the invention, the spacer region preferably is less than 500 bp and may encode bacterial replication origins or selectable markers, bacterial transcription terminators, bacterial supercoiling-induced DNA duplex destabilized (SIDD) structures. In replicative minicircle vectors of the invention, the spacer region may optionally encode eukaryotic sequences such as eukaryotic selectable markers, eukaryotic transcription terminators, supercoiling-induced DNA duplex destabilized (SIDD) structures, boundary elements, S/MARs, or other functionalities Rep protein dependent plasmid: A plasmid in which replication is dependent on a replication (Rep) protein provided in Trans. For example, R6K replication origin, ColE2-P9 replication origin and ColE2 related replication origin plasmids in which the Rep protein is expressed from the host strain genome. Numerous additional Rep protein dependent plasmids are known in the art, many of which are summarized in del Solar et al., 1998 *Microbiol. Mol. Biol. Rev* 62:434-464 which is included herein by reference RNA-IN: Insertion sequence 10 (IS10) encoded RNA-IN, an RNA complementary and antisense to a portion of RNA RNA-OUT. When RNA-IN is cloned in the untranslated leader of a mRNA, annealing of RNA-IN to RNA-OUT reduces translation of the gene encoded downstream of RNA-IN RNA-IN regulated selectable marker: A genomically expressed RNA-IN regulated selectable marker. In the presence of plasmid borne RNA-OUT (e.g. SEQ ID NO:21), expression of a protein encoded downstream of RNA-IN is repressed. An RNA-IN regulated selectable marker is configured such that RNA-IN regulates either 1) a protein that is lethal or toxic to said cell per se or by generating a toxic substance (e.g. SacB), or 2) a repressor protein that is lethal or toxic to said bacterial cell by repressing the transcription of a gene that is essential for growth of said cell (e.g. murA essential gene regulated by RNA-IN tetR repressor gene). For example, genomically expressed RNA-IN-SacB cell lines for RNA-OUT plasmid propagation are disclosed in Williams, Supra, 2008 and included herein by reference. Alternative selection markers described in the art may be substituted for SacB RNA-OUT: Insertion sequence 10 (IS10) encoded RNA-OUT, an antisense RNA that hybridizes to, and reduces translation of, the transposon gene expressed downstream of RNA-IN. The sequence of the RNA-OUT RNA (SEQ ID NO:21) and complementary RNA-IN SacB genomically expressed RNA-IN-SacB cell lines can be modified to incorporate alternative functional RNA-IN/RNA-OUT binding pairs such as those disclosed in Mutalik et al., 2012 *Nat Chem Biol* 8:447, including, but not limited to, the RNA-OUT A08/RNA-IN S49 pair, the RNA-OUT A08/RNA-IN S08 pair, and CpG free modifications of RNA-OUT A08 that modify the CG in the RNA-OUT 5' TT<u>CG</u>C SEQ ID NO: 21 sequence to a non-CpG sequence. An example of a CpG free RNA-OUT selection marker, in which the two CpG motifs in the RNA-OUT RNA (one of which is present in the RNA-IN complementary region) are removed, is given as SEQ ID NO:22. A multitude of alternative substitutions to remove the two CpG motifs (mutating each CpG to either CpA, CpC, CpT, ApG, GpG, or TpG) may be utilized to make a CpG free RNA-OUT RNA-OUT Selectable marker: An RNA-OUT selectable marker DNA fragment including *E. coli* transcription promoter and terminator sequences flanking an RNA-OUT RNA. An RNA-OUT selectable marker, utilizing the RNA-OUT promoter and terminator sequences, that is flanked by DraIII and KpnI restriction enzyme sites, and designer genomically expressed RNA-IN-SacB cell lines for RNA-OUT plasmid propagation, are disclosed in Williams, Supra, 2008 (SEQ ID NO:20) and included herein by reference. The RNA-OUT promoter and terminator sequences flanking the RNA-OUT RNA (SEQ ID NO:21) may be replaced with heterologous promoter and terminator sequences. For example, the RNA-OUT promoter may be substituted with a CpG free promoter known in the art, for example the I-EC2K promoter or the P5/6 5/6 or P5/6 6/6 promoters disclosed in Williams, Supra, 2008 and included herein by reference. An example of a CpG free RNA-OUT transcription unit, in which the two CpG motifs in the RNA-OUT RNA (one of which is present in the RNA-IN complementary region) and the two CpG motifs in the RNA-OUT promoter are removed is given as SEQ ID NO: 22. The DraIII flanking restriction site contains a CpG, so CpG free RNA-OUT selectable markers are cloned with an alternative flanking restriction site, such as KpnI, BglII or EcoRI (flanking SEQ ID NO: 22). Vectors incorporating the SEQ ID NO:22 CpG free RNA-OUT selectable marker may be selected for sucrose resistance using the RNA-IN-SacB cell lines for RNA-OUT plasmid propagation disclosed in Williams, Supra, 2008. Alternatively, the RNA-IN sequence in these cell lines can be modified to incorporate the 1 bp change needed to perfectly match the CpG free RNA-OUT region complementary to RNA-IN as described in Example 1.

RNA polymerase I promoter: Promoter that recruits RNA Polymerase I to synthesize ribosomal RNA RNA polymerase II promoter: Promoter that recruits RNA Polymerase II to synthesize mRNAs, most small nuclear RNAs and microRNAs. For example, constitutive promoters such as the human or murine CMV promoter, elongation factor 1 (EF1) promoter, the chicken β-actin promoter, the β-actin promoter from other species, the elongation factor-1 α (EF1 α) promoter, the phosphoglycerokinase (PGK) promoter, the Rous sarcoma virus (RSV) promoter, the human serum albumin (SA) promoter, the α-1 antitrypsin (AAT) promoter, the thyroxine binding globulin (TBG) promoter, the cytochrome P450 2E1 (CYP2E1) promoter, etc. The vectors may also utilize combination promoters such as the chicken β-actin/CMV enhancer (CAG) promoter, the human or murine CMV-derived enhancer elements combined with the elongation factor 1α (EF1α) promoters, CpG free versions of the human or murine CMV-derived enhancer elements combined with the elongation factor 1α (EF1α) promoters, the albumin promoter combined with an α-fetoprotein MERII enhancer, etc, or the diversity of tissue specific or inducible promoters know in the art such as the muscle specific promoters muscle creatine kinase (MCK), and C5-12 or the liver-specific promoter apolipoprotein A-I (ApoAI), etc.

RNA polymerase III promoter: Promoter that recruits RNA Polymerase III to synthesize tRNAs, 5S ribosomal RNA, and other small RNAs. For example, Class I promoters such as the 5s rRNA promoter, Class II promoter such as tRNA promoters, Class III promoters such as the U6 small nuclear RNA promoter or the H1 nuclear RNase P promoter, etc.

RNA selectable marker: An RNA selectable marker is a plasmid borne expressed non translated RNA that regulates a chromosomally expressed target gene to afford selection. This may be a plasmid borne nonsense suppressing tRNA that regulates a nonsense suppressible selectable chromosomal target as described by Crouzet J and Soubrier F 2005 U.S. Pat. No. 6,977,174 included herein by reference. This may also be a plasmid borne antisense repressor RNA, a non limiting list included herein by reference includes RNA-OUT that represses RNA-IN regulated targets, pMB 1 plasmid origin encoded RNAI (SEQ ID NO: 33; a selectable marker is given SEQ ID NO: 34) that represses RNAII regulated targets (Grabherr and Pfaffenzeller, Supra, 2006; Cranenburgh, Supra, 2009), IncB plasmid pMU720 origin encoded RNAI (SEQ ID NO: 35; a selectable marker is given SEQ ID NO: 36) that represses RNA II regulated targets (SEQ ID NO: 37; Wilson et al., Supra, 1997), ParB locus Sok of plasmid R1 that represses Hok regulated targets, Flm locus FlmB of F plasmid that represses flmA regulated targets (Morsey M A, 1999 U.S. Pat. No. 5,922, 583). An RNA selectable marker may be another natural antisense repressor RNAs known in the art such as those described in Wagner E G H, Altuvia S, Romby P. 2002. *Adv Genet* 46:361 and Franch T, and Gerdes K. 2000. *Current Opin Microbiol* 3:159. An RNA selectable marker may also be an engineered repressor RNAs such as synthetic small RNAs expressed SgrS, MicC or MicF scaffolds as described in Na D, Yoo S M, Chung H, Park H, Park J H, Lee S Y. 2013. *Nat Biotechnol* 31:170. An RNA selectable marker may also be an engineered repressor RNA such as SEQ ID NO: 38 as part of a selectable marker such as SEQ ID NO: 39 that represses a target RNA such as SEQ ID NO: 40 fused to a target gene to be regulated such as SacB in SEQ ID NO: 41 and SEQ ID NO:42

ROP: Repressor of primer

RSM: RNA selectable marker

SacB: Structural gene encoding *Bacillus subtilis* levansucrase. Expression of SacB in gram negative bacteria is toxic in the presence of sucrose SD: Standard deviation SEAP: Secreted alkaline phosphatase Selectable marker: A selectable marker, for example a kanamycin resistance gene or a RNA selectable marker Selection marker: A selectable marker, for example a kanamycin resistance gene or a RNA selectable marker SIDD: supercoiling-induced DNA duplex destabilized (SIDD) structures. These sites, when incorporated into a vector, may alter the susceptibility of other sequences within the vector to be destabilized. This can alter function. For example, addition of a SIDD site to a expression vector may reduce the helical destabilization of a promoter. This may increase or decrease promoter activity, depending on the promoter since some promoters have increased expression with promoter helical destabilization, while others will have reduced expression with promoter helical destabilization shRNA: Short hairpin RNA S/MAR: Scaffold/matrix attached region. Eukaryotic sequences that mediate DNA attachment to the nuclear matrix SR: Spacer region.

Spacer region: As used herein, spacer region is the region linking the 5' and 3' ends of the eukaryotic region sequences. The eukaryotic region 5' and 3' ends are typically separated by the bacterial replication origin and bacterial selectable marker in plasmid vectors. In simple single RNA Pol II promoter vectors this will be between the RNA Pol II promoter region (5' to either a promoter, enhancer, boundary element, S/MAR) and the RNA Pol II polyA region (3' to either a polyA sequence, eukaryotic terminator sequence, boundary element, S/MAR). For example, in NTC8485 (FIG. 1) the 1492 bp spacer region is the region between NheI site at 3737 and KpnI site at 1492. In dual RNA Pol II promoter vectors, the eukaryotic sequences separated by the spacer will depend on the orientation of the two transcription elements. For example, with divergent or convergent RNA Pol II transcription units, the spacer region may separate two polyA sequences or two enhancers respectively. In RNA Pol II promoter, RNA Pol III promoter dual expression vectors, the spacer region may separate an RNA Pol II enhancer and a RNA Pol III promoter. In replicative minicircle vectors of the invention, this spacer region preferably is less than 500 bp and may encode bacterial selectable markers, bacterial replication origins, bacterial transcription terminators, bacterial supercoiling-induced DNA duplex destabilized (SIDD) structures. In replicative minicircle vectors of the invention, this spacer region may optionally encode eukaryotic sequences such as eukaryotic selectable markers, eukaryotic transcription terminators, supercoiling-induced DNA duplex destabilized (SIDD) structures, boundary elements, S/MARs, or other functionalities ssi: Single stranded initiation sequences SV40 enhancer: Simian Virus 40 genomic DNA that contains the 72 bp and optionally the 21 bp enhancer repeats target antigen: Immunogenic protein or peptide epitope, or combination of proteins and epitopes, against which an immune response can be mounted. Target antigens may by derived from a pathogen for infectious disease or allergy applications, or derived from a host organism for applications such as cancer, allergy, or autoimmune diseases. Target antigens are well defined in the art. Some examples are disclosed in Williams, Supra, 2008 and are included herein by reference TE buffer: A solution containing approximately 10 mM Tris pH 8 and 1 mM EDTA TetR: Tetracycline repressor Transcription terminator: Bacterial: A DNA sequence that marks the end of a gene or operon for transcription. This may be an intrinsic transcription terminator or a Rho-dependent transcriptional terminator. For an intrinsic terminator, such as the trpA terminator, a hairpin structure forms within the transcript that disrupts the mRNA-DNA-RNA polymerase ternary complex. Alternatively, Rho-dependent transcriptional terminators require Rho factor, an RNA helicase protein complex, to disrupt the nascent mRNA-DNA-RNA polymerase ternary complex. Eukaryotic: PolyA signals are not 'terminators', instead internal cleavage at PolyA sites leaves an uncapped 5' end on the 3'UTR RNA for nuclease digestion. Nuclease catches up to RNA Pol II and causes termination. Termination can be promoted within a short region of the poly A site by introduction of RNA Pol II pause sites (eukaryotic transcription terminator). Pausing of RNA Pol II allows the nuclease introduced into the 3' UTR mRNA after PolyA cleavage to catch up to RNA Pol II at the pause site. A nonlimiting list of eukaryotic transcription terminators know in the art include the C2×4 terminator (Ashfield R, Patel A J, Bossone S A, Brown H, Campbell R D, Marcu K B, Proudfoot N J. 1994. *EMBO J* 13:5656) and the gastrin terminator (Sato K, Ito R, Baek K H, Agarwal K, 1986. *Mol. Cell. Biol.* 6:1032). Eukaryotic transcription terminators may elevate mRNA levels by enhancing proper 3'-end processing of mRNA (Kim D, Kim J D, Baek K, Yoon Y, Yoon J. 2003. *Biotechnol Prog* 19:1620)

Transgene: Gene of interest that is cloned into a vector for expression in a target organism ts: Temperature sensitive µg: Microgram µl: Microliter UTR: Untranslated region of a mRNA (5' or 3' to the coding region)

VARNA: Adenoviral virus associated RNA, including VARNAI (VAI or VA1) and or VARNAII (VAII or VA2) from any Adenovirus serotype, for example, serotype 2, serotype 5 or hybrids thereof VARNAI: Adenoviral virus associated RNAI, also referred to as VAI, or VA1, from any Adenovirus serotype, for example, serotype 2, serotype 5 or hybrids thereof Vector: A gene delivery vehicle, including viral (e.g. alphavirus, poxvirus, lentivirus, retrovirus, adenovirus, adenovirus related virus, etc) and nonviral (e.g. plasmid, MIDGE, transcriptionally active PCR fragment, minicircles, bacteriophage, etc) vectors. These are well known in the art and are included herein by reference Vector backbone: Eukaryotic region and bacterial region of a vector, without the transgene or target antigen coding region

DETAILED DESCRIPTION OF THE PREFERRED EMBODIMENTS

The invention relates generally to plasmid DNA vector methods and compositions that improve plasmid manufacture and expression. The invention can be practiced to improve expression and manufacturing of vectors such as eukaryotic expression plasmids useful for gene therapy, genetic immunization and or interferon therapy. Improved plasmid expression is defined herein as improved transgene expression level and/or expression duration in vitro or in vivo compared to a transgene encoding pUC plasmid containing a spacer region encoded pUC replication origin. It is to be understood that all references cited herein are incorporated by reference in their entirety.

According to one preferred embodiment, the present invention provides for method of increasing in vivo expression of transgene from covalently closed super-coiled plasmid DNA, which comprises modifying the plasmid DNA to replace the pMB1, ColE1 or pBR322 derived replication origin and selectable marker with a replication origin selected from the group consisting of an ColE2-P9 replication origin, ColE2 related replication origin, and R6K replication origin and a RNA selectable marker; transforming the modified plasmid DNA into a Rep protein producing bacterial cell line rendered competent for transformation; and isolating the resultant transformed bacterial cells. The modified plasmid produced from these cells has increased transgene expression in the target organism.

In one preferred embodiment, the spacer region encoded pMB1, ColE1 or pBR322 derived replication origin is replaced with a CpG free ColE2 origin to improve plasmid encoded transgene expression and manufacture. In another preferred embodiment, a primosome assembly site is incorporated into a ColE2 vector backbone to improve plasmid copy number. In yet another preferred embodiment, the spacer region encoded pMB1, ColE1 or pBR322 derived replication origin is replaced with a CpG free R6K origin to improve plasmid encoded transgene expression and manufacture.

According to one preferred embodiment, the present invention provides compositions of short spacer region covalently closed super-coiled plasmid DNA eukaryotic vectors with improved transgene expression and *E. coli* manufacture, which comprises modifying the plasmid DNA to replace the spacer region encoded replication origin in the vector spacer region with an intronic replication origin selected from the group consisting of an ColE2-P9 replication origin, ColE2 related replication origin, R6K replication origin, pUC replication origin and $P_{min}$ pUC replication origin; transforming the modified plasmid DNA as necessary into a Rep protein producing bacterial cell line rendered competent for transformation; and isolating the resultant transformed bacterial cells. The modified plasmid produced from these cells is a 'replicative minicircle' vector with improved manufacture and transgene expression.

In one preferred embodiment, the vector spacer region encoded replication origin is replaced with an intronic R6K replication origin to improve plasmid encoded transgene expression and manufacture. In another preferred embodiment, the vector spacer region encoded replication origin is replaced with an intronic pUC replication origin to improve plasmid encoded transgene expression and manufacture. In another preferred embodiment, the vector spacer region encoded replication origin is replaced with an intronic $P_{min}$ pUC replication origin to improve plasmid encoded transgene expression and manufacture. In yet another preferred embodiment, the vector spacer region encoded replication origin is replaced with an intronic ColE2 replication origin to improve plasmid encoded transgene expression and manufacture. In yet another preferred embodiment, the vector spacer region encoded replication origin is replaced with an intronic CpG free ColE2 replication origin to improve plasmid encoded transgene expression and manufacture. In yet another preferred embodiment, the vector spacer region encoded replication origin is replaced with an intronic CpG free R6K replication origin to improve plasmid encoded transgene expression and manufacture.

In yet another preferred embodiment, the vector spacer region encoded replication origin is replaced with an 3' UTR encoded R6K replication origin to improve plasmid encoded transgene expression and manufacture. In yet another preferred embodiment, the vector spacer region encoded replication origin is replaced with an 3' UTR encoded ColE2 replication origin to improve plasmid encoded transgene expression and manufacture. In yet another preferred embodiment, the vector spacer region encoded replication origin is replaced with an 3' UTR encoded CpG free ColE2 replication origin to improve plasmid encoded transgene expression and manufacture. In yet another preferred embodiment, the vector spacer region encoded replication origin is replaced with an 3' UTR encoded CpG free R6K replication origin to improve plasmid encoded transgene expression and manufacture.

In yet another preferred embodiment, the vector spacer region encoded selectable marker is replaced with an 3' UTR encoded RNA selectable marker to improve plasmid encoded transgene expression and manufacture. In yet another preferred embodiment, the vector spacer region encoded selectable marker is replaced with an intron encoded RNA selectable marker to improve plasmid encoded transgene expression and manufacture.

In yet another preferred embodiment, the vector spacer region directly links the eukaryotic region sequences that are typically separated by the bacterial replication origin and bacterial selectable marker. In yet another preferred embodiment, the vector eukaryotic region polyadenylation signal sequence is covalently linked directly to the enhancer of eukaryotic region promoter. In yet another preferred embodiment, a spacer region is included between the eukaryotic region sequences that are typically separated by the bacterial replication origin and bacterial selectable marker. In yet another preferred embodiment the spacer region between the sequences that are typically separated by the replication origin and selectable marker is 1 to 500 bp. In yet another preferred embodiment the spacer region between the sequences that are typically separated by the replication origin and selectable marker encode bacterial or eukaryotic selectable markers, bacterial transcription terminators, eukaryotic transcription terminators, supercoiling-induced DNA duplex destabilized (SIDD) structures, boundary elements, S/MARs, RNA Pol I or RNA Pol III expressed sequences or other functionalities. In yet another preferred embodiment, the spacer region is less than 500 bp and encodes an RNA selectable marker, with an R6K or ColE2 replication origin further encoded within an intron or a 3' UTR. In yet another preferred embodiment, the spacer region is less than 500 bp and encodes an R6K or ColE2 replication origin, with an RNA selectable marker further encoded within an intron or a 3' UTR. In yet another preferred embodiment, the spacer region is less than 500 bp and encodes an RNA selectable marker, with an R6K or ColE2 replication origin further encoded within the spacer region.

The methods of plasmid modification of the present invention have been surprisingly found to improve plasmid encoded transgene expression and manufacture.

Plasmid encoded transgene expression is preferably improved by employing specific constructs or compositions incorporated in a vector. According to one preferred embodiment, the present invention provides a composition for construction of a vector, comprising a RNA selectable marker and a ColE2 origin with at least 90% sequence identity to the sequences set forth as SEQ ID NO: 13, SEQ ID NO: 14, SEQ ID NO: 15, or SEQ ID NO: 16, and a plasmid DNA encoded eukaryotic region, wherein the ColE2 origin is operably linked within an intron of the plasmid DNA encoded eukaryotic region. The RNA selectable marker may be operably linked within an intron, a 3' UTR or the spacer region. This novel vector configuration enables high yield manufacture of short spacer region vectors. It has also been surprisingly found that this intronic ColE2 origin improves plasmid encoded transgene expression. According to another preferred embodiment, the eukaryotic region has at least 95% sequence identity to a sequence selected from the group consisting of: SEQ ID NO: 30, SEQ ID NO: 31.

According to another preferred embodiment, the present invention provides a composition for construction of a vector, comprising an RNA selectable marker and a R6K origin with at least 90% sequence identity to the sequences set forth as SEQ ID NO: 11, or SEQ ID NO: 12, and a plasmid DNA encoded eukaryotic region, wherein the R6K origin is operably linked to an intron within the plasmid DNA encoded eukaryotic region. The RNA selectable marker may be operably linked within an intron, a 3' UTR or the spacer region. This novel vector configuration enables high yield manufacture of short spacer region vectors. It has also been surprisingly found that this intronic R6K origin improves plasmid encoded transgene expression. According to another preferred embodiment, the eukaryotic region has at least 95% sequence identity to a sequence selected from the group consisting of: SEQ ID NO: 30, SEQ ID NO: 31.

According to another preferred embodiment, the present invention provides a composition for construction of a vector, comprising an RNA selectable marker and a pUC origin and a plasmid DNA encoded eukaryotic region, wherein the pUC origin is operably linked to an intron within the plasmid DNA encoded eukaryotic region. The RNA selectable marker may be operably linked within an intron, a 3' UTR or the spacer region. This novel vector configuration enables high yield manufacture of short spacer region vectors. It has also been surprisingly found that this intronic pUC origin improves plasmid encoded transgene expression. According to another preferred embodiment, the eukaryotic region has at least 95% sequence identity to a sequence selected from the group consisting of: SEQ ID NO: 30, SEQ ID NO: 31.

According to another preferred embodiment, the present invention provides a composition for construction of a vector, comprising an RNA selectable marker and a $P_{min}$ pUC origin with at least 90% sequence identity to the sequence set forth as SEQ ID NO: 45, and a plasmid DNA encoded eukaryotic region, wherein the $P_{min}$ pUC origin is operably linked to an intron within the plasmid DNA encoded eukaryotic region. The RNA selectable marker may be operably linked within an intron, a 3' UTR or the spacer region. This novel vector configuration enables high yield manufacture of short spacer region vectors. It has also been surprisingly found that this intronic $P_{min}$ pUC origin improves plasmid encoded transgene expression. According to another preferred embodiment, the eukaryotic region has at least 95% sequence identity to a sequence selected from the group consisting of: SEQ ID NO: 30, SEQ ID NO: 31.

Plasmid encoded transgene expression is preferably improved by employing specific constructs or compositions incorporated in a vector. According to one preferred embodiment, the present invention provides a composition for construction of a vector, comprising a ColE2 origin with at least 90% sequence identity to the sequences set forth as SEQ ID NO: 13, SEQ ID NO: 14, SEQ ID NO: 15, or SEQ ID NO: 16, and a plasmid DNA encoded eukaryotic region, wherein the ColE2 origin is operably linked within a 3' UTR of the plasmid DNA encoded eukaryotic region. An RNA selectable marker is incorporated into the vector either adjacent to the replication origin or within an intron or within the spacer region.

According to another preferred embodiment, the present invention provides a composition for construction of a vector, comprising a 3' UTR R6K origin with at least 90% sequence identity to the sequences set forth as SEQ ID NO: 11, or SEQ ID NO: 12, and a plasmid DNA encoded eukaryotic region, wherein the R6K origin is operably linked to a 3' UTR within the plasmid DNA encoded eukaryotic region. An RNA selectable marker is incorporated into the vector either adjacent to the replication origin or within an intron or within the spacer region. This novel vector configuration enables high yield manufacture of short spacer region vectors.

The methods of plasmid modification of the present invention have been surprisingly found to improve plasmid encoded transgene expression in the target organism. Increased expression vectors may find application to improve the magnitude of DNA vaccination mediated antigen reactive B or T cell responses for preventative or therapeutic vaccination, increase RNA and or protein transgene levels to improve gene replacement therapy or gene knockdown therapy, increase plasmid based expression levels of DNA vector expressed therapeutic antibodies that neutralize infectious diseases such as influenza, HIV, malaria, hepatitis C virus, tuberculosis, etc.

The methods of plasmid modification of the present invention have been surprisingly found to provide a solution to provide short spacer region vectors with efficient high yield manufacture.

As used herein, the term "sequence identity" refers to the degree of identity between any given query sequence, e.g. SEQ ID NO: 2, and a subject sequence. A subject sequence may, for example, have at least 90 percent, at least 95 percent, or at least 99 percent sequence identity to a given query sequence. To determine percent sequence identity, a query sequence (e.g. a nucleic acid sequence) is aligned to one or more subject sequences using any suitable sequence alignment program that is well known in the art, for instance, the computer program ClustalW (version 1.83, default parameters), which allows alignments of nucleic acid sequences to be carried out across their entire length (global alignment). Chema et al., 2003 *Nucleic Acids Res.*, 31:3497-500. In a preferred method, the sequence alignment program (e.g. ClustalW) calculates the best match between a query and one or more subject sequences, and aligns them so that identities, similarities, and differences can be determined. Gaps of one or more nucleotides can be inserted into a query sequence, a subject sequence, or both, to maximize sequence alignments. For fast pair-wise alignments of nucleic acid sequences, suitable default parameters can be selected that are appropriate for the particular alignment program. The output is a sequence alignment that reflects the relationship between sequences. To further determine percent identity of a subject nucleic acid sequence to a query sequence, the sequences are aligned using the alignment program, the number of identical matches in the alignment is divided by the length of the query sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Turning now to the drawings, FIG. 1. shows an annotated map of the antibiotic-free NTC8485 pUC origin expression vector with the locations of the pUC origin, PAS-BH primosomal assembly site, SV40 enhancer, HpaI site within the intron and other key elements indicated. The replication origin (PAS-BH and pUC origin) is from bp 32 to the DraIII (1345) site (1313 bp total). The antibiotic-free RNA-OUT selectable marker is between the DraIII (1345) and KpnI (1492) sites (147 bp total). The bacterial region (trpA terminator, replication origin and RNA-OUT selectable marker=spacer region) of this vector is 1492 bp. Below the map an annotated sequence of the vector encoded HTLV-IR-Rabbit β globin hybrid intron (SEQ IND NO:1) is shown. The HTLV-I R derived 5' intronic splice donor region and the Rabbit β globin 3' splice acceptor region functionalities are separated by a HpaI site (GTTAAC, bold uppercase). The 5' HTLV-I R derived splice donor (AGgtaagt; first 2 AG bases are exon 1) and rabbit β globin intron 1 derived 3' splice acceptor (cagG; last G is exon 2) sites are double underlined. The 3' splice acceptor poly-pyrimidine tract (starting with ctttttct) is single underlined. This poly-pyrimidine tract sequence was altered from the native rabbit β globin intron 1 sequence by replacing the native uppercase G and A residues in this region with t (ctGttttcA) to increase the poly-pyrimidine tract consensus. The rabbit B globin 3' acceptor branch site (tgctgac) is single underlined. This intron is 225 bp and is present in the NTC8385, NTC8485, NTC8685, NTC9385C, NTC9685C, NTC9385R, and NTC9685R vectors.

Figure 2:
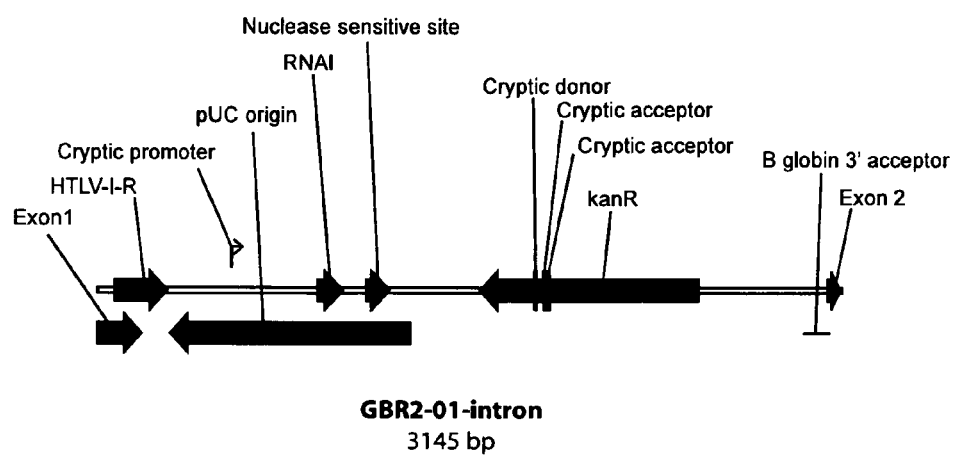
FIG. 2 depicts bioinformatics analysis of an intron containing the gWIZ bacterial region (GBR) encoded kanR selection marker-pUC origin.
Figure 3:
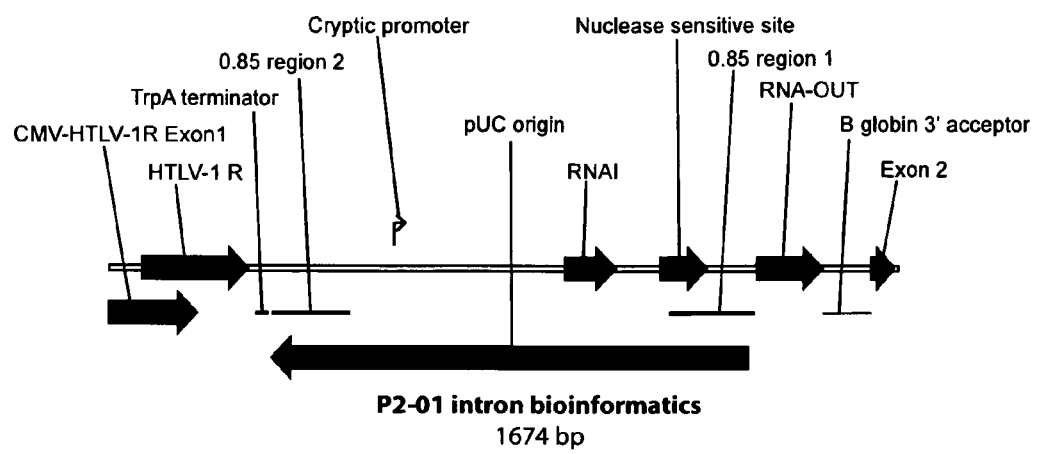
FIG. 3 depicts bioinformatics analysis of introns containing the NTC9385P2 bacterial region (P2) encoded RNA-OUT selectable marker—pUC origin in both orientations.
Figure 3:
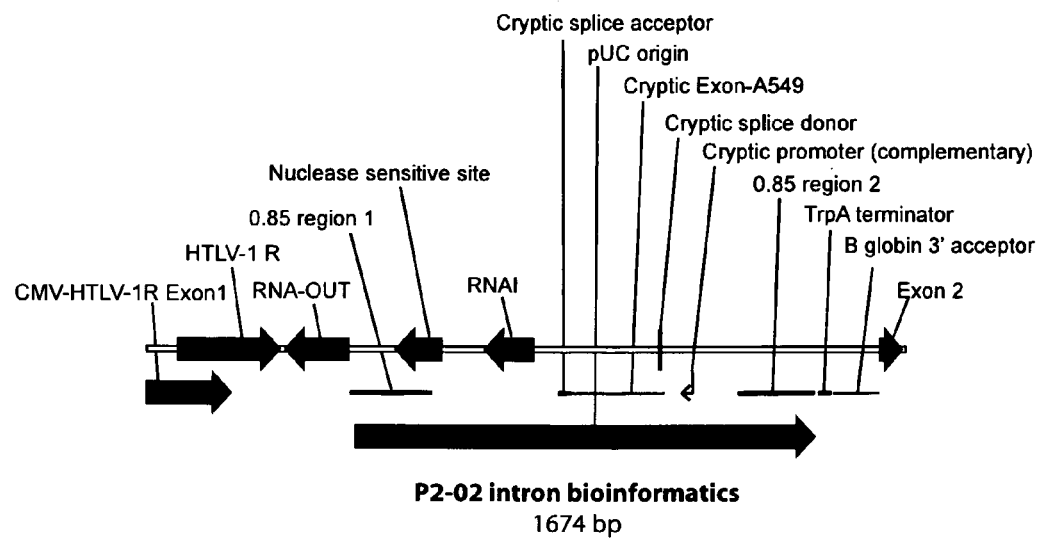

FIG. 2 shows bioinformatics analysis of an intron containing the gWIZ vector bacterial region (GBR2) encoded kanR selection marker-pUC origin. In this vector the kanR gene is antisense to the CMV promoter; the opposite sense orientation would be unacceptable due to safety concerns regarding the risk of kanR protein expression in the target organism. The kanR gene contains multiple cryptic splice acceptor and splice donor sites and potential sense and antisense promoters (not shown) predicted to interfere with intron function. The location and orientation of an experimentally verified cryptic pUC origin promoter (Lemp N A, Kiraoka K, Kasahara N, Logg C R. 2012. *Nucleic Acids Res* 40:7280) is shown (cryptic promoter). Splice signals were detected using the NetGene2 (Brunak, S., Engelbrecht, J., and Knudsen, S. 1991 *J Mol Biol* 220, 49-65) and Splicepredictor (Brendel, V., Xing, L. & Zhu, W. 2004. *Bioinformatics* 20, 1157-1169) programs while promoters were identified using the Softberry (Mount Kisco, N.Y.) TSSG and FPROM programs FIG. 3 shows bioinformatics analysis of introns containing the NTC9385P2 and NTC9385P2a bacterial region encoded RNA-OUT selectable marker-pUC origin in both orientations (P2-O1; P2-O2). A cryptic 209 bp exon derived from the pUC origin identified in A549 cells transfected with NTC9385P2-02 [and NTC9385P2(0.85)-O2] is indicated as well as the cryptic splice acceptor and cryptic splice donor used in this cryptic exon. The location and orientation of an experimentally verified cryptic pUC origin promoter (Lemp et al., Supra, 2012) is shown (cryptic promoter). Splice signals and promoters were detected as described in FIG. 2. The location of the regions removed in the NTC9385P2 (0.85)-O1, NTC9385P2a(0.85)-O1, NTC9385P2(0.85)-O2 and NTC9385P2a(0.85)-O2 vectors are indicated (0.85 region 1 and 0.85 region 2).

Figure 4:
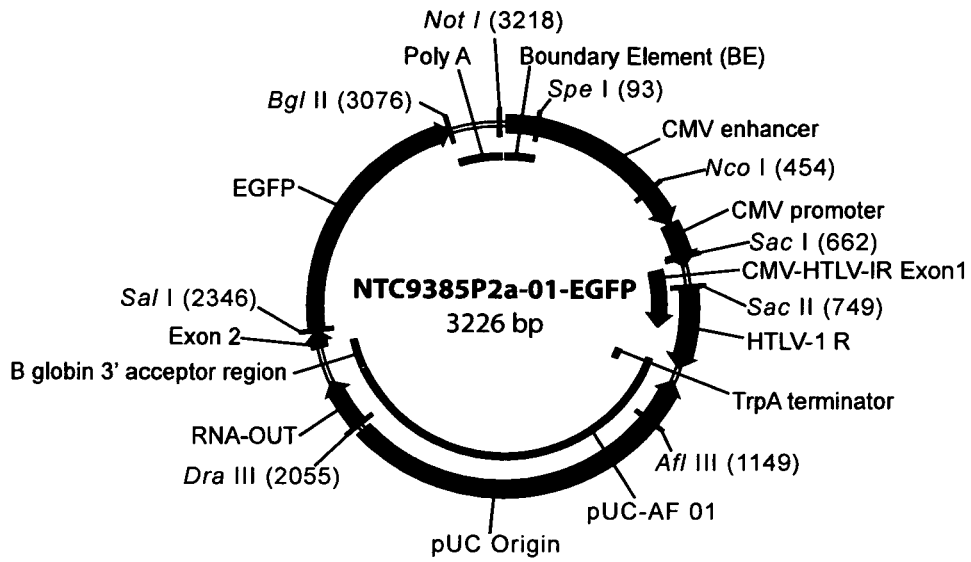
FIG. 4 depicts the NTC9385P2a-O1-EGFP and NTC9385P2a-O2-EGFP intronic pUC origin-RNA-OUT replicative minicircle expression vectors.
Figure 4:
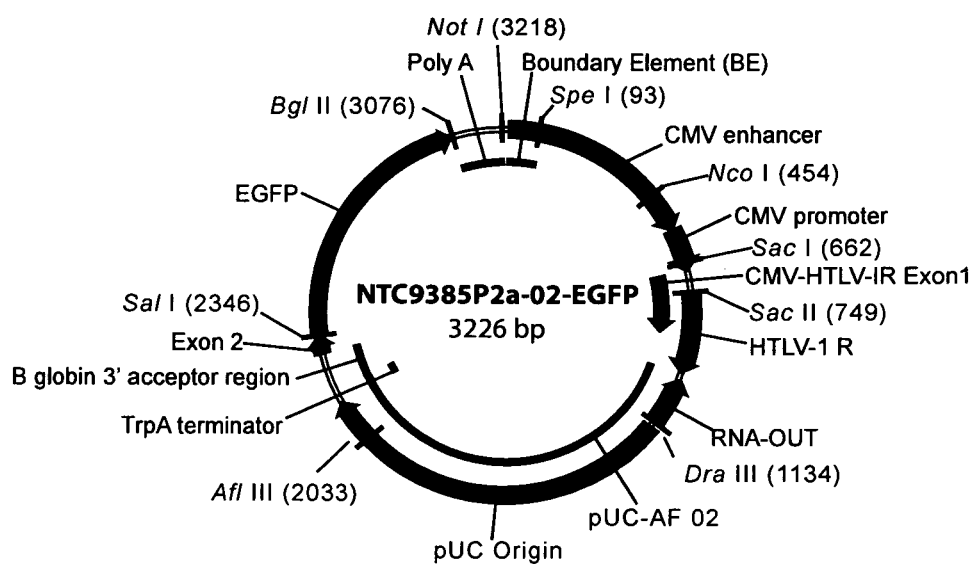

FIG. 4 shows an annotated map of the NTC9385P2a-O1-EGFP and NTC9385P2a-O2-EGFP intronic pUC origin- RNA-OUT replicative minicircle expression vectors with the locations and orientations of the intronic RNA-OUT selectable marker, pUC replication origin (pUC origin) trpA terminator (SEQ ID NO: 29) and other key elements indicated. These vectors contain a 1436 bp intron.

Figure 5:
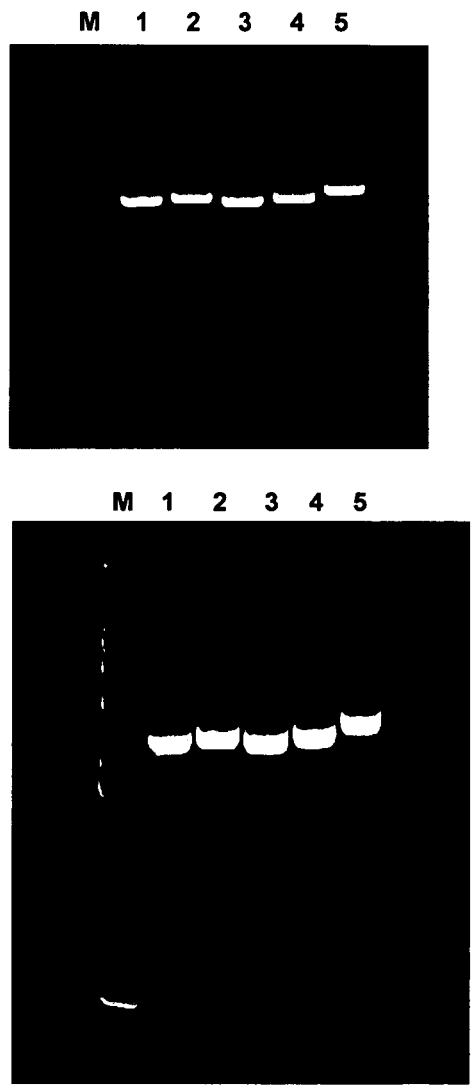
FIG. 5 shows plasmid quality from intronic pUC origin-RNA-OUT expression vectors NTC9385P2a-O1-EGFP, NTC9385P2a-O2-EGFP, NTC9385P2-O1-EGFP and NTC9385P2-O2-EGFP vectors versus a comparator spacer region encoded pUC origin-RNA-OUT expression vector NTC8385-EGFP.

FIG. 5 shows plasmid quality from intronic pUC origin-RNA-OUT expression vectors NTC9385P2a-O1-EGFP, NTC9385P2a-O2-EGFP, NTC9385P2-O1-EGFP and NTC9385P2-O2-EGFP vectors versus a comparator spacer region encoded pUC origin-RNA-OUT expression vector (NTC8385-EGFP). The top gel is a SYBR Green I prestain, the bottom gel is after SYBR Green II poststaining for 2 hrs followed by further electrophoresis to allow detection of shadow band or replication intermediates. SYBR Green I and II were obtained from Invitrogen (Carlsbad, Calif., USA).

Figure 6:
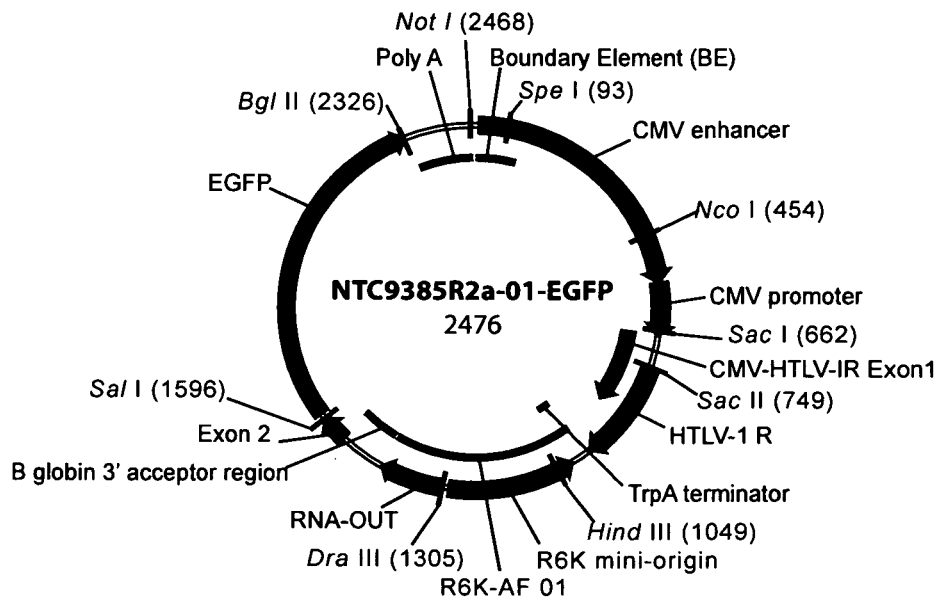
FIG. 6 depicts the NTC9385R2a-O1-EGFP and NTC9385R2a-O2-EGFP intronic R6K origin-RNA-OUT replicative minicircle expression vectors.
Figure 6:
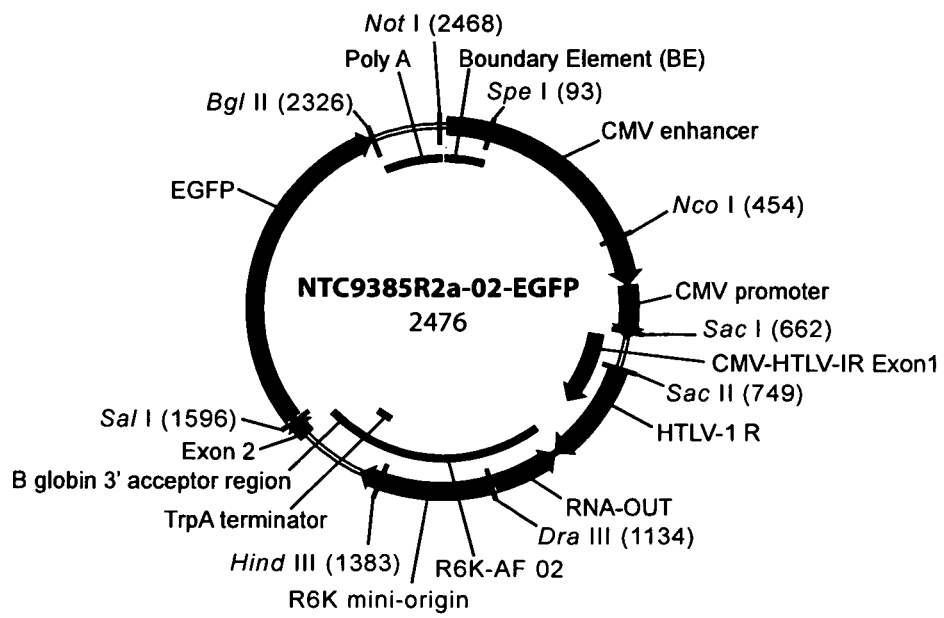

FIG. 6 depicts the NTC9385R2a-O1-EGFP and NTC9385R2a-O2-EGFP intronic R6K origin-RNA-OUT replicative minicircle expression vectors with the locations and orientations of the intronic RNA-OUT selectable marker, R6K gamma replication origin (R6K mini-origin) trpA terminator (SEQ ID NO: 27) and other key elements indicated. These vectors contain a 685 bp intron.

Figure 7:
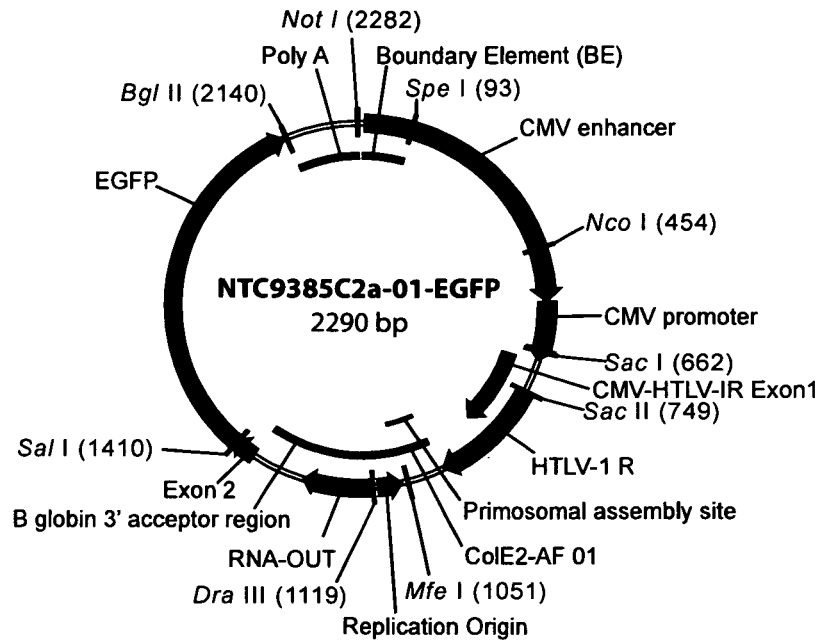
FIG. 7 depicts the NTC9385C2a-O1-EGFP and NTC9385C2a-O2-EGFP intronic ColE2 origin-RNA-OUT replicative minicircle expression vectors.
Figure 7:
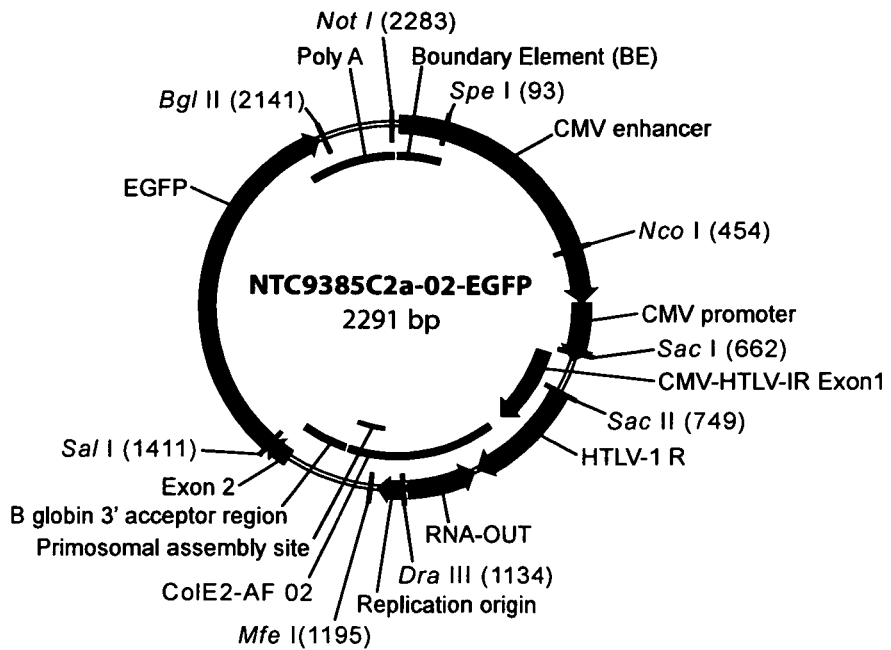

FIG. 7 depicts the NTC9385C2a-O1-EGFP and NTC9385C2a-O2-EGFP intronic ColE2 origin-RNA-OUT replicative minicircle expression vectors with the locations and orientations of the intronic RNA-OUT selectable marker, ColE2-P9 replication origin (Replication origin) primosomal assembly site (bacterial region is SEQ ID NO: 24) and other key elements indicated. These vectors contain a 499 bp intron.

Figure 8:
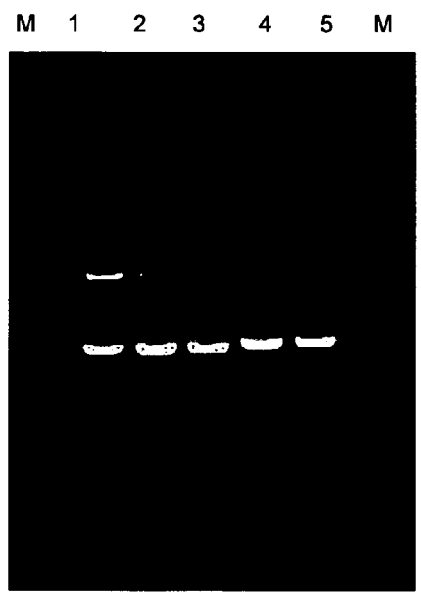
FIG. 8 shows plasmid quality from Table 7 fermentations of intronic R6K origin-RNA-OUT expression vectors NTC9385R2-O1-EGFP, NTC9385R2-O2-EGFP, NTC9385R2a-O1-EGFP and NTC9385R2a-O2-EGFP vectors, versus a comparator spacer region encoded R6K origin-RNA-OUT expression vector NTC9385R-EGFP.

FIG. 8 shows plasmid quality from Table 7 fermentations of intronic R6K origin-RNA-OUT expression vectors NTC9385R2-O1-EGFP, NTC9385R2-O2-EGFP, NTC9385R2a-O1-EGFP and NTC9385R2a-O2-EGFP vectors, versus a comparator spacer region encoded R6K origin-RNA-OUT expression vector (NTC9385R-EGFP). The gel is a SYBR Green I prestain. No replication intermediates or shadow band were detected after SYBR Green II poststain for 2 hrs followed by further electrophoresis.

Figure 9:
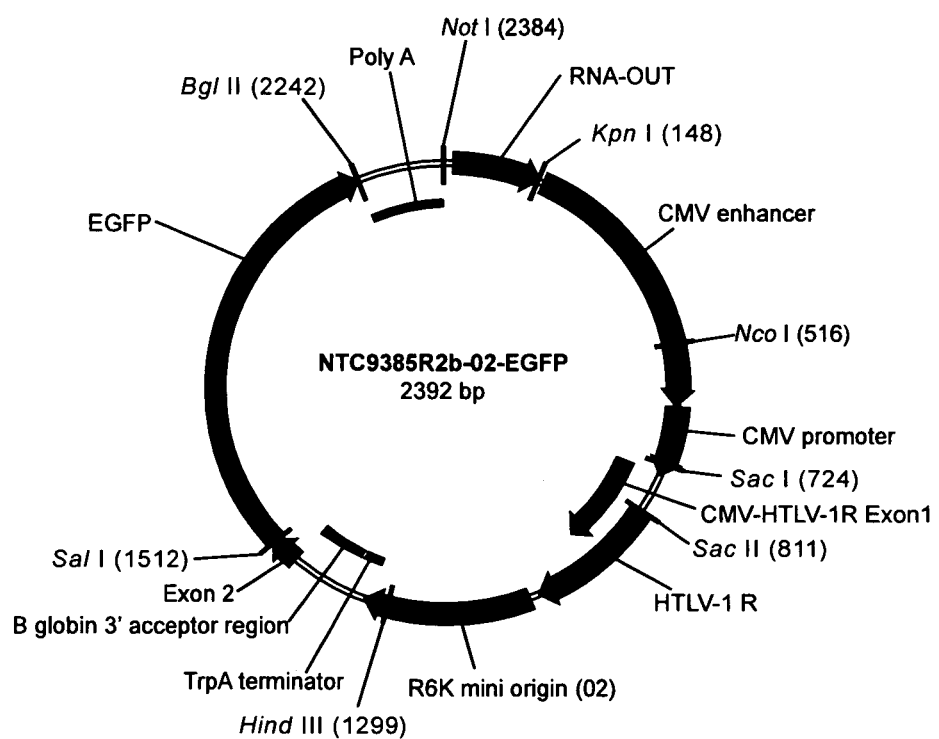
FIG. 9 depicts the NTC9385R2b-O2-EGFP intronic R6K origin-spacer region RNA-OUT replicative minicircle expression vectors.

FIG. 9 depicts the NTC9385R2b-O2-EGFP intronic R6K origin-spacer region RNA-OUT replicative minicircle expression vectors with the locations and orientations of the spacer region RNA-OUT selectable marker, intronic R6K gamma replication origin (R6K mini-origin SEQ ID NO: 11) trpA terminator and other key elements indicated. This vector contains a 539 bp intron.

Figure 10:
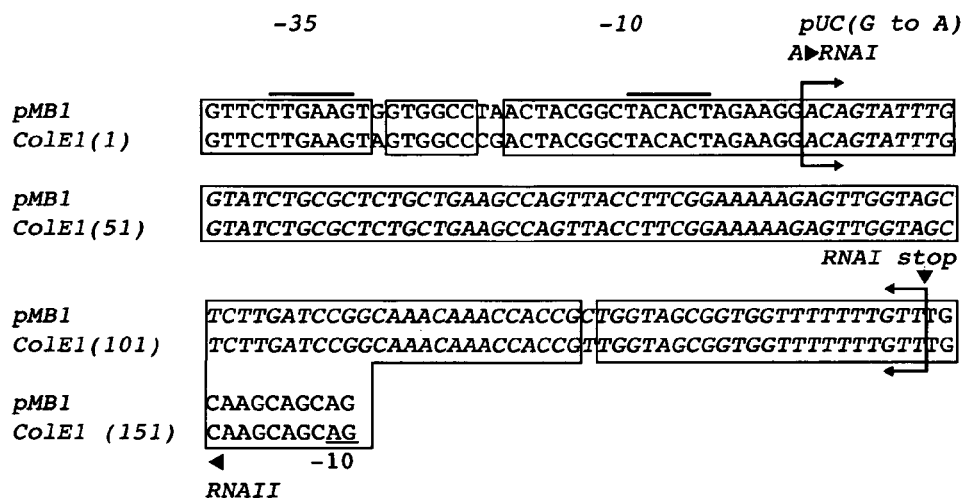
FIG. 10 depicts a pMB1 and ColE1 RNA I RNA selectable marker.

FIG. 10 shows pMB1 and ColE1 RNA I RNA selectable markers. The RNAI promoter (−35 and −10) and RNAI antisense repressor RNA (italics; SEQ ID NO:33) is shown as well the location of the pUC high copy number G to A mutation (RNAI selectable marker: SEQ ID NO: 34)

Figure 11:
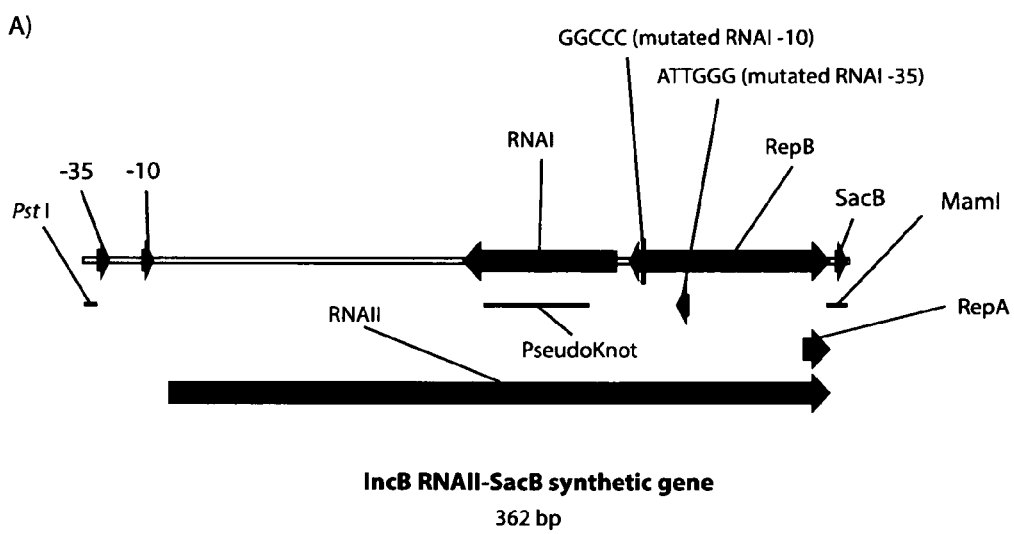
FIG. 11 depicts a IncB RNAI based RNA selectable marker.
Figure 11:
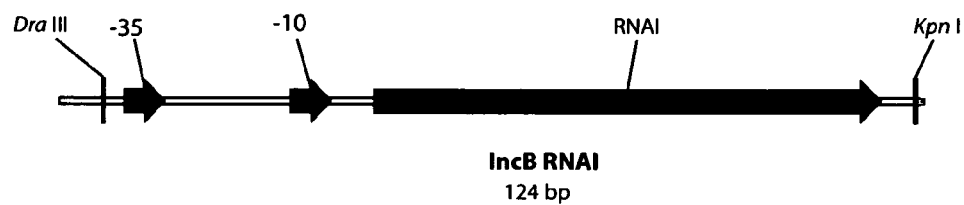

FIG. 11 shows an IncB RNAI based RNA selectable marker. A) Genomically expressed target of RNAI RNA selectable marker (SEQ ID NO: 37). Plasmid expressed RNAI binding to the pseudoknot in the complementary genomically expressed RNAII target prevents translation of the downstream SacB gene, conferring sucrose resistance. The RNAI −10 and −35 promoter elements are mutated to prevent RNAI expression. B) Structure of plasmid expressed IncB RNAI RNA selectable marker (SEQ ID NO: 36) encoding the IncB RNAI antisense repressor (SEQ ID NO: 35).

Figure 12:
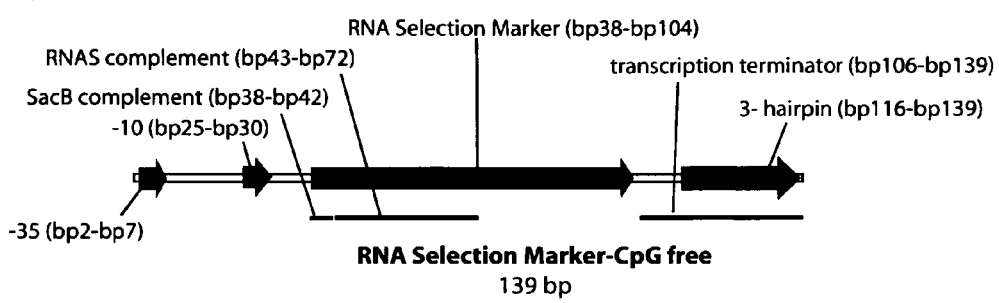
FIG. 12 depicts a designed synthetic CpG free RNA selectable marker.
Figure 12:
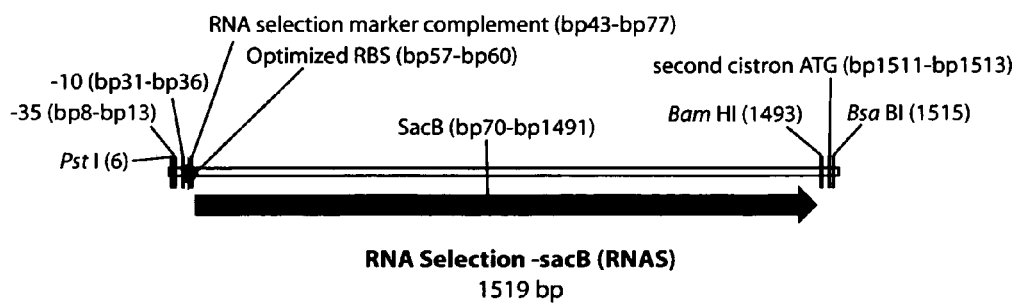

FIG. 12 shows a designed synthetic CpG free RNA selectable marker. A) Structure of plasmid expressed engineered CpG free RSM antisense RNA marker (SEQ ID NO: 39) encoding the CpG free antisense repressor RNA (SEQ ID NO: 38). B) Genomically expressed target of engineered CpG free RNA selectable marker, RNA selection-sacB (RNAS). Plasmid expressed engineered CpG free RNA selectable marker binding to the complementary genomically expressed RSM target (SEQ ID NO: 40) prevents translation of the downstream SacB gene, conferring sucrose resistance. Versions of RNA selection-SacB, in which the upstream promoter −35 and −10 promoter elements have either 5/6, 6/6 or 5/6, 5/6 or 5/6, 4/6 basepair match to the TTGACA or TAATAT consensus sequences were made (SEQ ID NO:41; SEQ ID NO: 42) and cloned into the pINT integration vector to create pINT-RNAS (P5/6 6/6), pINT-RNAS (P5/6 4/6) (SEQ ID NO: 43) and pINT-RNAS (P5/6 5/6) (SEQ ID NO: 44).

Figure 13:
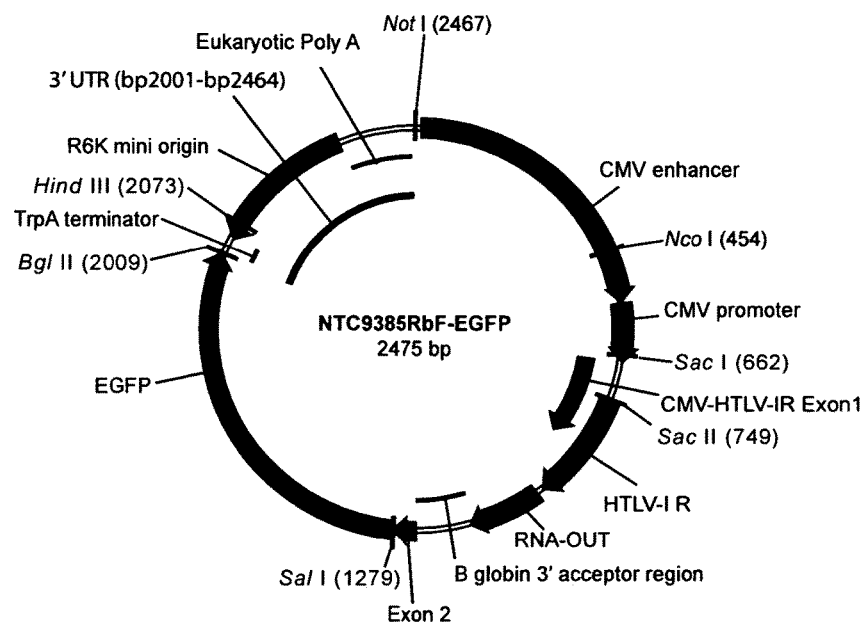
FIG. 13 depicts the NTC9385RbF-EGFP 3' UTR R6K, intronic RNA-OUT replicative minicircle expression vector.
Figure 13:
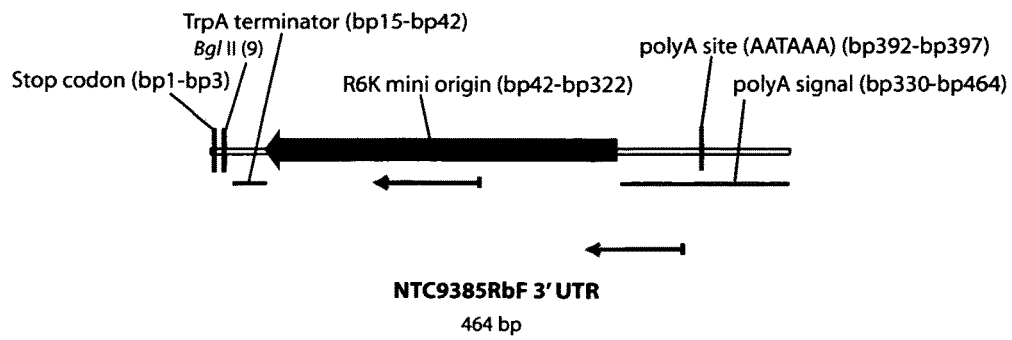

FIG. 13 shows the NTC9385RbF-EGFP 3' UTR R6K, intronic RNA-OUT replicative minicircle expression vector. A) the locations and orientations of the intronic RNA-OUT selectable marker, 3' UTR R6K gamma Replication origin (R6K mini-origin SEQ ID NO: 11) trpA terminator and other key elements indicated. This NTC9385RbF vector backbone (with EGFP excised, SalI and BglII transgene cloning sites juxtaposed) is presented as SEQ ID NO: 47. An alternative vector backbone, NTC9385RbF-RSM (with EGFP excised, SalI and BglII transgene cloning sites juxtaposed), in which the RNA-OUT selectable marker is substituted with the CpG free RSM antisense RNA marker (SEQ ID NO: 39) is presented as SEQ ID NO: 48. An alternative vector backbone, NTC9385RbF-RNAI (with EGFP excised, SalI and BglII transgene cloning sites juxtaposed), in which the RNA-OUT selectable marker is substituted with the RNAI selectable marker (SEQ ID NO: 34) is presented as SEQ ID NO: 49. B) Annotated map of the NTC9385RbF 3' UTR and polyA region. Open reading frames (cutoff of minimum 20 amino acids) on the complementary strand are indicated with arrowed lines. No open reading frames are present in the sense orientation.

The invention also relates to compositions and methods for producing short spacer region replicative minicircle plasmids with dramatically improved manufacturing yields and simplified manufacturing compared to alternative short spacer region vectors such as minicircles. The present invention also provides sequences that, when introduced into a vector backbone, increase plasmid encoded transgene expression.

The invention also relates to compositions and methods for producing high expression level plasmids. The present invention provides sequences that, when introduced into a vector backbone, increase plasmid encoded transgene expression.

The surprising observation that a ColE2 replication origin-RNA selection marker or R6K replication origin-RNA selectable marker can be utilized as a plasmid encoded transgene expression enhancer is disclosed.

As described herein, plasmid encoded transgene expression is increased by replacement of the pMB1, ColE1 or pBR322 derived origin-selection marker bacterial region with an R6K origin-RNA selectable marker in the plasmid spacer region. In yet another preferred embodiment, the R6K origin is CpG free. In yet another preferred embodiment, the R6K origin is included with an RNA-OUT selectable marker.

In yet another preferred embodiment, plasmid encoded transgene expression is increased by replacement of the pMB1, ColE1 or pBR322 derived origin-selection marker bacterial region with a ColE2 origin-RNA selectable marker in the plasmid spacer region. In yet another preferred embodiment, the ColE2 origin is CpG free. In yet another preferred embodiment, the ColE2 origin is included with an RNA-OUT selectable marker. In yet another preferred embodiment, the ColE2 origin is included with a primosome assembly site.

The surprising observation that a ColE2, R6K, pUC or $P_{min}$ pUC replication origin can be inserted into an intron of a eukaryotic RNA Pol II transcription unit without decreasing intron efficiency or transgene expression is disclosed.

The surprising observation that a ColE2 or R6K, replication origin can be inserted into an 3' UTR of a eukaryotic RNA Pol II transcription unit without decreasing transgene expression is disclosed.

As described herein, plasmid encoded transgene expression is improved by replacement of the vector spacer region encoded replication origin with an R6K origin in an intron or 3' UTR of a eukaryotic RNA Pol II transcription unit. In yet another preferred embodiment, the R6K origin is CpG free. In yet another preferred embodiment, the R6K origin is included with an RNA-OUT selectable marker.

In yet another preferred embodiment, plasmid encoded transgene expression is improved by replacement of the vector spacer region encoded replication origin with a ColE2 origin in an intron or 3' UTR of a eukaryotic RNA Pol II transcription unit. In yet another preferred embodiment, the ColE2 origin is CpG free. In yet another preferred embodiment, the ColE2 origin is included with an RNA-OUT selectable marker. In yet another preferred embodiment, the ColE2 origin is included with a primosome assembly site.

In yet another preferred embodiment, plasmid encoded transgene expression is improved by replacement of the vector spacer region encoded replication origin with a pUC origin in an intron of a eukaryotic RNA Pol II transcription unit. In yet another preferred embodiment, the pUC origin is included with an RNA-OUT selectable marker.

In yet another preferred embodiment, plasmid encoded transgene expression is improved by replacement of the vector spacer region encoded replication origin with a $P_{min}$ pUC origin in an intron of a eukaryotic RNA Pol II transcription unit. In yet another preferred embodiment, the $P_{min}$ pUC origin is included with an RNA-OUT selectable marker.

Improved plasmid encoded transgene expression is defined herein as improved transgene expression level and/or expression duration in vitro or in vivo compared to a transgene encoding pUC plasmid containing a spacer region encoded pUC replication origin.

EXAMPLES

The methods of the invention are further illustrated by the following examples. These are provided by way of illustration and are not intended in any way to limit the scope of the invention.

Example 1: pUC, R6K and ColE2 Replication Origin Plasmid Replication and Production pUC Origin Vector Replication and Production Background:

The vast majority of therapeutic plasmids use the pUC origin which is a high copy derivative of the pMB1 origin (closely related to the ColE1 origin). For pMB1 replication, plasmid DNA synthesis is unidirectional and does not require a plasmid borne initiator protein. The pUC origin is a copy up derivative of the pMB1 origin that deletes the accessory ROP (rom) protein and has an additional temperature sensitive mutation that destabilizes the RNAI/RNAII interaction. Shifting of a culture containing these origins from 30 to 42° C. leads to an increase in plasmid copy number. pUC plasmids can be produced in a multitude of *E. coli* cell lines. pUC plasmid propagation and fermentations reported herein were performed using cell line NTC48165=DH5α dcm atλ::P5/6 6/6-RNA-IN-SacB or NTC54208=XL1Blue dcm atλ::P5/6 6/6-RNA-IN-SacB the creation of which are disclosed in Carnes A E, Luke J M, Vincent J M, Schukar A, Anderson S, Hodgson C P, and Williams J A. 2011 *Biotechnol Bioeng* 108:354-363.

R6K Origin Vector Replication and Production Background:

The R6K gamma plasmid replication origin requires a single plasmid replication protein π that binds as a replication initiating monomer to multiple repeated 'iteron' sites (seven core repeats containing TGAGNG consensus) and as a replication inhibiting dimer to repressive sites (TGAGNG) and to iterons with reduced affinity. Replication requires multiple host factors including IHF, DnaA, and primosomal assembly proteins DnaB, DnaC, DnaG (Abhyankar et al., 2003 *J Biol Chem* 278:45476-45484). The R6K core origin contains binding sites for DnaA and IHF that affect plasmid replication since π, IHF and DnaA interact to initiate replication.

Different versions of the R6K gamma replication origin have been utilized in various eukaryotic expression vectors, for example pCOR vectors (Soubrier et al., 1999, *Gene Therapy* 6:1482) and a CpG free version in pCpGfree vectors (Invivogen, San Diego Calif.), and pGM169 (University of Oxford). Incorporation of the R6K replication origin per se does not improve transgene expression levels compared to an optimized pUC origin vector (Soubrier et al., Supra, 1999). However, use of a conditional replication origin such as R6K gamma that requires a specialized cell line for propagation adds a safety margin since the vector will not replicate if transferred to a patient's endogenous flora.

A highly minimalized R6K gamma derived replication origin (SEQ ID NO:11) that contains core sequences required for replication (including the DnaA box and stb 1-3 sites; Wu et al., 1995. *J Bacteriol.* 177: 6338-6345), but with the upstream π dimer repressor binding sites and downstream π promoter deleted (by removing one copy of the iterons) was disclosed in patent application PCT/US 13/00068 (Filing No. 61/743,219) entitled 'DNA plasmids with improved expression' and included herein by reference. The NTC9385R vector backbone (SEQ ID NO: 62) including this minimalized R6K origin and the RNA-OUT AF selectable marker in the spacer region, was disclosed in patent application PCT/US 13/00068 (Filing No. 61/743,219) entitled 'DNA plasmids with improved expression' and included herein by reference.

Typical R6K production strains express from the genome the π protein derivative PIR116 that contains a P106L substitution that increases copy number (by reducing π dimerization; π monomers activate while π dimers repress). Fermentation results with pCOR (Soubrier et al., Supra, 1999) and pCpG plasmids (Hebel H L, Cai Y, Davies L A, Hyde S C, Pringle I A, Gill D R. 2008. *Mol Ther* 16: 5110) were low, around 100 mg/L in PIR116 cell lines.

Mutagenesis of the pir-116 replication protein and selection for increased copy number has been used to make new production strains. For example, the TEX2pir42 strain contains a combination of P106L and P42L. The P42L mutation interferes with DNA looping replication repression. The TEX2pir42 cell line improved copy number and fermentation yields with pCOR plasmids with reported yields of 205 mg/L (Soubrier F. Circular DNA molecule having a conditional origin of replication, process for their preparation and their use in gene therapy. World Patent Application WO2004033664. 2004).

Other combinations of π copy number mutants that improve copy number include 'P42L and P113S' and 'P42L, P106L and F107S' (Abhyankar et al., 2004. *J Biol Chem* 279:6711-6719).

RNA-OUT selectable marker-R6K plasmid propagation and fermentations reported herein were performed using heat inducible 'P42L, P106L and F107S' π copy number mutant cell line NTC711231, the creation of which is disclosed in patent application PCT/US 13/00068 (Filing No. 61/743,219) entitled 'DNA plasmids with improved expression' and included herein by reference. NTC711231=NTC54208-pR pL (OL1-G to T) P42L-P106L-F107S (P3-). NTC54208=XL1Blue dcm attλ::P5/6 6/6-RNA-IN-SacB. Fermentations were additionally performed in the equivalent DH5α host strain NTC711772=NTC48165-pR pL (OL1-G to T) P42L-P106L-F107S (P3-). NTC48165=DH5α dcm attλ::P5/6 6/6-RNA-IN-SacB. Fermentations were also performed using host strain NTC731871, a 'P42L, P113S' π copy number mutant cell line which is equivalent to NTC711231 except for use of the alternative 'P42L, P113S' π copy number mutant disclosed in patent application PCT/US 13/00068 (Filing No. 61/743,219) entitled 'DNA plasmids with improved expression'.

ColE2 origin vector replication and production background: The ColE2 replication origin (for example, ColE2-P9) is highly conserved across the ColE2-related plasmid family. Fifteen members are compared in Hiraga et al., Supra, 1994, and fifty three ColE2 related plasmid members including ColE3 are compared in Yagura et al., Supra, both references are included herein by reference. Plasmids containing this origin are normally 10 copies/cell (low copy number). For gene therapy vector application, ColE2 replication origin vector copy number needs to be improved dramatically.

Expression of the ColE2-P9 replication (Rep) protein is regulated by antisense RNA (RNAI). Copy number mutations have been identified that interfere with this regulation and raise the copy number to 40/cell (Takechi et al., 1994 *Mol Gen Genet* 244:49-56).

RNA-OUT selectable marker-ColE2 plasmid propagation and fermentations were performed using heat inducible 'G194D' Rep protein copy number mutant cell line NTC710351 the creation of which is disclosed in patent application PCT/US 13/00068 (Filing No. 61/743,219) entitled 'DNA plasmids with improved expression' and included herein by reference.

The following vectors including NTC9385C (SEQ ID NO: 63) containing the minimal ColE2-P9 origin (Yagura and Itoh 2006 *Biochem Biophys Res Commun* 345:872-877) and various origin region modifications were disclosed in patent application PCT/US 13/00068 (Filing No. 61/743, 219) entitled 'DNA plasmids with improved expression' and included herein by reference.

+7-ssiA:

This combines the ColE2 origin (+7) (SEQ ID NO:13) with ssiA from plasmid R6K (SEQ ID NO:17). Thus ssiA vectors contain, in addition to the ColE2-P9 origin, a downstream primosome assembly site. Like most plasmid origins, the ColE2 origin contains a primosomal assembly site about 100 bp downstream of the origin (Nomura et al., Supra, 1991). This site primes lagging strand DNA replication (Masai et al., 1990 *J Biol Chem* 265:15124-15133) which may improve plasmid copy number or plasmid quality. The ColE2 PAS (ssiA) is similar to PAS-BH (ColE1 ssiA=PAS-BL Marians et al., 1982 *J Biol Chem* 257:5656-5662) and both sites (and PAS-BH) are CpG rich ØX174 type PAS. A CpG free PAS (ssiA from R6K; Nomura et al., Supra, 1991; SEQ ID NO:17) that acts as a dnaA, dnaB dnaC (ABC) primosome on a dnaA box hairpin sequence (Masai et al., Supra, 1990) was selected for inclusion in the +7-ssiA vectors. Alternative ABC or ØX174 type PAS sequences are functionally equivalent to ssiA from R6K, and may be substituted for ssiA in these ColE2 replication origin vectors. NTC9385C incorporates the +7-ssiA origin region.

+7 CpG Free-ssiA (SEQ ID NO:18):

This combines the ColE2 replication origin (+7 CpG free) (SEQ ID NO:16) with ssiA from plasmid R6K (SEQ ID NO:17). The single CpG in the ColE2 replication origin was removed from the vector by site directed mutagenesis. A version with flanking SphI and KpnI restriction sites for cloning is disclosed as SEQ ID NO: 19.

Yagura et al., Supra, 2006 have demonstrated that the Min ColE2 Replication origin (SEQ ID NO:14, which is reverse complement of residues 7-38, in FIG. 1 of Yagura et al., Supra, 2006) can be further deleted without eliminating replication function. Yagura et al., Supra, 2006, demonstrated that the core sequence is residues 8-35, with residues 5-36 are required for full activity. The +7 ColE2 Replication origin (SEQ ID NO:13; which is the reverse complement of residues 0-44 in FIG. 1 of Yagura et al., Supra, 2006) could therefore be reduced to span residues 8-35 or 5-36 of FIG. 1 of Yagura et al., Supra, 2006 (SEQ ID NO:15). Such vectors should replicate similarly to the disclosed vectors. As well, a number of base changes can be made within the core ColE2 origin 8-34 region that do not affect ColE2 replication (see changes to residues that retain function in Table 2; Yagura et al., Supra, 2006).

The +7(CpG free)-ssiA ColE2 origin (SEQ ID NO 18) or +7(CpG free) ColE2 origin (SEQ ID NO 16) are smaller CpG free replication origin alternatives to the 260 bp CpG free R6K replication origins (SEQ ID NO:12). CpG free ColE2 origins may be utilized to construct CpG free plasmid vectors. Combinations of a CpG free ColE2 or R6K replication origin with a CpG free RNA-OUT selectable marker (SEQ ID NO: 22) may be utilized to construct antibiotic-free CpG free bacterial regions for CpG free plasmid vectors (e.g. SEQ ID NO:25; SEQ ID NO:28). A CpG free R6K-RNA-OUT bacterial region was created by replacement of the kanR marker in a CpG free R6K replication origin (SEQ ID NO:12) vector with a CpG free RNA-OUT selectable marker (KpnI—SEQ ID NO: 22—BglII restriction fragment). This CpG free RNA-OUT selectable marker encoding R6K origin vector was successfully recovered as sucrose resistant colonies after transformation of R6K production host cell line NTC711231. This vector directly links the reverse complement of CpG free R6K replication origin (SEQ ID NO:12) through the KpnI site to the CpG free RNA-OUT selectable marker (SEQ ID NO: 22) in the orientation R6K origin>RNA-OUT> as opposed to the divergent orientation <R6K origin RNA-OUT> composition disclosed as SEQ ID NO:28. Expression of an EGFP transgene expressing version of this vector in A549 cells transfected as described in Example 2 was improved at 48 hrs post transfection compared to the kanR parent vector (4657±593 FU versus 3573±388 FU with the kanR parent vector). This demonstrates that various orientations of RNA- OUT and the replication origin may be utilized to create replicative minicircle vectors with improved expression, and that alternative RNA selectable markers can be utilized. Further, a CpG free ColE2-RNA bacterial region was created by replacement of the RNA-OUT marker and R6K origin in the CpG free R6K replication origin vector above with the +7(CpG free)-ssiA ColE2 origin (SEQ ID NO 19)-CpG free RNA-OUT selectable marker (SEQ ID NO: 22) as a SphI BglII restriction fragment (SEQ ID NO: 25). This CpG free RNA-OUT selectable marker encoding ColE2 origin vector was successfully recovered as sucrose resistant colonies after transformation of ColE2 production host cell line NTC710351. Expression of an EGFP transgene expressing version of this CpG free ColE2 origin-RNA-OUT vector in A549 cells transfected as described in Example 2 was improved at 48 hrs post transfection compared to the CpG free R6K-RNA-OUT-vector described above (1921±123 FU with the CpG free ColE2 origin-RNA-OUT vector versus 1579±207 FU with the CpG free R6K origin-RNA-OUT vector). The successful construction of these disclosed vectors demonstrate that CpG free ColE2 or R6K replication origins can be combined with a CpG free RNA-OUT selectable marker to construct antibiotic-free CpG free bacterial regions for CpG free plasmid vectors. The cell lines for selection (e.g. NTC711231, NTC711772, or NTC731871 for R6K and NTC710351 for ColE2) may be modified to alter the RNA-IN sequence in attλ::P5/6 6/6-RNA-IN-SacB to match the CpG free RNA-OUT encoded single base change that removes the CpG motif in the RNA-OUT RNA that is present in the RNA-IN complementary region (CpG free RNAIN). For example, robust sucrose selection and high plasmid yields and quality were obtained after transformation of CpG free RNA-OUT selectable marker (SEQ ID NO: 22) CpG free R6K origin (SEQ ID NO: 12) vectors into R6K production host NTC791342=XL1Blue dcm attλ::P5/6 6/6-CpG free RNA-IN-SacB-pR pL (OL1-G to T) P42L-P106L-F107S (P3-) which incorporates the one bp change in RNA-IN needed to perfectly complement the CpG free RNA-OUT. For example, CpG free RNA-OUT selectable marker (SEQ ID NO: 22) -CpG free ColE2 origin-CpG free ssiA (SEQ ID NO: 18) (incorporating the CpG free ColE2 RNA-OUT bacterial region; SEQ ID NO: 25) vectors may be propagated in ColE2 production host NTC791381=XL1Blue dcm attλ::P5/6 6/6-CpG free RNA-IN-SacB-pR pL (OL1-G to T) ColE2rep G194D which incorporates the one bp change in RNA-IN needed to perfectly complement the CpG free RNA-OUT.

An alternative CpG free RNA selectable marker that may be substituted for the CpG free RNA-OUT selectable marker in the creation of CpG free plasmid vectors is the RSM selectable marker (SEQ ID NO: 39) with flanking CpG free restriction sites (e.g. KpnI, BglII) replacing the CpG containing DraIII restriction site. Alternatively, the RSM antisense repressor RNA (SEQ ID NO: 38) with flanking CpG free promoter and terminator sequences could be substituted for the CpG free RNA-OUT selectable marker in the creation of CpG free plasmid vectors.

Use of a conditional replication origin such as these ColE2 origins that requires a specialized cell line for propagation adds a safety margin since the vector will not replicate if transferred to a patients endogenous flora.

Example 2: NTC9385R and NTC9385C Vector Construction, Manufacture and Expression The NTC9385C and NTC9385R AF eukaryotic expression vectors incorporating novel ColE2-P9 or R6K derived vector origins, respectively were made. To replace the spacer region encoded pUC origin with a ColE2 origin, the ColE2 origin (+7) (SEQ ID NO:13) combined with ssiA from plasmid R6K (SEQ ID NO:17) from Example 1 was used to make NTC9385C (SEQ ID NO: 63). To replace the spacer region encoded pUC origin with a R6K origin the R6K origin (SEQ ID NO:11) from Example 1 was used to make NTC9385R (SEQ ID NO: 62). The R6K gamma origin vector was constructed by swapping in the R6K gamma origin (SEQ ID NO:1) in a NotI-DraIII R6K origin synthetic gene for the corresponding NotI-DraIII pUC origin region. The ColE2 origin vector was constructed in a similar fashion, by swapping in the +7 ssiA ColE2 origin in a NheI-DraIII synthetic gene for the corresponding NheI-DraIII pUC origin region.

The 466 bp Bacterial region [NheI site-trpA terminator-R6K Origin-RNA-OUT-KpnI site] for NTC9385R and NTC9685R is shown in SEQ ID NO:26. The 281 bp Bacterial region [NheI site-ssiA-ColE2 Origin (+7)-RNA-OUT-KpnI site] for NTC9385C and NTC9685C is shown in SEQ ID NO:23.

High fermentation yields in HyperGRO media are obtained with these vectors. For example 392 mg/mL with NTC9385R-EGFP in R6K production cell line NTC711231 and 672 mg/L with NTC9385C-EGFP in ColE2 production cell line NTC710351 (Table 7).

These are just a few possible nonlimiting short spacer region vector configurations. Many alternative vector configurations incorporating the novel R6K or ColE2 origin vector modifications may also be made, including but not limited to vectors with alternative selection markers, alternative promoters, alternative terminators, and different orientations of the various vector-encoded elements or alternative R6K or ColE2 origins as described in Examples 1 to 11.

An example strategy for cloning into these vectors is outlined below.

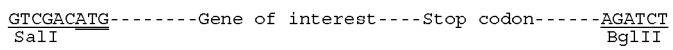

```
GTCGACATG--------Gene of interest----Stop codon------AGATCT
 SalI                                                  BglII
```

For the NTC9385C and NTC9385R vectors, the ATG start codon (double underlined) is immediately preceded by a unique SalI site. The SalI site is an effective Kozak sequence for translational initiation.

EGFP and muSEAP transgene versions of NTC9385C and NTC9385R were constructed by standard restriction fragment swaps. The muSEAP gene is secreted using its endogenous secretion signal, while EGFP is cell associated. Expression levels in vitro were determined using EGFP, while expression levels in vivo were determined using muSEAP. Expression levels were compared to the NTC8685 vector, the gWIZ vector, and a minicircle comparator.

NTC8685 and gWIZ are examples of vectors comprising a spacer region greater than 500 basepairs.

Adherent HEK293 (human embryonic kidney) and A549 (human lung carcinoma),cell lines were obtained from the American Type Culture Collection (Manassas, Va., USA). Cell lines were propagated in Dulbecco's modified Eagle's medium/F12 containing 10% fetal bovine serum and split (0.25% trypsin-EDTA) using Invitrogen (Carlsbad, Calif., USA) reagents and conventional methodologies. For transfections, cells were plated on 24-well tissue culture dishes, plasmids were transfected into cell lines using Lipofectamine 2000 following the manufacturer's instructions (Invitrogen).

Total cellular lysates for EGFP determination were prepared by resuspending cells in cell lysis buffer (BD Biosciences Pharmingen, San Diego, Calif., USA), lysing cells by incubating for 30 min at 37° C., followed by a freeze-thaw cycle at −80° C. Lysed cells were clarified by centrifugation and the supernatants assayed for EGFP by FLX800 microplate fluorescence reader (Bio-Tek, Winooski, Vt., USA). The results are summarized in Tables 3 and 8.

Groups of five mice were injected with plasmid DNA in an IACUC-approved study. Five micrograms of muSEAP plasmid in 25 or 50 μL of phosphate-buffered saline (PBS) was injected intramuscularly (IM) into a tibialis cranialis muscles of female BALB/c mice or ND4 Swiss Webster mice (8 to 10 weeks old) followed by Ichor TriGrid electroporation. SEAP levels in serum were determined using the Phospha-light SEAP Reporter Gene Assay System from Applied Biosystems (Foster City, Calif.) according to the manufacturer's instructions. The results are summarized below.

The NTC9385C and NTC9385R vectors had similar expression to the NTC8685 vector in vitro, and higher expression than the gWIZ comparator (Table 1). Thus substitution of the R6K or ColE2 replication origin for the pUC origin in the spacer region was not detrimental for eukaryotic cell expression. However, surprisingly, in vivo expression was dramatically improved compared to NTC8685 or gWIZ with the ColE2 and R6K origin vectors (Table 1). For example the NTC9385C vector was unexpectedly improved 1.5 to 3.8× that of NTC8385 or NTC8685 (Table 1) after IM delivery with EP.

This improved in vivo expression was not specific to the CMV promoter. Versions of NTC8685-muSEAP and NTC9385C-muSEAP were constructed in which the murine creatine kinase (MCK) promoter (3 copies of the MCK Enhancer upstream of the MCK promoter and 50 bp of the MCK exon 1 leader sequence; Wang B, Li J, Fu F H, Chen C, Zhu X, Zhou L, Jiang X, Xiao X. 2008. *Gene Ther* 15:1489) was substituted for the CMV promoter. The swaps replaced the entire CMV enhancer CMV promoter-exon 1 leader (NTC8685: from a XbaI site immediately after the SV40 enhancer to a SacII site in the CMV derived exon 1 leader sequence; NTC9385C: from the KpnI site to a SacII site in the CMV derived exon 1 leader sequence) with the MCK enhancer, MCK promoter-exon 1 leader retaining the HTLV-I R portion of exon 1. Purified plasmid DNA from the resultant vectors, NTC8685-MCK-muSEAP (4847 bp) and NTC9385C-MCK-muSEAP (3203 bp), was injected IM into one anterior tibialis muscle of 8-10 week old BALB/c female mice (5 mice/group), 5 μg dose in 50 μL, followed by Ichor TriGrid electroporation as described in Table 1. SEAP levels in serum was determined on day 28 (T=28) post delivery. The NTC9385C-MCK-muSEAP vector (98.4±55.8) had 4.5× higher average expression than NTC8685-MCK-muSEAP (22.0±10.9). All 5 NTC9385C-MCK-muSEAP injected mice had higher muSEAP levels than any of the NTC8685-muSEAP mice. This demonstrates that improved in vivo expression with the Nanoplasmid vectors of the invention is not specific to the CMV promoter.

Example 3: NTC9385P2, NTC9385P2a, NTC9385C2, NTC9385C2a, NTC9385R2, and NTC9385R2a Vector Construction A series of AF eukaryotic expression vectors incorporating intronic AF-pUC origin, AF-R6K origin or AF-ColE2 replication origins are disclosed.

FIG. 2 shows bioinformatics analysis of an intron containing the gWIZ vector bacterial region (GBR2) encoded kanR selection marker-pUC origin. This intron is predicted have reduced splicing efficiency and splicing precision due to the presence of numerous splice acceptor sites, splice donor sites, and eukaryotic promoters in the kanR gene. Replacement of the kanR gene with the RNA-OUT antibiotic-free marker results in an improved intron (FIG. 3) since

TABLE 1 gWIZ, NTC9385C and NTC9385R Nanoplasmid expression compared to NTC8685

| Plasmid | % NTC8685 expression in vitro [a] | % NTC8685 expression T = 7 days BALB/c [b] | % NTC8685 expression T = 7 days ND4 [b] | % NTC8685 expression T = 28 days BALB/c [b] | % NTC8685 expression T = 28 days ND4 [b] |
|---|---|---|---|---|---|
| gWIZ | 58 | 59 | 57 | 21 | 57 |
| NTC8385 | NA | NA | 101 | NA | 101 |
| NTC9385C | 92 | 377 | 349 | 150 | 233 |
| NTC9385R | NA | NA | 154 | NA | 216 |
| Minicircle [c] | NA | 89 | NA | 40 | NA |

[a] 100 ng/well EGFP transgene vectors transfected with lipofectamine into HEK293 cells
[b] murine SEAP (muSEAP) transgene vectors in 8-10 week old BALB/c or ND4 Swiss Webster female mice, 5 μg dose with EP intramuscular into one anterior tibialis muscle followed by Ichor TriGrid electroporation. 25 μL dose for ND4 mice, 50 μL dose for BALB/c.
[c] Minicircle equivalent to NTC9385C or NTC9385R, with NheI-KpnI region containing the replication origin and RNA-OUT selectable marker (bacterial region) removed from NTC8385-muSEAP by SpeI/NheI digestion, gel purification of the eukaryotic region, in vitro ligation and supercoiling with DNA gyrase. The SpeI site is the same site used to truncate the CMV promoter to make NTC8685, NTC9385C and NTC9385R vectors so the minicircle eukaryotic region is the same as NTC9385C-muSEAP and NTC9385R-muSEAP, the difference being the C2 and RNA-OUT region including the KpnI site is deleted in the minicircle.
NA = Not assayed the RNA-OUT sequence is not predicted to contain splice acceptor sites, splice donor sites, or eukaryotic promoters in either orientation.

However, the pUC origin does contain an experimentally verified cryptic eukaryotic promoter (FIG. 3) which likely would interfere with intron function. In addition, the close proximity of the pUC origin to the CMV enhancer repeats in an intronic vector is predicted to result in aberrant replication termination, resulting in replication intermediates which unacceptably reduce plasmid quality (Levy J. 2004. U.S. Pat. No. 6,709,844). So an intronically located pUC origin would be expected to interfere with eukaryotic intron function, and plasmid production quality.

The R6K and ColE2 origins do not contain predicted splice acceptor sites, splice donor sites, or eukaryotic promoters in either orientation. Replacement of the pUC origin with the R6K or ColE2 origins results in a improved intron design since the RNA-OUT-R6K and RNA-OUT-ColE2 bacterial region is not predicted to contain splice acceptor sites, splice donor sites, or eukaryotic promoters in either orientation.

NTC9385P2 and NTC9385P2a pUC Origin Replicative Minicircle Vectors:

NTC8485-EGFP (FIG. 1) disclosed in Williams, Supra, 2010 contains the CMV enhancer and promoter upstream of a chimeric HTLV-IR rabbit β globin intron (SEQ ID NO: 1). The NTC8485-EGFP vector (FIG. 1) was linearized with HpaI which cuts internally within the intron (FIG. 1; SEQ ID NO: 1) leaving a blunt end. The pUC origin-RNA-OUT bacterial region was excised from NTC8385 by digestion with NheI (4 bp protruding 5' sticky end was blunted by end filling using klenow enzyme) and KpnI (4 bp recessed 5' sticky end was blunted by end chewing using T4 DNA polymerase enzyme) (SEQ ID NO: 29). The two fragments were ligated and clones in either orientation (NTC8485P2-O1-EGFP or NTC8485P2-O2-EGFP) identified by restriction mapping and confirmed by DNA sequencing.

The NTC8485 encoded bacterial region and CMV enhancer encoded boundary element (NheI site to SpeI site; FIG. 1) was removed by digestion of NTC8485P2-O1-EGFP and NTC8485P2-O2-EGFP with NheI and SpeI and subsequent ligation (NheI and SpeI have compatible 4 bp sticky ends). Recombinant clones (NTC9385P2-O1-EGFP or NTC9385P2-O2-EGFP respectively) were identified by restriction mapping and confirmed by DNA sequencing.

The NTC8485 encoded bacterial region (NheI site to XbaI site; FIG. 1) was removed by digestion of NTC8485P2-O1-EGFP and NTC8485P2-O2-EGFP with NheI and XbaI and subsequent ligation (NheI and XbaI have compatible 4 bp sticky ends). Recombinant clones (NTC9385P2a-O1-EGFP or NTC9385P2a-O2-EGFP respectively; FIG. 4) were identified by restriction mapping and confirmed by DNA sequencing.

The construction and isolation of these four NTC9385P clones demonstrates that the pUC origin and RNA-OUT selectable marker can both function when located in an intron, in either orientation. Plasmid quality was evaluated by agarose gel analysis of plasmid preps from the four intronic pUC origin-RNA-OUT vectors, and the spacer region encoded pUC-RNA-OUT vector NTC8385. Surprisingly, plasmid quality was high, and no replication intermediates were identified (FIG. 5) despite the close proximity of the pUC origin to the CMV enhancer (Levy, Supra, 2004).

NTC9385R2 and NTC9385R2a Clones:

The NTC8485-EGFP vector (FIG. 1) was linearized with HpaI which cuts internally within the intron (FIG. 1; SEQ ID NO: 1) leaving a blunt end. The R6K origin-RNA-OUT bacterial region was excised from NTC9385R by digestion with NheI (4 bp protruding 5' sticky end was blunted by end filling using klenow enzyme) and KpnI (4 bp recessed 5' sticky end was blunted by end chewing using T4 DNA polymerase enzyme) (SEQ ID NO: 27). The two fragments were ligated and clones in either orientation (NTC8485R2-O1-EGFP or NTC8485R2-O2-EGFP) identified by restriction mapping and confirmed by DNA sequencing.

The NTC8485 encoded bacterial region and CMV enhancer encoded boundary element (NheI site to SpeI site; FIG. 1) was removed by digestion of NTC8485R2-O1-EGFP and NTC8485R2-O2-EGFP with NheI and SpeI and subsequent ligation (NheI and SpeI have compatible 4 bp sticky ends). Recombinant clones (NTC9385R2-O1-EGFP or NTC9385R2-O2-EGFP respectively) were identified by restriction mapping and confirmed by DNA sequencing.

The NTC8485 encoded bacterial region (NheI site to XbaI site; FIG. 1) was removed by digestion of NTC8485R2-O1-EGFP and NTC8485R2-O2-EGFP with NheI and XbaI and subsequent ligation (NheI and XbaI have compatible 4 bp sticky ends). Recombinant clones (NTC9385R2a-O1-EGFP or NTC9385R2a-O2-EGFP respectively; FIG. 6) were identified by restriction mapping and confirmed by DNA sequencing.

The construction and isolation of these four NTC9385R2 derived clones demonstrates that the R6K origin and RNA-OUT selectable marker can both function when located in an intron, in either orientation. Plasmid quality was evaluated by agarose gel analysis of plasmid preps from the four intronic R6K origin-RNA-OUT vectors. Surprisingly, plasmid quality was high, and no replication intermediates were identified (not shown) despite the close proximity of the origin to the CMV enhancer (Levy, Supra, 2004).

NTC9385C2 and NTC9385C2a Clones:

The NTC8485-EGFP vector (FIG. 1) was linearized with HpaI which cuts internally within the intron (FIG. 1; SEQ ID NO: 1) leaving a blunt end. The ColE2 origin-RNA-OUT bacterial region was excised from NTC9385C by digestion with NheI (4 bp protruding 5' sticky end was blunted by end filling using klenow enzyme) and KpnI (4 bp recessed 5' sticky end was blunted by end chewing using T4 DNA polymerase enzyme) (SEQ ID NO: 24). The two fragments were ligated and clones in either orientation (NTC8485C2-O1-EGFP or NTC8485C2-O2-EGFP) identified by restriction mapping and confirmed by DNA sequencing.

The NTC8485 encoded bacterial region and CMV enhancer encoded boundary element (NheI site to SpeI site; FIG. 1) was removed by digestion of NTC8485C2-O1-EGFP and NTC8485C2-O2-EGFP with NheI and SpeI and subsequent ligation (NheI and SpeI have compatible 4 bp sticky ends). Recombinant clones (NTC9385C2-O1-EGFP or NTC9385C2-O2-EGFP respectively) were identified by restriction mapping and confirmed by DNA sequencing.

The NTC8485 encoded bacterial region (NheI site to XbaI site; FIG. 1) was removed by digestion of NTC8485C2-O1-

EGFP and NTC8485C2-O2-EGFP with NheI and XbaI and subsequent ligation (NheI and XbaI have compatible 4 bp sticky ends). Recombinant clones (NTC9385C2a-O1-EGFP or NTC9385C2a-O2-EGFP respectively; FIG. 7) were identified by restriction mapping and confirmed by DNA sequencing.

The construction and isolation of these four NTC9385C clones demonstrates that the ColE2 origin and RNA-OUT selectable marker can both function when located in an intron, in either orientation. Plasmid quality was evaluated by agarose gel analysis of plasmid preps from the four intronic ColE2 origin-RNA-OUT vectors. Surprisingly, plasmid quality was high, and no replication intermediates were identified (not shown) despite the close proximity of the origin to the CMV enhancer (Levy, Supra, 2004).

Summary:

The NTC9385P2, NTC9385P2a, NTC9385C2, NTC9385C2a, NTC9385R2, and NTC9385R2a replicative minicircle vectors are just a few possible nonlimiting intronic bacterial region replicative minicircle vector configurations. Many alternative vector configurations incorporating the novel intronic pUC, R6K or ColE2 origin vector modifications may also be made, including but not limited to vectors with alternative selection markers, alternative promoters, alternative introns, alternative polyadenylation sequences, a spacer region preferably less than 500 bp between the eukaryotic polyadenylation signal and the eukaryotic promoter, a eukaryotic transcription terminator between the eukaryotic polyadenylation signal and the eukaryotic promoter, S/MAR, SIDD sites, boundary elements, multiple transcription units separated by a spacer region, and different orientations of the various vector-encoded elements or alternative R6K or ColE2 origins as described in Example 1.

An example strategy for cloning into the NTC9385R, NTC9385C, NTC9385P2, NTC9385P2a, NTC9385C2, NTC9385C2a, NTC9385R2, and NTC9385R2a etc vectors is outlined below.

```
GTCGACATG--------Gene of interest----Stop codon------AGATCT
SalI                                                 BglII
```

The ATG start codon (double underlined) may be immediately preceded by a unique SalI site (GTCGACATG). This SalI-ATG site is an effective kozak sequence for translational initiation. Alternatively, a kozak sequence-ATG (e.g. gccRccATG) may be included downstream of the SalI site. Alternatively, the SalI site may be downstream in frame with an optimized secretion sequence such as TPA or an alternative peptide leader such as ubiquitin, etc.

For precise cloning, genes are copied by PCR amplification from clones, cDNA, or genomic DNA using primers with SalI (5' end) and BglII (3' end) sites or Type IIS enzymes that create SalI or BglII compatible termini. Alternatively, genes are synthesized chemically to be compatible with the unique SalI/BglII cloning sites in these vectors.

For all vectors one or two stop codons (preferably TAA or TGA) may be included after the open reading frame, prior to the BglII site.

Example 4: NTC9385P2, NTC9385P2a, NTC9385C2, NTC9385C2a, NTC9385R2, and NTC9385R2a Vector Expression To determine intronic replicative minicircle vector eukaryotic region function, transgene expression levels were determined in vitro using the vector encoded EGFP transgene. EGFP mRNA, EGFP protein (EGFP fluorescence) and mRNA splice junctions were determined after plasmid transfection.

Adherent HEK293 (human embryonic kidney) and A549 (human lung carcinoma),cell lines were obtained from the American Type Culture Collection (Manassas, Va., USA). Cell lines were propagated in Dulbecco's modified Eagle's medium/F12 containing 10% fetal bovine serum and split (0.25% trypsin-EDTA) using Invitrogen (Carlsbad, Calif., USA) reagents and conventional methodologies. For transfections, cells were plated on 24-well tissue culture dishes. Plasmids were transfected into cell lines using Lipofectamine 2000 following the manufacturer's instructions (Invitrogen, Carlsbad Calif.).

Total cellular lysates for EGFP determination were prepared by resuspending cells in cell lysis buffer (BD Biosciences Pharmingen, San Diego, Calif., USA), lysing cells by incubating for 30 min at 37° C., followed by a freeze-thaw cycle at −80° C. Lysed cell supernatants were assayed for EGFP by FLX800 microplate fluorescence reader (Bio-Tek, Winooski, Vt., USA).

Cytoplasmic RNA was isolated from transfected HEK293 and A549 cells using the protein and RNA isolation system (PARIS kit, Ambion, Austin Tex.) and quantified by $A_{260}$. Samples were DNase treated (DNA-free DNase; Ambion, Austin Tex.) prior to reverse transcription using the Agpath-ID One step RT-PCR kit (Ambion, Austin Tex.) with the EGFP transgene specific complementary strand primer EGFPR (FIG. 1). Intron splicing was determined by PCR amplification of the reverse transcribed cytoplasmic RNA with the EGFP5Rseq and CMVF5seq primers (FIG. 1). EGFP mRNA levels in the reverse transcribed cytoplasmic RNA were quantified by quantitative PCR using a TaqMan EGFP transgene 6FAM-probe-MGBNFQ probe and flanking primers EGFPR and EGFPF (FIG. 1) in a TaqMan Gene expression assay using Applied Biosystems (Foster City, Calif.) TaqMan reagents and the Step One Real Time PCR System. Methods and primer and probe sequences are described in Luke J M, Vincent J M, Du S X, Gerdemann U, Leen A M, Whalen R G, Hodgson C P, and Williams J A. 2011. *Gene Therapy* 18:334-343 included herein by reference. Linearized vector was used for the RT-PCR standard curve.

The results are summarized in Tables 2-6. In Table 2 EGFP expression in HEK293 and A549 cell lines after transfection with NTC8485-EGFP (spacer region AF-pUC origin) or NTC8485 derivatives further including intronic AF-pUC, AF-ColE2 or AF-R6K origins (also with spacer region AF-pUC origin) is shown. The ColE2 and R6K intronic bacterial regions surprisingly had similar transgene expression levels comparable to the unaltered intron in NTC8485, while expression from the intronic pUC origin was slightly reduced.

TABLE 2

Intron encoded RNA-OUT selection/replication origin does not prevent transgene expression

| NTC8485 Vector (all EGFP) | Construct ID # | NTC8485 vector spacer region [a] | Vector Intron [a] (intron size) | A549 FU (T = 48 mean ± SD) [b] | HEK293 FU (T = 48 mean ± SD) [b] |
|---|---|---|---|---|---|
| NTC8485 | NTC-0200620 | T-BH-P-AF (SV40-BE) | HR-β (225 bp intron) | 5886 ± 249 (1×) | 32628 ± 1015 (1×) |
| NTC8485C2-O1 | 073-030-1H | T-BH-P-AF (SV40-BE) | HR ← C AF → β (499 bp intron) | 3638 ± 351 (0.62×) | 25231 ± 2124 (0.77×) |
| NTC8485C2-O2 | 073-030-1A | T-BH-P-AF (SV40-BE) | HR ← AF C → β (499 bp intron) | 4144 ± 275 (0.70×) | 26233 ± 1842 (0.80×) |
| NTC8485R2-O1 | 073-036-1B | T-BH-P-AF (SV40-BE) | HR ← T-R AF → β (685 bp intron) | 3656 ± 240 (0.62×) | 23905 ± 679 (0.73×) |
| NTC8485R2-O2 | 073-036-1A | T-BH-P-AF (SV40-BE) | HR ← AF R-T → β (685 bp intron) | 4062 ± 249 (0.69×) | 22165 ± 1281 (0.68×) |
| NTC8485P2-O1 | 073-041-2L | T-BH-P-AF (SV40-BE) | HR ← T-P-AF → β (1436 bp intron) | 2565 ± 294 (0.44×) | 20757 ± 1457 (0.64×) |
| NTC8485P2-O2 | 073-041-2E | T-BH-P-AF (SV40-BE) | HR ← AF P-T → β (1436 bp intron) | 2411 ± 320 (0.41×) | 15333 ± 1145 (0.47×) |

[a] trpA term = T; HTLV-IR = HR; B globin 3' acceptor site = β; RNA-OUT selectable marker = AF; PAS-BH = BH; pUC origin = P; R6K origin = R; ColE2 origin = C; CMV boundary element (XbaI-SpeI fragment) = BE; SV40 enhancer = SV40. Bracketed BE and or SV40 are spacer region flanking eukaryotic sequences
[b] Fluorescence units = FU ( ) Mean FU standardized to NTC8485

Conversion of the NTC8485C2, NTC8485R2 and NTC8485P2 (pUC origin-AF spacer region) vectors into replicative minicircles by removal of the pUC origin-AF spacer region to create the corresponding NTC9385C2, NTC9385R2 and NTC9385P2 vectors (Example 3) unexpectedly dramatically increased expression compared to the NTC8485C2, NTC8485R2 and NTC8485P2 parent vectors (Table 3). This demonstrates that the replicative minicircles of the invention unexpectedly improve expression through removal of vector spacer region encoded bacterial region.

TABLE 3

Improved expression with intron encoded RNA-OUT selection/replication origin

| Vector (all EGFP) | Construct ID # | Vector Spacer Region [a] | Vector Intron [a] | A549 FU [b] (T = 48 mean ± SD) | HEK293 FU [b] (T = 48 mean ± SD) |
|---|---|---|---|---|---|
| NTC8485 | NTC-0200620 | T-BH-P-AF (SV40-BE) | HR-β | 5886 ± 249 (1×) | 32628 ± 1015 (1×) |
| NTC9385C | 071-020-2D | C-AF | HR-β | 8591 ± 168 (1.46×) | 35293 ± 1798 (1.08×) |
| NTC8485C2-O1 | 073-030-1H | T-BH-P-AF (SV40-BE) | HR ← C AF → β | 3638 ± 351 (0.62×) | 25231 ± 2124 (0.77×) |
| NTC8485C2-O2 | 073-030-1A | T-BH-P-AF (SV40-BE) | HR ← AF C → β | 4144 ± 275 (0.70×) | 26233 ± 1842 (0.80×) |
| NTC9385C2-O1 | 073-032-5A | None | HR ← C AF → β | 6793 ± 521 (1.15x) | 24762 ± 1498 (0.76×) |
| NTC9385C2-O2 | 073-032-6A | None | HR ← AF C → β | 7330 ± 692 (1.25×) | 24811 ± 1256 (0.76×) |
| NTC9385C2a-O1 | 073-032-7A | None (BE) | HR ← C AF → β | 7515 ± 282 (1.28×) | 29444 ± 2193 (0.90×) |
| NTC9385C2a-O2 | 073-032-8A | None (BE) | HR ← AF C → β | 7255 ± 322 (1.23×) | 27055 ± 1850 (0.83×) |
| NTC9385R | 071-025-2C | T-R-AF | HR-β | 5813 ± 949 (0.99×) | 29822 ± 661 (0.91×) |
| NTC8485R2-O1 | 073-036-1B | T-BH-P-AF (SV40-BE) | HR ← T-R AF → β | 3656 ± 240 (0.62×) | 23905 ± 679 (0.73×) |
| NTC8485R2-O2 | 073-036-1A | T-BH-P-AF (SV40-BE) | HR ← AF R-T → β | 4062 ± 249 (0.69×) | 22165 ± 1281 (0.68×) |
| NTC9385R2-O1 | 073-038-1A | None | HR ← T-R-AF → β | 10959 ± 1278 (1.86×) | 34521 ± 3694 (1.06×) |
| NTC9385R2-O2 | 073-038-2A | None | HR ← AF R-T → β | 10652 ± 567 (1.81×) | 31586 ± 1121 (0.97×) |
| NTC9385R2a-O1 | 073-038-3A | None (BE) | HR ← T-R-AF → β | 10699 ± 674 (1.82×) | 37603 ± 2671 (1.15×) |
| NTC9385R2a-O2 | 073-038-4A | None (BE) | HR ← AF R-T → β | 10251 ± 1343 (1.74×) | 34086 ± 1518 (1.04×) |
| NTC8485P2-O1 | 073-041-2L | T-BH-P-AF (SV40-BE) | HR ← T-P-AF → β | 2565 ± 294 (0.44×) | 20757 ± 1457 (0.64×) |
| NTC8485P2-O2 | 073-041-2E | T-BH-P-AF (SV40-BE) | HR ← AF P-T → β | 2411 ± 320 (0.41×) | 15333 ± 1145 (0.47×) |
| NTC9385P2-O2 | 073-043-1A | None | HR ← AF P-T → β | 5561 ± 497 (0.94×) | 21838 ± 589 (0.67×) |

TABLE 3-continued

Improved expression with intron encoded RNA-OUT selection/replication origin

| Vector (all EGFP) | Construct ID # | Vector Spacer Region [a] | Vector Intron [a] | A549 FU [b] (T = 48 mean ± SD) | HEK293 FU [b] (T = 48 mean ± SD) |
|---|---|---|---|---|---|
| NTC9385P2a-O2 | 073-043-2A | None (BE) | HR ← AF P-T → β | 6291 ± 544 (1.07×) | 23808 ± 2411 (0.73×) |

[a] trpA term = T; HTLV-IR = HR; B globin 3' acceptor site = β; RNA-OUT selectable marker = AF; PAS-BH = BH; pUC origin = P; R6K origin = R; ColE2 origin = C; CMV boundary element (XbaI-SpeI fragment) = BE; SV40 enhancer = SV40. Bracketed BE and or SV40 are spacer region flanking eukaryotic sequences
[b] Fluorescence units = FU ( ) Mean FU standardized to NTC8485

Table 4 demonstrates that mRNA splicing is accurate and spliced mRNA export efficient with the intronic bacterial regions encoded in NTC9385C2, NTC9385R2 and NTC9385P2. A minor amount of a cryptic 209 bp pUC origin derived exon was identified with NTC9385P2-O2 (but not NTC9385P2-O1) in A549 cells but not HEK293 cells (Table 4; 490 bp band). The cryptic exon sequence was determined by sequencing of the PCR product and the cryptic 209 bp exon utilized cryptic splice donor and acceptor sites within the pUC origin (FIG. 3).

TABLE 4

Intron functional analysis - Splicing accuracy and export efficiency

| # | Plasmid | Cell line | EGFP mRNA RT-PCR (pg) | % EGFP mRNA [c] | Predicted spliced exon size (unspliced) | Actual spliced exon size (PCR) |
|---|---|---|---|---|---|---|
| 1 | NTC8685 | HEK293 | 448.3 ± 38.7 | 0.74% | 279 (514) | 279 [a] |
| 2 | NTC9385C2-O1 | HEK293 | 274.6 ± 10.3 | 0.44% | 279 (788) | 279 [a] |
| 3 | NTC9385C2-O2 | HEK293 | 227.4 ± 4.9 | 0.41% | 279 (788) | 279 [a] |
| 4 | NTC9385R2-O1 | HEK293 | 398.9 ± 14.8 | 0.64% | 279 (974) | 279 [a] |
| 5 | NTC9385R2-O2 | HEK293 | 350.7 ± 5.2 | 0.57% | 279 (974) | 279 [a] |
| 6 | NTC9385P2-O2 | HEK293 | 181.6 ± 5.5 | 0.30% | 279 (974) | 279 [a] |
| 7 | NTC8485P2-O1 | HEK293 | 160.1 ± 12.3 | 0.27% | 279 (1715) | 279 [a] |
| 8 | NTC8685 | A549 | 50.6 ± 4.3 | 0.128% | 279 (514) | 279 [a] |
| 9 | NTC9385C2-O1 | A549 | 29.2 ± 1.2 | 0.082% | 279 (788) | 279 |
| 10 | NTC9385C2-O2 | A549 | 23.9 ± 1.4 | 0.074% | 279 (788) | 279 |
| 11 | NTC9385R2-O1 | A549 | 41.9 ± 1.6 | 0.116% | 279 (974) | 279 |
| 12 | NTC9385R2-O2 | A549 | 35.8 ± 2.2 | 0.096% | 279 (974) | 279 [a] |
| 13 | NTC9385P2-O2 | A549 | 17.4 ± 0.6 | 0.050% | 279 (1715) | 279 [b] |
| 14 | NTC8485P2-O1 | A549 | 7.0 ± 0.2 | 0.024% | 279 (1715) | 279 |

[a] Correct splice junction verified by DNA sequencing of PCR product
[b] Faint extra bands at 490 and 650 bp, not present in 6 (HEK293 equivalent) or other samples
[c] % of total cytoplasmic RNA that is EGFP mRNA Table 5 further demonstrates unexpectedly robust expression is observed with all NTC9385C2, NTC9385R2 and NTC9385P2 replicative minicircle vectors (both orientations, with and without CMV boundary region). Overall, the highest expression is obtained with the R6K replicative minicircle vectors (NTC9385R2-O1; NTC9385R2-O2; NTC9385R2a-O1; NTC9385R2a-O2).

TABLE 5

Intron vector expression efficiency

| # | Vector (all EGFP) | Construct ID # | Vector Spacer Region [a] | Vector Intron [a] | A549 FU (T = 48 mean ± SD) [b] | HEK293 FU (T = 48 mean ± SD) [b] |
|---|---|---|---|---|---|---|
| 1 | NTC9385C2-O1 | 073-032-5A | None | HR ← C AF → β | 7581 ± 1145 | 20868 ± 9153 |
| 2 | NTC9385C2-O2 | 073-032-6A | None | HR ← AF C → β | 6012 ± 503 | 12902 ± 2356 |
| 3 | NTC9385C2a-O1 | 073-032-7A | (BE) | HR ← C AF → β | 6018 ± 979 | 13564 ± 799 |
| 4 | NTC9385C2a-O2 | 073-032-8A | (BE) | HR ← AF C → β | 6633 ± 136 | 16119 ± 729 |
| 5 | NTC9385R2-O1 | 073-038-1A | None | HR ← T-R AF → β | 9626 ± 304 | 18627 ± 999 |
| 6 | NTC9385R2-O2 | 073-038-2A | None | HR ← AF R-T → β | 8513 ± 235 | 12660 ± 348 |
| 7 | NTC9385R2a-O1 | 073-038-3A | (BE) | HR ← T-R AF → β | 8295 ± 188 | 15601 ± 2550 |
| 8 | NTC9385R2a-O2 | 073-038-4A | (BE) | HR ← AF R-T → β | 8724 ± 188 | 19219 ± 1763 |
| 9 | NTC9385P2-O1 | 073-126-1A | None | HR ← T-P-AF → β | 6086 ± 704 | 16967 ± 2237 |
| 10 | NTC9385P2-O2 | 073-043-1A | None | HR ← AF P-T → β | 4941 ± 283 | 11604 ± 2580 |

TABLE 5-continued

Intron vector expression efficiency

| Vector # (all EGFP) | Construct ID # | Vector Spacer Region [a] | Vector Intron [a] | A549 FU (T = 48 mean ± SD) [b] | HEK293 FU (T = 48 mean ± SD) [b] |
|---|---|---|---|---|---|
| 11 NTC9385P2a-O1 | 073-126-2A | (BE) | HR ← T-P-AF → β | 5277 ± 114 | 13073 ± 1779 |
| 12 NTC9385P2a-O2 | 073-043-2A | (BE) | HR ← AF P-T → β | 5122 ± 608 | 11182 ± 870 |

[a] trpA term = T; HTLV-IR = HR; B globin 3' acceptor site = β; RNA-OUT selectable marker = AF; pUC origin = P; R6K origin = R; ColE2 origin = C; CMV boundary element (XbaI-SpeI fragment) = BE. Bracketed BE is spacer region flanking eukaryotic sequences
[b] Fluorescence units = FU Table 6 demonstrates in vivo expression after intradermal delivery with the intronic bacterial region vectors of the invention was improved compared to an optimized plasmid comparator (NTC8685). NTC9385R2a-O2 expression was surprisingly improved 1.9-4.1 fold compared to NTC8685 while NTC9385P2a-O1 was unexpectedly improved 5.0-8.0 fold. NTC9385R2-O2 expression was also improved (1.3-1.5 fold compared to NTC8685) but less than NTC9385R2a- using growth factors such as hypoxia inducible factor, hypoxia inducible factor 1α, keratinocyte growth factor, vascular endothelial growth factor (VEGF), fibroblast growth factor-1 (FGF-1, or acidic FGF), FGF-2 (also known as basic FGF), FGF-4, placental growth factor (P1GF), angiotensin-1 (Ang-1), hepatic growth factor (HGF), Developmentally Regulated Endothelial Locus (Del-1), stromal cell derived factor-1 (SDF-1), etc.

TABLE 6

Replicative minicircle vector expression in vitro (lipofectamine) and in vivo (intradermal delivery with electroporation)

| muSEAP Vector [b] | SR [a] | SR (bp) | Intron [a] | A549 ($A_{405}$) [d] | HEK-293 ($A_{405}$) [d] | ID + EP [c] (pg/mL) T = 4 day mean ± SD | ID + EP [c] (pg/mL) T = 7 day mean ± SD | ID + EP [c] (pg/mL) T = 14 day mean ± SD |
|---|---|---|---|---|---|---|---|---|
| NTC8685 | T-VA1-BH-P-AF (SV40) | 1695 | HR-β | 0.240 ± 0.029 (1.0×) | 3.002 ± 0.188 (1.0×) | 1.9 ± 1.2 (1.0×) | 6.7 ± 4.1 (1.0×) | 5.0 ± 3.9 (1.0×) |
| NTC9385 P2a-O1 | None (BE) | 0 | HR T ← P AF → -β | 0.467 ± 0.047 (2.0×) | 2.890 ± 0.085 (1.0×) | 9.5 ± 6.2 (5.0×) | 53.4 ± 51.5 (8.0×) | 34.8 ± 29.6 (7.0×) |
| NTC9385 R2a-O2 | None (BE) | 0 | HR ← AF R → T-β | 0.409 ± 0.039 (1.7×) | 2.561 ± 0.038 (0.9×) | 6.5 ± 6.1 (3.4×) | 27.6 ± 25.9 (4.1×) | 9.5 ± 11.2 (1.9×) |
| NTC9385 R2-O2 | None | 0 | HR ← AF R → T-β | 0.564 ± 0.008 (2.4×) | 2.999 ± 0.106 (1.0×) | 2.8 ± 3.8 (1.5×) | 8.8 ± 15.7 (1.3×) | 7.0 ± 8.5 (1.4×) |

[a] Prokaryotic terminator = T; HTLV-IR = HR; B globin 3' acceptor site = β; RNA-OUT = AF; pUC origin = P; R6Kγ origin = R; ColE2-P9 origin = C; CMV boundary element (XbaI-SpeI fragment) = BE; SV40 enhancer = SV40; PAS-BH = BH. Bracketed BE or SV40 are spacer region flanking eukaryotic sequences
[b] P vectors produced in dcm- XL1B1ue NTC54208; R vectors produced in dcm- R6K Rep cell line NTC711231; C vectors produced in dcm- ColE2 Rep cell line NTC710351
[c] Dose = 50 μg in 50 μL saline injected intradermally (ID) with EP. 6 mice/group. Mean ± SD pg/mL muSEAP on indicated day post EP reported. ( ) Mean muSEAP standardized to NTC8685
[d] muSEAP plasmid DNA transfected with Lipofectamine 2000. Mean ± SD 48 hr post transfection $A_{405}$ reported. ( ) Mean $A_{405}$ standardized to NTC8685

O2 suggesting that the CMV promoter derived boundary element adjacent to the spacer region is beneficial. Replicative minicircle expression is surprisingly much higher relative to plasmid comparator in vivo compared to in vitro (Table 6). While not limiting the application of the invention, this may be an unexpected benefit of removal of the large spacer region encoded replication origin and selectable marker, perhaps through rapid spacer region directed heterochromatin formation that is more prevalent in vivo than in vitro.

The improved transgene expression level after intradermal delivery demonstrates the application of Nanoplasmid and replicative minicircle vectors of the invention for cutaneous DNA vaccination and gene therapy applications. For example, for intradermal DNA vaccination, epidermal DNA vaccination, or transcutaneous DNA vaccination using a variety of antigens. For example, for gene therapy applications such as wound healing, burns, diabetic foot ulcer, critical limb ischemia therapies, or cosmetic treatment for different dermatological conditions, including anti-aging (anti-wrinkle), scar revision, radiation induced lesions, hair growth, surgical skin graft enhancement, or hemangioma, Reduction of the vector spacer region size as described herein by removal of the bacterial region replication origin and addition of an intronic R6K, ColE2, pUC or $P_{min}$ pUC origin vectors of the invention will also increase the duration of in vivo expression since expression duration is improved with plasmid vectors in which the bacterial region is removed (minicircle) or replaced with a spacer region of up to at least 500 bp (Lu et al., Supra, 2012). Thus the replicative minicircle vectors of the invention also have additional utility for applications requiring extended duration expression, such as: liver gene therapy using hydrodynamic delivery with transgenes such as α-1 antitrypsin (AAT) for AAT deficiency, Coagulation Factor VIII for Hemophilia A Therapy or Coagulation Factor IX for Hemophilia B Therapy etc: lung gene therapy with transgenes such as Cystic fibrosis transmembrane conductance regulator (CFTR) for cystic fibrosis etc; muscle gene therapy with transgenes such as the GNE gene for Hereditary inclusion body myopathies (HIBM), or dystrophin or dystrophin minigenes for duchenne muscular dystrophy (DMD), etc.

The intronic replicative minicircles of the invention spacer region between the 5' and 3' ends of the eukaryotic region may optionally encode up to 500 bp of sequence. This spacer region may include a number of functional sequences such as bacterial or eukaryotic selectable markers, bacterial or eukaryotic replication origins, bacterial transcription terminators, eukaryotic transcription terminators, supercoiling-induced DNA duplex destabilized (SIDD) structures, boundary elements, S/MARs, RNA Pol I or RNA Pol III expressed sequences or other functionalities.

Example 5: Replicative Minicircle Vector Fermentation Production

Fermentation:

Fermentations were performed using proprietary fed-batch media (NTC3019, HyperGRO media) in New Brunswick BioFlo 110 bioreactors as described (Carnes and Williams, Supra, 2011). The seed cultures were started from glycerol stocks or colonies and streaked onto LB medium agar plates containing 6% sucrose. The plates were grown at 30-32° C.; cells were resuspended in media, and used to provide approximately 0.1% inoculums for the fermentations that contained 0.5% sucrose to select for RNA-OUT plasmids.

Production Hosts:

Antibiotic-free pUC origin RNA-OUT plasmid fermentations were performed in *E. coli* strain XL1Blue [recA1 endA1 gyrA96 thi-1 hsdR17 supE44 relA1 lac [F′ proAB lacIqZΔM15 Tn10 (Tet')] (Stratagene, La Jolla, Calif.)] dcm or DH5α [F-Φ80lacZΔM15 Δ(lacZYA-argF) U169 recA1 endA1 hsdR17 (rK−, mK+) phoA supE44 λ-thi-1 gyrA96 relA1] (Invitrogen, Carlsbad Calif.) dcm containing chromosomally integrated pCAH63-CAT RNA-IN-SacB (P5/6 6/6) as disclosed in Williams, Supra, 2008. SacB (*Bacillus subtilis* levansucrase) is a counterselectable marker which is lethal to *E. coli* cells in the presence of sucrose. Translation of SacB from the RNA-IN-SacB transcript is inhibited by plasmid encoded RNA-OUT. This facilitates plasmid selection in the presence of sucrose, by inhibition of SacB mediated lethality. These production strains are NTC54208=XL1Blue dcm attλ::P5/6 6/6-RNA-IN-SacB and NTC48165=DH5α dcm attλ::P5/6 6/6-RNA-IN-SacB Antibiotic-free R6K plasmid propagation and fermentations were performed using pL promoter heat inducible 'P42L, P106L and F107S' or 'P42L, P113S' π copy number mutant cell line lines, the creation of which is disclosed in patent application PCT/US 13/00068 (Filing No. 61/743,219) entitled 'DNA plasmids with improved expression' and included herein by reference. NTC711231 is NTC54208-pR pL (OL1-G to T) P42L-P106L-F107S (P3-). NTC54208=XL1Blue dcm attλ::P5/6 6/6-RNA-IN-SacB. NTC731871=NTC54208-pR pL (OL1-G to T) P42L-P113S (P3-). NTC711772=NTC48165-pR pL (OL1-G to T) P42L-P106L-F107S (P3-). NTC48165=DH5α dcm attλ::P5/6 6/6-RNA-IN-SacB.

Antibiotic-free ColE2 plasmid propagation and fermentations were performed using pL promoter heat inducible 'G194D' Rep protein copy number mutant cell line NTC710351 the creation of which is disclosed in patent application PCT/US 13/00068 (Filing No. 61/743,219) entitled 'DNA plasmids with improved expression' and included herein by reference. NTC710351=NTC54208-pR pL (OL1-G to T) ColE2 Rep G194D Analytical Methods:

Culture samples were taken at key points and at regular intervals during all fermentations. Samples were analyzed immediately for biomass ($OD_{600}$) and for plasmid yield. Plasmid yield was determined by quantification of plasmid obtained from Qiagen Spin Miniprep Kit preparations as described (Carnes and Williams, Supra, 2011). Briefly, cells were alkaline lysed, clarified, plasmid was column purified, and eluted prior to quantification. Agarose gel electrophoresis analysis (AGE) was performed on 0.8-1% Tris/acetate/EDTA (TAE) gels as described in Carnes and Williams, Supra, 2011.

Results:

Fermentation yields are summarized in Table 7. The results demonstrated that the replicative minicircle vectors of the invention have efficient manufacture. Manufacture was effective with ColE2, R6K and pUC replicative minicircles with yield of 184-745 mg/L, up to >100 fold improved compared to reported yields of 5 mg/L with alternative short spacer region minicircle vectors (Kay et al., Supra, 2010). Additionally, the replicative minicircle vectors of the invention do not require the complicated difficult to scale expensive additional manufacturing steps required to remove the large bacterial region between the eukaryotic polyA and promoter with minicircle vectors (Kay et al., Supra, 2010) since replicative minicircles have less than 500 bp between the eukaryotic polyA and the promoter which does not need to be removed.

TABLE 7

Intronic RNA-OUT AF selection plasmid fermentation yields [a]

| Plasmid | Plasmid size (kb) | Origin/ host strain | Vector type [f] | Growth phase Specific yield (mg/L/ OD600) | Production phase final Specific yield (mg/ L/OD$_{600}$) | Production phase final biomass (OD$_{600}$) | Production phase final yield (mg/L) [e] |
|---|---|---|---|---|---|---|---|
| NTC9385R-EGFP | 2.4 | R6K [b] | SR | 1.4-1.5 | 4.4 | 89 | 392 |
| NTC9385R-L-CF | 3.4 | R6K [b] | SR | 2.2-2.4 | 8.5 | 72 | 615 |
| NTC9385R-L-CF | 3.4 | DR6K [b] | SR | 2.3-2.6 | 7.8 | 98 | 745 |
| NTC9385R2-O1-EGFP | 2.4 | R6K [b] | Intron | 1.4-1.5 | 6.3 | 66 | 414 |
| NTC9385R2-O2-EGFP | 2.4 | R6K [b] | Intron | 1.1-1.8 | 3.8 | 70 | 269 |
| NTC9385R2-O2-EGFP | 2.4 | DR6K [b] | Intron | 1.4 | 4.1 | 93 | 376 |
| NTC9385R2a-O1-EGFP | 2.5 | R6K [b] | Intron | 1.7-1.9 | 4.8 | 74 | 356 |
| NTC9385R2a-O2-EGFP | 2.5 | R6K [b] | Intron | 1.0-1.8 | 3.5 | 69 | 244 |
| NTC9385R2b-O2-EGFP | 2.4 | R6K [b] | Intron (AF-SR) | 2.6-3.0 | 7.2 | 61 | 440 |
| NTC9385Ra-O1-EGFP | 2.4 | R6K [b] | SR (AF-intron) | 2.8-3.4 | 7.0 | 49 | 340 |
| NTC9385Ra-O1-EGFP | 2.4 | DR6K [b] | SR (AF-intron) | 1.9-2.2 | 6.3 | 99 | 623 |

TABLE 7-continued

Intronic RNA-OUT AF selection plasmid fermentation yields [a]

| Plasmid | Plasmid size (kb) | Origin/ host strain | Vector type [f] | Growth phase Specific yield (mg/L/ OD600) | Production phase final Specific yield (mg/ L/OD$_{600}$) | Production phase final biomass (OD$_{600}$) | Production phase final yield (mg/L) [e] |
|---|---|---|---|---|---|---|---|
| NTC9385Ra-O2-EGFP | 2.4 | R6K [b] | SR (AF-intron) | 1.2-1.7 | 4.6 | 40 | 184 |
| NTC9385RbF-EGFP | 2.5 | R6K [b] | 3' UTR (AF-intron) | 2.9 | 4.5 | 56 | 258 |
| NTC9385RbF-EGFP | 2.5 | DR6K [b] | 3' UTR (AF-intron) | 2.0-2.4 | 4.2 | 99 | 420 |
| NTC9385C-EGFP | 2.2 | ColE2 [c] | SR | 0.6-1.0 | 5.8 | 115 | 672 |
| NTC9385C2a-O1-EGFP | 2.3 | ColE2 [c] | Intron | 0.8-1.1 | 3.7 | 87 | 323 |
| NTC9385C2a-O2-EGFP | 2.3 | ColE2 [c] | Intron | 0.8-1.0 | 3.7 | 64 | 235 |
| NTC9385P2a-O1-EGFP | 3.2 | pUC [d] | Intron | 1.2-1.3 | 8.6 | 82 | 703 |
| NTC9385P2a(0.85)-O1-EGFP | 2.9 | P$_{min}$ [d] | Intron | 0.9-1.0 | 5.6 | 84 | 468 |
| NTC9385P2a(0.85)-O2-EGFP | 2.9 | P$_{min}$ [d] | Intron | 0.8-1.05 | 5.7 | 77 | 439 |
| NTC8385(0.85)-EGFP | 2.8 | P$_{min}$ [d] | SR | 0.9 | 6.4 | 105 | 667 |

[a] 30° C. growth phase to 50-60 OD600. Plasmid copy number then induced by temperature shift to 42° C. and subsequent 7-10.5 hr growth post induction (production phase)
[b] R6K plasmid produced in: R6K = cell line NTC711231 = NTC54208-pR pL (OL1-G to T) P42L-P106L-F107S (P3-). NTC54208 = XL1Blue dcm attλ::P5/6 6/6-RNA-IN- SacB. DR6K = NTC711772 = NTC48165-pR pL (OL1-G to T) P42L-P106L-F107S (P3-). NTC48165 = DH5α dcm attλ::P5/6 6/6-RNA-IN- SacB.
[c] ColE2 plasmid produced in cell line NTC710351 = NTC54208-pR pL (OL1-G to T) ColE2 Rep G194D
[d] pUC and P$_{min}$ plasmid produced in cell line NTC54208 = XL1Blue dcm attλ::P5/6 6/6-RNA-IN- SacB
[e] By comparison, minicircle manufacturing final volumetric yield are 5 mg/L (Kay et al., Supra, 2010)
[f] SR = Replication origin and selectable marker in spacer region. Intron = Replication origin and selectable marker in intron. NTC9385R2b has RNA-OUT in SR and R6K origin in intron. NTC9385Ra has RNA-OUT in SR and R6K origin in SR. NTC9385RbF has R6K in 3' UTR and RNA-OUT in SR.

As well, fermentation plasmid DNA was high quality with ColE2, R6K and pUC replicative minicircles. A comparison of plasmid production with the 4 R6K intronic selection vectors (NTC9385R2-O1-EGFP; NTC9385R2-O2-EGFP; NTC9385R2a-O1-EGFP; NTC9385R2a-O2-EGFP) versus a standard R6K spacer region vector NTC9385R-EGFP demonstrated no differences in yield (Table 7) or quality (FIG. 8).

Example 6: High Level Expression with Replicative Minicircle Vectors Modified to Include an RNA Selectable Marker or a Eukaryotic Transcriptional Terminator in the Spacer Region Minicircle vectors contain a spacer region between the eukaryotic region polyA and promoter sequences; this spacer region may be at least 500 bp (Lu et al., Supra, 2012). To determine if the spacer region may encode a selectable marker, bacterial transcription terminator, eukaryotic transcription terminator or other functionality, replicative minicircle vectors were created that included either a RNA-OUT selectable marker or a Gastrin eukaryotic terminator. FIG. 9 shows NTC9385R2b-O2-EGFP, an example intronic R6K origin replicative minicircle vector in which the RNA-OUT RNA selectable marker is located in the spacer region between the eukaryotic polyA and the eukaryotic promoter rather than within the intron. The vector has a 148 bp spacer region, well below 500 bp. The vector was transfected into HEK293 and A549 cell lines, and EGFP expression and splicing were analyzed as described in Example 4. High level expression (Table 8) and accurate splicing (Table 9) were observed with this vector. This vector could be further modified to replace RNA-OUT with a different RNA selectable marker, such as pMB1 RNAI, ColE2 RNAI, IncB RNAI, RSM, etc.

Improved transgene expression was observed when the gastrin eukaryotic transcription terminator was inserted into the spacer region (NTC9385R2a-O2-Gt versus NTC9385R2a-O2; Table 8). Collectively, these results demonstrate additional functionalities may be added to the spacer region without interfering with replicative minicircle performance Additional sequences that may be added to the spacer include bacterial selectable markers (e.g. RNA-OUT or RNAI or alternative RNA selectable markers; see Examples 7 and 9), eukaryotic selectable markers, bacterial transcription terminators, eukaryotic transcription terminators (e.g. gastrin terminator), boundary elements, supercoiling-induced DNA duplex destabilized (SIDD) structures, S/MARs, RNA Pol I or RNA Pol III expressed sequences or other functionalities. As well, additional sequences could be encoded within the intron, such as SIDD structures, RNA Pol III transcription units expressing short hairpin RNA's or immunostimulatory RNAs such as those disclosed in Williams, Supra, 2008, included herein by reference.

Example 7: RNAI Regulated Vectors

Alternative RNA selectable markers known in the art may be utilized in replicative minicircle vectors. For example, RNA-OUT (RNA-IN regulated chromosomal selection marker) may be replaced with the pMB1 plasmid origin encoded RNAI (RNAII regulated chromosomal selection marker Grabherr and, Pfaffenzeller Supra, 2006; Cranenburgh, Supra, 2009), plasmid pMU720 origin encoded RNAI (SEQ ID NO: 35) that represses RNA II regulated targets (Wilson et al., Supra, 1997), plasmid R1ParB locus Sok (Hok regulated chromosomal selection marker; Morsey, Supra, 1999), F plasmid Flm locus FlmB (flmA regulated chromosomal selection marker; Morsey, Supra, 1999) or other RNA selectable markers described in the art. The use of alternative RNA selectable markers to construct replicative minicircles was demonstrated here by substitution of RNA-OUT with the pMB1 plasmid origin encoded RNAI and assessing expression and splicing accuracy.

RNAI is present within the intron of the NTC9385P2 and NTC9385P2a vectors (FIG. 3; FIG. 4) and NTC9385P2 (0.85) and NTC9385P2a(0.85) vectors (Example 8). The observed accurate splicing (Table 4) and robust expression (Table 5) of NTC9385P2 clones with RNAI in either orientation demonstrated that intronic pMB1 plasmid origin encoded RNAI expression is compatible with replicative minicircle function. The increased in vivo expression observed with NTC9385P2a-O1-muSEAP (Table 6) further demonstrates that intronic pMB1 plasmid origin encoded RNAI expression is compatible with replicative minicircle function. The observed accurate splicing (Table 9) and robust expression (Table 11) of NTC9385P2(0.85) clones with RNAI in either orientation demonstrated that intronic pMB1 plasmid origin encoded RNAI expression is compatible with replicative minicircle function (see Example 10).

Nanoplasmid variants with the pMB1 antisense RNA RNAI (SEQ ID NO:33) with promoter and terminator region (RNAI selectable marker: SEQ ID NO:34 flanked by DraIII-KpnI restriction sites for cloning as described previously for RNA-OUT) substituted for RNA-OUT were constructed as described in Example 3 and tested for expression to determine if alternative selectable markers may be utilized in place of RNA-OUT. The results (Table 8) demonstrate alternative RNA selectable markers may be substituted for RNA-OUT. Substitution of RNAI for RNA-OUT in the vector spacer region (NTC9385Ra-RNAI-O1) or in the intron in either orientation (NTC9385R-RNAI-O1 and NTC9385R-RNAI-O2) did not reduce expression relative to the corresponding RNA-OUT construct. To determine splicing accuracy, NTC9385R-RNAI-O1-EGFP and NTC9385R-RNAI-O2-EGFP were transfected into the A549 cell line and cytoplasmic RNA isolated from transfected A549 cells using the protein and RNA isolation system (PARIS kit, Ambion, Austin Tex.) and quantified by $A_{260}$. Samples were DNase treated (DNA-free DNase; Ambion, Austin Tex.) prior to reverse transcription using the Agpath-ID One step RT-PCR kit (Ambion, Austin Tex.) with the EGFP transgene specific complementary strand primer EGFPR (FIG. 1). Intron splicing was determined by PCR amplification of the reverse transcribed cytoplasmic RNA with the EGFP5Rseq and CMVF5seq primers (FIG. 1). The resultant PCR product (a single band in each case) was determined by sequencing to be the correct spliced exon1-exon2 fragment (Table 9). This demonstrated that, like intronic RNA-OUT, intronic RNAI in either orientation is accurately removed by splicing and does not interfere with splicing accuracy. This further demonstrates that alternative RNA based selectable markers may be substituted for RNA-OUT in the spacer region or the intron and that pMB1 RNAI is a preferred RNA based selectable marker for replicative minicircle vectors.

Alternatively, the 108 bp RNAI antisense repressor RNA (SEQ ID NO: 33) may be substituted for the 70 bp RNA-OUT antisense repressor RNA (SEQ ID NO: 21) retaining the flanking RNA-OUT transcription control sequences in any of the constructs described in Examples 2-11. RNAI regulated replicative minicircle vectors may be grown in RNAII-SacB regulated cell lines further expressing, as required, R6K, ColE2-P9, or ColE2 related Rep protein. RNAII-SacB regulated cell lines may be made replacing the RNA-IN sequence in pCAH63-CAT RNA-IN-SacB (P5/6 6/6) with a RNAII target sequence as described in Williams, Supra, 2008 included herein by reference. Alternatively, RNAI regulated replicative minicircle vectors may be grown in any of the RNAII regulated chromosomal selection marker cell lines disclosed in Grabherr and Pfaffenzeller, Supra, 2006 and Cranenburgh, Supra, 2009. These cell lines would be modified for expression, as required, of R6K, ColE2-P9, or ColE2 related Rep protein.

TABLE 8

High level expression with vectors with pMB1 RNAI encoded in the spacer region or intron

| Vector (all EGFP) | Spacer region [a] | SR [d] (bp) | Intron [a] | A549 FU[c] (T = 48 mean + SD) | HEK293 FU[c] (T = 48 mean + SD) |
|---|---|---|---|---|---|
| NTC8685 | T-VA1 BH-P-AF (SV40) | 1465 | HR-β [b] | 8546 ± 1163 (1.00×) | 62068 ± 1760 (1.00×) |
| NTC8385 (0.85 kb) [e] | T-P$_{min}$-AF | 866 | HR-β [b] | 9364 ± 966 (1.10×) | 31482 ± 1822 (0.51×) |
| NTC9385C | ← C-AF → | 281 | HR-β [b] | 8860 ± 382 (1.04×) | 33356 ± 1489 (0.54×) |
| NTC9385R | ← T-R-AF → | 466 | HR-β [b] | 16237 ± 2520 (1.90×) | 55919 ± 6371 (0.90×) |
| NTC9385Ra-O2 | ← T-R | 306 | HR- ← AF-β | 14510 ± 835 (1.70×) | 49526 ± 2179 (0.80×) |
| NTC9385R2-O2 | None | 0 | HR ← AF R-T → -β | 15394 ± 683 (1.80×) | 30995 ± 4487 (0.50×) |
| NTC9385R2a-O2 | (BE) | 0 | HR ← AF R-T → -β | 11383 ± 253 (1.33×) | 36382 ± 1086 (0.59×) |
| NTC9385R2a-O2-Gt | TT-(BE) | 73 | HR ← AF R-T → -β | 15076 ± 321 (1.76×) | 49289 ± 2672 (0.79×) |
| NTC9385R2b-O2 | AF→ | 148 | HR ← R-T → -β | 10721 ± 1039 (1.25×) | 42507 ± 5321 (0.68×) |
| NTC9385Ra-O1 dual | ← T-R-AF → | 466 | HR-AF → -β | 13929 ± 1291 (1.63×) | 56552 ± 2714 (0.91×) |
| NTC9385Ra-O2 dual | ← T-R-AF → | 466 | HR- ← AF-β | 12543 ± 245 (1.47×) | 54379 ± 1244 (0.89×) |
| NTC9385Ra-RNAI-O1 | ← T-R-RNAI → | 488 | HR-AF → -β | 15773 ± 238 (1.85×) | 55468 ± 6619 (0.89×) |
| NTC9385R-RNAI-O1 | ← T-R-AF → | 466 | HR- ← RNAI-β | 14296 ± 287 (1.67×) | 60630 ± 2176 (0.98×) |

TABLE 8-continued

High level expression with vectors with pMB1 RNAI encoded in the spacer region or intron

| Vector (all EGFP) | Spacer region [a] | SR [d] (bp) | Intron [a] | A549 FU[c] (T = 48 mean + SD) | HEK293 FU[c] (T = 48 mean + SD) |
|---|---|---|---|---|---|
| NTC9385R-RNAI-O2 | ← T-R-AF → | 466 | HR-RNAI → -β | 12271 ± 466 (1.44×) | 60691 ± 6482 (0.98×) |

[a] trpA term = T; Gastrin (Gt) eukaryotic terminator = TT; HTLV-IR = HR; B globin 3' acceptor site = β; RNA-OUT selectable marker = AF; pUC origin RNAI antisense RNA selectable marker = RNAI; pUC origin = P; R6K origin = R; ColE2 origin = C; CMV boundary element = BE; PAS-BH = BH; SV40 enhancer = SV40. Bracketed BE or SV40 are spacer region flanking eukaryotic sequences
[b] HR β intron is 225 bp
[c] EGFP plasmid DNA transfected with Lipofectamine 2000. Mean ± SD Fluorescence units (FU) at 48 hrs post transfection reported. ( ) Mean FU standardized to NTC8685
[d] Spacer Region (SR) size (bp) is total bp of components between polyA and CMV or SV40 enhancer, and does not include the SV40 enhancer or BE.
[e] $P_{min}$ minimal pUC origin (SEQ ID NO: 45) and RNA-OUT (bacterial region = SEQ ID NO: 46)

TABLE 9

Accurate splicing with replicative minicircle vectors with pMB1 RNAI and minimal pUC origin encoded in the intron

| Plasmid | Cell line | EGFP RT-PCR (pg) | % EGFP mRNA | Predicted spliced exon size (unspliced) | Actual spliced exon size (PCR) |
|---|---|---|---|---|---|
| NTC9385R | A549 | 87.5 ± 3.8 | 0.260% | 279 (514) | 279 [c] |
| NTC9385R-RNAI-O1 | A549 | 45.9 ± 3.0 | 0.142% | 279 (667) | 279 [c] |
| NTC9385R-RNAI-O2 | A549 | 43.1 ± 2.1 | 0.121% | 279 (667) | 279 [c] |
| NTC9385R2-O2 | A549 | 26.8 ± 2.2 | 0.094% | 279 (974) | 279 [c] |
| NTC9385Ra-O2 | A549 | 60.2 ± 6.1 | 0.198% | 279 (648) | 279 [c] |
| NTC9385R2b-O2 | A549 | 42.1 ± 1.2 | 0.148% | 279 (819) | 279 [c] |
| NTC9385P2a-O1 | A549 | 15.8 ± 1.3 | 0.054% | 279 (1715) | 279 [c] |
| NTC9385P2a-O2 | A549 | 11.6 ± 0.2 | 0.037% | 279 (1715) | 279 [a] |
| NTC9385P2a (0.85)-O1 | A549 | 20.1 ± 1.6 | 0.085% | 279 (1366) | 279 [c] |
| NTC9385P2a (0.85)-O2 | A549 | 6.7 ± 0.5 | 0.027% | 279 (1366) | 279 [b] |
| NTC9385C-C2x4-muSEAP (negative control) | A549 | 0.003 | 0.000 | No band | No band |

[a] Faint extra bands at 490 and 650 bp (previously observed with transfection of NTC9385P2a-O2 into A549; (see Table 4). Correct splice junction verified by DNA sequencing of PCR product. Faint band at 490 bp corresponds to mRNA with an additional pUC derived exon (see FIG. 3)
[b] Very faint extra bands at 490 and 650 bp. Correct splice junction verified by DNA sequencing of PCR product. Faint band at 490 corresponds to mRNA with an additional pUC derived exon (see FIG. 3)
[c] Correct splice junction verified by DNA sequencing of PCR product Example 8: Spacer Region and Intron Modified Nanoplasmid Vectors NTC8685 (SR=1465 bp) has much lower in vivo expression than NTC9385R (SR=466 bp) and NTC9385C (SR=281 bp) (Table 1). A minimal pUC origin vector was constructed with an 866 bp spacer region (NTC8385-Min; contains $P_{min}$ minimal pUC origin-RNA-OUT). These vectors were tested for expression in vitro (lipofectamine 2000 delivery) and in vivo after intradermal or intramuscular electroporation delivery. As with Intramuscular injection (Example 2, Table 1), the results with intradermal delivery (Table 10) demonstrated ColE2 and R6K origin vectors dramatically improved in vivo expression compared to NTC8685. For example transgene expression from the NTC9385C vector was unexpectedly improved 2.7 to 3.1× on days 4, 7, and 14 compared to NTC8685 after intradermal delivery (Table 10) and improved by 1.5 to 3.8× on days 1, 4, 7, 14, 28 and 56 after intramuscular delivery. Transgene expression from the NTC9385R vector was unexpectedly improved 5.3 to 6.3× on days 4, 7, and 14 compared to NTC8685 after intradermal delivery (Table 10) and improved by 1.5 to 2.3× on days 1, 4, 7, 14, 28 and 56 after intramuscular delivery. The 866 bp minimal pUC origin vector also improved transgene expression to 1.4-1.9× that of NTC8685 after intradermal delivery. This demonstrates improved in vivo expression with the NTC9385C and NTC9385R vectors is not tissue specific since expression improvement was obtained after intradermal and intramuscular delivery. Additionally, improved in vivo expression of the invention is not specific to the CMV promoter since improved transgene expression was also observed with an NTC9385C-muSEAP vector with the murine creatine kinase (MCK) promoter substituted for the CMV promoter (NTC9385C-MCK-muSEAP, see Example 2). NTC9385C-MCK-muSEAP expression was improved 4.5× compared to NTC8685-MCK-muSEAP on day 28 after intramuscular delivery with EP (98.4±55.8 versus 22.0±10.9 pg/mL) (see Example 2). Inclusion of the C2×4 eukaryotic transcription terminator in the NTC9385C vector further improved in vivo expression to 2.9 to 4.1× compared to NTC8685 after intradermal delivery (Table 10). These results collectively demonstrate improved in vivo expression with Nanoplasmid vectors may be obtained in various tissues and with alternative eukaryotic promoters or with alternative/additional sequences flanking the spacer region encoded bacterial region.

Nanoplasmid vectors additionally encoding RNA-OUT in the HTLV-1R Rabbit β globin hybrid intron (both orientations of RNA-OUT SEQ ID NO:20 inserted into the unique HpaI site in the intron (SEQ ID NO:1) (NTC9385Ra-O1 dual and NTC9385Ra-O2 dual) were constructed. Robust expression with RNA-OUT in either orientation in the intron was observed (Table 8). The spacer region RNA-OUT was excised from these vectors (KpnI and DraIII digestion to excise RNA-OUT, ends blunted by T4 DNA polymerase treatment, blunt end ligation), to create NTC9385Ra-O1 (SEQ ID NO:50) and NTC9385Ra-O2 (SEQ ID NO:51) which have opposite orientations of intronic RNA-OUT marker and only the R6K replication origin in the spacer region (SR=306 bp). Similarly high level expression with both clones was observed (Table 8). To determine splicing accuracy NTC9385Ra-O2-EGFP was transfected into the A549 cell line and cytoplasmic RNA isolated and splice junctions characterized as described in Example 4. The RNA was reverse transcribed using an EGFP specific primer, and PCR amplified using Exon 1 and Exon 2 specific primers. The resultant PCR product (a single band) was determined by sequencing to be the correct spliced exon1-exon2 fragment. This demonstrated that intronic RNA-OUT is accurately removed by splicing and does not interfere with splicing accuracy. NTC9385Ra-O2-EGFP also demonstrated improved in vivo expression compared to NTC8685 (Table 10: 1.6-3.5×). Additionally, high yield manufacture was obtained with NTC9385Ra vectors (Table 7). This demonstrates that Nanoplasmid vectors with improved transgene expression of the current invention may encode the RNA selectable marker in the intron rather than the spacer region.

variety of antigens. For example, for gene therapy applications such as wound healing, burns, diabetic foot ulcer, critical limb ischemia therapies, or cosmetic treatment for different dermatological conditions, including anti-aging (anti-wrinkle), scar revision, radiation induced lesions, hair growth, surgical skin graft enhancement, or hemangioma, using growth factors such as hypoxia inducible factor, hypoxia inducible factor 1α, keratinocyte growth factor, vascular endothelial growth factor (VEGF), fibroblast growth factor-1 (FGF-1, or acidic FGF), FGF-2 (also known as basic FGF), FGF-4, placental growth factor (P1GF), angiotensin-1 (Ang-1), hepatic growth factor (HGF), Developmentally Regulated Endothelial Locus (Del-1), stromal cell derived factor-1 (SDF-1), etc.

Example 9: Alternative RNA Selectable Marker Nanoplasmid Vectors

The RNAI transcription unit (FIG. 10; SEQ ID NO: 34) was demonstrated in Example 7 as an acceptable substitute for the RNA-OUT selectable marker (SEQ ID NO: 20) in any of the constructs described in Examples 2-11. This may utilize the example pMB1 RNAI or the highly related ColE1 RNAI.

Another preferred RNA based selectable marker, IncB plasmid RNAI (SEQ ID NO:35) encoded within a selectable marker (SEQ ID NO:36), is shown in FIG. 11B. The promoter and terminator sequences flanking the IncB plasmid RNAI may be substituted with the plurality of promoter and terminator sequences know in the art. A cell line for antibiotic-free sucrose selection of IncB RNAI expressing plasmid vectors may be created by modification of the genomically expressed RNA-IN-SacB cell lines for RNA-OUT plasmid propagation disclosed in Williams, Supra, 2008 by replacement of the 68 bp RNA-IN regulator in a

TABLE 10

SR vector expression in vitro and in vivo

| muSEAP Vector [b] | SR [a] | SR (bp) | Intron [a] | A549 ($A_{405}$) [d] | HEK-293 ($A_{405}$) [d] | ID + EP [c] (pg/mL) T = 4 | ID + EP [c] (pg/mL) T = 7 | ID + EP [c] (pg/mL) T = 14 |
|---|---|---|---|---|---|---|---|---|
| NTC8685 | T-VA1-BH-P-AF→ | 1465 | HR-β | 0.240 ± 0.029 (1.0×) | 3.002 ± 0.188 (1.0×) | 1.9 ± 1.2 (1.0×) | 6.7 ± 4.1 (1.0×) | 5.0 ± 3.9 (1.0×) |
| NTC8385-Min [e] | T-$P_{min}$-AF→ | 866 | HR-β | 0.495 ± 0.027 (2.1×) | 2.713 ± 0.177 (0.9×) | 3.7 ± 2.7 (1.9×) | 12.4 ± 8.1 (1.9×) | 7.1 ± 5.2 (1.4×) |
| NTC9385R | T ← R-AF→ | 466 | HR-β | 0.604 ± 0.04 (2.5×) | 3.036 ± 0.169 (1.0×) | 12.0 ± 7.4 (6.3×) | 35.5 ± 31.1 (5.3×) | 29.9 ± 23.4 (6.0×) |
| NTC9385C | ←C-AF→ | 281 | HR-β | 0.267 ± 0.053 (1.1×) | 2.720 ± 0.228 (0.9×) | 5.8 ± 3.0 (3.1×) | 20.8 ± 9.6 (3.1×) | 13.5 ± 9.8 (2.7×) |
| NTC9385C C2x4 | ←C-AF→ | 281 | HR-β | 0.214 ± 0.017 (0.89×) | 2.472 ± 0.197 (0.82×) | 5.6 ± 2.3 (2.9×) | 27.7 ± 20.3 (4.1×) | 16.0 ± 14.3 (3.2×) |
| NTC9385R a-O2 | T ←R | 306 | HR- ← AF-β | 0.524 ± 0.071 (2.2×) | 3.065 ± 0.220 (1.0×) | 3.6 ± 2.8 (1.9×) | 23.4 ± 16.5 (3.5×) | 7.8 ± 8.0 (1.6×) |

[a] Prokaryotic terminator = T; HTLV-IR = HR; β globin 3' acceptor site = β; RNA-OUT = AF; pUC origin = P; minimal pUC origin = $P_{min}$; R6Kγ origin = R; ColE2-P9 origin = C; C2x4 eukaryotic transcription terminator = C2x4; PAS-BH = BH
[b] All plasmids produced in XL1Blue dcm- host strains. P vectors were produced in dcm- XL1Blue NTC54208; R vectors were produced in dcm- R6K Rep cell line NTC711231 (OL1 G to T); C vectors were produced in dcm- ColE2 Rep cell line NTC710351 (OL1 G to T).
[c] Dose = 50 μg in 50 μl saline injected intradermal (ID) with EP on day 0. 6 mice/group. Mean ± SD pg/mL muSEAP reported for day 4, 7 and 14. ( ) Mean muSEAP standardized to NTC8685
[d] muSEAP plasmid DNA transfected with Lipofectamine 2000. Mean ± SD $A_{405}$ reported at 48 hrs post transfection. ( ) Mean $A_{405}$ standardized to NTC8685
[e] $P_{min}$ minimal pUC origin (SEQ ID NO: 45) and RNA-OUT (bacterial region = SEQ ID NO:46)

The improved transgene expression level after intradermal delivery demonstrates the application of Nanoplasmid and replicative minicircle vectors of the invention for cutaneous DNA vaccination and gene therapy applications. For example, for intradermal DNA vaccination, epidermal DNA vaccination, or transcutaneous DNA vaccination using a PstI-MamI restriction fragment with a 362 bp PstI-MamI IncB RNAII regulator (SEQ ID NO:37) (FIG. 11A).

Another preferred RNA based selectable marker, an engineered CpG free repressor RNA (SEQ ID NO: 38) encoded as part of a selectable marker (SEQ ID NO: 39), is shown in FIG. 12A. The promoter and terminator sequences flanking the CpG free repressor RNA may be substituted with the plurality of promoter and terminator sequences know in the art. This RSM represses a target RNA such as SEQ ID NO: 40 encoded upstream of a target gene to be regulated such as SacB in SEQ ID NO: 41 and SEQ ID NO:42 (FIG. 12B; RNAS). pINT-RNAS expression vectors encoding SEQ ID NO:41 (P5/6 4/6 promoter driven expression of RNAS) and SEQ ID NO:42 (P5/6 5/6 promoter driven expression of RNAS) RNAS PstI-BamHI (FIG. 12B) were constructed (SEQ ID NO: 43, SEQ ID NO: 44) as well as pINT-RNAS vectors with a P5/6 6/6 promoter driving expression of RNAS. The P5/6 4/6, P5/6 5/6, P5/6 6/6 promoters, the pCAH63-CAT integration vector, and cloning and integration of pCAH63-CAT vector derivatives were as described (Luke J, Carnes A E, Hodgson C P, Williams J A. 2009 Vaccine 27:6454-6459). The P5/6 6/6 promoter contains a TAGACA-35 region that is 5/6 match with the TTGACA-35 consensus sequence, separated, by the optimal 17 bp spacing, from a TATAAT consensus-10 region. Briefly, the pCAH63-CAT integration vector was digested with BamHI and PstI and ligated with a P5/6 6/6 promoter RNA-selection-SacB (RNAS) synthetic gene (Genscript, Piscataway, N.J.) which was excised as a 2487 bp PstI-BamHI restriction fragment. Clones (pINT-RNAS integration vector P5/6 6/6) were verified by restriction digestion and integrated into NTC54208 (XL1Blue dcm-) as described (Luke et al., Supra, 2009). The resultant cell line, NTC781953 was demonstrated to be sucrose sensitive as predicted. The 147 bp RNA-OUT selectable marker in NTC8685-EGFP was excised with DraIII/KpnI and the CpG free RNA selectable marker synthetic gene (Genscript, Piscataway, N.J.) excised as a 147 bp DraIII/KpnI restriction fragment (DraIII-SEQ ID NO: 39-KpnI) and ligated to the 3672 bp NTC8685-EGFP DraIII/KpnI restriction fragment. Clones (NTC8685-RSM-EGFP) were identified as sucrose resistant colonies after transformation into NTC781953 and sequence validated.

This demonstrates that this alternative designed RNA selectable marker (SEQ ID NO: 38) may be substituted for the RNA-OUT RNA selectable marker in the vectors of the current invention. RSM plasmids may be selected in alternative cell lines, for example, in which the 6/6 consensus TATAAT-10 promoter region in pINT-RNAS integration vector P5/6 6/6 was altered using synthetic oligonucleotides to 5/6 consensus TATGAT (P5/6 5/6) (pINT-RNAS P5/6 5/6; SEQ ID NO: 44) or 4/6 consensus TAGATT (P5/6 4/6) (pINT-RNAS P5/6 4/6; SEQ ID NO: 43). Alternatively, optimal promoter strength can be determined by other alterations in the −10 region that change the consensus sequence, or alternations in the −35 region TTGACA consensus, or changes in the spacing between the −10 and −35 regions from the optimal 17 bp. Engineered CpG free repressor RNA selectable marker replicative minicircle vectors may be grown in RNA-selection-SacB (RNAS) regulated cell lines further expressing, as required, R6K, ColE2-P9, or ColE2 related Rep protein. RNA-selection-SacB (RNAS) regulated cell lines may also be made replacing the RNA-IN sequence in pCAH63-CAT RNA-IN-SacB (P5/6 6/6) with the target RNA SEQ ID NO: 40 as described in Williams, Supra, 2008 included herein by reference.

Example 10: Minimal pUC Origin Replicative Minicircles

Replicative minicircle vectors NTC8485P2 (0.85)-O1, NTC8485P2 (0.85)-O2, NTC9385P2a(0.85)-O1 and NTC9385P2a(0.85)-O2 containing the $P_{min}$ pUC replication origin (SEQ ID NO: 45) and the RNA-OUT RNA selectable marker (0.85 kb Bacterial region=SEQ ID NO: 46) within the intron were constructed as described in Example 3, and characterized for expression in HEK293 and A549 (Table 11) and splicing accuracy in A549 (Table 9) as described in Example 4.

TABLE 11

Robust expression with P2-(0.85) replicative minicircles

| Vector (EGFP) | Spacer region [a] | Intron [a] | A549 FU[b] (T = 48 mean + SD) | HEK293 FU[b] (T = 48 mean + SD) |
|---|---|---|---|---|
| NTC8485 | T BH ← P-AF→ (SV40-BE) | HR-β | 4311 ± 458 (1×) | 40236 ± 1851 (1×) |
| NTC8485C2-O1 | T BH ← P-AF→ (SV40-BE) | HR ← C AF → -β | 5001 ± 2724 (1.16×) | 41334 ± 14098 (1.03×) |
| NTC8485C2-O2 | T BH ← P-AF→ (SV40-BE) | HR ← AF C → -β | 2962 ± 495 (0.69×) | 28849 ± 2421 (0.72×) |
| NTC8485R2-O1 | T BH ← P-AF→ (SV40-BE) | HR ← T-R AF → -β | 2888 ± 180 (0.67×) | 29395 ± 1054 (0.73×) |
| NTC8485R2-O2 | T BH ← P-AF→ (SV40-BE) | HR ← AF R-T → -β | 3187 ± 851 (0.74×) | 33044 ± 3515 (0.82×) |
| NTC8485P2-O1 | T BH ← P-AF→ (SV40-BE) | HR ← T-P-AF → -β | 1143 ± 392 (0.27×) | 20775 ± 6777 (0.52×) |
| NTC8485P2-O2 | T BH ← P-AF→ (SV40-BE) | HR ← AF P-T → -β | 1500 ± 169 (0.35×) | 16575 ± 2483 (0.41×) |
| NTC8485P2 (0.85)-O1 | T BH ← P-AF→ (SV40-BE) | HR ← T-$P_{min}$-AF → -β | 1969 ± 591 (0.46×) | 31883 ± 2750 (0.79×) |
| NTC8485P2- (0.85)-O2 | T BH ← P-AF→ (SV40-BE) | HR ← AF $P_{min}$-T → -β | 2171 ± 410 (0.50×) | 24733 ± 1417 (0.61×) |
| NTC9385P2a-O1 | None (BE) | HR ← T-P-AF → -β | 4445 ± 217 (1.03×) | 26181 ± 1643 (0.65×) |
| NTC9385P2a-O2 | None (BE) | HR ← AF P -T →-β | 3457 ± 426 (0.80×) | 23829 ± 1514 (0.59×) |
| NTC9385P2a (0.85)-O1 | None (BE) | HR ← T-$P_{min}$ -AF → -β | 6175 ± 258 (1.43×) | 38169 ± 2245 (0.95×) |
| NTC9385P2a- (0.85)-O2 | None (BE) | HR←AF $P_{min}$ -T → -β | 6756 ± 583 (1.57×) | 35363 ± 3532 (0.88×) |
| NTC9385C2a-O1 | None (BE) | HR ← C AF → -β | 5793 ± 820 (1.34×) | 36804 ± 6725 (0.91×) |

TABLE 11-continued

Robust expression with P2-(0.85) replicative minicircles

| Vector (EGFP) | Spacer region [a] | Intron [a] | A549 FU[b] (T = 48 mean + SD) | HEK293 FU[b] (T = 48 mean + SD) |
|---|---|---|---|---|
| NTC9385R2a-O1 | None (BE) | HR ← T-R-AF → -β | 7498 ± 859 (1.74×) | 37595 ± 5497 (0.93×) |
| NTC9385R2a-O2 | None (BE) | HR ← AF R-T → -β | 5815 ± 456 (1.35×) | 36926 ± 2001 (0.92×) |

[a] Prokaryotic terminator = T; HTLV-IR = HR; B globin 3' acceptor site = β; RNA-OUT = AF; pUC origin = P; $P_{min}$ minimalized pUC origin = $P_{min}$; R6Kγ origin = R; ColE2-P9 origin = C; Boundary element = BE; 2 × 72 bp repeat of SV40 enhancer = SV40. Bracketed BE and or SV40 are spacer region flanking eukaryotic sequences
[b] EGFP plasmid DNA transfected with Lipofectamine 2000. Mean ± SD Fluorescence units (FU) at 48 hrs post transfection reported. ( ) Mean FU standardized to NTC8485

As with NTC9385P2a-O1 (Example 4) splicing was accurate with NTC9385P2a(0.85)-O1. Minor amounts of a cryptic $P_{min}$ derived exon were detected with NTC9385P2a (0.85)-O2; the sequence of the cryptic exon matches the previously identified pUC derived cryptic exon observed with NTC9385P2a-O2, (Table 9; FIG. 3). Expression from both orientations was unexpectedly higher with NTC9385P2a(0.85)-O1 and NTC9385P2a(0.85)-O2 compared to NTC9385P2a-O1 and NTC9385P2a-O2 (Table 11) as well as NTC8485P2a(0.85)-O1 and NTC8485P2a(0.85)-O2 compared to NTC8485P2a-O1 and NTC8485P2a-O2 (Table 11). While not limiting the application of this invention, the higher expression with the intronic $P_{min}$ replicative minicircles versus intronic pUC replicative minicircles may be due to smaller intron size or deletion of inhibitory sequences, such as the pUC origin nuclease sensitive site (FIG. 3). High yield manufacture was obtained with these intronic $P_{min}$ pUC replication origin vectors (Table 7) with high quality plasmid surprisingly without detectable replication intermediates despite the close proximity of the $P_{min}$ pUC replication origin and the CMV promoter enhancer.

Example 11: 3' UTR Nanoplasmid Vectors

The R6K origin (SEQ ID NO: 11), RNA-OUT selectable marker (SEQ ID NO: 20), or R6K-RNA-OUT bacterial region (SEQ ID NO: 26) were cloned into the 3' UTR of the NTC7485 and NTC9385C vectors. NTC7485 is a kanamycin resistant (kanR) derivative of the NTC8485 vector in which RNA-OUT is substituted with kanR NTC7485 was used to test expression of vectors with the RNA-OUT selectable marker and R6K-RNA-OUT bacterial region in the 3' UTR to avoid duplication of RNA-OUT within a vector backbone. Likewise, NTC9385C was used to test expression with the R6K origin encoded in the 3' UTR since this vector does not encode the R6K origin.

NTC7485-EGFP-R-OUT O1 and O2 were constructed by cloning the RNA-OUT selectable marker as a 147 bp DraIII/KpnI (blunted with T4 DNA polymerase) restriction fragment into BglII digested (blunted by filling with Klenow), CIP treated NTC7485-EGFP (4508 bp restriction fragment). Recombinant clones of both orientations were identified as sucrose resistant colonies in cell line NTC54208 and confirmed by restriction mapping and sequencing. The orientation 2 clone that was tested contained two copies of RNA-OUT (Table 12). NTC7485-EGFP R6K-R-OUT O1 and O2 were constructed by cloning the R6K-RNA-OUT bacterial region as a 447 bp BsrBI/KpnI (blunted with T4 DNA polymerase) restriction fragment into BglII digested (blunted by filling with Klenow), CIP treated NTC7485-EGFP (4508 bp restriction fragment). Recombinant clones of both orientations were identified as sucrose resistant colonies in cell line NTC54208 and confirmed by restriction mapping and sequencing. NTC9385C-EGFP-R6K O1 and 2 were constructed by cloning the R6K origin as a 300 bp BsrBI/DraIII (blunted with T4 DNA polymerase) restriction fragment into BglII digested (blunted by filling with Klenow), CIP treated NTC9385C-EGFP (2206 bp restriction fragment). Recombinant clones of both orientations were identified as sucrose resistant colonies in R6K production cell line NTC711231 and confirmed by restriction mapping and sequencing.

Transgene (EGFP) expression of these 3' UTR selection, replication or selection-replication vectors, compared to the parent vectors, was determined in HEK293 and A549 cell lines as described in Example 4 (Table 12). The observed robust expression of 3'UTR clones with RNA-OUT, R6K-RNA-OUT or R6K in either orientation demonstrated that 3' UTR encoded replication and or selection is compatible with replicative minicircle function and high level expression. Additionally, the results further demonstrate that 3'UTR selection can be combined with spacer region replication (NTC7485-R-OUT O1, O2) or that 3' UTR replication can be combined with spacer region selection (NTC9385C-R6K-O1, O2).

The ←R-AF→, AF→, ←R orientations are preferred since these contain no open reading frames which could be translated by read through of the transgene stop codon (Table 12).

TABLE 12

High level expression with R6K replication origin and/or RNA-OUT encoded in the 3' UTR

| Plasmid (all EGFP) | Spacer [a] | 3' UTR [a] | A549 EGFP [b] | HEK EGFP [b] |
|---|---|---|---|---|
| NTC7485 | T-BH-P-kanR (SV40-BE) | None [c] | 3418 ± 739 (1×) | 24066 ± 1169 (1×) |
| NTC7485-R6K-R-OUT O1 | T-BH-P-kanR (SV40-BE) | ← R-AF → [c] | 2110 ± 233 (0.61×) | 23822 ± 2430 (0.99×) |

TABLE 12-continued

High level expression with R6K replication origin and/or RNA-OUT encoded in the 3' UTR

| Plasmid (all EGFP) | Spacer [a] | 3' UTR [a] | A549 EGFP [b] | HEK EGFP [b] |
|---|---|---|---|---|
| NTC7485-R6K-R-OUT O2 | T-BH-P-kanR (SV40-BE) | ← AF R → | 1666 ± 228 (0.49×) | 18230 ± 823 (0.76×) |
| NTC7485-R-OUT O1 | T-BH-P-kanR (SV40-BE) | AF→ [c] | 2709 ± 332 (0.79×) | 25609 ± 1430 (1.06×) |
| NTC7485-R-OUT O2 (2x) | T-BH-P-kanR (SV40-BE) | ← AF ← AF | 2151 ± 207 (0.63×) | 19471 ± 1221 (0.81×) |
| NTC9385C | C-AF→ | None [c] | 4044 ± 592 (1.18×) | 28546 ± 1370 (1.19×) |
| NTC9385C-R6K O1 | C-AF→ | ←R [c] | 7897 ± 961 (2.31×) | 37645 ± 1264 (1.56×) |
| NTC9385C-R6K O2 | C-AF→ | R→ | 8305 ± 317 (2.43×) | 36707 ± 1024 (1.53) |

[a] Prokaryotic terminator = T; RNA-OUT = AF; pUC origin = P; R6Kγ origin = R; ColE2-P9 origin = C; 2 × 72 bp repeat of SV40 enhancer = SV40; PAS-BH = BH. Bracketed BE or SV40 are spacer region flanking eukaryotic sequences
[b] EGFP plasmid DNA transfected with Lipofectamine 2000. Mean ± SD Fluorescence units (FU) at 48 hrs post transfection reported. ( ) Mean FU standardized to NTC7485
[c] No open reading frames in 3'UTR (cutoff of minimum 20 amino acids)

A vector, NTC9385RbF (FIG. 13; SEQ ID NO: 47), that contains the R6K miniorigin in the 3'UTR in the ←R (orientation 1) configuration (which has no 3' UTR open reading frames), and intronic RNA-OUT was created as follows. First, NTC9385C-Rbf-EGFP was constructed by cloning the R6K origin as a 316 bp BfaI (klenow heat killed) then DraIII (blunted with T4 DNA polymerase) restriction fragment into BglII digested (blunted by filling with Klenow), CIP treated NTC9385C-EGFP (2206 bp restriction fragment). Recombinant clones of the correct orientation were identified as sucrose resistant colonies in R6K production cell line NTC711231 and confirmed by restriction mapping and sequencing. This construct was digested with AlwNI and SacII to excise the intron, and the 2217 bp restriction fragment was ligated to the 449 bp RNA-OUT intron from NTC9385Ra-O1-EGFP similarly digested with AlwNI and SacII. The resultant construct (NTC9385C-RbF-EGFP Intron RNA-OUT) was sequence verified then digested with NotI and NcoI to excise the spacer region encoded ColE2 origin-RNA-OUT. The resultant 2014 bp fragment was ligated to the spacer region and boundary element from NTC9385R2a-O1-muSEAP as a compatible 462 bp NotI and NcoI digested restriction fragment. The resultant clone, NTC9385RbF-EGFP was sequence validated, and surprisingly robust expression (Table 13) and high fermentation yields (Table 7) verified. This demonstrates the surprising observation that replication and selection functions may be encoded within the 3' UTR and intron respectively. Collectively, these results demonstrate that 3'UTR selection can be combined with spacer region or intronic replication or that 3' UTR replication can be combined with spacer region or intronic selection. The RNA-OUT selectable marker may be substituted with alternative RNA selectable markers as described in Examples 7 and 9.

TABLE 13

High level expression with R6K replication origin encoded in the 3' UTR

| Vector (all EGFP) | Spacer [a,b] | Intron [a] | 3' UTR [a] | A549 EGFP [b] | HEK EGFP [b] |
|---|---|---|---|---|---|
| NTC9385C | ← C-AF → | HR-β | None | 2661 ± 489 (3.25×) | 15722 ± 2235 (4.74×) |
| NTC9385R | T ← R AF → | HR-β | None | 4803 ± 298 (5.86×) | 18396 ± 2231 (5.55×) |
| NTC8685 | T-VA1-BH-P-AF (SV40) | HR-β | None | 2164 ± 364 (2.64×) | 18153 ± 2251 (5.47×) |
| NTC9385R2a-O2 | (BE) | HR ← AF R → T-β | None | 2967 ± 476 (3.62×) | 12581 ± 852 (3.79×) |
| NTC9385R2a-O1 | (BE) | HR ← T-R-AF → -β | None | 3416 ± 283 (4.17×) | 15059 ± 2639 (4.54×) |
| NTC9385Ra-O1 | ←R | HR-AF → -β | None | 2727 ± 315 (3.33×) | 19124 ± 4212 (5.77×) |
| NTC9385RbF | (BE) | HR-AF → -β | ←R | 2427 ± 184 (2.96×) | 13257 ± 2720 (4.00×) |
| pVAX1 | P-kanR | None | None | 820 ± 82 (1×) | 3317 ± 83 (1×) |

[a] trpA term = T; HTLV-IR = HR; B globin 3' acceptor site = β; RNA-OUT selectable marker = AF; pUC origin = P; R6K origin = R; ColE2 origin = C; CMV boundary element = BE; PAS-BH = BH. Bracketed BE or SV40 are spacer region flanking eukaryotic sequences
[b] EGFP plasmid DNA transfected with Lipofectamine 2000. Mean ± SD Fluorescence units (FU) at 48 hrs post transfection reported. ( ) Mean FU standardized to pVAX1

To demonstrate alternative RNA selectable markers can be substituted for RNA-OUT in the 3' UTR, and that the ColE2 origin can be substituted for the R6K origin in the 3' UTR, NTC9385R-EGFP derivatives were made with the RNAI selectable marker (SEQ ID NO: 34) or the ColE2 origin (+7) (SEQ ID NO: 13)-CpG free ssiA (SEQ ID NO:

16) inserted in the 3' UTR. Control NTC9385R-EGFP constructs with the pUC origin or the $P_{min}$ minimalized pUC origin (SEQ ID NO: 45) inserted in the 3' UTR were also constructed and expression tested. NTC9585R was used to test expression of vectors with the RNAI selectable marker and ColE2 and pUC replication origins in the 3' UTR to avoid duplication of RNAI, ColE2 or pUC sequences within a vector backbone. All RNAI, ColE2 or pUC sequences were cloned as blunt ended restriction fragments into the 3' UTR of the NTC9385R-EGFP vector that had been digested with BglII, blunted by filling with klenow (2391 bp restriction fragment), and CIP treated. RNAI selectable marker (SEQ ID NO: 34) was excised with HpaI as a 162 bp restriction fragment from a synthetic gene (Genscript, Piscataway, N.J.). The ColE2 origin (+7) (SEQ ID NO: 13)-CpG free ssiA (SEQ ID NO: 16) was excised from NTC9385C-EGFP as a 132 bp NheI (heat kill, klenow filled to blunt)/DraIII (heat kill, T4 DNA polymerase treatment to remove protruding sticky end) restriction fragment. The pUC origin was excised from NTC8385-EGFP as an 1067 bp NheI (heat kill, klenow filled to blunt)/DraIII (heat kill, T4 DNA polymerase treatment to remove protruding sticky end) restriction fragment. The $P_{min}$ minimalized pUC origin was excised from NTC8385-EGFP as an 720 bp AflIII/BspHI (heat kill, klenow filled to blunt) restriction fragment. Recombinant clones were identified as sucrose resistant colonies in R6K replication cell line NTC711231 and confirmed by restriction mapping and sequencing. Transgene (EGFP) expression of these 3' UTR selection or replication or vectors, compared to the parent NTC9385R-EGFP vector, was determined in HEK293 and A549 cell lines. The results demonstrated robust expression with constructs with 3' UTR encoded RNAI selectable marker or ColE2 origin-ssiA replication origin but not with constructs encoded the pUC origin or $P_{min}$ minimalized pUC origin (Table 14). This demonstrates that robust expression replicative minicircle vectors can be constructed with the ColE2 or R6K origin, and/or RNA selectable markers encoded in the 3' UTR.

The ←R-AF→, AF→←R, AF→, ←R, ←R-RNAI→, RNAI→←R, ←R←RNAI, ←RNAI←R, RNAI→, and ←RNAI compositions and orientations are preferred in the 3' UTR since these contain no open reading frames which could be translated by read through of the transgene stop codon (Table 14). RNA-OUT selectable marker (SEQ ID NO: 20), CpG free RNA-OUT selectable marker (SEQ ID NO: 22) and RSM (SEQ ID NO: 39) are preferred RNA selectable markers in the 3' UTR in the AF→ orientation since these RNA selectable markers contain no open reading frames which could be translated by read through of the transgene stop codon. The RNAI selectable marker (SEQ ID NO: 34) is preferred in either orientation since both orientations do not contain open reading frames which could be translated by read through of the transgene stop codon.

TABLE 14

High level expression with RNAI encoded in the 3' UTR

| Vector (all EGFP) | Spacer [a, b] | Intron [a] | 3' UTR [a] | A549 EGFP [b] | HEK EGFP [b] |
|---|---|---|---|---|---|
| NTC8685 | T-VA1-BH-P-AF (SV40) | HR-β | None [c] | 5519 ± 483 (2.76x) | 51594 ± 1019 (8.36x) |
| NTC8685-RSM | T-VA1-BH-P-RSM(SV40) | HR-β | None [c] | 5655 ± 512 (2.83x) | 48511 ± 4272 (7.86x) |
| NTC9385R-Intron | T ← R-AF → | CMV-β | None [c] | 12361 ± 742 (6.18x) | 39832 ± 1273 (6.45x) |
| NTC9385R | T ← R-AF → | HR-β | None [c] | 12036 ± 2401 (6.01x) | 50208 ± 1084 (8.14x) |
| NTC9385R-3'UTR pUC O2 | T ← R-AF → | HR-β | P→ | 3470 ± 362 (1.73x) | 9827 ± 595 (1.59x) |
| NTC9385R-3'UTR pMIN O1 | T ← R-AF → | HR-β | ←$P_{min}$ | 2950 ± 130 (1.47x) | 10828 ± 715 (1.75x) |
| NTC9385R-3'UTR pMIN O2 | T ← R-AF → | HR-β | $P_{min}$→ | 2010 ± 88 (1.00x) | 6523 ± 476 (1.06x) |
| NTC9385R-3'UTR C2 O1 | T ← R-AF → | HR-β | ←C | 9569 ± 682 (4.78x) | 40691 ± 1421 (6.59x) |
| NTC9385R-3'UTR RNAI O2 | T ← R-AF → | HR-β | ←RNAI [c] | 9064 ± 295 (4.53x) | 35543 ± 2829 (5.76x) |
| NTC9385RbF | (BE) | HR-AF → -β | ←R [c] | 8500 ± 1618 (4.23x) | 39407 ± 4006 (6.39x) |
| pVAX1 | P-kanR | None | None | 2001 ± 299 (1x) | 6170 ± 778 (1x) |

[a] trpA term = T; HTLV-IR = HR; B globin 3' acceptor site = β; RNA-OUT selectable marker = AF; pUC origin RNAI antisense RNA selectable repressor RNA marker = RNAI; RSM antisense repressor RNA marker = RSM; pUC origin = P; pMIN origin = $P_{min}$; R6K origin = R; ColE2 origin = C; CMV boundary element = BE; PAS-BH = BH; CMV B globin 3' acceptor site = CMV- β = SEQ ID NO: 10. Bracketed BE or SV40 are spacer region flanking eukaryotic sequences
[b] EGFP plasmid DNA transfected with Lipofectamine 2000. Mean ± SD Fluorescence units (FU) at 48 hrs post transfection reported. ( ) Mean FU standardized to pVAX1
[c] No open reading frames in 3'UTR (cutoff of minimum 20 amino acids)

Summary

While the above description contains many examples, these should not be construed as limitations on the scope of the invention, but rather should be viewed as an exemplification of preferred embodiments thereof. Many other variations are possible. For example, a replication origin and/or a selectable marker may be inserted into the 3' UTR at any site between the transgene stop codon and the polyadenylation signal. The polyadenylation signal may be from a variety of polyadenylation signals known in the art, including the rabbit β globin, the human β globin, SV40 early, SV40 late, bovine growth hormone, etc, polyadenylation signals. Additionally, a replication origin and/or a selectable marker may be inserted into the HTLV-I R-Rabbit β globin hybrid intron (SEQ ID NO:1) at any site between the 5' splice acceptor and the 3' acceptor branch site (FIG. 1) rather than the HpaI site. Alternatively, a replication origin and/or a selectable marker may be inserted at two different sites within an intron between the 5' splice acceptor and the 3' acceptor branch site. Alternatively, a replication origin and a selectable marker may be inserted into two different introns, each insertion at any site between the 5' splice acceptor and the 3' acceptor branch site. Alternatively, a replication origin and a selectable marker may be inserted into alternative introns at any site between the 5' splice acceptor and the 3' acceptor branch site. A non limiting list of alternative introns for insertion of a bacterial region to create an intron encoded bacterial region of the invention are SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:32. Replacement of the HTLV-IR-rabbit β globin 3' acceptor site intron (SEQ ID NO: 1) with the CMV-rabbit β globin 3' acceptor site intron (SEQ ID NO:10) in the NTC9385R vector (NTC9385R-intron; SEQ ID NO: 64) resulted in high level expression, comparable with the HTLV-IR-rabbit β globin 3' acceptor site intron containing NTC9385R vector (Table 14). This demonstrates that various introns can be utilized to practice the invention.

Additionally, the RNA-OUT selectable marker may be substituted with an alternative RNA-OUT sequence variant that functionally binds RNA-IN to repress expression. Likewise, the RNA-OUT promoter and/or terminator could be substituted with an alternative promoter and/or terminator. Further, an alternative RNA based selectable marker could be substituted for RNA-OUT. This may be a plasmid borne nonsense suppressing tRNA that regulates a nonsense suppressible selectable chromosomal target as described by Crouzet and Soubrier, Supra, 2005 included herein by reference. This may also be a plasmid borne antisense repressor RNA, a non limiting list included herein by reference includes pMB1 plasmid origin encoded RNAI (SEQ ID NO: 33) that represses RNAII regulated targets (as described in Grabherr and Pfaffenzeller, Supra, 2006; Cranenburgh, Supra, 2009), plasmid pMU720 origin encoded RNAI (SEQ ID NO: 35) that represses RNA II regulated targets (Wilson et al., Supra, 1997) ParB locus Sok of plasmid R1 that represses Hok regulated targets, Flm locus FlmB of F plasmid that represses flmA regulated targets (Morsey, Supra, 1999) or other antisense repressor RNAs known in the art.

For example, the pMB1 plasmid origin encoded RNAI (SEQ ID NO: 33) as a selectable marker (SEQ ID NO:34) flanked by restriction sites for cloning purposes can substituted for RNA-OUT in any of the vectors disclosed in Examples 2-11. For example, NTC9385RbF (FIG. 13; SEQ ID NO: 47) substituted with the RNAI selectable marker (SEQ ID NO: 34) is shown as SEQ ID NO:49. NTC9385Ra-O1 (SEQ ID NO:50) or NTC9385Ra-O2 (SEQ ID NO:51) substituted with the RNAI selectable marker (SEQ ID NO: 34) are shown as SEQ ID NO:54 and SEQ ID NO:55 respectively. NTC9385RaF (SEQ ID NO: 56) in which the R6K origin is positioned in the spacer region and the RNA-OUT selectable marker is positioned in the 3' UTR, substituted with the RNAI selectable marker (SEQ ID NO: 34) is shown as SEQ ID NO:58.

RNAI (SEQ ID NO: 33) expressing vectors can be selected in cell lines that encode RNAII regulated targets as described in Grabherr and Pfaffenzeller, Supra, 2006; Cranenburgh, Supra, 2009. In these cell lines, binding of RNAI to RNAII target sequences inserted in an mRNA upstream of the target gene start codon represses expression of the target gene. The target gene can encode a repressor protein, that itself suppresses expression of a second gene. In this manner, RNAI repressor RNA repression of the RNAII regulated target gene leads to expression of the second gene. If the second gene is essential for growth, then plasmid containing cells can be selected under conditions wherein second gene expression is required for growth. Alternatively, the target gene can encode a selectable conditionally toxic molecule, such as SacB. In this manner, RNAI repressor RNA mediated repression of the RNAII regulated target gene leads to repression of toxin gene expression allowing selection of plasmid containing cells under conditions wherein toxin gene expression eliminates cells without plasmid. The RNAII that is used to regulate target gene expression can be the entire anti-RNAI (1-108) region, or be a RNAII fragment that contains the three loop RNAII region complementary to RNAI, for example anti-RNAI (10-108) (SEQ ID NO: 59) or be one or two RNAII loops complementary to RNAI as disclosed in Grabherr and Pfaffenzeller, Supra, 2006. A non limiting list of configurations of these RNAII molecules that can be used to regulate target gene expression are: 1) A RNAII-target gene fusion, in which the RNAII is positioned downstream of a ribosome binding site and ATG start codon, and is in frame with the target gene start codon, such that the RNAII is translated in frame as an N terminal extension of the target protein as described in Grabherr and Pfaffenzeller, Supra, 2006. Plasmid borne RNAI binds expressed RNAII inhibiting translation of the fusion protein; 2) A RNAII-target gene dual cistron, in which the RNAII is positioned downstream of a ribosome binding site and ATG start codon and upstream of an in frame stop codon and second ribosome binding site which is upstream of the target gene start codon, such that the RNAII is translated as a first cistron, followed by translation of the target protein in a second cistron. Plasmid borne RNAI binds expressed RNAII inhibiting translation of the first cistron, which prevents ribosome binding to the second ribosome binding site, reducing target gene expression; 3) RNAII leader upstream of target gene, in which the RNAII is positioned upstream or overlapping the ribosome binding site of the target gene such that plasmid borne RNAI binds expressed RNAII RNA preventing ribosome binding to the ribosome binding site, reducing target gene expression. Configurations for RNAII leaders using an anti-RNAI (4-108) are disclosed in Cranenburgh, Supra, 2009. Alternative RNAII leaders using an anti-RNAI(10-108) (SEQ ID NO: 59) with a weak ribosome binding site (TCGA) upstream of the target gene ATG or a strong ribosome binding site (AGGAGA) upstream of the target gene ATG are shown as SEQ ID NO:60 and SEQ ID NO:61 respectively. These cassettes can be expressed from a variety of promoters, for example the P5/6 6/6, P5/6 5/6, or P5/6 4/6 promoters disclosed herein, regulate a variety of target genes, for example SacB or tetR disclosed herein, and integrated into the genome using PCR products or integration vectors, for example the pINT integration vector disclosed herein.

Alternatively, an engineered RNA selectable marker such as the RSM antisense repressor RNA (SEQ ID NO: 38) may be substituted for RNA-OUT. The RSM antisense repressor RNA selectable marker (SEQ ID NO: 39) may be flanked by DraIII and KpnI restriction sites to allow precise replacement of the RNA-OUT selectable marker (SEQ ID NO: 20) flanked by DraIII and KpnI sites. For example, the RNA-OUT marker was replaced with the RSM antisense RNA marker (SEQ ID NO: 39) in NTC8685-RSM-EGFP (see Example 9). The resultant vector had high expression in A549 and HEK293 cells comparable to the RNA-OUT comparator (Table 14) demonstrating that alternative RNA selectable markers can be utilized in the practice of the current invention. NTC9385RbF (FIG. 13; SEQ ID NO: 47) substituted with the RSM antisense repressor RNA marker (SEQ ID NO: 39) is shown as SEQ ID NO:48. NTC9385Ra-O1 (SEQ ID NO:50) or NTC9385Ra-O2 (SEQ ID NO:51) substituted with the RSM antisense repressor RNA marker (SEQ ID NO: 39) are shown as SEQ ID NO:52 and SEQ ID NO:53 respectively. NTC9385RaF (SEQ ID NO: 56) in which the R6K origin is positioned in the spacer region and the RNA-OUT selectable marker is positioned in the 3' UTR, substituted with the RSM antisense repressor RNA marker (SEQ ID NO: 39) is shown as SEQ ID NO:57.

For CpG free vector applications, the CpG free RNA-OUT selectable marker (SEQ ID NO: 22) or RSM antisense repressor RNA marker (SEQ ID NO: 39) may be flanked by CpG free restriction enzyme sites, for example BglII or EcoRI for cloning, or may be incorporated into the vector by PCR, or by synthesizing the new vector de novo using gene synthesis. The CpG free RNA selectable marker may be incorporated within an intron, a 3' UTR or the spacer region of a vector. CpG free replication origins may be incorporated within an intron, a 3' UTR or the spacer region of a vector. The CpG free RNA selectable markers and replication origins may be incorporated together or separately with introns, a 3' UTR or the spacer region of a vector. A CpG free RNA selectable marker may be combined with a CpG free R6K replication origin (e.g. SEQ ID NO: 12) in any orientation to make a CpG free bacterial region, for example SEQ ID NO: 28. A CpG free RNA selectable marker may be combined with a CpG free ColE2 replication origin (e.g. SEQ ID NO: 16) in any orientation, optionally incorporating a CpG free ssi (e.g. SEQ ID NO: 17), to make a CpG free bacterial region, for example SEQ ID NO: 25. These CpG free bacterial regions may be incorporated into the spacer region, the intron or the 3' UTR of a vector.

In the vectors of the invention, the ColE2-P9 or R6K replication origin may be substituted with a ColE2 related replication origin, and propagated in a strain expressing the ColE2 related replication origin replication protein. Likewise, the ColE2-P9 or R6K Rep protein dependent origin may be substituted with an origin from one of the numerous alternative Rep protein dependent plasmids that are know in the art, for example the Rep protein dependent plasmids described in del Solar et al., Supra, 1998 which is included herein by reference. Likewise, the various orientations of the replication origin, and the RNA selectable marker, may be utilized. For example, Table 15 summarizes the eight orientations of the replication origin, and the RNA selectable marker in vectors of the current invention in which the replication origin and RNA selectable marker are both encoded together within either the spacer region, a intron, or the 3' UTR. Table 16 summarizes twenty four orientations of the replication origin, and the RNA selectable marker in vectors of the current invention in which the replication origin and RNA selectable marker are encoded separately within the spacer region, a intron, or the 3' UTR. Vectors in which the replication origin and RNA selectable marker are encoded separately within the spacer region and the 3' UTR do not need to include an intron. However, one or more introns may optionally be included in vectors in which the replication origin and RNA selectable marker are encoded separately within the spacer region and the 3' UTR.

TABLE 15

Spacer region, intron or 3' UTR encoded RSM selection/replication origin short spacer region replicative minicircle vector configurations

| # | Vector Intron configurations [a,b] | Vector Spacer region configurations [a,c] | Vector 3' UTR configurations [a,c] |
|---|---|---|---|
| 1 | SD ← Rep RSM → SA | PA ← Rep RSM → EP | Stop ← Rep RSM → PA |
| 2 | SD ← Rep ← RSM SA | PA ← Rep ← RSM EP | Stop ← Rep ← RSM PA |
| 3 | SD Rep → RSM → SA | PA Rep → RSM → EP | Stop Rep → RSM → PA |
| 4 | SD Rep → ← RSM SA | PA Rep → ← RSM EP | Stop Rep → ← RSM PA |
| 5 | SD ← RSM Rep → SA | PA ← RSM Rep → EP | Stop ← RSM Rep → PA |
| 6 | SD ← RSM ← Rep SA | PA ←RSM ← Rep EP | Stop ← RSM ← Rep PA |
| 7 | SD RSM → Rep → SA | PA RSM → Rep → EP | Stop RSM → Rep → PA |
| 8 | SD RSM → ← Rep SA | PA RSM → ← Rep EP | Stop RSM → ← Rep PA |

[a] SD = Splice donor; SA = Splice acceptor; Rep = replication origin, selected from the group R6K gamma replication origin, a ColE2-P9 replication origin, a ColE2-P9 related replication origin, a pUC replication origin (intron only, not in SR or 3' UTR), a $P_{min}$ pUC replication origin (intron only, not in SR or 3' UTR); RSM = RNA selectable marker; Stop = transgene stop codon; PA = polyadenylation signal; EP = RNA polymerase I, II or III enhancer promoter
[b] Additional functional groups may be encoded within the intron, including bacterial transcriptional terminators, eukaryotic promoters, eukaryotic enhancers, eukaryotic intronic splicing enhancers, nuclear localizing sequences, supercoiling-induced DNA duplex destabilized (SIDD) structures, microRNAs and/or immunostimulatory RNA elements etc
[c] Additional functional groups may be encoded within the spacer region or 3' UTR, including bacterial transcriptional terminators, eukaryotic transcriptional terminators, eukaryotic enhancers, boundary elements, nuclear localizing sequences, supercoiling-induced DNA duplex destabilized (SIDD) structures, microRNAs, mRNA export sequences (3' UTR), and/or immunostimulatory RNA elements etc

TABLE 16

Spacer region, intron or 3' UTR encoded separated RSM selection/replication origin short spacer region replicative minicircle vector configurations

| # | Vector Intron configurations [a,b] | Vector Spacer region configurations [a,c] | Vector 3' UTR configurations [a,c] |
|---|---|---|---|
| 1 | SD ← Rep SA | PA RSM → EP | Stop PA |
| 2 | SD ← Rep SA | PA ← RSM EP | Stop PA |
| 3 | SD ← Rep SA | PA EP | Stop RSM → PA |
| 4 | SD ← Rep SA | PA EP | Stop ← RSM PA |
| 5 | SD Rep → SA | PA RSM → EP | Stop PA |
| 6 | SD Rep → SA | PA ← RSM EP | Stop PA |
| 7 | SD Rep → SA | PA EP | Stop RSM → PA |
| 8 | SD Rep → SA | PA EP | Stop ← RSM PA |
| 9 | SD ← RSM SA | PA Rep → EP | Stop PA |
| 10 | SD ← RSM SA | PA ← Rep EP | Stop PA |
| 11 | SD ← RSM SA | PA EP | Stop Rep → PA |
| 12 | SD ← RSM SA | PA EP | Stop ← Rep PA |
| 13 | SD RSM → SA | PA Rep → EP | Stop PA |
| 14 | SD RSM → SA | PA ← Rep EP | Stop PA |
| 15 | SD RSM → SA | PA EP | Stop Rep → PA |
| 16 | SD RSM → SA | PA EP | Stop ← Rep PA |
| 17 | SD SA | PA Rep → EP | Stop RSM → PA |
| 18 | SD SA | PA Rep → EP | Stop ← RSM PA |
| 19 | SD SA | PA ← Rep EP | Stop RSM → PA |
| 20 | SD SA | PA ← Rep EP | Stop ← RSM PA |
| 21 | SD SA | PA RSM → EP | Stop Rep → PA |
| 22 | SD SA | PA RSM → EP | Stop ← Rep PA |

TABLE 16-continued

Spacer region, intron or 3' UTR encoded separated
RSM selection/replication origin short spacer region
replicative minicircle vector configurations

| # | Vector Intron configurations [a,b] | Vector Spacer region configurations [a,c] | Vector 3' UTR configurations [a,c] |
|---|---|---|---|
| 23 | SD SA | PA ← RSM EP | Stop Rep → PA |
| 24 | SD SA | PA ← RSM EP | Stop ← Rep PA |

[a] SD = Splice donor; SA = Splice acceptor; Rep = replication origin, selected from the group R6K gamma replication origin, a ColE2-P9 replication origin, a ColE2-P9 related replication origin, a pUC replication origin (intron only, not in SR or 3' UTR), a $P_{min}$ pUC replication origin (intron only, not in SR or 3' UTR); RSM = RNA selectable marker; Stop = transgene stop codon; PA = polyadenylation signal; EP = RNA polymerase I, II or III enhancer promoter
[b] Additional functional groups may be encoded within the intron, including bacterial transcriptional terminators, eukaryotic promoters, eukaryotic enhancers, eukaryotic intronic splicing enhancers, nuclear localizing sequences, supercoiling-induced DNA duplex destabilized (SIDD) structures, microRNAs and/or immunostimulatory RNA elements etc
[c] Additional functional groups may be encoded within the spacer region or 3' UTR, including bacterial transcriptional terminators, eukaryotic transcriptional terminators, eukaryotic enhancers, mRNA export sequences (3' UTR), boundary elements, supercoiling-induced DNA duplex destabilized (SIDD) structures, nuclear localizing sequences, microRNAs and/or immunostimulatory RNA elements etc The vectors may encode a diversity of transgenes different from the examples provided herein, for example, antigen genes for a variety of pathogens, or therapeutic genes such as hypoxia inducible factor, keratinocyte growth factor, factor IX, factor VIII, etc, or RNA genes such as microRNAs or shRNA. Likewise, the vectors may utilize a diversity of RNA Pol II promoters different from the CMV promoter examples provided herein, for example, constitutive promoters such as the elongation factor 1 (EF1) promoter, the chicken β-actin promoter, the β-actin promoter from other species, the elongation factor-1α (EF1α) promoter, the phosphoglycerokinase (PGK) promoter, the Rous sarcoma virus (RSV) promoter, the human serum albumin (SA) promoter, the α-1 antitrypsin (AAT) promoter, the thyroxine binding globulin (TBG) promoter, the cytochrome P450 2E1 (CYP2E1) promoter, etc. The vectors may also utilize combination promoters such as the chicken β-actin/CMV enhancer (CAG) promoter, the human or murine CMV-derived enhancer elements combined with the elongation factor 1α (EF1α) promoters, CpG free versions of the human or murine CMV-derived enhancer elements combined with the elongation factor 1α (EF1α) promoters, the albumin promoter combined with an α-fetoprotein MERII enhancer, etc, or the diversity of tissue specific or inducible promoters know in the art such as the muscle specific promoters muscle creatine kinase (MCK), and C5-12 or the liver-specific promoter apolipoprotein A-I (ApoAI). The orientation of the various vector-encoded elements may also be changed relative to each other.

The vectors may optionally contain additional functionalities, such as nuclear localizing sequences, and/or immunostimulatory RNA elements as disclosed in Williams, Supra, 2008 as part of the eukaryotic region or alternatively within introns or within the spacer region.

Additional sequences may be added to the spacer, for example a eukaryotic selectable marker, bacterial transcription terminators, eukaryotic transcription terminators, boundary elements, supercoiling-induced DNA duplex destabilized (SIDD) structures, S/MARs, RNA Pol I or RNA Pol III expressed sequences or other functionalities. For example, improved transgene expression was observed when the gastrin eukaryotic transcription terminator was inserted into the spacer region (NTC9385R2a-O2-Gt versus NTC9385R2a-O2; Table 8). As well, additional sequences could be encoded within the intron, such as RNA Pol III transcription units expressing short hairpin RNA's, microRNAs or immunostimulatory RNAs such as those disclosed in Williams, Supra, 2008, included herein by reference.

Any eukaryotic expression vector can be converted into replicative minicircle expression vector of the invention by: 1) Cloning a RNA selectable marker and/or replication origin into an intron, 3' UTR, or spacer region; and 2) removing the existing vector spacer region encoded selection marker and/or replication origin. If the vector does not contain an intron, an intron for insertion of the bacterial region can be added by standard cloning methodologies known in the art. More than one intron can be used to make a replicative minicircle, by cloning the replication origin into one intron and the selectable marker into a second intron. Alternatively, the replication origin can be cloned into an intron or UTR, and the selection marker encoded within the spacer region created from excision of the existing vector encoded bacterial region. Cloning may be performed using restriction enzyme fragment ligation or ligation independent cloning, or the various PCR amplification based cloning strategies known in the art. Alternatively, the vectors of the invention can be created de novo using gene synthesis to make the entire vector or fragments of the vector.

Thus, the reader will see that the improved replicative minicircle expression vectors of the invention provide for an approach to improve plasmid encoded transgene expression (i.e. through incorporation of a short spacer region preferably less than 500 bp) while dramatically improving manufacture compared to alternative short spacer region vectors such as minicircles.

Accordingly, the scope of the invention should be determined not by the embodiments illustrated, but by the appended claims.

What is claimed is:

1. A method of constructing a eukaryotic replicative minicircle expression vector and expressing a gene of interest therefrom comprising:
   a) combining i) a eukaryotic region with 5' and 3' ends encoding a gene of interest and comprising an intron, the intron comprising a 5' splice donor and a 3' acceptor branch site, a bacterial replication origin selected from the group consisting of R6K replication origin, and ColE2-P9 replication origin, and an RNA selectable marker; with ii) a spacer region linking the 5' and 3' ends of the eukaryotic region, said spacer region being less than 500 basepairs in length, to create a eukaryotic replicative minicircle expression vector; and
   b) introducing said replicative minicircle expression vector into a target eukaryotic cell or a eukaryotic organism comprising the target eukaryotic cell, under conditions wherein the target eukaryotic cell is transfected and said gene of interest is expressed.

2. The method of claim 1, wherein said RNA selectable marker is an RNA-IN regulating RNA-OUT functional variant with at least 95% sequence identity to a sequence selected from the group consisting of SEQ ID NO:20, and SEQ ID NO:22.

3. The method of claim 1, wherein said RNA selectable marker is selected from the group consisting of:
   an RNA-OUT selectable marker that encodes an RNA-IN regulating RNA-OUT RNA with at least 95% sequence identity to SEQ ID NO: 21;
   an RNAI selectable marker that encodes an RNAII regulating RNAI RNA with at least 95% sequence identity to SEQ ID NO: 33;
   an IncB RNAI selectable marker encoding an RNAII regulating RNAI RNA with at least 95% sequence identity to SEQ ID NO: 35; and
   an synthetic RNA selectable marker encoding an RNA selectable marker complement regulating RNA with at least 95% sequence identity to SEQ ID NO: 38.

4. The method of claim 1, wherein said intron with a 5' splice donor and a 3' acceptor branch site is a functional variant with at least 95% sequence identity to a sequence selected from the group consisting of: SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10.

5. The method of claim 1, wherein said pUC replication origin and said RNA selectable marker positioned within said intron is a functional variant with at least 95% sequence identity to SEQ ID NO: 29.

6. A method of constructing a eukaryotic replicative minicircle expression vector comprising:
   a) combining i) a eukaryotic region with 5' and 3' ends encoding a gene of interest and comprising an intron the intron comprising a 5' splice donor and a 3' acceptor branch site, a bacterial region comprising an R6K origin or a ColE2-P9 bacterial replication origin, and a RNA selectable marker with ii) a spacer region linking the 5' and 3' ends of the eukaryotic region sequences, said spacer region being less than 500 basepairs in length, to create a eukaryotic replicative minicircle expression vector;
b) transforming said replicative minicircle expression vector into cells of an RNA selectable marker regulated bacterial cell line;
c) isolating the resultant transformed bacterial cells by selection; and
d) propagating the resultant transformed bacterial cells in culture.

7. The method of claim 6, wherein said RNA selectable marker is an RNA-IN regulating RNA-OUT functional variant with at least 95% sequence identity to a sequence selected from the group consisting of SEQ ID NO:20, and SEQ ID NO:22.

8. The method of claim 6, wherein said RNA selectable marker is selected from the group consisting of:
an RNA-OUT selectable marker that encodes an RNA-IN regulating RNA-OUT RNA with at least 95% sequence identity to SEQ ID NO: 21;
an RNAI selectable marker that encodes an RNAII regulating RNAI RNA with at least 95% sequence identity to SEQ ID NO: 33;
an IncB RNAI selectable marker encoding an RNAII regulating RNAI RNA with at least 95% sequence identity to SEQ ID NO: 35; and
an synthetic RNA selectable marker encoding an RNA selectable marker complement regulating RNA with at least 95% sequence identity to SEQ ID NO: 38.

9. The method of claim 6, wherein said intron with a 5' splice donor and a 3' acceptor branch site is a functional variant with at least 95% sequence identity to a sequence selected from the group consisting of: SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10.

10. The method of claim 6, wherein said pUC replication origin and said RNA selectable marker positioned within said intron is a functional variant with at least 95% sequence identity to SEQ ID NO: 29.

11. A eukaryotic replicative minicircle expression vector comprising i) a eukaryotic region sequence with 5' and 3' ends encoding a gene of interest and comprising an intron, the intron comprising a 5' splice donor and a 3' acceptor branch site, a bacterial replication origin selected from the group consisting of R6K replication origin, and ColE2-P9 replication origin, and an RNA selectable marker; and ii) a spacer region of less than 500 basepairs in length linking the 5' and 3' ends of the eukaryotic region sequences.

12. The vector of claim 11, wherein said RNA selectable marker is an RNA-IN regulating RNA-OUT functional variant with at least 95% sequence identity to a sequence selected from the group consisting of SEQ ID NO:20, and SEQ ID NO:22.

13. The vector of claim 11, wherein said RNA selectable marker is selected from the group consisting of: an RNA-OUT selectable marker that encodes an RNA-IN regulating RNA-OUT RNA with at least 95% sequence identity to SEQ ID NO: 21; an RNAI selectable marker that encodes an RNAII regulating RNAI RNA with at least 95% sequence identity to SEQ ID NO: 33; an IncB RNAI selectable marker encoding an RNAII regulating RNAI RNA with at least 95% sequence identity to SEQ ID NO: 35; an synthetic RNA selectable marker encoding an RNA selectable marker complement regulating RNA with at least 95% sequence identity to SEQ ID NO: 38.

14. The vector of claim 11, wherein said intron with a 5' splice donor and a 3' acceptor branch site is a functional variant with at least 95% sequence identity to a sequence selected from the group consisting of: SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10.

15. The vector of claim 11, wherein said pUC replication origin and said RNA selectable marker positioned within said intron is a functional variant with at least 95% sequence identity to SEQ ID NO: 29.

* * * * *